(12) United States Patent
Shimazaki et al.

(10) Patent No.: US 6,426,345 B1
(45) Date of Patent: Jul. 30, 2002

(54) HETEROBICYCLIC DERIVATIVES

(75) Inventors: Norihiko Shimazaki, Tsuchiura; Shinya Watanabe; Akihiko Sawada, both of Tsukuba; Keiji Hemmi, deceased, late of Tsukuba, all of (JP), by Mitsue Hemmi, Keiichiro Hemmi, Yusuke Hemmi, heirs

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 08/793,451

(22) PCT Filed: Jul. 10, 1995

(86) PCT No.: PCT/JP95/01366

§ 371 (c)(1),
(2), (4) Date: Jan. 8, 1998

(87) PCT Pub. No.: WO96/01825

PCT Pub. Date: Jan. 25, 1996

(30) Foreign Application Priority Data

Jul. 11, 1989 (GB) .............................. 9413975

(51) Int. Cl.[7] .................... C07D 487/04; A61K 3/4985; A61D 11/06
(52) U.S. Cl. .................... 514/234.2; 514/249; 544/117; 544/350
(58) Field of Search .............................. 514/234.2, 249; 544/117, 350

(56) References Cited

U.S. PATENT DOCUMENTS 4,296,114 A * 10/1981 Appleton ............... 424/248.52

FOREIGN PATENT DOCUMENTS

EP  008 864  3/1980

OTHER PUBLICATIONS

Hayashi, S. et al, Chem. Pharm. Bull, 23(4), 1975, 810–816.*

* cited by examiner

Primary Examiner—Richard L. Raymond
Assistant Examiner—Thomas C McKenzie
(74) Attorney, Agent, or Firm—Oblon, Spivak, McClelland, Maier & Neustadt, P.C.

(57) ABSTRACT

Heterobicyclic derivatives of the formula:

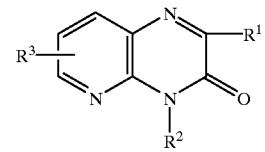

wherein
$R^1$ is aryl which may have suitable substituent(s), ar(lower)alkyl which may have suitable substituent(s), halo(lower)alkyl, protected carboxy(lower)alkyl, acyl (lower)alkyl, heterocyclic group or heterocyclic(lower) alkyl which may have suitable substituent(s), $R^2$ is aryl which may have suitable substituent(s) or heterocyclic group, and $R^3$ is hydrogen, lower alkoxy or arylthio, and a pharmaceutically acceptable salt thereof which are useful as a medicament.

23 Claims, No Drawings

HETEROBICYCLIC DERIVATIVES

This application is a 371 of PCT/JP95/01366, filed Jul. 10, 1995.

TECHNICAL FIELD

This invention relates to new heterobicyclic derivatives and pharmaceutically acceptable salts thereof which are useful as a medicament.

BACKGROUND ART

Some heterobicyclic derivatives have been known as described, for example, in EP 0 008 864 A2.

DISCLOSURE OF INVENTION

This invention relates to new heterobicyclic derivatives.

One object of this invention is to provide the new and useful pyridopyrazine derivatives and pharmaceutically acceptable salts thereof which possess a strong phosphodiesterase IV (PDE IV)-inhibitory activity and a strong inhibitory activity on the production of tumor necrosis factor (TNF).

Another object of this invention is to provide processes for preparation of the pyridopyrazine derivatives and salts thereof.

A further object of this invention is to provide a pharmaceutical composition comprising said pyridopyrazine derivatives or a pharmaceutically acceptable salt thereof.

Still further object of this invention is to provide a use of said pyridopyrazine derivatives or a pharmaceutically acceptable salt thereof as a medicament for prophylactic and therapeutic treatment of PDE-IV and TNF mediated diseases such as chronic inflammatory diseases, specific autoimmune diseases, sepsis-induced organ injury, and the like in human being and animals.

The object pyridopyrazine derivatives of the present invention are novel and can be represented by the following general formula (I):

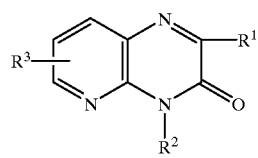

(I)

wherein $R^1$ is aryl which may have suitable substituent(s), ar(lower)alkyl which may have suitable substituent(s), halo(lower)alkyl, protected carboxy(lower)alkyl, acyl(lower)alkyl, heterocyclic group or heterocyclic(lower)alkyl which may have suitable substituent(s), $R^2$ is aryl which may have suitable substituent(s) or heterocyclic group, and $R^3$ is hydrogen, lower alkoxy or arylthio.

The object compound (I) of the present invention can be prepared by the following processes.

Process (1)

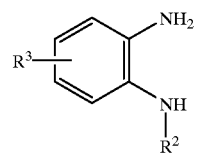

(II)
or a salt thereof

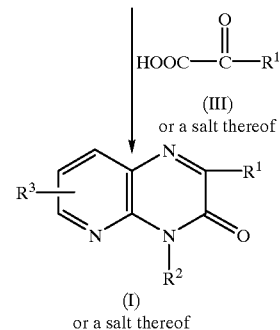

(III)
or a salt thereof (I)
or a salt thereof

Process (2)

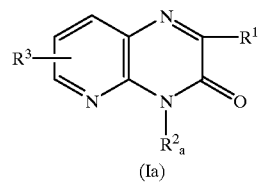

(Ia)
or its reactive derivative
at the amino group, or a salt thereof

↓ acylation

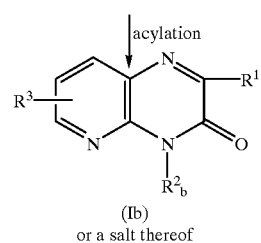

(Ib)
or a salt thereof

Process (3)

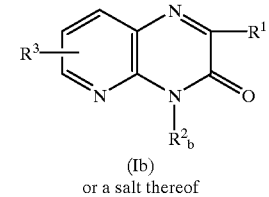

(Ib)
or a salt thereof

↓ deacylation

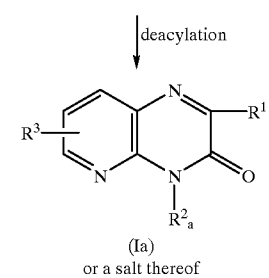

(Ia)
or a salt thereof

Process (4)

[Chemical structure (XI) or a salt thereof]

↓ halogenation

[Chemical structure (Ic) or a salt thereof]

Process (5)

[Chemical structure (Id) or a salt thereof]

① ↓ [Reagent (VIII) or a salt thereof]

[Chemical structure (IX) or a salt thereof]

② ↓ elimination of N-protective group

[Chemical structure (Ie) or a salt thereof]

wherein
$R^1$, $R^2$ and $R^3$ are each as defined above,
$R_a^1$ is halo(lower)alkyl,
$R_a^2$ is aryl having amino or aryl having aminoaryl,
$R_b^2$ is aryl having acylamino or aryl having acylaminoaryl,
$R^4$ is lower alkyl, $R^5$ is N-protective group,
Y is halogen,
$Y^{\ominus}$ is halide, and
A is lower alkylene.

The starting compound (II) of the present invention can be prepared by the following processes.

Process (A)

[Chemical structure (IV) or a salt thereof]

① ↓ $H_2N-R^2$ (V) or salt thereof

[Chemical structure (VI) or a salt thereof]

② ↓ reduction

[Chemical structure (II) or a salt thereof]

Process (B)

[Chemical structure (II) or a salt thereof]

↓ HOOC—C(=O)—$R^4$ (X) or a salt thereof

[Chemical structure (XI) or a salt thereof]

Process (C)

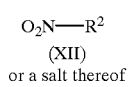
(XII)
or a salt thereof

↓ reduction

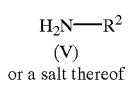
(V)
or a salt thereof

Process (D)

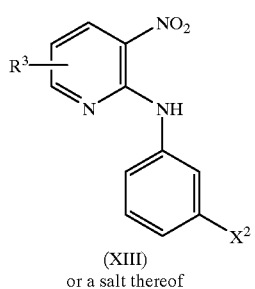
(XIII)
or a salt thereof $H_2C=CH-R^6$
(XIV)
or a salt thereof

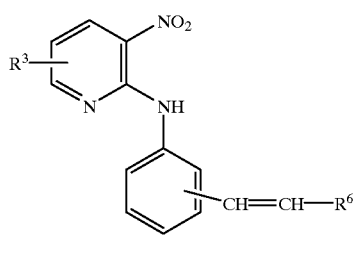
(VIa)
or a salt thereof

Process (E)

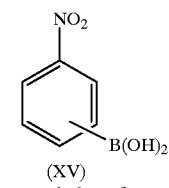
(XV)
or a salt thereof $X^3-R^7$
(XVI)
or a salt thereof

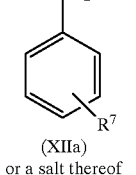
(XIIa)
or a salt thereof

Process (F)

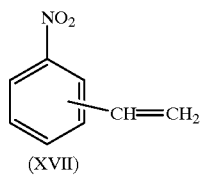
(XVII)

$X^4-R^6$
(XVIII)
or a salt thereof

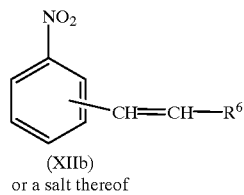
(XIIb)
or a salt thereof

Process (G)

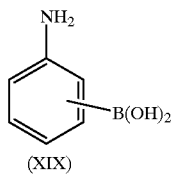
(XIX)
or a salt thereof $X^5-R^8$
(XX)
or a salt thereof

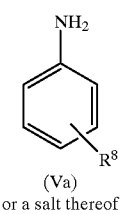
(Va)
or a salt thereof

Process (H)

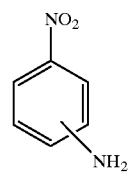
(XIIc)
or a salt thereof

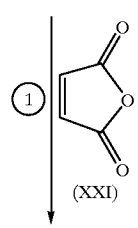
(XXI)

↓

-continued

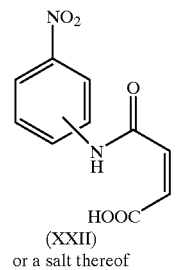

(XXII)
or a salt thereof

↓ 2 dehydration

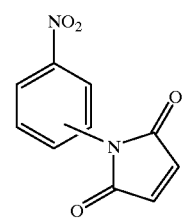

(XXIII)
or a salt thereof

Process (I)

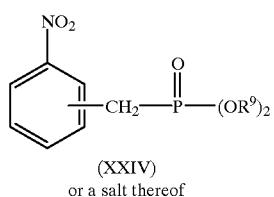

(XXIV)
or a salt thereof

↓

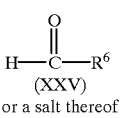

(XXV)
or a salt thereof

↓

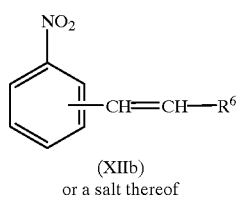

(XIIb)
or a salt thereof wherein
$R^2$, $R^3$ and $R^4$ are each as defined above,
$R^6$ is heterocyclic group which may have 1 to 3 halogen,
$R^7$ is aryl,
$R^8$ is aryl having acylamino,
$R^9$ is lower alkyl, and
$X^1$, $X^2$, $X^3$, $X^4$ and $X^5$ are each a leaving group.

Suitable pharmaceutically acceptable salts of the object compound (I) are conventional non-toxic salts and may include a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.); an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, fumarate, methanesulfonate, benzenesulfonate, toluenesulfonate, etc.); a salt with a basic or acidic amino acid (e.g., arginine, aspartic acid, glutamic acid, etc.).

In the above and subsequent descriptions of the present specification, suitable examples and illustration of the various definitions which the present invention intends to include within the scope thereof are explained in detail as follows.

The term "lower" is used to intend a group having 1 to 6, preferably 1 to 4, carbon atom(s), unless otherwise provided.

The term "higher" is used to intend a group having 7 to 20 carbon atoms, unless otherwise provided.

Suitable "lower alkyl" and "lower alkyl moiety" in the terms "ar(lower)alkyl", halo(lower)alkyl, "protected carboxy(lower)alkyl", "acyl(lower)alkyl", "heterocyclic (lower)alkyl" and "heterocyclicoxycarbonyl(lower)alkyl" may include straight or branched one having 1 to 6 carbon atom(s), such as methyl, ethyl, propyl, isopropyl, butyl, isobutyl, sec-butyl, tert-butyl, pentyl, tert-pentyl, hexyl, and the like, and in which more preferable example may be $C_1$–$C_4$ alkyl.

Suitable "lower alkenyl" may include vinyl, 1-(or 2-)propenyl, 1-(or 2- or 3-)butenyl, 1-(or 2- or 3- or 4-)pentenyl, 1-(or 2- or 3- or 4- or 5-)hexenyl, methylvinyl, ethylvinyl, 1-(or 2- or 3-)methyl-1-(or 2-)propenyl, 1-(or 2- or 3-)ethyl-1-(or 2-)propenyl, 1-(or 2- or 3- or 4-)methyl-1-(or 2- or 3-)butenyl, and the like, in which more preferable example may be $C_2$–$C_4$ alkenyl.

Suitable "lower alkynyl" may include ethynyl, 1-propynyl, propargyl, 1-methylpropargyl, 1 or 2 or 3-butynyl, 1 or 2 or 3 or 4-pentynyl, 1 or 2 or 3 or 4 or 5-hexynyl, and the like.

Suitable "lower alkoxy" may include methoxy, ethoxy, propoxy, isopropoxy, butoxy, isobutoxy, t-butoxy, pentyloxy, t-pentyloxy, hexyloxy and the like.

Suitable "lower alkylene" may include straight or branched one such as methylene, ethylene, trimethylene, tetramethylene, pentamethylene, hexamethylene, methylmethylene, ethylethylene, propylene, and the like, in which more preferable example may be $C_1$–$C_4$ alkylene and the most preferable one may be methylene.

Suitable "cyclo(lower)alkyl" may include cyclopentyl, cyclohexyl and the like.

Suitable "cyclo(lower)alkenyl" may include cyclohexenyl, cyclohexadienyl and the like.

Suitable "aryl" and "aryl moiety" in the terms "ar(lower)alkyl", "arylthio", "aminoaryl" and "acylaminoaryl" may include phenyl, naphthyl and the like.

Suitable "halogen" and "halogen moiety" in the term "halo(lower)alkyl" may include fluorine, bromine, chlorine and iodine.

Suitable "leaving group" may include acid residue, lower alkoxy as exemplified above, and the like.

Suitable "acid residue" may include halogen as exemplified above, acyloxy and the like.

Suitable "halide" may include fluoride, bromide, chloride and the like.

Suitable "protected carboxy" and "protected carboxy moiety" in the term "protected carboxy(lower)alkyl" may include esterified carboxy and the like. And suitable example of said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, etc.); lower alkenyl ester (e.g., vinyl ester, allyl ester, etc.); lower alkynyl ester (e.g. ethynyl ester, propynyl ester, etc.); lower alkoxy(lower)alkyl ester (e.g., methoxymethyl ester, ethoxymethyl ester, isopropoxymethyl ester, 1-methoxyethyl ester, 1-ethoxyethyl ester, etc.); lower alkylthio(lower)alkyl ester (e.g., methylthiomethyl ester, ethylthiomethyl ester, ethylthioethyl ester, isopropoxythiomethyl ester, etc.); mono(or di or tri)halo(lower) alkyl ester (e.g., 2-iodoethyl ester, 2,2,2-trichloroethyl ester, etc.); lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 1-acetoxyethyl ester, 2-acetoxyethyl ester, 2-propionyloxyethyl ester, etc.); lower alkoxycarbonyloxy(lower)alkyl ester (e.g., methoxycarbonyloxymethyl ester, ethoxycarbonyloxymethyl ester, propoxycarbonyloxymethyl ester, 1-(or 2-)-[methoxycarbonyloxy]ethyl ester, 1-(or 2-)-[ethoxycarbonyloxy]ethyl ester, 1-(or 2-)-[propoxycarbonyloxy]ethyl ester, 1-(or 2-)-[isopropoxycarbonyloxy]ethyl ester, etc.); lower alkanesulfonyl(lower)alkyl ester (e.g., mesylmethyl ester, 2-mesylethyl ester, etc.); lower alkoxycarbonyloxy(lower) alkyl ester (e.g., methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-)isopropoxycarbonyloxyethyl ester, etc.); phthalidylidene (lower)alkyl ester; (5-lower alkyl-2-oxo-1,3-dioxol-4-yl) (lower)alkyl ester [e.g., (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.]; mono(or di or tri)alkyl(lower)alkyl ester, for example, mono(or di or tri)phenyl(lower)alkyl ester which may have one or more suitable substituent(s) (e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have one or more suitable substituent(s) such as substituted or unsubstituted phenyl ester (e.g., phenyl ester, tolyl ester, t-butylphenyl ester, xylyl ester, mesityl ester, cumenyl ester, 4-chlorophenyl ester, 4-methoxyphenyl ester, etc.); tri(lower)alkylsilyl ester; lower alkylthioester (e.g. methylthioester, ethylthioester, etc.) and the like.

Suitable "hydroxy protective group" in the term "protected hydroxy" may include acyl, mono(or di or tri)phenyl (lower)alkyl which may have one or more suitable substituent(s) (e.g., benzyl, 4-methoxybenzyl, trityl, etc.), trisubstituted silyl [e.g., tri(lower)alkylsilyl (e.g., trimethylsilyl, t-butyldimethylsilyl, etc.), etc.], tetrahydropyranyl and the like.

Suitable "N-protective group" may include acyl or a conventional protecting group such as mono (or di or tri)aryl(lower)alkyl, for example, mono(or di or tri)phenyl (lower)alkyl (e.g., benzyl, trityl, etc.) or the like.

Suitable "protected amino" may include acylamino or an amino group substituted by a conventional protecting group such as mono (or di or tri)aryl(lower)alkyl, for example, mono(or di or tri)phenyl(lower)alkyl (e.g., benzyl, trityl, etc.) or the like.

Suitable "acyl" and "acyl moiety" in the terms "acylamino", "acyloxy" and "acyl(lower)alkyl" may include carbamoyl, thiocarbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

Carbamoyl; Thiocarbamoyl; Aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.); lower or higher alkenoyl (e.g., acryloyl, 2-(or 3-)butenoyl, 2-(or 3- or 4-)pentenoyl, 2-(or 3- or 4- or 5-)hexenoyl, etc.); lower or higher alkoxycarbonyl (e.g., methoxycarbonyl, ethoxycarbonyl, isopropoxycarbonyl, t-butoxycarbonyl, t-pentyloxycarbonyl, heptyloxycarbonyl, etc.); lower or higher alkylsulfonyl (e.g., methylsulfonyl, ethylsulfonyl, etc.); lower or higher alkoxysulfonyl (e.g., methoxysulfonyl, ethoxysulfonyl, etc.); lower alkadienoyl (e.g., heptadienoyl, hexadienoyl, etc.); cyclo(lower) alkylcarbonyl (e.g., cyclopropylcarbonyl, cyclopentylcarbonyl, cyclohexylcarbonyl, etc.); cyclo (lower)alkylidene(lower)alkanoyl (e.g., cycloheptylideneacetyl, cycloheptylidenepropanoyl, cyclohexylideneacetyl, cyclohexylidenepropanoyl, etc.); cyclo(lower)alkyloxycarbonyl (e.g., cyclopentyloxycarbonyl, cyclohexyloxycarbonyl, etc.); lower alkylglyoxyloyl (e.g., methylglyoxyloyl, ethylglyoxyloyl, propylglyoxyloyl, etc.); lower alkoxyglyoxyloyl (e.g., methoxyglyoxyloyl, ethoxyglyoxyloyl, propoxyglyoxyloyl, etc.); or the like;

Aromatic acyl such as aroyl (e.g., benzoyl, toluoyl, naphthoyl, etc.); ar(lower) alkanoyl [e.g., phenyl(lower)alkanoyl (e.g., phenylacetyl, phenylpropanoyl, phenylbutanoyl, phenylisobutanoyl, phenylpentanoyl, phenylhexanoyl, etc.), naphthyl(lower) alkanoyl (e.g., naphthylacetyl, naphthylpropanoyl, naphthylbutanoyl, etc.), etc.]; ar(lower)alkenoyl [e.g., phenyl(lower)alkenoyl (e.g., phenylpropenoyl, phenylbutenoyl, phenylmethacryloyl, phenylpentenoyl, phenylhexenoyl, etc.), naphthyl(lower)alkenoyl (e.g., naphthylpropenoyl, naphthylbutenoyl, etc.), etc.]; ar(lower)alkoxycarbonyl [e.g., phenyl(lower) alkoxycarbonyl (e.g., benzyloxycarbonyl, etc.), etc.]; aryloxycarbonyl (e.g., phenoxycarbonyl, naphthyloxycarbonyl, etc.); aryloxy(lower)alkanoyl (e.g., phenoxyacetyl, phenoxypropionyl, etc.); arylglyoxyloyl (e.g., phenylglyoxyloyl, naphthylglyoxyloyl, etc.); arylsulfonyl (e.g., phenylsulfonyl, p-tolylsulfonyl, etc.); ar(lower)alkylsulfonyl [e.g., phenyl(lower)alkylsulfonyl (e.g., benzylsulfonyl, phenylethylsulfonyl, etc.), naphthyl (lower)alkylsulfonyl (e.g., naphthylmethylsulfonyl, naphthylethylsulfonyl, etc.), etc.]; or the like;

Heterocyclic acyl such as heterocycliccarbonyl; heterocyclic(lower)alkanoyl (e.g., heterocyclicacetyl, heterocyclicpropanoyl, heterocyclicbutanoyl, heterocyclicpentanoyl, heterocyclichexanoyl, etc.); heterocyclic(lower)alkenoyl (e.g., heterocyclicpropenoyl, heterocyclicbutenoyl, heterocyclicpentenoyl, heterocyclichexenoyl, etc.); heterocyclicglyoxyloyl; heterocyclicoxycarbonyl; or the like; in which suitable "heterocyclic moiety" in the terms "heterocycliccarbonyl", "heterocyclic(lower)alkanoyl", heterocyclic(lower)alkenoyl", heterocyclicoxycarbonyl and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like.

And, especially preferable heterocyclic group may be heterocyclic group such as unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidinyl, pyrazinyl, pyridazinyl, triazolyl (e.g., 1H-1,2,4-triazolyl, 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, tetrahydroquinolyl (e.g., 1,2,3,4-tetrahydroquinolyl, etc.), isoquinolyl, indazolyl, benzotriazolyl, benzopyrimidinyl (e.g., benzo[b]pyrimidinyl, etc.), etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl, etc.;

unsaturated condensed heterocyclic group containing 1 to 2 oxygen atom(s), for example, benzodioxolyl (e.g. methylenedioxyphenyl, etc.), benzofuryl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl (e.g., benzo[b]thienyl, etc.), benzodithiinyl, etc.;

unsaturated condensed heterocyclic group containing an oxygen atom and 1 to 2 sulfur atom(s), for example, benzoxathiinyl, etc.; and the like.

The acyl moiety as stated above may have one to ten, same or different, suitable substituent(s) such as lower alkyl as exemplified above, lower alkoxy as exemplified above, lower alkylthio wherein lower alkyl moiety is as exemplified above, cyclo(lower)alkyl as exemplified above, cyclo(lower)alkenyl as exemplified above, cyclo(lower)alkyloxy wherein cyclo(lower)alkyl moiety is as exemplified above, halogen as exemplified above, amino, protected amino as exemplified above, hydroxy, protected hydroxy as exemplified above, cyano, nitro, carboxy, protected carboxy as exemplified above, sulfo, sulfamoyl, imino, oxo, amino(lower)alkyl wherein lower alkyl moiety is as exemplified above, carbamoyloxy, mono(or di or tri)halo(lower)alkyl wherein halogen moiety and lower alkyl moiety are each as exemplified above, hydroxy(lower)alkyl wherein lower alkyl moiety is as exemplified above, heterocyclic group as exemplified above, heterocyclicoxy wherein heterocyclic moiety is as exemplified above, heterocyclicamino which may have nitro wherein heterocyclic moiety is as exemplified above, aryl which may have suitable substituent(s) wherein aryl moiety is as exemplified above, arylsulfonyl wherein aryl moiety is as exemplified above, ar(lower)alkyl wherein aryl moiety and lower alkyl moiety are each as exemplified above, protected carboxy(lower)alkenyl wherein protected carboxy moiety and lower alkenyl moiety are each as exemplified above, acyl as exemplified above, acylamino wherein acyl moiety is as exemplified above, or the like.

Suitable "heterocyclic group" and "heterocyclic moiety" in the terms "heterocyclic(lower)alkyl" and "heterocyclicoxycarbonyl(lower)alkyl" can be referred to the ones as mentioned above.

Suitable "substituent" in the term "ar(lower)alkyl which may have suitable substituent(s)" may include lower alkyl as exemplified above, lower alkoxy as exemplified above, lower alkenyl as exemplified above, lower alkynyl as exemplified above, mono(or di or tri)halo(lower)alkyl wherein halogen moiety and lower alkyl moiety are each as exemplified above, cyclo(lower)alkyl as exemplified above, cyclo(lower)alkenyl as exemplified above, halogen as exemplified above, carboxy, protected carboxy as exemplified above, hydroxy, protected hydroxy as exemplified above, aryl as exemplified above, ar(lower)alkyl wherein aryl moiety and lower alkyl moiety are each as exemplified above, carboxy(lower)alkyl wherein lower alkyl moiety is as exemplified above, protected carboxy(lower)alkyl wherein protected carboxy moiety and lower alkyl moiety are each as exemplified above, nitro, amino, protected amino as exemplified above, di(lower)alkylamino wherein lower alkyl moiety is as exemplified above, amino(lower)alkyl wherein lower alkyl moiety is as exemplified above, protected amino(lower)alkyl wherein protected amino moiety and lower alkyl moiety are each as exemplified above, hydroxy(lower)alkyl wherein lower alkyl moiety is as exemplified above, protected hydroxy(lower)alkyl wherein protected hydroxy moiety and lower alkyl moiety are each as exemplified above, acyl as exemplified above, cyano, sulfo, sulfamoyl, carbamoyloxy, mercapto, lower alkylthio wherein lower alkyl moiety is as exemplified above, imino, and the like.

Suitable "substituent" in the term "aryl which may have suitable substituent(s)" may include lower alkyl as exemplified above, lower alkoxy as exemplified above, lower alkenyl as exemplified above, lower alkynyl as exemplified above, mono(or di or tri)halo(lower)alkyl wherein halogen moiety and lower alkyl moiety are each as exemplified above, cyclo(lower)alkyl as exemplified above, cyclo(lower)alkenyl as exemplified above, halogen as exemplified above, cyclo(lower)alkyloxy wherein cyclo(lower)alkyl moiety is as exemplified above, carboxy, protected carboxy as exemplified above, hydroxy, protected hydroxy as exemplified above, aryl as exemplified above, ar(lower)alkyl wherein aryl moiety and lower alkyl moiety are each as exemplified above, carboxy(lower)alkyl wherein lower alkyl moiety as exemplified above, protected carboxy(lower)alkyl wherein protected carboxy moiety and lower alkyl moiety are each as exemplified above, nitro, amino, protected amino as exemplified above, acylamino wherein acyl moiety is as exemplified above, di(lower)alkylamino wherein lower alkyl moiety is as exemplified above, amino(lower)alkyl wherein lower alkyl moiety is as exemplified above, protected amino(lower)alkyl wherein protected amino moiety and lower alkyl moiety are each as exemplified above, hydroxy(lower)alkyl wherein lower alkyl moiety is as exemplified above, protected hydroxy(lower)alkyl wherein protected hydroxy moiety and lower alkyl moiety are each as exemplified above, acyl as exemplified above, cyano, sulfo, sulfamoyl, carbamoyloxy, mercapto, lower alkylthio wherein lower alkyl moiety is as exemplified above, lower alkylamino wherein lower alkyl moiety is as exemplified above, N-acyl-N-lower alkylamino wherein acyl moiety and lower alkyl moiety are each as exemplified above, acyl(lower)alkyl wherein acyl moiety and lower alkyl moiety are each as exemplified above, ar(lower)alkenyl which may have 1 to 3 halogen wherein aryl moiety, lower alkenyl moiety and halogen moiety are each as exemplified above, acyl(lower)alkenyl wherein acyl moiety, and lower alkenyl moiety are each as exemplified above, protected carboxy(lower)alkenyl wherein protected carboxy moiety and lower alkenyl moiety are each as exemplified above, cyano(lower)alkenyl wherein lower alkenyl moiety is as exemplified above, heterocyclicoxy which may have 1 to 3 aryl wherein heterocyclic moiety and aryl moiety are each as exemplified above, imino, [heterocyclicamino which may have 1 to 3 substituent(s) selected from the group consisting of lower alkyl and aryl] wherein heterocyclic moiety, lower alkyl moiety and aryl moiety are each as exemplified above; [aryl which may have 1 to 3 substituent(s) selected from the group consisting of carboxy(lower)alkenyl, protected carboxy(lower)alkenyl, aryl, lower alkoxy, cyclo(lower)alkyloxy, halogen, carboxy, protected carboxy, amino, acylamino, diacylamino and acyl] wherein aryl moiety, lower alkenyl moiety, protected carboxy moiety, lower alkoxy moiety, cyclo(lower)alkyl moiety, halogen moiety and acyl moiety are each as exemplified above; heterocyclic(lower)alkenyl which may have 1 to 3 halogen wherein heterocyclic moiety, lower alkenyl moiety and halogen moiety are each as exemplified above; [heterocyclic group which may have 1 to 3 substituent(s) selected from the group consisting of halogen, cyano, carboxy, protected carboxy, oxo, acyl, amino, protected amino and heterocyclic group] wherein heterocyclic moiety, halogen moiety, protected carboxy moiety, acyl moiety and protected amino moiety are each as exemplified above; and the like.

Suitable "substituent" in the term "heterocyclic(lower)alkyl which may have suitable substituent(s)" may include lower alkyl as exemplified above, lower alkoxy as exemplified above, lower alkenyl as exemplified above, lower alkynyl as exemplified above, mono(or di or tri)halo(lower)alkyl wherein halogen moiety and lower alkyl moiety are each as exemplified above, cyclo(lower)alkyl as exemplified above, cyclo(lower)alkenyl as exemplified above, halogen as exemplified above, carboxy, protected carboxy as exemplified above, hydroxy, protected hydroxy as exemplified above, aryl as exemplified above, ar(lower)alkyl wherein aryl moiety and lower alkyl moiety are each as exemplified above, carboxy(lower)alkyl wherein lower alkyl moiety as exemplified above, protected carboxy(lower)alkyl wherein protected carboxy moiety and lower alkyl moiety are each as exemplified above, nitro, amino, protected amino as exemplified above, di(lower)alkylamino wherein lower alkyl moiety is as exemplified above, amino(lower)alkyl wherein lower alkyl moiety is as exemplified above, protected amino(lower)alkyl wherein protected amino moiety and lower alkyl moiety are each as exemplified above, hydroxy(lower)alkyl wherein lower alkyl moiety is as exemplified above, protected hydroxy(lower)alkyl wherein protected hydroxy moiety and lower alkyl moiety are each as exemplified above, acyl as exemplified above, cyano, sulfo, sulfamoyl, carbamoyloxy, mercapto, lower alkylthio wherein lower alkyl moiety is as exemplified above, imino, and the like.

The processes for preparing the object and the starting compounds are explained in detail in the following.

Process (1)

The compound (I) or a salt thereof can be prepared by reacting the compound (II) or a salt thereof with the compound (III) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, diethyl ether or any other solvent which does not adversely affect the reaction.

The reaction temperature is not critical and the reaction is usually carried out under warming to heating.

Process (2)

The compound (Ib) or a salt thereof can be prepared by subjecting the compound (Ia) or its reactive derivative at the amino group or a salt thereof to acylation reaction.

Suitable acylating agent to be used in the present acylation reaction may include the compound of the formula:

$$R^{10}\text{—OH} \quad\quad\quad (VII)$$

(wherein $R^{10}$ is acyl) or its reactive derivative or a salt thereof.

Suitable reactive derivative at the amino group of the compound (Ia) may include Schiff's base type imino or its tautomeric enamine type isomer formed by the reaction of the compound (Ia) with a carbonyl compound such as aldehyde, ketone or the like; a silyl derivative formed by the reaction of the compound (Ia) with a silyl compound such as N,O-bis(trimethylsilyl)acetamide, N-trimethylsilylacetamide or the like; a derivative formed by the reaction of the compound (Ia) with phosphorus trichloride or phosgene, and the like.

Suitable reactive derivative of the compound (VII) may include an acid halide, an acid anhydride, an activated ester, isocyanate, and the like. The suitable example may be an acid chloride; acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfuric acid (e.g., methanesulfonic acid, ethanesulfonic acid, etc.), sulfuric acid, alkylcarbonic acid, aliphatic carboxylic acid (e.g, pivalic acid, pentanoic acid, isopentanoic acid, 2-ethylbutyric acid, trichloroacetic acid, etc.); aromatic carboxylic acid (e.g., benzoic acid, etc.); a symmetrical acid anhydride; an activated amide with imidazole, 4-substituted imidazole, dimethylpyrazole, triazole or tetrazole; an activated ester (e.g., cyanomethyl ester, methoxymethyl ester, dimethyliminomethyl

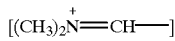

ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthio ester, p-nitrophenyl thioester, p-cresyl thioester, carboxymethyl thioester, pyranyl ester, pyridyl ester, piperidyl ester, 8-quinolyl thioester, etc.); an ester with a N-hydroxy compound (e.g., N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.); substituted or unsubstituted aryl isocyanate; substituted or unsubstituted aryl isothiocyanate, and the like. These reactive derivatives can optionally be selected from them accordingly to the kind of the compound (VII) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (VII) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diisopropylcarbodiimide; N-ethyl-N'-(3-dimethylaminopropyl)carbodiimide; N,N-carbonyl-bis(2-methylimidazole); pentamethyleneketene-N-cyclohexylimine; diphenylketene-N-cyclohexylimine; ethoxyacetylene; 1-alkoxy-1-chloroethylene; trialkyl phosphite; isopropyl polyphosphate; phosphorous oxychloride (phosphoryl chloride); phosphorous trichloride; thionyl chloride; oxalyl chloride; triphenylphosphite; 2-ethyl-7-hydroxybenzisoxazolium salt; 2-ethyl-5-(m-sulfophenyl) isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorous oxychloride, etc.; or the like.

The reaction may also be carried out in the presence of an organic or inorganic base such as an alkali metal bicarbonate, tri(lower)alkylamine, pyridine, N-(lower)alkylmorphorine, N,N-di(lower)alkylbenzylamine, or the like.

The reaction temperature is not critical, and the reaction is usually carried out under cooling to heating.

Process (3)

The compound (Ia) or a salt thereof can be prepared by subjecting the compound (Ib) or a salt thereof to deacylation reaction.

Suitable method of this deacylation reaction may include conventional one such as hydrolysis, reduction and the like.

(i) For Hydrolysis

The hydrolysis is preferably carried out in the presence of a base or an acid including Lewis acid.

Suitable base may include an inorganic base and an organic base such as an alkali metal [e.g., sodium, potassium, etc.], an alkaline earth metal [e.g., magnesium, calcium, etc.], the hydroxide or carbonate or hydrogencarbonate thereof, trialkylamine [e.g., trimethylamine, triethylamine, etc.], picoline, 1,5-diazabicyclo[4.3.0]non-5-ene, or the like.

Suitable acid may include an organic acid [e.g., formic acid, acetic acid, propionic acid, trichloroacetic acid, trifluoroacetic acid, etc.], and an inorganic acid [e.g., hydrochloric acid, hydrobromic acid, sulfuric acid, hydrogen chloride, hydrogen bromide, etc.].

The elimination using Lewis acid such as trihaloacetic acid [e.g., trichloroacetic acid, trifluoroacetic acid, etc.], or the like is preferably carried out in the presence of cation trapping agents [e.g., anisole, phenol, etc.].

The reaction is usually carried out in a conventional solvent such as water, alcohol (e.g., methanol, ethanol, isopropyl, alcohol, etc.), tetrahydrofuran, dioxane, toluene, methylene chloride, ethylene dichloride, chloroform, N,N-dimethylformamide, N,N-dimethylacetamide or any other organic solvents which do not adversely affect the reaction, or the mixture thereof.

The reaction temperature is not critical and the reaction is usually carried out under cooling to warming.

(ii) For Reduction

Reduction is carried out in a conventional manner, including chemical reduction and catalytic reduction.

Suitable reducing reagent to be used in chemical reduction are hydrides (e.g., hydrogen iodide, hydrogen sulfide, lithium aluminum hydride, sodium borohydride, sodium cyanoborohydride, etc.), or a combination of a metal (e.g., tin, zinc, iron, etc.) or metallic compound (e.g., chromium chloride, chromium acetate, etc.) and an organic acid or an inorganic acid (e.g., formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g., platinum plate, spongy platinum, platinum black, colloidal platinum, platinum oxide, platinum wire, etc.), palladium catalysts (e.g., spongy palladium, palladium black, palladium oxide, palladium on carbon, colloidal palladium, palladium on barium sulfate, palladium on barium carbonate, etc.), nickel catalysts (e.g., reduced nickel, nickel oxide, Raney nickel, etc.), cobalt catalysts (e.g., reduced cobalt, Raney cobalt, etc.), iron catalysts (e.g., reduced iron, Raney iron, Ullman iron, etc.), and the like.

The reduction is usually carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvents which do not adversely affect the reaction, or the mixture thereof.

Additionally, in case that the above-mentioned acids to be used in chemical reduction are in liquid, they can also be used as a solvent.

The reaction temperature of this reduction is not critical and the reaction is usually carried out under cooling to warming.

Process (4)

The compound (Ic) or a salt thereof can be prepared by subjecting the compound (XI) or a salt thereof to halogenation reaction.

This halogenation is usually carried out by using a conventional halogenating agent such as halogen (e.g., chlorine, bromine, etc.), phosphorus trihalide (e.g., phosphorus tribromide, phosphorus trichloride, etc.), phosphorus pentahalide (e.g., phosphorus pentachloride, phosphorus pentabromide, etc.), phosphorus oxychloride (e.g., phosphoryl trichloride, phosphoryl monochloride, etc.), thionyl halide (e.g., thionyl chloride, thionyl bromide, etc.), oxalyl halide (e.g., oxalyl chloride, oxalyl bromide, etc.), N-halosuccinimide (e.g. N-bromosuccinimide, N-chlorosuccinimide, etc.) and the like.

This reaction is usually carried out in a solvent such as water, alcohol (e.g., methanol, ethanol, isopropyl alcohol, etc.), benzene, dioxane, N,N-dimethylformamide, tetrahydrofuran, methylene chloride, ethylene dichloride, chloroform, diethyl ether or any other solvent which does not adversely affect the reaction.

The reaction temperature is not critical and the reaction is usually carried out under cooling to warming.

Process (5)-①

The compound (IX) or a salt thereof can be prepared by reacting the compound (Id) or a salt thereof with the compound (VIII) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvents which do not adversely affect the reaction, or the mixture thereof.

The reaction temperature is not critical and the reaction is usually carried out under cooling to heating.

The reaction is usually carried out in the presence of an acid including Lewis acid.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, zinc halide (e.g. zinc chloride, zinc bromide, etc.), etc.] and the like.

The reaction may be also carried out in the presence of an inorganic or an organic base such as an alkali metal (e.g., sodium, potassium, etc.), an alkali metal hydroxide (e.g., sodium hydroxide, potassium hydroxide, etc.), an alkali metal hydrogencarbonate (e.g., sodium hydrogencarbonate, potassium hydrogencarbonate, etc.), alkali metal carbonate (e.g., sodium carbonate, potassium carbonate, etc.), tri(lower)alkylamine (e.g., trimethylamine, triethylamine, diisopropylethylamine, etc.), alkali metal hydride (e.g., sodium hydride, etc.), alkali metal (lower)alkoxide (e.g., sodium methoxide, sodium ethoxide, etc.), pyridine, lutidine, picoline, dimethylaminopyridine, N-(lower) alkylmorpholine, N,N-di(lower)alkylbenzylamine, N,N-di(lower)alkylaniline or the like.

When the base, the acid and/or the starting compound are in liquid, they can be used also as a solvent.

Process (5)-②

The compound (Ie) or a salt thereof can be prepared by subjecting the compound (IX) or a salt thereof to elimination reaction of N-protective group.

This reaction can be carried out in a similar manner to that of the aforementioned Process (3), and therefore the reagents to be used and the reaction conditions (e.g., solvent, reaction temperature, etc.) can be referred to those of the Process (3).

Process (A)-①

The compound (VI) or a salt thereof can be prepared by reacting the compound (IV) or a salt thereof with the compound (V) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, diethyl ether or any other solvent which does not adversely affect the reaction.

The reaction temperature is not critical and the reaction is usually carried out under warming to heating.

When the starting compound is in liquid, it can be also used as a solvent.

Process (A)-②

The compound (II) or a salt thereof can be prepared by subjecting the compound (VI) or a salt thereof to reduction reaction.

Reduction is carried out in a conventional manner, including chemical reduction and catalytic reduction.

Suitable reducing reagent to be used in chemical reduction are hydrides (e.g., hydrogen iodide, hydrogen sulfide, lithium aluminum hydride, sodium borohydride, sodium cyanoborohydride, etc.) or a combination of a metal (e.g., tin, zinc, iron, etc.) or metallic compound (e.g., chromium chloride, chromium acetate, etc.) and an organic acid or an inorganic acid (e.g., formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g., platinum plate, spongy platinum, platinum black, colloidal platinum, platinum oxide, platinum wire, etc.), palladium catalysts (e.g., spongy palladium, palladium black, palladium oxide, palladium on carbon, colloidal palladium, palladium on barium sulfate, palladium on barium carbonate, etc.), nickel catalysts (e.g., reduced nickel, nickel oxide, Raney nickel, etc.), cobalt catalysts (e.g., reduced cobalt, Raney cobalt, etc.), iron catalysts (e.g., reduced iron, Raney iron, etc.), copper catalysts (e.g., reduced copper, Raney copper, Ullman copper, etc.) and the like.

The reduction is usually carried out in a conventional solvent which does not adversely influence the reaction such as water, alcohol (e.g., methanol, ethanol, propanol, etc.), tetrahydrofuran, dioxane, N,N-dimethylformamide, etc., or a mixture thereof.

The reaction temperature is not critical and the reaction is usually carried out under cooling to warming.

Process (B)

The compound (XI) or a salt thereof can be prepared by reacting the compound (II) or a salt thereof with the compound (X) or a salt thereof.

This reaction can be carried out in a similar manner to that of the aforementioned Process (1), and therefore the reagents to be used and the reaction conditions (e.g., solvent, reaction temperature, etc.) can be referred to those of the Process (1).

Process (C)

The compound (V) or a salt thereof can be prepared by subjecting the compound (XII) or a salt thereof to reduction reaction.

This reaction can be carried out in a similar manner to that of the aforementioned Process (A)-②, and therefore the reagents to be used and the reaction conditions (e.g., solvent, reaction temperature, etc.) can be referred to those of the Process (A)-②.

The present invention includes, within the scope of the invention, the case that a maleimidophenyl group is transformed into a succinimidophenyl group during the reaction.

Process (D)

The compound (VIa) or a salt thereof can be prepared by reacting the compound (XIII) or a salt thereof with the compound (XIV) or a salt thereof.

The reaction can be carried out in the manner disclosed in Preparation 51 or similar manners thereto.

Process (E)

The compound (XIIa) or a salt thereof can be prepared by reacting the compound (XV) or a salt thereof with the compound (XVI) or a salt thereof.

The reaction can be carried out in the manner disclosed in Preparation 41 or similar manners thereto.

Process (F)

The compound (XIIb) or a salt thereof can be prepared by reacting the compound (XVII) with the compound (XVIII) or a salt thereof.

The reaction can be carried out in the manner disclosed in Preparation 38 or similar manners thereto.

Process (G)

The compound (Va) or a salt thereof can be prepared by reacting the compound (XIX) or a salt thereof with the compound (XX) or a salt thereof.

The reaction can be carried out in the manner disclosed in Preparation 4, 61, 62 or 63, or similar manners thereto.

Process (H)-①

The compound (XXII) or a salt thereof can be prepared by reacting the compound (XIIc) or a salt thereof with the compound (XXI).

The reaction can be carried out in the manner disclosed in Preparation 77 or similar manners thereto.

Process (H)-②

The compound (XXIII) or a salt thereof can be prepared by subjecting the compound (XXII) or a salt thereof to dehydration reaction.

The reaction can be carried out in the manner disclosed in Preparation 78 or similar manners thereto.

Process (I)

The compound (XIIb) or a salt thereof can be prepared by reacting the compound (XXIV) or a salt thereof with the compound (XXV) or a salt thereof.

The reaction can be carried out in the manner disclosed in Preparation 42 or similar manners thereto.

Suitable salts of the object and the starting compounds in Processes (1)~(5) and (A)~(I) can be referred to the ones as exemplified for the compound (I).

The new pyridopyrazine derivatives (I) and pharmaceutically acceptable salts thereof hardly possess a strong inhibitory activity against phosphodiesterase III (PDE III), but possess a strong inhibitory activity against phosphodiesterase IV (PDE IV) and a strong inhibitory activity on the tumor necrosis factor (TNF).

That is, the pyridopyrazine derivatives (I) and pharmaceutically acceptable salts thereof are selective inhibitors of phosphodiesterase IV (PDE IV) and inhibitors on the production of tumor necrosis factor (TNF).

Accordingly, the new pyridopyrazine derivatives (I) and a pharmaceutically acceptable salt thereof can be used for prophylactic and therapeutic treatment of PDE-IV and TNF mediated diseases such as chronic inflammatory diseases (e.g., rheumatoid arthritis, osteoarthritis, emphysema, chronic bronchiolitis, etc.), osteoporosis, rejection by transplantation, asthma, eosinophilia, cystic fibrosis, hepatitis, pancreatitis, nephritis, endotoxin shock, specific autoimmune diseases [e.g., ankylosing spondylitis, autoimmune hematological disorders (e.g., hemolyticodo anaemia, aplastic anaemia, pure red cell anaemia, idiopathic thrombocytopenia, etc.), systemic lupus erythematosus, polychondritis, scleroderma, Wegener granulamotosis, dermatomyositis, chronic active hepatitis, myasthenia gravis, atopic dermatitis, psoriasis, idiopathic sprue, autoimmune inflammatory bowel disease (e.g., ulcerative colitis, Crohn's disease, etc.), endocrine ophthalmopathy, Grave's disease, sarcoidosis, multiple sclerosis, primary biliary cirrhosis, juvenile diabetes (diabetes mellitus type I), Reiter's syndrome, non infection uveitis, autoimmune keratitis (e.g., keratoconjunctivitis sicca, vernal keratoconjunctivitis, etc.), interstitial lung fibrosis, psoriatic arthritis, etc.], cancer cachexia, AIDS cachexia, thrombosis, and the like.

In order to show the utilities of the pyridopyrazine derivatives (I) and a pharmaceutically acceptable salt thereof of the present invention, pharmacological test data of the representative compound of the pyridopyrazine derivatives (I) are illustrated in the following.

(a) Inhibition of U937 Phosphodiesterase IV (PDE IV)

1. Test Method

Harvested U937 was freezed in −80° C. and throwed to destroy the cell body. The pellet of destroyed cell was washed by Phosphate-buffered saline (PBS).

The washed cell pellet was homogenized with Dounce homogenizer (20 strokes) in homogenizing buffer (0.5% deoxycholate [DOC], 5 mM 2-mercaptoethanol, 1 $\mu$M leupeptin, 100 $\mu$M PMSF, 20 $\mu$M p-tosyl-L-lysine-chloromethyl ketone [TLCK] in PBS). The homogenate was centrifuged at 100,000 g×90 minutes (4° C.) and the supernatant containing PDE IV activity was dialyzed against dialysis buffer, which was the same component as homogenizing buffer without DOC. The dialyzed supernatant of homogenate was stored in freezer (−80° C.) as PDE IV enzyme preparation.

Enzyme preparation was diluted in assay buffer (10 mM Tris-HCl, 5 mM MgCl, 1 mM 2-Mercaptoethanol [pH 8.0]). In advance the rate of dilution was choosen every new lot of homogenizing preparation. For blank, a part of the enzyme preparation was boiled for 10 minutes.

Test compounds were dissolved in dimethylsulfoxide (DMSO) at a concentration of 4×10(−2)[M] (final conc. 1×10(−5)M), then serial dilutions were made in DMSO to achieve desired concentrations. The diluted compounds of each concentration were further diluted 1:500 in assay buffer (0.2% DMSO). Final DMSO concentration in assay tube was 0.025%.

In duplicate, the followings were added to a glass tube, in order, at 0° C. (all concentrations are given as final concentrations in assay tube).

50 $\mu$l compound or assay buffer for control or blank

50 $\mu$l 8×10(−5)[M] CI-930 (final 10 $\mu$M): (CI-930 is PDE III inhibitor)

200 $\mu$l enzyme preparation or boiled enzyme preparation for blank.

The reaction tube was preincubated in a water bath (30° C.) for 5 minutes, then 100 $\mu$l [³H]-cAMP (37.0 MBq/ml [³H]-cAMP: 4 $\mu$M cold cAMP=1:800) was added thereto. After 15 minutes, 2.5 units/ml alkaline phosphatase was added to the reaction mixture and the reaction was continued for 15 minutes. Dowex 1×8 gel was added to the reaction mixture and was vortexed well. The mixture was centrifuged at 1000 rpm×5 minutes, and then 500 $\mu$l of the supernatant was added to 10 ml scintillation fluid in appropriate vial, vortexed, and counted for [³H].

The inhibitory activity was calculated according to the following equation:

$$\% \text{ Inhibition} = 100 - \frac{\text{avg. cpm [test compound]} - \text{avg. cpm [blank (boiled enzyme)]}}{\text{avg. cpm [control (no compound)]} - \text{avg. cpm [blank (boiled enzyme)]}} \times 100$$

2. Test Compound (a) 4-[3-[3-(1-Naphthyl)ureido]phenyl]-2-benzyl-3-oxo-3,4-dihydropyrido[2,3-b]pyrazine 3. Test Result

| Test compound | IC$_{50}$ (M) |
| --- | --- |
| (a) | $3.1 \times 10^{-8}$ |

(b) Inhibition on TNF-α production in human mononuclear cells

1. Test Method

Blood was drawn from healthy volunteers with heparin. The mononuclear cell (MNC) fraction was obtained by gradient centrifugation (1800 rpm, 15 minutes), diluted with the same volume of RPMI-1640 culture medium, over Ficoll-Paque (Pharmacia LKB Biotechnology). MNC were washed twice with RPMI-1640. Then, MNC were resuspended in RPMI-1640 culture medium supplemented with 2 mM L-glutamine and 1% fetal bovine serum. MNC were incubated at 37° C. for 16 hours in 96-well micro culture plate at a concentration of $3 \times 10^{-5}$ cells/well with or without 1 μg/ml lipopolysaccharide (LPS)(from *E. coli*) and various amounts of test compound. At the end of incubation, the supernatant was obtained and its TNF-α active was measured by enzyme-linked immunosorbent assay (ELISA). ELISA was performed with TNF-α ELISA kit (Otsuka Pharmaceutical Co., Ltd.).

2. Test Compound (a) 4-[3-[3-(1-Naphthyl)ureido]phenyl]-2-benzyl-3-oxo-3,4-dihydropyrido[2,3-b]pyrazine 3. Test Result

| Test compound | IC$_{50}$ (M) |
| --- | --- |
| (a) | $5.6 \times 10^{-8}$ |

For therapeutic administration, the object compounds (I) of the present invention and pharmaceutically acceptable salts thereof are used in a form of the conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as granule, capsule, tablet, dragee or suppository, or in a liquid form such as solution, suspension or emulsion for injection, ingestion, eye drops, etc. If needed, there may be included in the above preparation auxiliary substance such as stabilizing agent, wetting or emulsifying agent, buffer or any other commonly used additives.

The effective ingredient may usually be administered with a unit dose of 0.001 mg/kg to 500 mg/kg, preferably 0.01 mg/kg to 10 mg/kg, 1 to 4 times a day. However, the above dosage may be increased or decreased according to age, weight and conditions of the patient or the administering method.

Preferred embodiments of the object compound (I) are as follows.

$R^1$ is phenyl which may have 1 to 3 (more preferably one or two; most preferably one) suitable substituent(s) (more preferably nitro); phenyl(lower)alkyl which may have 1 to 3 (more preferably one or two;

most preferably one) suitable substituent(s) [more preferably substituent selected from the group consisting of nitro, amino, protected amino (more preferably acylamino), hydroxy and protected hydroxy (more preferably acyloxy; most preferably lower alkanoyloxy)]; halo(lower)alkyl; protected carboxy(lower)alkyl (more preferably esterified carboxy(lower)alkyl; most preferably lower alkoxycarbonyl (lower)alkyl); carbamoyl(lower)alkyl which may have one or two suitable substituent(s) [more preferably substituent selected from the group consisting of lower alkyl and heterocyclic group (more preferably pyrrolidinyl)]; heterocyclicoxycarbonyl(lower)alkyl (more preferably pyrrolidinyloxycarbonyl(lower)alkyl) which may have 1 to 3 (more preferably one or two) suitable substituent(s) (more preferably oxo); heterocycliccarbonyl(lower)alkyl (more preferably pyrrolidinylcarbonyl(lower)alkyl or piperazinylcarbonyl(lower)alkyl) which may have 1 to 3 (more preferably one or two; most preferably one) substituent(s) selected from the group consisting of protected carboxy (more preferably esterified carboxy; most preferably lower alkoxycarbonyl) and lower alkyl; indolyl; or indolyl(lower)alkyl, pyridyl(lower)alkyl, imidazolyl (lower)alkyl, morpholinyl(lower)alkyl or triazolyl(lower) alkyl, each of which may have 1 to 3 (more preferably one or two; most preferably one) suitable substituent(s) [more preferably substituent selected from the group consisting of lower alkyl, N-oxide and aryl (more preferably phenyl)];

$R^2$ is phenyl or naphthyl, each of which may have 1 to 3 (more preferably one or two) suitable substituent(s) {more preferably substituent selected from the group consisting of lower alkyl; halogen; mono(or di or tri)halo(lower)alkyl (more preferably trihalo(lower) alkyl); hydroxy; protected hydroxy (more preferably acyloxy; most preferably lower alkanoyloxy); carboxy; protected carboxy (more preferably esterified carboxy; most preferably lower alkoxycarbonyl or phenyl (lower)alkoxycarbonyl); carboxy(lower)alkyl; protected carboxy(lower)alkyl (more preferably esterified carboxy(lower)alkyl; most preferably lower alkoxycarbonyl(lower)alkyl); lower alkoxy; cyano; nitro; amino; acylamino [more preferably lower alkanoylamino; aryloxycarbonylamino (more preferably phenyl(lower)alkoxycarbonylamino); lower alkoxycarbonylamino; lower alkoxyglyoxyloyl; cyclo (lower)alkylcarbonylamino; cyclo(lower) alkyloxycarbonylamino; cyclo(lower)alkylidene (lower)alkanoylamino; aroylamino (more preferably benzoylamino or naphthoylamino) which may have 1 to 3 (more preferably one or two) substituent(s) selected from the group consisting of lower alkyl, halogen, lower alkoxy, carboxy, protected carboxy (more preferably esterified carboxy; most preferably lower alkoxycarbonyl), nitro, hydroxy, protected hydroxy (more preferably acyloxy; most preferably lower alkanoyloxy), mono(or di or tri)halo(lower)alkyl (more preferably trihalo(lower)alkyl), cyclo(lower) alkyloxy, aryl (more preferably phenyl), carboxy (lower)alkenyl, protected carboxy(lower)alkenyl (more preferably esterified carboxy(lower)alkenyl; most preferably lower alkoxycarbonyl(lower)alkenyl), amino, protected amino (more preferably aroylamino; most preferably benzoylamino), heterocyclicoxy (more preferably pyrimidinyloxy), and heterocyclicamino (more preferably pyridylamino) which may have nitro; arylsulfonylamino (more preferably phenylsulfonylamino) which may have one or two halogen; ar(lower) alkylsulfonylamino (more preferably phenyl(lower) alkylsulfonylamino); cyclo(lower)alkylcarbonylamino; [mono(or di)ar(lower)alkanoyl]amino (more preferably [mono (or di)phenyl(lower) alkanoyl]amino or [naphthyl(lower)alkanoyl]amino); lower alkadienoylamino; heterocycliccarbonylamino (more preferably furylcarbonylamino, pyridylcarbonylamino, thienylcarbonylamino, indolylcarbonylamino, indolinylcarbonylamino, quinolylcarbonylamino, tetrahydroquinolylcarbonylamino, benzofurylcarbonylamino, benzothienylcarbonylamino, methylenedioxybenzoylamino or morpholinylcarbonylamino) which may have 1 to 3 (more preferably one or two) substituent(s) selected from the group consisting of lower alkyl and halogen; ar(lower)alkenoylamino (more preferably phenyl(lower)alkenoylamino) which may have 1 to 3 (more preferably one or two; most preferably one) substituent(s) selected from the group consisting of lower alkyl, halogen, carboxy, protected carboxy (more preferably esterified carboxy; most preferably lower alkoxycarbonyl) and nitro; heterocyclic(lower)alkenoylamino (more preferably pyridyl(lower)alkenoylamino); carbamoylamino which may have one or two substituent(s) selected from the group consisting of lower alkyl; aryl (more preferably phenyl or naphthyl) which may have 1 to 3 (more preferably one or two) substituent(s) selected from the group consisting of nitro, amino, protected amino (more preferably acylamino), lower alkoxy, lower alkylthio, lower alkyl, aryl (more preferably phenyl), carboxy, protected carboxy (more preferably esterified carboxy; most preferably lower alkoxycarbonyl), di(lower)alkylamino, mono(or di or tri)halo(lower)alkyl (more preferably trihalo(lower)alkyl) and halogen; arylsulfonyl (more preferably phenylsulfonyl); ar(lower)alkyl (more preferably phenyl(lower)alkyl); cyclo(lower)alkyl; and heterocyclic group (more preferably thiazolyl, pyridyl, quinolyl or morpholinyl); or thiocarbamoylamino which may have one or two (more preferably one) substituent(s) selected from the group consisting of aryl (more preferably phenyl or naphthyl) and acyl (more preferably aroyl; most preferably benzoyl)]; lower alkylamino; N-acyl-N-lower alkylamino [more preferably N-lower alkanoyl-N-lower alkylamino, N-aroyl-N-lower alkylamino (more preferably N-benzoyl-N-lower alkylamino), N-arylcarbamoyl-N-lower alkylamino (more preferably N-phenylcarbamoyl-N-lower alkylamino) or N-protected carboxyar(lower)alkenoyl-N-lower alkylamino (more preferably N-[esterified carboxyphenyl](lower)alkenoyl-N-lower alkylamino; most preferably N-[lower alkoxycarbonylphenyl](lower)alkenoyl-N-lower alkylamino)]; heterocyclicamino (more preferably thiazolylamino or pyrimidinylamino) which may have 1 to 3 (more preferably one or two; most preferably one) substituent(s) selected from the group consisting of lower alkyl and aryl (more preferably phenyl); acyl [more preferably lower alkanoyl, carbamoyl which may have one or two substituent(s) selected from the group consisting of lower alkyl and aryl (more preferably phenyl) which may have one or two halogen, aroyl (more preferably benzoyl) which may have lower alkoxy or heterocycliccarbonyl (more preferably morpholinylcarbonyl or indolizinylcarbonyl)]; acyl(lower)alkyl [more preferably carbamoyl(lower)alkyl which may have one or two (more preferably one) aryl (more preferably phenyl or naphthyl)]; aryl (more preferably phenyl or naphthyl) which may have 1 to 3 (more preferably one or two) substituent(s) selected from the group consisting of carboxy(lower)alkenyl, protected carboxy(lower)alkenyl (more preferably esterified carboxy(lower)alkenyl; most preferably lower alkoxycarbonyl(lower)alkenyl), aryl (more preferably phenyl), lower alkoxy, cyclo(lower)alkyloxy, halogen, carboxy, protected carboxy (more preferably esterified carboxy; most preferably lower alkoxycarbonyl), amino, acylamino [more preferably lower alkanoylamino, aroylamino (more preferably benzoylamino) which may have protected carboxy (more preferably esterified carboxy) or carboxy, lower alkylsulfonylamino, mono(or di or tri)halo(lower)alkanoylamino (more preferably trihalo(lower)alkanoylamino), lower alkoxycarbonylamino, aryloxycarbonylamino (more preferably phenoxycarbonylamino), carboxy(lower)alkanoylamino, protected carboxy(lower)alkanoylamino (more preferably esterified carboxy(lower)alkanoylamino; most preferably lower alkoxycarbonyl(lower)alkanoylamino), carboxy(lower)alkenoylamino, protected carboxy(lower)alkenoylamino (more preferably esterified carboxy(lower)alkenoylamino; most preferably lower alkoxycarbonyl(lower)alkenoylamino), cyclo(lower)alkylcarbonylamino, lower alkylglyoxyloylamino, arylsulfonylamino (more preferably phenylsulfonylamino) which may have one or two halogen, ar(lower)alkenoylamino (more preferably phenyl(lower)alkenoylamino) which may have protected carboxy (more preferably esterified carboxy) or carboxy, heterocyclic(lower)alkenoylamino (more preferably pyridyl(lower)alkenoylamino), heterocycliccarbonylamino (more preferably quinoxalinylcarbonylamino or benzothienylcarbonylamino), carbamoylamino which may have one or two substituent(s) selected from the group consisting of lower alkyl and aryl (more preferably phenyl)], diacylamino (more preferably bis(lower alkylsulfonyl)amino) and acyl (more preferably carbamoyl which may have one or two substituent(s) selected from the group consisting of lower alkyl and aryl (more preferably phenyl or naphthyl); ar(lower)alkyl (more preferably phenyl(lower)alkyl or naphthyl(lower)alkyl); ar(lower)alkenyl (more preferably phenyl(lower)alkenyl or naphthyl(lower)alkenyl) which may have 1 to 3 (more preferably one or two) halogen; acyl(lower)alkenyl (more preferably aroyl(lower)alkenyl; most preferably benzoyl(lower)alkenyl); protected carboxy(lower)alkenyl (more preferably esterified carboxy(lower)alkenyl; most preferably lower alkoxycarbonyl(lower)alkenyl); cyano(lower)alkenyl; heterocyclic(lower)alkenyl (more preferably pyridyl(lower)alkenyl which may have 1 to 3 (more preferably one or two; most preferably one) halogen, pyrimidinyl(lower)alkenyl or quinolyl(lower)alkenyl); heterocyclic group (more preferably pyridyl, thienyl, pyrrolyl, pyrrolidinyl, indolyl, quinolyl, isoquinolyl, imidazolyl, thiazolyl, benzothiazolyl or triazolyl) which may have 1 to 3 (more preferably one or two) substituent(s) selected from the group consisting of halogen, cyano, carboxy, protected carboxy (more preferably esterified carboxy; most preferably lower alkoxycarbonyl), oxo, acyl (more preferably lower alkanoyl), amino, protected amino (more preferably acylamino) and heterocyclic group (more preferably pyridyl); and heterocyclicoxy (more preferably pyrimidinyloxy) which may have 1 to 3 (more preferably one or two; most preferably one) aryl (more preferably phenyl)}, or pyridyl, $R^3$ is hydrogen, lower alkoxy or arylthio (more preferably phenylthio).

More preferred embodiments of the object compound (I) are as follows.

R$^1$ is phenyl, nitrophenyl, phenyl(lower)alkyl, nitrophenyl(lower)alkyl, aminophenyl(lower)alkyl, hydroxyphenyl(lower)alkyl, lower alkanoyloxyphenyl (lower)alkyl, halo(lower)alkyl, lower alkoxycarbonyl (lower)alkyl, [pyrrolidinylcarbamoyl](lower)alkyl, [N,N-di(lower)alkylcarbamoyl](lower)alkyl, pyrrolidinylcarbonyl(lower)alkyl, [dioxopyrrolidinyloxycarbonyl](lower)alkyl, [lower alkoxycarbonylpyrrolidinylcarbonyl](lower)alkyl, [lower alkylpiperazinylcarbonyl](lower)alkyl, indolyl, indolyl(lower)alkyl, pyridyl(lower)alkyl which may have N-oxide, imidazolyl(lower)alkyl which may have lower alkyl or phenyl, or morpholinyl(lower)alkyl, R$^2$ is phenyl, lower alkylphenyl, halophenyl, trihalo (lower)alkylphenyl, hydroxyphenyl, lower alkanoyloxyphenyl, carboxyphenyl, lower alkoxycarbonylphenyl, [phenyl(lower)alkoxycarbonyl] phenyl, [carboxy(lower)alkyl]phenyl, [lower alkoxycarbonyl(lower)alkyl]phenyl, lower alkoxyphenyl, cyanophenyl, nitrophenyl, aminophenyl, [lower alkanoylamino]phenyl, [phenoxycarbonylamino]phenyl, [lower alkoxycarbonylamino]phenyl, [lower alkoxyglyoxyloylamino]phenyl, [cyclo(lower) alkyloxycarbonylamino]phenyl, [cyclo(lQwer) alkylcarbonylamino]phenyl, [cyclo(lower)alkylidene (lower)alkanoylamino]phenyl, [benzoylamino]phenyl, [mono(or di)(lower alkyl)benzoylamino]phenyl, [mono(or di)halobenzoylamino]phenyl, [di(lower alkoxy)benzoylamino]phenyl, [bis(lower alkoxycarbonyl)benzoylamino]phenyl, [mono(or di)nitrobenzoylamino]phenyl, [hydroxybenzoylamino] phenyl, [lower alkanoyloxybenzoylamino]phenyl, [bis [trihalo(lower)alkyl]benzoylamino]phenyl, phenyl having benzoylamino substituted with lower alkoxy-carbonyl and nitro, phenyl having benzoylamino substituted with lower alkoxy and cyclo(lower)alkyloxy, [phenylbenzoylamino]phenyl, [[lower alkoxycarbonyl (lower)alkenyl]benzoylamino]phenyl, [[benzoylamino]benzoylamino]phenyl, [pyrimidinyloxybenzoylamino]phenyl, [[nitropyridylamino]benzoylamino]phenyl, [naphthoylamino]phenyl, [hydroxynaphthoylamino] phenyl, [[lower alkanoyloxynaphthoyl]amino]phenyl, [[lower alkoxycarbonylnaphthoyl]amino]phenyl, [phenylsulfonylamino]phenyl, [dihalophenylsulfonylamino]phenyl, [phenyl(lower) alkylsulfonylamino]phenyl, [cyclo(lower) alkylcarbonylamino]phenyl, [mono(or di)phenyl (lower)alkanoylamino]phenyl, [naphthyl(lower) alkanoylamino]phenyl, [lower alkadienoylamino] phenyl, [furylcarbonylamino]phenyl, [pyridylcarbonylamino]phenyl, [dihalopyridylcarbonylamino]phenyl, [thienylcarbonylamino]phenyl, [indolinylcarbonylamino]phenyl, [quinolylcarbonylamino]phenyl, [tetrahydroquinolylcarbonylamino]phenyl, [benzofurylcarbonylamino]phenyl, [lower alkylindolylcarbonylamino]phenyl, [benzothienylcarbonylamino]phenyl, [methylenedioxybenzoylamino]phenyl, [morpholinylcarbonylamino]phenyl, [phenyl(lower) alkenoylamino]phenyl, [[lower alkylphenyl(lower) alkenoyl]amino]phenyl, [[mono(or di)halophenyl (lower)alkenoyl]amino]phenyl, [[lower alkoxycarbonylphenyl(lower)alkenoyl]amino]phenyl, [[nitrophenyl(lower)alkenoyl]amino]phenyl, [pyridyl (lower)alkenoylamino]phenyl, ureidophenyl, [lower alkylureido]phenyl, [phenylureido]phenyl, [[aminophenyl]ureido]phenyl, [[halophenylureido] phenyl, [[nitrophenyl]ureido]phenyl, [[lower alkoxyphenyl]ureido]phenyl, [[lower alkylthiophenyl] ureido]phenyl, [[mono(or di)(lower alkyl)phenyl] ureido]phenyl, [biphenylylureido]phenyl, [[carboxyphenyl]ureido]phenyl, [[lower alkoxycarbonylphenyl]uredio]phenyl, [[di(lower) alkylaminophenyl]ureido]phenyl, [[trihalo(lower) alkylphenyl]ureido]phenyl, [[dihalophenyl]ureido] phenyl, [naphthylureido]phenyl, [phenylsulfonylureido]phenyl, [phenyl(lower) alkylureido]phenyl, [cyclo(lower)alkylureido]phenyl, [thiazolylureido]phenyl, [pyridylureido]phenyl, [quinolylureido]phenyl, [morpholinylureido]phenyl, [N-phenyl-N-lower alkylureido]phenyl, [phenyl (thioureido)]phenyl, [naphthyl(thioureido)]phenyl, [benzoyl(thioureido)]phenyl, [lower alkylamino] phenyl, [N-lower alkanoyl-N-lower alkylamino] phenyl, [N-benzoyl-N-lower alkylamino]phenyl, [N-phenylcarbamoyl-N-lower alkylamino]phenyl, [N-lower alkoxycarbonylphenyl(lower)alkenoyl-N-lower alkylamino]phenyl, [lower alkylthiazolylamino] phenyl, [phenylthiazolylamino]phenyl, [pyrimidinylamino]phenyl, lower alkanoylphenyl, carbamoylphenyl, [lower alkylcarbamoyl]phenyl, [phenylcarbamoyl]phenyl, [dihalophenylcarbamoyl] phenyl, [N-dihalophenyl-N-lower alkylcarbamoyl] phenyl, benzoylphenyl, [lower alkoxybenzoyl]phenyl, morpholinylcarbonylphenyl, indolizinylcarbonylphenyl, [phenylcarbamoyl(lower) alkyl]phenyl, [naphthylcarbamoyl(lower)alkyl]phenyl, phenylphenyl, [[lower alkoxycarbonyl(lower)alkenyl] phenyl]phenyl,, biphenylylphenyl, phenyl having phenyl substituted with lower alkoxy and cyclo(lower) alkyloxy, [halophenyl]phenyl, [carboxyphenyl]phenyl, [lower alkoxycarbonylphenyl]phenyl, [aminophenyl] phenyl, [[lower alkanoylamino]phenyl]phenyl, [[benzoylamino]phenyl]phenyl, [[carboxybenzoylamino]phenyl]phenyl, [[mono(or bis) (lower alkylsulfonyl)amino]phenyl]phenyl, [[trihalo (lower)alkanoylamino]phenyl]phenyl, [[lower alkoxycarbonylamino]phenyl]phenyl, [[phenoxycarbonylamino]phenyl]phenyl, [[carboxy (lower)alkanoylamino]phenyl]phenyl, [[lower alkoxycarbonyl(lower)alkanoylamino]phenyl]phenyl, [[lower alkoxycarbonyl(lower)alkenoylamino]phenyl] phenyl, [[cyclo(lower)alkylcarbonylamino]phenyl] phenyl, [[lower alkylglyoxyloylamino]phenyl]phenyl, [[dihalophenylsulfonylamino]phenyl]phenyl, [[phenyl (lower)alkenoylamino]phenyl]phenyl, phenylphenyl substituted with (lower)alkenoylamino having phenyl and carboxy, [[pyridyl(lower)alkenoylamino]phenyl] phenyl, [[quinoxalinylcarbonylamino]phenyl]phenyl, [[benzothienylcarbonylamino]phenyl]phenyl, [[lower alkylcarbamoylamino]phenyl]phenyl, [[phenylcarbamoylamino]phenyl]phenyl, [[naphthylcarbamoyl]phenyl]phenyl, naphthylphenyl, [lower alkoxynaphthyl]phenyl, [phenyl(lower)alkyl] phenyl, [naphthyl(lower)alkyl]phenyl, [phenyl(lower) alkenyl]phenyl, [dihalophenyl(lower)alkenyl]phenyl, [naphthyl(lower)alkenyl]phenyl, [benzoyl(lower) alkenyl]phenyl, [lower alkoxycarbonyl(lower)alkenyl]

phenyl, [cyano(lower)alkenyl]phenyl, [pyridyl(lower)alkenyl]phenyl, [(halopyridyl)(lower)alkenyl]phenyl, [pyrimidinyl(lower)alkenyl]phenyl, [quinolyl(lower)alkenyl]phenyl, pyridylphenyl, thienylphenyl, halothienylphenyl, pyrrolylphenyl, [dihalopyrrolyl]phenyl, [cyanopyrrolyl]phenyl, [lower alkoxycarbonylpyrrolyl]phenyl, [dioxopyrrolidinyl]phenyl, indolylphenyl, [lower alkoxycarbonylindolyl]phenyl, [lower alkanoylindolyl]phenyl, quinolylphenyl, isoquinolylphenyl, imidazolylphenyl, [aminothiazolyl]phenyl, [pyridylthiazolyl]phenyl, benzothiazolylphenyl, triazolylphenyl, pyrimidinyloxyphenyl, [phenylpyrimidinyloxy]phenyl, phenyl having halogen and amino, phenyl having halogen and (halophenyl)ureido, phenyl having halogen and (lower alkoxypheny l)ureido, phenyl having halogen and lower alkanoylamino, bis(lower alkoxycarbonyl)phenyl, phenyl having lower alkoxycarbonyl and amino, phenyl having lower alkoxycarbonyl and lower alkanoylamino, phenyl having lower alkoxycarbonyl and naphthoylamino, phenyl having halogen and naphthoylamino, phenyl having cyclo(lower)alkyloxy and lower alkoxy, naphthyl or pyridyl, and $R^3$ is hydrogen, lower alkoxy or phenylthio.

The following Preparations and Examples are given for the purpose of illustrating the present invention in more detail.

Preparation 1

A mixture of 2-chloro-3-nitropyridine (1.59 g) and m-toluidine (1.07 g) was heated at 100° C. for 20 minutes. The mixture was cooled and dissolved in ethyl acetate. The organic solution was washed with water and brine, dried over magnesium sulfate and concentrated. The residue was subjected to silica gel column chromatography (hexane-ethyl acetate, 4:1) to afford 3-nitro-2-[(m-tolyl)amino]pyridine (834 mg) as an orange solid.

NMR (CDCl$_3$, δ): 2.49 (3H, s), 6.83 (1H, dd, J=5 Hz, 8 Hz), 7.02 (1H, d, J=8 Hz), 7.29 (1H, t, J=8 Hz), 7.4–7.5 (2H, m), 8.45–8.6 (2H, m), 10.08 (1H, br s)

Preparation 2

The following compounds were obtained according to a similar manner to that of Preparation 1.
(1) 3-Nitro-2-[(pyridin-3-yl)amino]pyridine
NMR (CDCl$_3$, δ): 6.93 (1H, dd, J=5 Hz, 8 Hz), 7.35 (1H, dd, J=5 Hz, 8 Hz), 8.17 (1H, dt, J=8 Hz, 1.5 Hz), 8.42 (1H, dd, J=1.5 Hz, 5 Hz), 8.45–8.6 (2H, m), 8.87 (1H, d, J=3 Hz), 10.10 (1H, s)
(2) 3-Nitro-2-[(pyridin-2-yl)amino]pyridine
NMR (CDCl$_3$, δ): 6.96 (1H, dd, J=5 Hz, 8 Hz), 7.05 (1H, m), 7.23 (1H, dt, J=1.5 Hz, 8 Hz), 8.3–8.65 (4H, m)
(3) 2-(1-Naphthyl)amino-3-nitropyridine
NMR (CDCl$_3$, δ): 6.82 (1H, dd, J=1.5 Hz, 8 Hz), 7.45–7.65 (3H, m), 7.79 (1H, d, J=8 Hz), 7.85–8.1 (4H, m), 8.41 (1H, dd, J=1.5 Hz, 5 Hz), 8.48 (1H, dd, J=1.5 Hz, 8 Hz)
(4) 2-(3-Ethoxycarbonylphenyl)amino-3-nitropyridine
NMR (CDCl$_3$, δ): 1.42 (3H, t, J=7 Hz), 4.41 (2H, q, J=7 Hz), 6.89 (1H, dd, J=5 Hz, 8 Hz), 7.48 (1H, t, J=8 Hz), 7.8–8.0 (2H, m), 8.28 (1H, s), 8.45–8.6 (2H, m), 10.17 (1H, br s)
(5) 2-(4-Methoxycarbonylphenyl)amino-3-nitropyridine
NMR (CDCl$_3$, δ): 3.93 (3H, s), 6.96 (1H, dd, J=5 Hz, 8 Hz), 7.82 (2H, d, J=9 Hz), 8.08 (2H, d, J=9 Hz), 8.5–8.6 (2H, m)
(6) 2-(4-Methoxycarbonylmethylphenyl)amino-3-nitropyridine
NMR CDCl$_3$, δ): 3.64 (2H, s), 3.71 (3H, s), 6.83 (1H, dd, J=5 Hz, 8 Hz), 7.32 (2H, d, J=9 Hz), 7.62 (2H, d, J=9 Hz), 8.45–8.6 (2H, m), 10.11 (1H, br s)
(7) 2-(3-Methoxycarbonylmethylphenyl)amino-3-nitropyridine
NMR (CDCl$_3$, δ): 3.68 (2H, s), 3.72 (3H, s), 6.85 (1H, dd, J-5 Hz, 8 Hz), 7.11 (1H, d, J=8 Hz), 7.37 (1H, t, J=8 Hz), 7.60 (2H, d, J=8 Hz), 8.45–8.6 (2H, m), 10.12 (1H, br s)
(8) 2-(4-Acetylphenyl)amino-3-nitropyridine
NMR CDCl$_3$, δ): 2.61 (3H, s), 6.95 (1H, dd, J=5 Hz, 8 Hz), 7.83 (2H, d, J=9 Hz), 8.00 (2H, d, J=9 Hz), 8.5–8.6 (2H, m)
(9) 2-(3-Acetylphenyl)amino-3-nitropyridine
NMR (CDCl$_3$, δ): 2.65 (3H, s), 6.90 (1H, dd, J=5 Hz, 8 Hz), 7.50 (1H, t, J=8 Hz), 7.77 (1H, d, J=8 Hz), 7.90 (1H, dd, J=1.5 Hz, 8 Hz), 8.25 (1H, s), 8.45–8.6 (2H, m), 10.19 (1H, br s)
(10) 2-(3-Fluorophenyl)amino-3-nitropyridine
NMR (CDCl$_3$, δ): 6.8–6.95 (2H, m), 7.25–7.4 (2H, m), 7.73 (1H, m), 8.5–8.6 (2H, m), 10.19 (1H, br s)
(11) 2-(3-Hydroxyphenyl)amino-3-nitropyridine
NMR (DMSO-d$_6$, δ): 6.55 (1H, m), 6.95–7.25 (4H, m), 8.5–8.6 (2H, m), 9.48 (1H, s), 9.88 (1H, s)
(12) 2-(4-Methoxyphenyl)amino-3-nitropyridine
NMR (CDCl$_3$, δ): 3.83 (3H, s), 6.78 (1H, dd, J=5 Hz, 8 Hz), 6.95 (2H, d, J=9 Hz), 7.48 (2H, d, J=9 Hz), 8.45 (1H, dd, J=1.5 Hz, 5 Hz), 8.51 (1H, dd, J=1.5 Hz, 8 Hz), 9.97 (1H, br s)
(13) 2-(3-Methoxyphenyl)amino-3-nitropyridine
NMR (CDCl$_3$, δ): 3.85 (3H, s), 6.74 (1H, m), 6.87 (1H, dd, J=5 Hz, 8 Hz), 7.18 (1H, m), 7.25–7.4 (2H, m), 8.45–8.6 (2H, m), 10.13 (1H, br s)

Preparation 3

A mixture of 3-nitro-2-[(m-tolyl)amino]pyridine (825 mg) and 10% palladium carbon (0.3 g) in ethanol (15 ml) and 1,4-dioxane (15 ml) was stirred under hydrogen (3 atm) at room temperature for 30 minutes. The catalyst was removed and the solvent was evaporated. The solids were collected and washed with isopropyl ether to give 3-amino-2-[(m-tolyl)amino]pyridine (660 mg).

NMR (CDCl$_3$, δ): 3.15 (2H, br s), 6.18 (1H, br s), 6.77 (1H, dd, J=5 Hz, 8 Hz), 6.95–7.3 (5H, m), 7.83 (1H, dd, J=1.5 Hz, 5 Hz)

Preparation 4

The following compounds were obtained according to a similar manner to that of Preparation 3.
(1) 3-Amino-2-[(pyridin-3-yl)amino]pyridine
NMR (DMSO-d$_6$, δ): 5.12 (2H, s), 6.67 (1H, dd, J=5 Hz, 8 Hz), 6.93 (1H, dd, J=1.5 Hz, 8 Hz), 7.24 (1H, dd, J=5 Hz, 8 Hz), 7.50 (1H, dd, J=1.5 Hz, 5 Hz), 7.95 (1H, s), 8.0–8.15 (2H, m), 8.76 (1H, d, J=3 Hz)
(2) 3-Amino-2-[(pyridin-2-yl)amino]pyridine
NMR (DMSO-d$_6$, δ): 5.23 (2H, s), 6.74 (1H, dd, J=5 Hz, 8 Hz), 6.83 (1H, m), 6.98 (1H, dd, J=1.5 Hz, 8 Hz), 7.5–7.7 (2H, m), 8.00 (1H, d, J=8 Hz), 8.18 (1H, m), 8.39 (1H, s)
(3) 3-Amino-2-[(1-naphthyl)amino]pyridine
NMR (DMSO-d$_6$, δ): 5.12 (2H, s), 6.64 (1H, dd, J=5 Hz, 8 Hz), 6.98 (1H, dd, J=1.5 Hz, 8 Hz), 7.35–7.65 (6H, m), 7.76 (1H, s), 7.90 (1H, m), 8.05 (1H, m)
(4) 2-(3-Acetamidophenyl)amino-3-aminopyridine
NMR (DMSO-d$_6$, δ): 2.03 (3H, s), 5.09 (2H, s), 6.63 (1H, dd, J=5 Hz, 8 Hz), 6.89 (1H, dd, J=1.5 Hz, 8 Hz), 7.0–7.25

(2H, m), 7.33 (1H, m), 7.49 (1H, dd, J=1.5 Hz, 5 Hz), 7.71 (1H, s), 7.87 (1H, s), 9.80 (1H, s)

(5) 3-Amino-2-[(3-ethoxycarbonylphenyl)amino]pyridine

NMR (DMSO-d$_6$, δ): 1.33 (3H, t, J=7 Hz), 4.31 (2H, q, J=7 Hz), 5.12 (2H, s), 6.68 (1H, dd, J=5 Hz, 8 Hz), 6.93 (1H, dd, J=1.5 Hz, 8 Hz), 7.3–7.5 (2H, m), 7.52 (1H, dd, J=1.5 Hz, 5 Hz), 7.95–8.1 (2H, m), 8.17 (1H, s)

(6) 3-Amino-2-[(4-methoxycarbonylphenyl)amino]pyridine

NMR (DMSO-d$_6$, δ): 3.86 (3H, s), 5.19 (2H, s), 6.74 (1H, dd, J=5 Hz, 8 Hz), 6.98 (1H, dd, J=1.5 Hz, 8 Hz), 7.58 (1H, dd, J=1.5 Hz, 5 Hz), 7.70 (2H, d, J=9 Hz), 7.83 (2H, d, J=9 Hz), 8.28 (1H, s)

(7) 3-Amino-2-[(4-methoxycarbonylmethylphenyl)amino]pyridine

NMR (DMSO-d$_6$, δ): 3.58 (2H, s), 3.61 (3H, s), 5.07 (2H, s), 6.61 (1H, dd, J=5 Hz, 8 Hz), 6.89 (1H, dd, J=1.5 Hz, 8 Hz), 7.11 (2H, d, J=9 Hz), 7.49 (1H, dd, J=1.5 Hz, 5 Hz), 7.57 (2H, d, J=9 Hz), 7.70 (1H, s)

(8) 3-Amino-2-[(3-methoxycarbonylmethylphenyl)amino]pyridine

NMR (CDCl$_3$, δ): 3.41 (2H, br s), 3.61 (2H, s), 3.69 (3H, s), 6.21 (1H, br s), 6.78 (1H, dd, J=5 Hz, 8 Hz), 6.87 (1H, m), 7.01 (1H, dd, J=1.5 Hz, 8 Hz), 7.15–7.3 (3H, m), 7.85 (1H, dd, J=1.5 Hz, 5 Hz)

(9) 2-(4-Acetylphenyl)amino-3-aminopyridine

NMR (DMSO-d$_6$, δ): 2.49 (3H, s), 5.19 (2H, s), 6.75 (1H, dd, J=5 Hz, 8 Hz), 6.98 (1H, dd, J=1.5 Hz, 8 Hz), 7.57 (1H, dd, J=1.5 Hz, 5 Hz), 7.69 (2H, d, J=9 Hz), 7.86 (2H, d, J=9 Hz), 8.27 (1H, s)

(10) 2-(3-Acetylphenyl)amino-3-aminopyridine

NMR (DMSO-d$_6$, δ): 2.57 (3H, s), 5.11 (2H, s), 6.67 (1H, dd, J=5 Hz, 8 Hz), 6.93 (1H, dd, J=1.5 Hz, 8 Hz), 7.2–7.55 (3H, m), 7.95–8.05 (2H, m), 8.13 (1H, s)

(11) 3-Amino-2-[(3-fluorophenyl)amino]pyridine

NMR (DMSO-d$_6$, δ): 5.11 (2H, s), 6.55–6.75 (2H, m), 6.93 (1H, dd, J=1.5 Hz, 8 Hz), 7.15–7.35 (2H, m), 7.54 (1H, dd, J=1.5 Hz, 5 Hz), 7.72 (1H, dt, J=13 Hz, 1.5 Hz), 7.98 (1H, s)

(12) 3-Amino-2-[(3-hydroxyphenyl)amino]pyridine

NMR (DMSO-d$_6$, δ): 5.12 (2H, br s), 6.27 (1H, m), 6.61 (1H, dd, J=1.5 Hz, 8 Hz), 6.85–7.05 (3H, m), 7.71 (1H, s), 7.49 (1H, dd, J=1.5 Hz, 5 Hz), 7.63 (1H, s), 9.12 (1H, s)

(13) 3-Anino-2-[(4-methoxyphenyl)amino]pyridine

NMR CDCl$_3$, δ): 3.07 (2H, br s), 3.79 (3H, s), 6.19 (1H, br s), 6.70 (1H, dd, J=5 Hz, 8 Hz), 6.87 (2H, d, J=9 Hz), 7.23 (2H, d, J=9 Hz), 7.78 (1H, dd, J=1.5 Hz, 5 Hz)

(14) 3-Amino-2-[(3-methoxyphenyl)amino]pyridine

NMR (CDCl$_3$, δ): 3.42 (2H, br s), 3.79 (3H, s), 6.21 (1H, s), 6.51 (1H, m), 6.75–6.85 (2H, m), 6.92 (1H, m), 7.02 (1H, dd, J=1.5 Hz, 8 Hz), 7.18 (1H, t, J=8 Hz), 7.85 (1H, dd, J=1.5 Hz, 5 Hz)

Preparation 5

A mixture of 2-chloro-3-nitropyridine (6.12 g), 3'-aminoacetanilide (5.80 g) and potassium carbonate (5.34 g) in toluene (50 ml) was refluxed for 5 hours. The mixture was cooled, and the solids were collected and washed with water, ethanol and isopropyl ether successively to give 2-(3-acetamidophenyl)amino-3-nitropyridine (5.88 g) as an orange solid.

NMR (DMSO-d$_6$, δ): 2.06 (3H, s), 6.99 (1H, dd, J=5 Hz, 8 Hz), 7.2–7.4 (3H, m), 7.91 (1H, s), 8.5–8.6 (2H, m), 9.93 (1H, s), 9.99 (1H, s)

Preparation 6

To a mixture of ethyl 3-aminobenzoate (996 mg) and triethylamine (0.85 ml) in dichloromethane (10 ml) was added benzoyl chloride (0.70 ml). The mixture was stirred at room temperature for 15 minutes, poured into a mixture of ethyl acetate and water. The organic phase was washed with brine, dried over magnesium sulfate and concentrated. The resultant solid was collected and washed with isopropyl ether to give ethyl 3-benzoylaminobenzoate (1.36 g).

NMR (DMSO-d$_6$, 300 MHz, δ): 1.33 (3H, t, J=7 Hz), 4.33 (2H, q, J=7 Hz), 7.45–7.75 (5H, m), 7.98 (2H, d, J=8 Hz), 8.08 (1H, d, J=8 Hz)

Preparation 7

To a suspension of sodium hydride (60% in oil, 5.19 g) in N,N-dimethylformamide (30 ml) was added a solution of 3'-nitroacetanilide (214 mg) in N,N-dimethylformamide (30 ml) at 0° C. The mixture was stirred at room temperature for 30 minutes, then iodomethane (3.59 ml) was added. After 30 minutes, 1N hydrochloric acid was poured into the mixture and extracted with ethyl acetate. The organic solution was washed with water and brine, dried over magnesium sulfate and concentrated. The resultant solid was collected and washed with isopropyl ether to give N-methyl-3'-nitroacetanilide (4.64 g).

NMR (DMSO-d$_6$, 200 MHz, δ): 1.92 (3H, s), 3.25 (3H, s), 7.65–7.9 (2H, m), 8.1–8.3 (2H, m)

Preparation 8

A mixture of ammonium thiocyanate (2.79 g) and benzoyl chloride (3.86 ml) in acetone (30 ml) was refluxed for 5 minutes. Then a solution of 3'-aminoacetanilide (5.00 g) in acetone (40 ml) was added thereto. The mixture was poured into water, and the resulting precipitate was separated by filtration. The crystals were heated at 50° C. for 3 hours with 1N sodium hydroxide (150 ml) solution. The mixture was poured into a mixture of ethyl acetate and water, and the resulting precipitate was collected and washed with ethyl acetate and water to give N-(3-acetylaminophenyl)thiourea (4.22 g).

NMR (DMSO-d$_6$, 300 MHz, δ): 2.03 (3H, s), 7.12 (1H, d, J=8 Hz), 7.22 (1H, t, J=8 Hz), 7.33 (1H, d, J=8 Hz), 7.62 (1H, s), 9.68 (1H, s), 9.95 (1H, s)

Preparation 9

A mixture of 3-nitroaniline (6.14 g), 2-chloropyrimidine (4.85 g) and potassium carbonate (6.15 g) in dimethylsulfoxide (50 ml) was heated at 170° C. for 5 hours. The mixture was cooled and poured into a mixture of ethyl acetate and water. The organic phase was washed with brine, dried over magnesium sulfate and concentrated. The resulting solid was collected and washed with isopropyl ether to give 2-(3-nitrophenylamino)pyrimidine (1.92 g).

NMR (DMSO-d$_6$, 300 MHz, δ): 6.97 (1H, t, J=5 Hz), 7.57 (1H, t, J=8 Hz), 7.78 (1H, d, J=8 Hz), 8.09 (1H, d, J=8 Hz), 8.58 (2H, d, J=5 Hz), 8.85 (1H, s)

Preparation 10

A mixture of 3-nitrophenol (6.85 g), 2-chloropyrimidine (5.13 g) and potassium carbonate (6.81 g) in dimethylsulfoxide (50 ml) was heated at 150° C. for 30 minutes. The mixture was cooled and poured into a mixture of ethyl acetate and water. The organic phase was washed with brine, dried over magnesium sulfate and concentrated. The resulting solid was collected and washed with isopropyl ether to give 2-(3-nitrophenoxy)pyrimidine (7.41 g).

NMR (DMSO-d$_6$, 300 MHz, δ): 7.35 (1H, t, J=5 Hz), 7.7–7.8 (2H, m), 8.1–8.2 (2H, m), 8.69 (2H, d, J=5 Hz)

Preparation 11

A mixture of methyl 3-hydroxybenzoate (3.4 g), 2-chloropyrimidine (2.29 g) and potassium carbonate (3.04 g) in dimethylsulfoxide (30 ml) was stirred at 150° C. for 1 hour. The mixture was poured into a mixture of ethyl acetate and water. The organic phase was washed with water and brine, dried over magnesium sulfate and concentrated. The resultant solid was collected and washed with isopropyl ether to give methyl 3-(pyrimidine-2-yl)oxybenzoate (3.66 g).

NMR (CDC13, 300 MHz, δ): 3.92 (3H, s), 7.07 (1H, t, J=5 Hz), 7.41 (1H, m), 7.52 (1H, t, J=8 Hz), 7.88 (1H, t, J=1.5 Hz), 7.96 (1H, d, J=8 Hz), 8.58 (2H, d, J=5 Hz)

Preparation 12

The following compound was obtained according to similar manners to those of Preparations 10 and 11.

2-(3-Nitrophenoxy)-4-phenylpyrimidine

NMR (DMSO-$d_6$, 300 MHz, δ): 7.5–7.65 (3H, m), 7.75–7.9 (2H, m), 7.93 (1H, d, J=5 Hz), 8.1–8.25 (4H, m), 8.73 (1H, d, J=5 Hz)

Preparation 13

To a solution of iodobenzene (3.53 ml) in ether (10 ml) was added n-butyllithium (1.6M in hexane, 20 ml), and the mixture was stirred at room temperature for 20 minutes. The above solution was added to a solution of 2-chloropyrimidine (3.52 g) in ether (90 ml) at −30° C. The mixture was stirred at −30° C. for 30 minutes and then at 0° C. for 30 minutes, quenched with a solution of acetic acid (1.83 ml) and water (0.31 ml) in tetrahydrofuran (6 ml), and treated with 2,3-dichloro-5,6-dicyanobenzoquinone (DDQ) (7.26 g) in tetrahydrofuran (30 ml). The mixture was stirred at 0° C. for 5 minutes, cooled to 0° C., treated with a cold aqueous solution of sodium hydroxide (3M, 9.2 ml), and stirred at 0° C. for 5 minutes. The organic phase was separated, washed with water and brine, dried over magnesium sulfate, concentrated and subjected to silica gel column chromatography (hexane-ethyl acetate, 7:3) to afford 2-chloro-4-phenylpyrimidine (3.39 g) as a solid.

NMR (DMSO-$d_6$, 300 MHz, δ): 7.55–7.7 (3H, m), 8.15–8.25 (3H, m), 8.83 (1H, d, J=5 Hz)

Preparation 14

A mixture of 2-bromo-3'-nitroacetophenone (12.2 g) and thiourea (3.81 g) in ethanol (100 ml) was stirred at room temperature for 15 minutes. The reaction mixture was poured into a mixture of ethyl acetate and an aqueous sodium bicarbonate solution. The organic phase was washed with brine, dried over magnesium sulfate and concentrated. The resultant solid was collected and washed with isopropyl ether to give 2-amino-4-(3-nitrophenyl)thiazole (10.21 g).

NMR (DMSO-$d_6$, 300 MHz, δ): 7.24 (2H, s), 7.36 (1H, s), 7.67 (1H, t, J=8 Hz), 8.10 (1H, dt, J=8 Hz, 1.5 Hz), 8.24 (1H, dt, J=8 Hz, 1.5 Hz), 8.62 (1H, t, J=1.5 Hz)

Preparation 15

A mixture of 2-bromo-3'-nitroacetophenone (3.66 g) and 3-thiocarbamoylpyridine (2.07 g) in ethanol (40 ml) was refluxed for 1 hour. The reaction mixture was poured into a mixture of ethyl acetate and an aqueous sodium bicarbonate solution. The organic phase was washed with brine, dried over magnesium sulfate and concentrated. The resultant solid was collected and washed with isopropyl ether to give 4-(3-nitrophenyl)-2-(pyridin-3-yl)thiazole (2.91 g).

NMR (DMSO-$d_6$, 300 MHz, δ): 7.55 (1H, m), 7.78 (1H, t, J=8 Hz), 8.22 (1H, d, J=8 Hz), 8.41 (1H, m), 8.50 (1H, d, J=8 Hz), 8.59 (1H, s), 8.70 (1H, dd, J=1.5 Hz, 5 Hz), 8.83 (1H, s), 9.22 (1H, d, J=1.5 Hz)

Preparation 16

A mixture of 2-bromo-3'-nitroacetophenone (4.88 g.) and formamide (50 ml) was stirred at 185° C. for 2 hours. The reaction mixture was poured into a mixture of ethyl acetate and an aqueous sodium bicarbonate solution. The organic phase was washed with brine, dried over magnesium sulfate and concentrated. The resultant solid was collected and washed with ethyl acetate to give 4-(3-nitrophenyl) imidazole (2.32 g).

NMR (DMSO-$d_6$, 300 MHz, δ): 7.63 (1H, t, J=8 Hz), 7.78 (1H, s), 7.90 (1H, s), 8.02 (1H, d, J=8 Hz), 8.21 (1H, d, J=8 Hz), 8.58 (1H, s), 12.36 (1H, br s)

Preparation 17

A mixture of 3-nitrobenzoyl chloride (3.71 g), anisole (2.0 ml) and aluminum chloride (2.67 g) in dichloromethane (50 ml) was refluxed for 1 hour. The reaction mixture was poured into a mixture of ethyl acetate and water. The organic phase was washed with brine, dried over magnesium sulfate and concentrated. The resultant solid was collected and washed with ethyl acetate to give 1-(3-nitrobenzoyl)-4-methoxybenzene (955 mg).

NMR (DMSO-$d_6$, 300 MHz, δ): 3.88 (3H, s), 7.12 (2H, d, J=8 Hz), 7.75–7.9 (3H, m), 8.12 (1H, d, J=8 Hz), 8.39 (1H, s), 8.48 (1H, m)

Preparation 18

A mixture of 3-nitrobenzoyl chloride (4.50 g) and indolizine (2.84 g) in dichloromethane (30 ml) was stirred at room temperature for 30 minutes. The reaction mixture was poured into a mixture of ethyl acetate and water. The organic phase was separated, washed with brine, dried over magnesium sulfate and concentrated. The resultant solid was collected and washed with ethyl acetate to give 3-(3-nitrobenzoyl)indolizine (4.51 g).

NMR (DMSO-$d_6$, 300 MHz, δ): 6.74 (1H, d, J=5 Hz), 7.18 (1H, m), 7.35–7.45 (2H, m), 7.8–7.9 (2H, m), 8.09 (1H, d, J=8 Hz), 8.4–8.5 (2H, m), 9.85 (1H, d, J=7 Hz)

Preparation 19

To a suspension of sodium hydride (60% in oil, 1.48 g) in N,N-dimethylformamide (40 ml) was added a solution of diethyl benzylphosphonate (7.69 g) in N,N-dimethylformamide (40 ml) at 0° C. The mixture was stirred at room temperature for 30 minutes, then a solution of 3-nitrobenzaldehyde (5.09 g) was added thereto. After stirring at 50° C. for 1 hour, the mixture was poured into dilute hydrochloric acid, and extracted with ethyl acetate 3 times. The combined organic solution was washed with water and brine, dried over magnesium sulfate and concentrated. The resultant solid was collected and washed with isopropyl ether to give (E)-3-nitrostilbene (3.97 g).

NMR (CDCl$_3$, 300 MHz, δ): 7.1–7.6 (8H, m), 7.80 (1H, d, J=8 Hz), 8.10 (1H, dd, J=1.5 Hz, 8 Hz), 8.38 (1H, s)

Preparation 20

The following compounds were obtained according to a similar manner to that of Preparation 19.

(1) 2-((E)-3-Nitrostyryl)naphthalene

NMR (CDCl$_3$, 300 MHz, δ): 7.25 (1H, d, J=16 Hz), 7.35–7.6 (4H, m), 7.7–7.95 (6H, m), 8.10 (1H, dd, J=1.5 Hz, 8 Hz), 8.41 (1H, s)

(2) (E)-3-Nitrostyryl phenyl ketone

NMR (CDCl$_3$, 300 MHz, δ): 7.5–7.7 (5H, m), 7.86 (1H, d, J=16 Hz), 7.93 (1H, d, J=8 Hz), 8.06 (2H, d, J=8 Hz), 8.28 (1H, dd, J=1.5 Hz, 8 Hz), 8.52 (1H, s)

(3) (E)-3-(3-Nitrophenyl)propenonitrile

NMR (CDCl$_3$, 300 MHz, δ): 6.07 (1H, d, J=16 Hz), 7.48 (1H, d, J=16 Hz), 7.64 (1H, t, J=8 Hz), 7.78 (1H, d, J=8 Hz), 8.25–8.4 (2H, m)

(4) (E)-Methyl 3-(3-nitrophenyl)propenoate

NMR (CDCl$_3$, 300 MHz, δ): 3.84 (3H, s), 6.57 (1H, d, J=16 Hz), 7.59 (1H, t, J=8 Hz), 7.73 (1H, d, J=16 Hz), 7.83 (1H, d, J=8 Hz), 8.24 (1H, dd, J=1.5 Hz, 8 Hz), 8.39 (1H, t, J=1.5 Hz)

Preparation 21

A mixture of N-methyl-3$^1$-nitroacetanilide (5.13 g) and 10% palladium carbon (0.6 g) in methanol (50 ml) and 1,4-dioxane (50 ml) and stirred under hydrogen (3 atm) at room temperature for 2 hours. The catalyst was removed by filtration and the solvent was evaporated. The resultant solid was collected and washed with isopropyl ether to give 3'-amino-N-methylacetanilide (4.06 g).

NMR (DMSO-d$_6$, 200 MHz, δ): 1.78 (3H, s), 3.08 (3H, s), 5.28 (2H, s), 6.35–6.6 (3H, m), 7.05 (1H, t, J=8 Hz)

Preparation 22

The following compounds were obtained according to a similar manner to that of Preparation 21.

(1) 3-(Pyrimidin-2-yl)aminoaniline

NMR (DMSO-d$_6$, 300 MHz, δ): 4.96 (2H, s), 6.28 (1H, m), 6.78 (1H, m), 6.8–6.95 (2H, m), 7.05 (1H, s), 8.42 (2H, d, J=5 Hz), 9.28 (1H, s)

(2) 3-(Pyrimidin-2-yl) oxyaniline

NMR (DMSO-d$_6$, 300 MHz, δ): 5.23 (2H, s), 6.2–6.35 (2H, m), 6.43 (1H, d, J=8 MHz), 7.02 (1H, t, J=8 Hz), 7.23 (1H, t, J=5 Hz), 8.62 (2H, d, J=5 Hz)

(3) 3-(4-Phenylpyrimidin-2-yl)oxyaniline

NMR (DMSO-d$_6$, 300 MHz, δ): 5.27 (2H, s), 6.3–6.5 (3H, m), 7.07 (1H, t, J=8 Hz), 7.45–7.65 (3H, m), 7.82 (1H, d, J=5 Hz), 8.05–8.2 (2H, m), 8.67 (1H, d, J–5 Hz)

Preparation 23

A mixture of (E)-3-nitrostilbene (3.63 g), hydrochloric acid (35%, 10 ml) and iron powder (3.6 g) in ethanol (30 ml) was refluxed for 1 hour. The mixture was poured into aqueous sodium bicarbonate solution and extracted with ethyl acetate twice. The combined organic solution was washed with aqueous sodium bicarbonate and brine, dried over magnesium sulfate and concentrated. The resultant solid was collected and washed with isopropyl ether to give (E)-3-aminostilbene (2.05 g).

NMR (DMSO-d$_6$, 300 MHz, δ): 5.09 (2H, s), 6.49 (1H, d, J=8 Hz), 6.7–6.85 (2H, m), 7.0–7.15 (3H, m), 7.2–7.45 (3H, m), 7.58 (2H, d, J=8 Hz)

Preparation 24

The following compounds were obtained according to a similar manner to that of Preparation 23.

(1) 2-Amino-4-(3-aminophenyl)thiazole

NMR (DMSO-d$_6$, 300 MHz, δ): 5.02 (2H, s), 6.45 (1H, m), 6.76 (1H, s), 6.9–7.05 (5H, m)

(2) 3-[2-(Pyridin-3-yl)thiazol-4-yl]aniline

NMR (DMSO-d$_6$, 300 MHz, δ): 5.20 (2H, s), 6.58 (1H, d, J=8 Hz), 7.05–7.2 (2H, m), 7.30 (1H, s), 7.58 (1H, m), 8.05 (1H, s), 8.35 (1H, d, J=8 Hz), 8.68 (1H, d, J=5 Hz), 9.19 (1H, d, J=1.5 Hz)

(3) 3-(Imidazol-4-yl)aniline

NMR (DMSO-d$_6$, 300 MHz, δ): 4.96 (2H, s), 6.38 (1H, d, J=8 Hz), 6.85–7.1 (3H, m), 7.40 (1H, s), 7.64 (1H, s), 12.04 (1H, br s)

(4) 3-Amino-4'-methoxybenzophenone

NMR (DMSO-d$_6$, 300 MHz, δ): 3.84 (3H, s), 5.37 (2H, s), 6.75–6.85 (2H, m), 6.89 (1H, t, J=1.5 Hz), 7.07 (2H, dt, J=8 Hz, 1.5 Hz), 7.16 (1H, t, J=8 Hz), 7.72 (2H, dt, J=8 Hz, 1.5 Hz)

(5) 3-(3-Indolizinylcarbonyl)aniline

NMR (DMSO-d6, 300 MHz, δ): 5.32 (2H, s), 6.65 (1H, d, J=5 Hz), 6.75 (1H, m), 7.86 (1H, d, J=8 Hz), 6.97 (1H, s), 7.05–7.2 (2H, m), 7.25–7.4 (2H, m), 7.77 (1H, d, J=8 Hz), 9.81 (1H, d, J=7 Hz)

(6) 3-[(E)-2-(2-Naphthyl)vinyl]aniline

NMR (DMSO-d$_6$, 300 MHz, δ): 5.09 (2H, s), 6.50 (1H, d, J=8 Hz), 6.75–6.85 (2H, m), 7.03 (1H, t, J=8 Hz), 7.23 (2H, s), 7-.4–7.55 (2H, m), 7.8–7.95 (4H, m), 7.98 (1H, s)

(7) (E)-3-Aminostyryl phenyl ketone

NMR (DMSO-d$_6$, 300 MHz, δ): 5.21 (2H, s), 6.68 (1H, d, J=8 Hz), 6.95–7.15 (3H, m), 7.5–7.8 (5H, m), 8.10 (2H, d, J=8 Hz)

(8) (E)-3-(3-Aminophenyl)propenonitrile

NMR (DMSO-d$_6$, 300 MHz, δ): 5.26 (2H, s), 6.23 (1H, d, J=16 Hz), 6.64 (1H, d, J=8 Hz), 6.73 (1H, s), 6.79 (1H, d, J=8 Hz), 7.08 (1H, t, J=8 Hz), 7.48 (1H, d, J=16 Hz)

(9) (E)-Methyl 3-(3-aminophenyl)propenoate

NMR (DMSO-d$_6$, 300 MHz, δ): 3.72 (3H, s), 5.19 (2H, S), 6.41 (1H, d, J=16 Hz), 6.64 (1H, dd, J=1.5 Hz, 8 Hz), 6.75–6.85 (2H, m), 7.06 (1H, t, J=8 Hz), 7.48 (1H, d, J=16 Hz)

Preparation 25

A mixture of N-(3-acetylaminophenyl)thiourea (0.84 g) and 2-bromoacetophenone (0.84 g) in ethanol (10 ml) was refluxed for 15 minutes. After evaporation of the solvent, 3N hydrochloric acid was added thereto and the mixture was refluxed for 30 minutes. The mixture was made basic with sodium bicarbonate and extracted with ethyl acetate. The organic solution was washed with water and brine, dried over magnesium sulfate and concentrated. The residue was crystallized from ethanol to give 3-(4-phenylthiazol-2-yl)aminoaniline (0.88 g).

NMR (DMSO-d$_6$, 300 MHz, δ): 5.11 (2H, s), 6.20 (1H, d, J=8 Hz), 6.82 (1H, m), 6.9–7.0 (2H, m), 7.25–7.35 (2H, m), 7.42 (2H, t, J=8 Hz), 7.93 (2H, d, J=8 Hz)

Preparation 26

The following compound was obtained according to a similar manner to that of Preparation 25.

3-(4-Methylthiazol-2-yl)aminoaniline

NMR (DMSO-d$_6$, 300 MHz, δ): 2.19 (3H, s), 5.02 (2H, s), 6.15 (1H, d, J=8 Hz), 6.37 (1H, s), 6.65–6.8 (2H, m), 6.90 (1H, t, J=8 Hz), 9.73 (1H, s)

Preparation 27

A mixture of 2-chloro-3-nitropyridine (1.96 g) and 3'-amino-N-methylacetanilide (2.03 g) in toluene (20 ml) was refluxed for 7 hours. The mixture was poured into a mixture of ethyl acetate and aqueous sodium bicarbonate solution. The organic phase was separated, washed with brine, dried over magnesium sulfate and concentrated. The resultant solid was collected and washed with isopropyl ether to give 2-[3-(N-methylacetamido)phenylamino]-3-nitropyridine (872 mg).

NMR (DMSO-$d_6$, 200 MHz, δ): 1.85 (3H, s), 3.18 (3H, s), 7.0–7.15 (2H, m), 7.42 (1H, t, J=8 Hz), 7.66 (2H, m), 8.5–8.6 (2H, m), 10.01 (1H, s)

Preparation 28

A mixture of 2-chloro-3-nitropyridine (2.27 g), 3-chloroaniline (1.5 ml) and potassium carbonate (2.2 g) in 1,4-dioxane (30 ml) was refluxed for 20 hours. The insoluble materials were removed by filtration and the filtrate was concentrated. Silica gel column chromatography (chloroform-methanol, 50:1) afforded 2-(3-chlorophenylamino)-3-nitropyridine (404 mg) as an orange solid.

NMR (CDCl$_3$, 300 MHz, δ): 6.90 (1H, dd, J=5 Hz, 8 Hz), 7.15 (1H, dt, J=8 Hz, 1.5 Hz), 7.31 (1H, t, J=8 Hz), 7.45 (1H, dt, J=8 Hz, 1.5 Hz), 7.88 (1H, t, J=1.5 Hz), 8.5–8.6 (2H, m), 10.14 (1H, s)

Preparation 29

The following compounds were obtained according to similar manners to those of Preparations 1, 5 and 28.

(1) 2-(3-Cyanophenylamino)-3-nitropyridine

NMR (CDCl$_3$, 300 MHz, δ): 6.97 (1H, dd, J=5 Hz, 8 Hz), 7.4–7.55 (2H, m), 7.7–7.8 (1H, m), 8.32 (1H, s), 8.5–8.65 (2H, m), 10.22 (1H, s)

(2) 2-(3-Biphenylylamino)-3-nitropyridine

NMR (CDCl$_3$, 300 MHz, δ): 6.85 (1H, dd, J=5 Hz, 8 Hz), 7.2–7.5 (5H, m), 7.55–7.7 (3H, m), 7.86 (1H, t, J=1.5 Hz), 8.45–8.6 (2H, m), 10.19 (1H, s)

(3) 3-Nitro-2-[3-(4-phenylthiazol-2-yl)aminophenylamino]pyridine

NMR (DMSO-$d_6$, 300 MHz, δ): 7.05 (1H, dd, J=5 Hz, 8 Hz), 7.21 (1H, d, J=8 Hz), 7.25–7.5 (6H, m), 7.92 (2H, d, J=8 Hz), 8.37 (1H, s), 8.5–8.6 (2H, m)

(4) 3-Nitro-2-[3-(4-methylthiazol-2-yl)aminophenylamino]pyridine

NMR (DMSO-$d_6$, 300 MHz, δ): 2.22 (3H, s), 6.45 (1H, s), 6.99 (1H, dd, J=5 Hz, 8 Hz), 7.17 (1H, d, J=8 Hz), 7.27 (1H, t, J=8 Hz), 7.41 (1H, d, J=8 Hz), 8.01 (1H, s), 8.5–8.6 (2H, m)

(5) 3-Nitro-2-[3-(pyrimidin-2-yl)aminophenylamino]pyridine

NMR (DMSO-$d_6$, 300 MHz, δ): 6.84 (1H, t, J=5 Hz), 6.98 (1H, m), 7.2–7.3 (2H, m), 7.54 (1H, m), 8.05 (1H, s), 8.45–8.55 (4H, m), 9.67 (1H, s)

(6) 3-Nitro-2-[3-(pyrimidin-2-yl)oxyphenylamino]pyridine

NMR (DMSO-$d_6$, 300 MHz, δ): 6.9–7.5 (2H, m), 7.28 (1H, t, J=5 Hz), 7.41 (1H, t, J=8 Hz), 7.53 (1H, d, J=8 Hz), 7.66 (1H, t, J=1.5 Hz), 8.5–8.6 (2H, m), 8.66 (2H, d, J=5 Hz)

(7) 3-Nitro-2-[3-[(4-phenylpyrimidin-2-yl)oxy]phenylamino]pyridine

NMR (DMSO-$d_6$, 300 MHz, δ): 6.95–7.1 (2H, m), 7.43 (1H, t, J=8 Hz), 7.5–7.65 (4H, m), 7.74 (1H, t, J=1.5 Hz), 7.87 (1H, d, J=5 Hz), 8.1–8.2 (2H, m), 8.45–8.6 (2H, m), 8.69 (1H, d, J=5 Hz)

(8) 2-[3-(2-Aminothiazol-4-yl)phenylamino]-3-nitropyridine

NMR (DMSO-$d_6$, 300 MHz, δ): 6.9–7.1 (4H, m), 7.36 (1H, t, J=8 Hz), 7.55–7.65 (2H, m), 7.98 (1H, s), 8.5–8.6 (2H, m), 9.99 (1H, s)

(9) 3-Nitro-2-[3-[2-(pyridin-3-yl)thiazol-4-yl]phenylamino]pyridine

NMR (DMSO-$d_6$, 300 MHz, δ): 7.01 (1H, m), 7.48 (1H, t, J=8 Hz), 7.57 (1H, m), 7.74 (1H, d, J=8 Hz), 7.84 (1H, d, J=8 Hz), 8.29 (1H, s), 8.39 (1H, dd, J=1.5 Hz, 8 Hz), 8.5–8.6 (2H, m), 8.69 (1H, d, J=5 Hz), 9.22 (1H, s), 10.05 (1H, s)

(10) 2-[3-(Imidazol-4-yl)phenylamino]-3-nitropyridine

NMR (DMSO-$d_6$, 300 MHz, δ): 6.98 (1H, dd, J=5 Hz, 8 Hz), 7.3–7.75 (4H, m), 7.99 (1H, s), 8.5–8.6 (2H, m), 9.99 (1H, s), 12.18 (1H, br s)

(11) 2-[3-(4-Methoxybenzoyl)phenylamino]-3-nitropyridine

NMR (CDCl$_3$, 300 MHz, δ): 3.91 (3H, s), 6.88 (1H, dd, J=5 Hz, 8 Hz), 6.98 (2H, dt, J=8 Hz, 1.5 Hz), 7.45–7.6 (2H, m), 7.8–7.95 (3H, m), 8.09 (1H, s), 8.50 (1H, d, J=5 Hz), 8.55 (1H, d, J=8 Hz), 10.20 (1H, s)

(12) 2-[3-(3-Indolizinylcarbonyl)phenylamino]-3-nitropyridine

NMR (CDCl$_3$, 300 MHz, δ): 6.55 (1H, d, J=5 Hz), 6.86 (1H, dd, J=5 Hz, 8 Hz), 6.96 (1H, t, J=8 Hz), 7.22 (1H, t, J=8 Hz), 7.45–7.65 (4H, m), 7.79 (1H, d, J=8 Hz), 8.17 (1H, s), 8.5–8.6 (2H, m), 9.98 (1H, d, J=7 Hz), 10.22 (1H, s)

(13) 3-Nitro-2-[(E)-3-styrylphenylamino]pyridine

NMR (CDCl$_3$, 300 MHz, δ): 6.85 (1H, dd, J=5 Hz, 8 Hz), 7.13 (2H, s), 7.20–7.45 (5H, m), 7.5–7.65 (3H, m), 7.78 (1H, s), 8.5–8.6 (2H, m), 10.16 (1H, s)

(14) 2-[3-[(E)-2-(2-Naphthyl)vinyl]phenylamino]-3-nitropyridine

NMR (DMSO-$d_6$, 300 MHz, δ): 7.00 (1H, dd, J=5 Hz, 8 Hz), 7.35–7.55 (6H, m), 7.63 (1H, d, J=8 Hz), 7.85–7.95 (5H, m), 8.02 (1H, s), 8.5–8.6 (2H, m), 10.02 (1H, s)

(15) 2-[3-((E)-2-Benzoylvinyl)phenylamino]-3-nitropyridine

NMR (DMSO-$d_6$, 300 MHz, δ): 7.10 (1H, dd, J=5 Hz, 8 Hz), 7.5–7.95 (7H, m), 8.03 (1H, d, J=16 Hz), 8.15–8.3 (3H, m), 8.6–8.7 (2H, m), 10.12 (1H, s)

(16) 2-[3-((E)-2-Cyanovinyl)phenylamino]-3-nitropyridine

NMR (CDCl$_3$, 300 MHz, δ): 5.93 (1H, d, J=16 Hz), 6.91 (1H, dd, J=5 Hz, 8 Hz), 7.35–7.5 (2H, m), 7.67 (1H, dd, J=1.5 Hz, 8 Hz), 7.91 (1H, t, J=1.5 Hz), 8.45–8.6 (2H, m), 10.18 (1H, s)

(17) 2-[3-((E)-2-Methoxycarbonylvinyl)phenylamino]-3-nitropyridine

NMR (CDCl$_3$, 300 MHz, δ): 3.82 (3H, s), 6.48 (1H, d, J=16 Hz), 6.89 (1H, dd, J=5 Hz, 8 Hz), 7.33 (1H, d, J=8 Hz), 7.41 (1H, t, J=8 Hz), 7.63 (1H, d, J=8 Hz), 7.72 (1H, d, J=16 Hz), 8.5–8.6 (2H, m), 10.16 (1H, s)

Preparation 30

A mixture of 3-amino-2-chloropyridine (2.57 g) and 3-nitroaniline (2.76 g) was heated at 200° C. for 1 hour. The mixture was cooled and partitioned between aqueous sodium bicarbonate solution and chloroform. The organic layer was washed with brine, dried over magnesium sulfate, concentrated and subjected to silica gel column chromatography (chloroform-methanol, 40:1) to afford 3-amino-2-(3-nitrophenylamino)pyridine (141 mg) as an orange solid.

NMR (DMSO-$d_6$, 200 MHz, δ): 5.18 (2H, s), 6.74 (1H, dd, J=5 Hz, 8 Hz), 6.99 (1H, dd, J=1.5 Hz, 8 Hz), 7.45–7.7 (3H, m), 8.02 (1H, m), 8.33 (1H, s), 8.66 (1H, t, J=1.5 Hz)

Preparation 31

A mixture of 3-nitro-2-((E)-3-styrylphenylamino)pyridine (1.03 g) and 10% palladium on carbon (0.3 g) in methanol (20 ml) and 1,4-dioxane (20 ml) was stirred under hydrogen (3 atm) at room temperature for 1.5 hours. The catalyst was removed by filtration and the solvent was evaporated. The resulting solid was collected and washed with isopropyl ether to give 3-amino-2-(3-phenethylphenylamino)pyridine (835 mg).

NMR (DMSO-d$_6$, 300 MHz, δ): 2.8–2.95 (4H, m), 5.05 (2H, s), 6.61 (1H, dd, J=5 Hz, 8 Hz), 6.72 (1H, d, J=8 Hz), 6.89 (1H, d, J=8 Hz), 7.1–7.35 (6H, m), 7.43 (1H, s), 7.50 (1H, d, J=5 Hz), 7.55 (1H, dd, J=1.5 Hz, 8 Hz), 7.67 (1H, s)

Preparation 32

The following compounds were obtained according to similar manners to those of Preparations 3 and 31.

(1) 2-(3-Acetamidophenylamino)-3-amino-6-ethoxypyridine

NMR (DMSO-d$_6$, δ): 1.35 (3H, t, J=7 Hz), 2.02 (3H, s), 4.35 (2H, q, J=7 Hz), 6.29 (1H, d, J=7 Hz), 6.82 (1H, m), 6.90 (1H, d, J=7 Hz), 7.05 (1H, dd, J=8 Hz, 8 Hz), 7.20 (1H, m), 7.75 (1H, s), 8.35 (1H, s), 9.71 (1H, s)

(2) 3-Amino-2-[3-[2-(2-naphthyl)ethyl]phenylamino]pyridine

NMR (DMSO-d$_6$, 300 MHz, δ): 2.9–3.1 (4H, m), 5.07 (2H, s), 6.61 (1H, dd, J=5 Hz, 8 Hz), 6.76 (1H, d, J=8 Hz), 6.89 (1H, dd, J=1.5 Hz, 8 Hz), 7.12 (1H, t, J=8 Hz), 7.4–7.6 (6H, m), 7.68 (1H, s), 7.75 (1H, s), 7.8–7.9 (3H, m)

Preparation 33

A mixture of 2-(3-chlorophenylamino)-3-nitropyridine (394 mg), hydrochloric acid (35% 1.3 ml) and iron powder (0.44 g) in ethanol (5 ml) was refluxed for 15 minutes. The mixture was poured into aqueous sodium bicarbonate solution and extracted with ethyl acetate twice. The combined organic solution was washed with aqueous sodium bicarbonate solution and brine, dried over magnesium sulfate and concentrated. The resultant solid was collected and washed with isopropyl ether to give 3-amino-2-(3-chlorophenylamino)pyridine (281 mg).

NMR (DMSO-d$_6$, 200 MHz, δ): 5.12 (2H, s), 6.68 (1H, dd, J=5 Hz, 8 Hz), 6.8–7.0 (2H, m), 7.23 (1H, t, J=8 Hz), 7.45–7.6 (2H, m), 7.89 (1H, t, J=2 Hz), 7.96 (1H, s)

Preparation 34

The following compounds were obtained according to a similar manner to that of Preparation 33.

(1) 3-Amino-2-(3-cyanophenylamino)pyridine

NMR (DMSO-d$_6$, 300 MHz, δ): 5.13 (2H, s), 6.71 (1H, dd, J=5 Hz, 8 Hz), 6.97 (1H, dd, J=1.5 Hz, 8 Hz), 7.25 (1H, d, J=8 Hz), 7.42 (1H, t, J=8 Hz), 7.57 (1H, dd, J=1.5 Hz, 5 Hz), 7.82 (1H, dd, J=1.5 Hz, 8 Hz), 8.13 (1H, s), 8.18 (1H, t, J=1.5 Hz)

(2) 3-Amino-2-(3-biphenylylamino)pyridine

NMR (DMSO-d$_6$, 300 MHz, δ): 5.09 (2H, s), 6.6–6.7 (1H, m), 6.92 (1H, dt, J=8 Hz, 1.5 Hz), 7.12 (1H, d, J=8 Hz), 7.25–7.4 (2H, m), 7.45–7.6 (3H, m), 7.63 (2H, d, J=8 Hz), 7.69 (1H, d, J=8 Hz), 7.83 (1H, s), 7.89 (1H, s)

(3) 3-Amino-2-[3-(2-aminothiazol-4-yl)phenylamino]pyridine

NMR (DMSO-d$_6$, 300 MHz, δ): 5.08 (2H, s), 6.61 (1H, dd, J=5 Hz, 8 Hz), 6.8–6.9 (2H, m), 6.98 (2H, s), 7.15–7.3 (2H, m), 7.49 (1H, m), 7.65 (1H, d, J=8 Hz), 7.76 (1H, s), 7.91 (1H, s)

(4) 3-Amino-2-[3-[2-(pyridin-3-yl)thiazol-4-yl]phenylamino]pyridine

NMR (DMSO-d$_6$, 300 MHz, δ): 5.12 (2H, s), 6.65 (1H, dd, J=5 Hz, 8 Hz), 6.92 (1H, d, J=8 Hz), 7.33 (1H, t, J=8 Hz), 7.45–7.6 (3H, m), 7.82 (1H, dd, J=1.5 Hz, 8 Hz), 7.89 (1H, s), 8.14 (1H, s), 8.22 (1H, s), 8.38 (1H, m), 8.69 (1H, d, J=5 Hz), 9.22 (1H, d, J=1.5 Hz)

(5) 3-Amino-2-[3-(imidazol-4-yl)phenylamino]pyridine

NMR (DMSO-d$_6$, 5, 300 MHz, δ): 5.07 (2H, s), 6.61 (1H, dd, J=5 Hz, 8 Hz), 6.90 (1H, d, J=8 Hz), 7.15–7.25 (2H, m), 7.4–7.8 (5H, m), 7.94 (1H, s), 12.18 (1H, br s)

(6) 3-Amino-2-[3-(4-methoxybenzoyl)phenylamino]pyridine

NMR (DMSO-d$_6$, 300 MHz, δ): 3.87 (3H, s), 5.09 (2H, s), 6.65 (1H, dd, J=5 Hz, 8 Hz), 6.91 (1H, d, J=8 Hz), 7.05–7.2 (3H, m), 7.38 (1H, t, J=8 Hz), 7.49 (1H, m), 7.80 (2H, dt, J=8 Hz, 1.5 Hz), 7.9–8.05 (3H, m)

(7) 3-Amino-2-[3-(3-indolizinylcarbonyl)phenylamino]pyridine

NMR (DMSO-d$_6$, 300 MHz, δ): 5.10 (2H, s), 6.60–6.75 (2H, m), 6.94 (1H, d, J=8 Hz), 7.11 (1H, m), 7.22 (1H, d, J=8 Hz), 7.25–7.45 (2H, m), 7.5–7.55 (2H, m), 7.75–7.85 (2H, m), 8.00 (1H, s), 8.08 (1H, s), 9.86 (1H, d, J=7 Hz)

(8) 3-Amino-2-((E)-3-styrylphenylamino)pyridine

NMR (DMSO-d$_6$, 300 MHz, δ): 5.07 (2H, s), 6.63 (1H, dd, J=5 Hz, 8 Hz), 6.90 (1H, d, J=8 Hz), 7.05–7.4 (7H, m), 7.5–7.65 (4H, m), 7.78 (2H, d, J=8 Hz)

(9) 3-Amino-2-[3-[(E)-2-(2-naphthyl)vinyl]phenylamino]pyridine

NMR (DMSO-d$_6$, 300 MHz, δ): 5.10 (2H, s), 6.67 (1H, dd, J=5 Hz, 8 Hz), 6.92 (1H, d, J=8 Hz), 7.17 (1H, d, J=8 Hz), 7.2–7.65 (7H, m), 7.81 (1H, s), 7.85–8.0 (5H, m), 8.02 (1H, s)

(10) 3-Amino-2-[3-((E)-2-benzoylvinyl)phenylamino]pyridine

NMR (DMSO-d$_6$, 300 MHz, δ): 5.10 (2H, s), 6.67 (1H, dd, J=5 Hz, 8 Hz), 6.94 (1H, dd, J=1.5 Hz, 8 Hz), 7.34 (1H, t, J=8 Hz), 7.42 (1H, d, J=8 Hz), 7.5–7.9 (8H, m), 7.98 (1H, s), 8.12 (2H, dd, J=1.5 Hz, 8 Hz)

(11) 3-Amino-2-[3-((E)-2-cyanovinyl)phenylamino]pyridine

NMR (DMSO-d$_6$, 300 MHz, δ): 5.09 (2H, s), 6.32 (1H, d, J=16 Hz), 6.67 (1H, dd, J=5 Hz, 8 Hz), 6.92 (1H, dd, J=1.5 Hz, 8 Hz), 7.17 (1H, d, J=8 Hz), 7.30 (1H, t, J=8 Hz), 7.5–7.95 (5H, m)

(12) 3-Amino-2-[3-((E)-2-methoxycarbonylvinyl)phenylamino]pyridine

NMR (DMSO-d$_6$, 300 MHz, δ): 3.73 (3H, s), 5.08 (2H, s), 6.49 (1H, d, J=16 Hz), 6.66 (1H, dd, J=5 Hz, 8 Hz), 6.93 (1H, d, J=8 Hz), 7.15–7.35 (2H, m), 7.5–7.75 (3H, m), 7.85 (1H, s), 7.90 (1H, s)

(13) 3-Amino-2-[3-(N-methylacetamido)phenylamino]pyridine

NMR (DMSO-d$_6$, 200 MHz, δ): 1.83 (3H, s), 3.16 (3H, s), 5.09 (2H, s), 6.65 (1H, dd, J=5 Hz, 8 Hz), 6.77 (1H, d, J=8 Hz), 6.92 (1H, dd, J=1.5 Hz, 8 Hz), 7.28 (1H, t, J=8 Hz), 7.5–7.65 (3H, m), 7.90 (1H, s)

(14) 3-Amino-2-[3-(4-phenylthiazol-2-yl)aminophenylamino]pyridine

NMR (DMSO-d$_6$, 300 MHz, δ): 5.09 (2H, s), 6.67 (1H, dd, J=5 Hz, 8 Hz), 6.92 (1H, m), 7.0–7.55 (6H, m), 7.53 (1H, d, J=5 Hz), 7.73 (1H, s), 7.91 (2H, d, J=8 Hz), 8.19 (1H, s)

(15) 3-Amino-2-[3-(4-methylthiazol-2-yl)aminophenylamino]pyridine

NMR (DMSO-d$_6$, 300 MHz, δ): 2.21 (3H, s), 5.09 (2H, s), 6.39 (1H, s), 6.62 (1H, dd, J=5 Hz, 8 Hz), 6.89 (1H, d, J=8 Hz), 7.05–7.3 (3H, m), 7.49 (1H, d, J=5 Hz), 7.68 (1H, s), 7.89 (1H, s)

(16) 3-Amino-2-[3-(pyrimidin-2-yl)aminophenylamino]pyridine

NMR (DMSO-d$_6$, 300 MHz, δ): 5.08 (2H, s), 6.60 (1H, dd, J=5 Hz, 8 Hz), 6.79 (1H, d, J=5 Hz), 6.88 (1H, d, J=8 Hz), 7.10 (1H, t, J=8 Hz), 7.22 (1H, m), 7.30 (1H, m), 7.48 (1H, d, J=5 Hz), 7.66 (1H, s), 7.92 (1H, t, J=1.5 Hz), 8.45 (2H, d, J=5 Hz), 9.47 (1H, s)

(17) 3-Amino-2-[3-(pyrimidin-2-yl)oxyphenylamino]pyridine

NMR (DMSO-d$_6$, 300 MHz, δ): 5.10 (2H, s), 6.6–6.7 (2H, m), 6.91 (1H, d, J=8 Hz), 7.2–7.3 (2H, m), 7.4–7.55 (2H, m), 7.60 (1H, s), 7.89 (1H, s), 8.65 (2H, d, J=5 Hz)

(18) 3-Amino-2-[3-(4-phenylpyrimidin-2-yl)oxyphenylamino]pyridine

NMR (DMSO-d$_6$, 300 MHz, δ): 5.10 (2H, s), 6.63 (1H, dd, J=5 Hz, 8 Hz), 6.72 (1H, d, J=8 Hz), 6.93 (1H, d, J=8 Hz), 7.30 (1H, t, J=8 Hz), 7.45–7.6 (5H, m), 7.69 (1H, s), 7.84 (1H, d, J=5 Hz), 7.91 (1H, s), 8.1–8.2 (2H, m), 8.68 (1H, d, J=5 Hz)

Preparation 35

4N Aqueous solution of sodium hydroxide (2 ml) was added to a solution of ethyl 3-(benzoylamino)benzoate (695 mg) in ethanol (5 ml) and 1,4-dioxane (5 ml). After stirred at 50° C. for 1 hour, the mixture was acidified with dilute hydrochloric acid and extracted with ethyl acetate. The organic phase was washed with dilute hydrochloric acid and brine, dried over magnesium sulfate and concentrated to give 3-(benzoylamino)benzoic acid (595 mg) as solid.

NMR (DMSO-d$_6$, 300 MHz, δ): 7.45–7.75 (5H, m), 7.99 (2H, d, J=8 Hz), 8.05 (1H, d, J=8 Hz), 8.44 (1H, s)

Preparation 36

The following compound was obtained according to a similar manner to that of Preparation 35.

3-(Pyrimidin-2-yl)oxybenzoic acid

NMR (DMSO-d$_6$, 300 MHz, δ): 7.30 (1H, t, J=5 Hz), 7.48 (1H, d, J=8 Hz), 7.58 (1H, t, J=8 Hz), 7.69 (1H, s), 7.84 (1H, d, J=8 Hz), 8.67 (2H, d, J=5 Hz)

Preparation 37

4N Aqueous solution of sodium hydroxide (1 ml) was added to a solution of ethyl 3-[(3-nitropyridin-2-yl)amino]benzoate (322 mg) in ethanol (2 ml) and 1,4-dioxane (2 ml). After stirred at room temperature for 1 hour, the mixture was acidified with dilute hydrochloric acid and extracted with ethyl acetate. The organic phase was washed with water and brine, dried over magnesium sulfate and concentrated to give 3-[(3-nitropyridin-2-yl)amino]benzoic acid (263 mg) as solid.

NMR (DMSO-d$_6$, 300 MHz, δ): 7.03 (1H, dd, J=5 Hz, 8 Hz), 7.49 (1H, t, J=8 Hz), 7.72 (1H, d, J=8 Hz), 7.88 (1H, d, J=8 Hz), 8.26 (1H, s), 8.5–8.6 (2H, m), 10.03 (1H, s)

Preparation 38

A mixture of 3-nitrostyrene (4.6 ml), 3-bromopyridine (2.6 ml), palladium(II) acetate (0.20 g), tetrabutylammonium chloride (8.4 g) and sodium bicarbonate (6.3 g) in N,N-dimethylformamide (40 ml) was stirred at 110° C. for 3 hours. Then the mixture was poured into aqueous sodium bicarbonate and extracted with ethyl acetate twice. The combined organic phase was washed with aqueous sodium bicarbonate and brine, dried over magnesium sulfate and concentrated. The resultant solid was collected and washed with isoprbpyl ether to give 3-[(E)-2-(3-nitrophenyl)vinyl]pyridine (5.34 g).

NMR (CDCl$_3$, 300 MHz, δ): 7.21 (2H, s), 7.33 (1H, dd, J=5 Hz, 8 Hz), 7.57 (1H, t, J=8 Hz), 7.8–7.9 (2H, m), 8.13 (1H, dd, J=2 Hz, 8 Hz), 8.38 (1H, t, J=2 Hz), 8.55 (1H, d, J=5 Hz), 8.78 (1H, d, J=2 Hz)

Preparation 39

The following compound was obtained according to a similar manner to that of Preparation 38.

5-[(E)-2-(3-Nitrophenyl)vinyl]pyrimidine

NMR (DMSO-d$_6$, 300 MHz, δ): 7.51 (1H, d, J=16 Hz), 7.7–7.8 (2H, m), 8.09 (1H, d, J=8 Hz), 8.18 (1H, dd, J=2 Hz, 8 Hz), 8.47 (1H, s), 9.10 (3H, m)

Preparation 40

A mixture of 1-iodo-3-nitrobenzene (7.47 g), 2-vinylpyridine (4.73 g), palladium(II) acetate (0.20 g), tetrabutylammonium chloride (8.34 g) and sodium bicarbonate (6.3 g) in N,N-dimethylformamide (50 ml) was stirred at 110° C. for 5 hours. Then the mixture was poured into aqueous sodium bicarbonate and extracted with ethyl acetate twice. The combined organic phase was washed with aqueous sodium bicarbonate and brine, dried over magnesium sulfate and concentrated. The resultant solid was collected and washed with isopropyl ether to give 2-[(E)-2-(3-nitrophenyl)vinyl]pyridine (3.37 g).

NMR (CDCl$_3$, 300 MHz, δ): 7.15–7.3 (2H, m), 7.41 (1H, d, J=8 Hz), 7.54 (1H, t, J=8 Hz), 7.65–7.75 (2H, m), 8.13 (1H, dd, J=2 Hz, 8 Hz), 8.43 (1H, s), 8.64 (1H, d, J=5 Hz)

Preparation 41

To a solution of 2-bromonaphthalene (5.0 g) and tetrakis(triphenylphosphine)palladium(0) (0.56 g) in toluene (50 ml) was added a solution of dihydroxy(3-nitrophenyl)borane (4.44 g) in methanol and 2M sodium carbonate solution in water (12 ml). The resulting mixture was stirred at 80° C. for 4 hours and extracted with ethyl acetate. After evaporation of the solvent, the crude residue was crystallized from hexane to give 3-(2-naphthyl)-1-nitrobenzene (5.4 g).

NMR (CDCl$_3$, δ): 7.54 (2H, m), 7.65 (1H, t, J=8 Hz), 7.75 (1H, d, J=8 Hz), 7.91 (2H, m), 7.98 (1H, d, J=8 Hz), 8.05 (1H, dd, J=9 Hz, 2 Hz), 8.11 (1H, s), 8.23 (1H, dd, J=8 Hz, 2 Hz), 8.59 (1H, s)

Preparation 42

To a suspension of sodium hydride (60% in oil, 0.75 g) in N,N-dimethylformamide (20 ml) was added a solution of diethyl 3-nitrobenzylphosphonate (4.40 g) in N,N-dimethylformamide (20 ml). The mixture was stirred at room temperature for 15 minutes, then a solution of 4-quinolinecarbaldehyde (2.81 g) in N,N-dimethylformamide (20 ml) was added thereto. After stirring at 50° C. fbr 30 minutes, the mixture was poured into aqueous sodium bicarbonate, and extracted with ethyl acetate twice. The combined organic solution was washed with aqueous sodium bicarbonate and brine, dried over magnesium sulfate and concentrated. The residue was chromatographed on silica gel column (chloroform-methanol (50:1)) to give 4-[(E)-2-(3-nitrochenyl)vinyl]quinoline (1.57 g) as a solid.

NMR (DMSO-d$_6$, 300 MHz, δ): 7.65–7.85 (4H, m), 7.89 (1H, d, J=5 Hz), 8.07 (1H, d, J=8 Hz), 8.21 (1H, dd, J=2 Hz, 8 Hz), 8.3–8.4 (2H, m), 8.62 (1H, d, J=8 Hz), 8.70 (1H, t, J=2 Hz), 8.94 (1H, d, J=5 Hz)

Preparation 43

The following compound was obtained according to a similar manner to that of Preparation 42.

2-](E)-2-(3-Nitrophenyl)vinyl]quinoline

NMR (DMSO-d$_6$, 300 MHz, δ): 7.60 (1H, t, J=8 Hz), 7.65–7.85 (3H, m), 7.9–8.05 (4H, m), 8.15–8.3 (2H, m), 8.41 (1H, d, J=8 Hz), 8.57 (1H, t, J=2 Hz)

Preparation 44

A mixture of 3-[(E)-2-(3-nitrophenyl)vinyl]pyridine (3.64 g), iron powder (3.6 g) and hydrochloric acid (35%, 11 ml)

in ethanol (30 ml) was stirred at 80° C. for 4 hours. Then the mixture was poured into aqueous sodium bicarbonate and extracted with ethyl acetate twice. The combined organic phase was washed with aqueous sodium bicarbonate and brine, dried over magnesium sulfate and concentrated. The resultant solid was collected and washed with isopropyl ether to give 3-[(E)-2-(3-aminophenyl)vinyl]pyridine (1.25 g).

NMR (DMSO-$d_6$, 300 MHz, δ): 5.12 (2H, s), 6.52 (1H, dd, J=2 Hz, 8 Hz), 6.75–6.85 (2H, m), 7.0–7.15 (2H, m), 7.23 (1H, d, J=16 Hz), 7.39 (1H, m), 8.02 (1H, m), 8.45 (1H, d, J=5 Hz), 8.75 (1H, d, J=2 Hz)

Preparation 45

A mixture of 3-(2-naphthyl)-1-nitrobenzene (5.4 g), iron (3.63 g) and acetic acid (13.0 g) in ethanol (50 ml) was stirred under reflux for 3 hours. The reaction mixture was diluted with chloroform, filtered and treated with saturated sodium bicarbonate solution. The chloroform layer was separated, dried, evaporated and chromatographed on silica gel to give 3-(2-naphthyl)aniline (5.2 g).

NMR (CDCl$_3$, δ): 3.75 (2H, br s), 6.70 (1H, dd, J=8 Hz, 2 Hz), 7.03 (1H, s), 7.12 (1H, d, J=8 Hz), 7.27 (1H, dd, J=8 Hz, 8 Hz), 7.47 (2H, m), 7.70 (1H, dd, J=8 Hz, 2 Hz), 7.87 (3H, m), 8.01 (1H, s)

Preparation 46

The following compounds were obtained according to a similar manner into that of Preparation 3, 21, 23, 44 or 45.

(1) 2-[(E)-2-(3-Aminophenyl)vinyl]pyridine NMR (DMSO-$d_6$, 300 MHz, δ): 5.12 (2H, s), 6.53 (1H, dd, J=2 Hz, 8 Hz), 6.75–6.85 (2H, m), 7.0–7.15 (2H, m), 7.23 (1H, dd, J=5 Hz, 8 Hz), 7.45–7.6 (2H, m), 7.78 (1H, t, J=8 Hz), 8.56 ($_1$H, d, J=5 Hz)

(2) 5-[(E)-2-(3-Aminophenyl)vinyl]pyrimidine

NMR (DMSO-$d_6$, 300 MHz, δ): 5.17 (2H, s), 6.55 (1H, dd, J=2 Hz, 8 Hz), 6.79 (2H, m), 7.0–7.1 (2H, m), 7.39 (1H, d, J=16 Hz), 9.03 (3H, m)

(3) 4-[(E)-2-(3-Aminophenyl)vinyl]quinoline

NMR (DMSO-$d_6$, 300 MHz, δ): 5.15 (2H, s), 6.60 (1H, dd, J=2 Hz, 8 Hz), 6.95–7.05 (2H, m), 7.11 (1H, t, J=8 Hz), 7.45 (1H, d, J=16 Hz), 7.67 (1H, t, J=8 Hz), 7.75–7.95 (3H, m), 8.05 (1H, d,, J=8 Hz), 8.44 (1H, d, J=8 Hz), 8.88 (1H, d, J=5 Hz)

(4) 2-[(E)-2-(3-Aminophenyl)vinyl]quinoline

NMR (DMSO-$d_6$, 300 MHz, δ): 5.18 (2H, s), 6.59 (1H, d, J=8 Hz), 6.85–6.95 (2H, m), 7.10 (1H, t, J=8 Hz), 7.31 (1H, d, J=16 Hz), 7.56 (1H, t, J=8 Hz), 7.65–7.8 (2H, m), 7.85–8.0 (3H, m), 8.33 (1H, d, J=8 Hz)

(5) 3-(3-Biphenylyl)aniline

NMR (CDCl$_3$, δ): 3.74 (2H, s), 6.69 (1H, dd, J=8 Hz, 2 Hz), 6.95 (1H, t, J=2 Hz), 7.02 (1H, d, J=8 Hz), 7.24 (1H, m), 7.35 (1H, m), 7.4–7.6 (5H, m), 7.64 (2H, m), 7.79 (1H, s)

Preparation 47

A mixture of 2-chloro-3-nitropyridine (1.15 g), 3-[(E)-2-(3-aminophenyl)vinyl]pyridine (1.23 g) and potassium carbonate (1.1 g) in 1,4-dioxane (15 ml) was stirred under reflux for 22 hours. After cooling, insoluble materials were removed by filtration and the filtrate was concentrated. The residue was chromatographed on silica gel column (2% methanol in chloroform) to give 3-nitro-2-[3-[(E)-2-(3-pyridyl)vinyl]phenylamino]pyridine (510 mg) as an orange solid.

NMR (DMSO-$d_6$, 300 MHz, δ): 7.02 (1H, m), 7.3–7.5 (5H, m), 7.65 (1H, m), 7.89 (1H, s), 8.08 (1H, d, J=8 Hz), 8.48 (1H, d, J=5 Hz), 8.5–8.6 (2H, m), 8.80 (1H, d, J=2 Hz)

Preparation 48

A mixture of 3-(2-naphthyl)aniline (5.0 g), 2-chloro-3-nitropyridine (3.62 g) and potassium carbonate (6.31 g) in dioxane (50 ml) was stirred under reflux for 6 days. The reaction mixture was extracted with chloroform and evaporated. Crude residue was chromatographed on silica gel to give 2-[3-(2-naphthyl)phenylamino]-3-nitropyridine as an orange crystal (5.23 g).

NMR (DMSO-$d_6$, δ): 7.02 (1H, dd, J=8 Hz, 5 Hz), 7.55 (4H, m), 7.75 (1H, m), 7.85–8.1 (5H, m), 8.26 (1H, s), 8.55 (2H, m)

Preparation 49

A mixture of 2-chloro-3-nitropyridine (8.5 g), 3-iodoaniline (12.5 g) and potassium carbonate (9.0 g) in 1,4-dioxane (100 ml) was stirred under reflux for 20 hours. After cooling, insoluble materials were removed by filtration and the filtrate was concentrated. The resultant solid was collected and washed with isopropyl ether to give 2-(3-iodophenylamino)-3-nitropyridine (3.88 g) as an orange solid.

NMR (CDCl$_3$, 300 MHz, δ): 6.89 (1H, dd, J=5 Hz, 8 Hz), 7.11 (1H, t, J=8 Hz), 7.50 (1H, d, J=8 Hz), 7.60 (1H, dd, J=2, 8 Hz), 8.12 (1H, s), 8.45–8.6 (2H, m)

Preparation 50

The following compounds were obtained according to a similar manner to that of Preparation 1, 5, 27, 28, 47, 48 or 49.

(1) 3-Nitro-2-[3-[(E)-2-(2-pyridyl)vinyl]phenylamino] pyridine

NMR (CDCl$_3$, 300 MHz, δ): 6.87 (1H, dd, J=2 Hz, 8 Hz), 7.4–7.8 (7H, m), 7.98 (1H, s), 8.05–8.2 (2H, m), 8.5–8.6 (2H, m)

(2) 3-Nitro-2-[3-[(E)-2-(5-pyrimidinyl)vinyl]phenylamino] pyridine

NMR (DMSO-$d_6$, 300 MHz, δ): 7.02 (1H, dd, J=5 Hz, 8 Hz), 7.28 (1H, d, J=16 GHz), 7.49–7.5 (2H, m), 7.58 (1H, d, J=16 Hz), 7.68 (1H, m), 7.90 (1H, s), 8.5–8.6 (2H, m), 9.0–9.1 (3H, m)

(3) 3-Nitro-2-[3-[(E)-2-(4-quinolyl)vinyl]phenylamino] pyridine

NMR (DMSO-$d_6$, 300 MHz, δ): 7.02 (1H, dd, J=5, 8 Hz), 7.47 (1H, t, J=8 Hz), 7.55–7.85 (6H, m), 7.89 (1H, d, J=5 Hz), 8.05–8.2 (6H, m), 8.5–8.6 (3H, m), 8.90 (1H, d, J=5 Hz)

(4) 3-Nitro-2-[3-[(E)-2-(2-quinolyl)vinyl]phenylamino] pyridine

NMR (DMSO-$d_6$, 300 MHz, δ): 7.03 (1H, dd, J=5, 8 Hz), 7.4–7.6 (4H, m), 7.7–8.05 (7H, m), 8.37 (1H, d, J=8 Hz), 8.55–8.6 (2H, m)

(5) 2-[3-(2-Cyanopyrrol-1-yl)phenylamino]-3-nitropyridine

NMR (DMSO-$d_6$, δ): 6.46 (1H, m), 7.06 (1H, m), 7.25 (1H, m), 7.31 (1H, m), 7.56 (1H, m), 7.78 (1H, m), 8.03 (1H, m), 8.56 (2H, m)

(6) 2-[3-(Benzothiazol-2-yl)phenylamino]-3-nitropyridine

NMR (DMSO-$d_6$, δ): 7.06 (1H, dd, J=8 Hz, 4 Hz), 7.50 (1H, dd, J=8 Hz, 8 Hz), 7.57 (2H, dd, J=8 Hz, 8 Hz), 7.88 (2H, m), 8.09 (1H, d, J=8 Hz), 8.18 (1H, d, J=8 Hz), 8.46 (1H, m), 8.57 (2H, m)

(7) 2-(3-Benzoylphenylamino)-3-nitropyridine

NMR (CDCl$_3$, δ): 6.88 (1H, dd, J=8 Hz, 5 Hz), 7.51 (3H, m), 7.60 (2H, m), 7.88 (3H, m), 8.14 (1H, m), 8.49 (1H, dd, J=5 Hz, 2 Hz), 8.55 (1H, dd, J=8 Hz, 2 Hz)

(8) 2-(3-Trifluoromethylphenylamino)-3-nitropyridine

NMR (DMSO-$d_6$, δ): 7.05 (1H, dd, J=8 Hz, 4 Hz), 7.45 (1H, d, J=8 Hz), 7.60 (1H, dd, J=8 Hz, 8 Hz), 7.92 (1H, d, J=8 Hz), 8.12 (1H, s), 8.53 (2H, m)

(9) 2-[3-(Indol-1-yl)phenylamino]-3-nitropyridine

NMR (CDCl$_3$, δ): 6.70 (1H, d, J=3 Hz), 6.89 (1H, dd, J=8 Hz, 4 Hz), 7.17 (1H, m), 7.21 (1H, m), 7.30 (1H, m), 7.39 (1H, d, J=3 Hz), 7.50 (2H, m), 7.72 (2H, m), 8.10 (1H, m), 8.50 (1H, m), 8.55 (1H, m)

(10) 2-(3-Carboxyphenylamino)-3-nitropyridine

NMR (DMSO-$d_6$, δ): 7.03 (1H, dd, J=8 Hz, 5 Hz), 7.50 (1H, dd, J=8 Hz, 8 Hz), 7.71 (1H, m), 7.88 (1H, m), 8.25 (1H, m), 8.55 (2H, m)

(11) 2-[(5-Acetamido-2-fluorophenyl)amino]-3-nitropyridine

NMR (CDCl$_3$, δ): 2.15 (3H, s), 6.92 (1H, dd, J=8 Hz, 5 Hz), 7.11 (1H, dd, J=8 Hz, 8 Hz), 7.35 (1H, m), 8.55 (3H, m)

(12) 2-[3-(1-Naphthyl)phenylamino]-3-nitropyridine

NMR (CDCl$_3$, δ): 6.83 (1H, dd, J=8 Hz, 5 Hz), 7.31 (1H, d, J=7 Hz), 7.4–7.55 (5H, m), 7.74 (1H, dd, J=8 Hz, 2 Hz), 7.79 (1H, m), 7.90 (2H, m), 8.00 (1H, d, J=8 Hz), 8.47 (1H, m), 8.53 (1H, d, J=8 Hz)

(13) 2-[3-(3-Biphenylyl)phenylamino]-3-nitropyridine

NMR (CDCl$_3$, δ): 6.86 (1H, dd, J=8 Hz, 6 Hz), 7.39 (1H, m), 7.4–7.7 (11H, m), 7.83 (1H, s), 7.89 (1H, s), 8.50 (2H, m)

Preparation 51

A mixture of 2-(3-iodophenylamino)-3-nitropyridine (3.86 g), 4-vinylpyridine (1.78 g), palladium(II) acetate (80 mg), tetrabutylammonium chloride (3.14 g) and sodium bicarbonate (2.4 g) in N,N-dimethylformamide (20 ml) was stirred at 110° C. for 22 hours. Then the mixture was poured into aqueous sodium bicarbonate and extracted with ethyl acetate twice. The combined organic phase was washed with aqueous sodium bicarbonate and brine, dried over magnesium sulfate and concentrated. The residue was chromatographed on silica gel column (chloroform-methanol (50:1)) to give 3-nitro-2-[3-[(E)-2-(4-pyridyl)vinyl]phenylamino]pyridine (1.41 g) as an orange solid.

NMR (CDCl$_3$, 300 MHz, δ): 6.88 (1H, dd, J=5 Hz, 8 Hz), 7.07 (1H, d, J=16 Hz), 7.3–7.5 (5H, m), 7.62 (1H, d, J=8 Hz), 7.85 (1H, s), 8.5–8.65 (4H, m)

Preparation 52

A mixture of 3-nitro-2-[3-[(E)-2-(3-pyridyl)vinyl]phenylamino]pyridine (493 mg), iron powder (0.35 g) and hydrochloric acid (35%, 1 ml) in methanol (5 ml) was stirred under reflux for 4 hours. Then the mixture was poured into aqueous sodium bicarbonate and extracted with ethyl acetate twice. The combined organic phase was washed with aqueous sodium bicarbonate and brine, dried over magnesium sulfate and concentrated. The resultant solid was collected and washed with isopropyl ether to give 3-amino-2-[3-[(E)-2-(3-pyridyl)vinyl]phenylamino]pyridine (291 mg).

NMR (DMSO-$d_6$, 300 MHz, δ): 5.10 (2H, s), 6.66 (1H, dd, J=5 Hz, 8 Hz), 6.92 (1H, d, J=8 Hz), 7.1–7.45 (5H, m), 7.54 (1H, d, J=5 Hz), 7.62 (1H, d, J=8 Hz), 7.80 (2H, d, J=8 Hz), 8.08 (1H, d, J=8 Hz), 8.47 (1H, d, J=5 Hz), 8.79 (1H, d, J=2 Hz)

Preparation 53

A mixture of 3-nitro-2-[3-[(E)-2-(4-pyridyl)vinyl]phenylamino]pyridine (1.38 g), iron powder (1.0 g) and hydrochloric acid (35%, 3.0 ml) in ethanol (10 ml) was stirred at 80° C. for 2 hours. Then the mixture was poured into aqueous sodium bicarbonate and extracted with ethyl acetate twice. The combined organic phase was washed with aqueous sodium bicarbonate and brine, dried over magnesium sulfate and concentrated. The residue was chromatographed on silica gel column (8% methanol in chloroform) to give 3-amino-2-[3-[(E)-2-(4-pyridyl)vinyl]phenylamino]pyridine (1.14 g) as powder.

NMR (DMSO-$d_6$, 300 MHz, δ): 5.09 (2H, s), 6.65 (1H, dd, J=5 Hz, 8 Hz), 6.93 (1H, d, J=8 Hz), 7.1–7.2 (2H, m), 7.28 (1H, t, J=8 Hz), 7.45–7.7 (5H, m), 7.82 (1H, s), 7.88 (1H, s), 8.54 (2H, d, J=5 Hz)

Preparation 54

A mixture of 2-[3-(2-naphthyl)phenylamino]-3-nitropyridine (3.0 g), iron (2.46 g) and acetic acid (5.28 g) in ethanol (14 ml) was stirred under reflux for 6 hours. The reaction mixture was diluted with chloroform, filtered and treated with saturated sodium bicarbonate solution. The chloroform layer was separated, dried, evaporated and chromatographed on silica gel to give 2-[3-(2-naphthyl)phenylamino]-3-aminopyridine (1.2 g, 43.9%).

NMR (CDCl$_3$, δ): 5.10 (2H, s), 6.65 (1H, dd, J=8 Hz, 6 Hz), 6.94 (1H, dd, J=8 Hz, 2 Hz), 7.28 (1H, m), 7.37 (1H, dd, J=8 Hz, 8 Hz), 7.53 (3H, m), 7.77 (1H, m), 7.81 (1H, d, J=8 Hz), 7.90 (1H, s), 7.95 (1H, m), 8.00 (3H, m), 8.16 (1H, s)

Preparation 55

The following compounds were obtained according to a similar manner to that of Preparation 3, 31, 33, 52, 53 or 54.

(1) 3-Amino-2-[3-[(E)-2-(2-pyridyl)vinyl]phenylamino]pyridine

NMR (DMSO-$d_6$, 300 MHz, δ): 5.10 (2H, s), 6.66 (1H, dd, J=5 Hz, 8 Hz), 6.93 (1H, d, J=8 Hz), 7.1–7.3 (4H, m), 7.55–7.7 (4H, m), 7.75–7.85 (2H, m), 7.90 (1H, s), 8.59 (1H, d, J=5 Hz)

(2) 3-Amino-2-[3-[(E)-2-(5-pyrimidinyl)vinyl]phenylamino]pyridine

NMR (DMSO-$d_6$, 300 MHz, δ): 5.10 (2H, s), 6.66 (1H, dd, J=5 Hz, 8 Hz), 6.92 (1H, d, J=8 Hz), 7.1–7.2 (2H, m), 7.29 (1H, t, J=8 Hz), 7.45–7.55 (2H, m), 7.62 (1H, d, J=8 Hz), 7.83 (2H, d, J=8 Hz), 9.0–9.1 (1H, m)

(3) 3-Amino-2-[3-[(E)-2-(2-quinolyl)vinyl]phenylamino]pyridine

NMR (DMSO-$d_6$, 300 MHz, δ): 5.10 (2H, s), 6.68 (1H, dd, J=5 Hz, 8 Hz), 6.95 (1H, d, J=8 Hz), 7.2–7.45 (3H, m), 7.5–7.6 (2H, m), 7.65 (1H, d, J=8 Hz), 7.7–8.05 (7H, m), 8.36 (1H, d, J=8 Hz)

(4) 3-Amino-2-[3-[(E)-2-(4-quinolyl)vinyl]phenylamino]pyridine

NMR (DMSO-$d_6$, 300 MHz, δ): 5.10 (2H, s), 6.67 (1H, dd, J=5 Hz, 8 Hz), 6.94 (1H, d, J=8 Hz), 7.3–7.45 (2H, m), 7.5–7.6 (2H, m), 7.65–8.1 (8H, m), 8.48 (1H, d, J=8 Hz), 8.89 (1H, d, J=5 Hz)

(5) 2-[3-(Benzothiazol-2-yl)phenylamino]-3-aminopyridine

NMR (DMSO-$d_6$, δ): 5.15 (2H, s), 6.70 (1H, dd, J=8 Hz, 5 Hz), 6.97 (1H, dd, J=8 Hz, 2 Hz), 7.4–7.5 (2H, m), 7.56 (3H, m), 7.96 (1H, dd, J=8 Hz, 2 Hz), 8.08 (2H, m), 8.16 (1H, d, J=8 Hz), 8.40 (1H, m)

(6) 2-[3-(3-Acetylindol-1-yl)phenylamino]-3-aminopyridine

NMR (CDCl$_3$, δ): 2.57 (3H, s), 3.49 (2H, br s), 6.49 (1H, s), 6.80 (1H, dd, J=8 Hz, 5 Hz), 7.05 (2H, m), 7.30 (4H, m), 7.45 (1H, dd, J=9 Hz, 8 Hz), 7.61 (1H, m), 7.68 (1H, m), 7.87 (1H, m), 7.95 (1H, s), 8.44 (1H, m)

(7) 2-[3-(2-Cyanopyrrol-1-yl)phenylamino]-3-aminopyridine

NMR (DMSO-d$_6$, δ): 5.13 (2H, s), 6.43 (1H, m), 6.67 (1H, m), 6.95 (2H, m), 7.20 (1H, m), 7.40 (1H, dd, J=8 Hz, 8 Hz), 7.48 (1H, m), 7.52 (1H, m), 7.66 (1H, m), 7.98 (1H, m), 8.10 (1H, s)

(8) 2-(3-Benzoylphenylamino)-3-aminopyridine

NMR (CDCl$_3$, δ): 3.45 (2H, br s), 6.37 (1H, s), 6.79 (1H, dd, J=8 Hz, 5 Hz), 7.02 (1H, dd, J=8 Hz, 2 Hz), 7.38 (2H, m), 7.49 (2H, m), 7.60 (2H, m), 7.69 (1H, m), 7.84 (3H, m)

(9) 2-(3-Trifluoromethylphenylamino)-3-aminopyridine

NMR (CDCl$_3$, δ): 3.41 (2H, br s), 6.38 (1H, br s), 6.82 (1H, dd, J=8 Hz, 5 Hz), 7.05 (1H, dd, J=8 Hz, 2 Hz), 7.18 (1H, d, J=8 Hz), 7.37 (1H, dd, J=8 Hz, 8 Hz), 7.49 (1H, d, J=8 Hz), 7.55 (1H, br s), 7.85 (1H, dd, J=5 Hz, 2 Hz)

(10) 2-(3-Methoxycarbonylphenylamino)-3-aminopyridine

NMR (DMSO-d$_6$, δ): 3.83 (3H, s), 5.30 (2H, br s), 6.68 (1H, dd, J=8 Hz, 6 Hz), 6.95 (1H, d, J=8 Hz), 7.37 (1H, dd, J=8 Hz, 8 Hz), 7.44 (1H, d, J=8 Hz), 7.51 (1H, d, J=6 Hz), 7.99 (1H, d, J=8 Hz), 8.09 (1H, s), 8.18 (1H, s)

(11) 2-[(5-Acetamido-2-fluorophenyl)amino]-3-aminopyridine

NMR (CDCl$_3$, δ): 2.09 (3H, s), 6.80 (1H, dd, J=8 Hz, 5 Hz), 7.00 (1H, dd, J=8 Hz, 8 Hz), 7.05 (1H, dd, J=8 Hz, 2 Hz), 7.22 (1H, m), 7.72 (2H, m)

(12) 2-[3-(1-Indolyl)phenylamino]-3-aminopyridine

NMR (CDCl$_3$, δ): 3.43 (2H, br s), 6.35 (1H, s), 6.67 (1H, m), 6.80 (1H, m), 7.05 (2H, m), 7.20 (3H, m), 7.38 (2H, m), 7.55 (1H, s), 7.69 (1H, dd, J=8 Hz, 8 Hz), 7.83 (1H, d, J=3 Hz)

(13) 2-[3-(1-Naphthyl)phenylamino]-3-aminopyridine

NMR (CDCl$_3$, δ): 3.40 (2H, br s), 6.29 (1H, s), 6.75 (1H, dd, J=8 Hz, 6 Hz), 6.97 (1H, d, J=8 Hz), 7.08 (1H, m), 7.30 (1H, s), 7.35–7.55 (6H, m), 7.85 (3H, m), 8.01 (1H, d, J=8 Hz)

(14) 2-[3-(3-Biphenylyl)phenylamino]-3-aminopyridine

NMR (CDCl$_3$, δ): 3.45 (2H, br s), 6.30 (1H, s), 6.80 (1H, dd, J=8 Hz, 6 Hz), 7.03 (1H, d, J=8 Hz), 7.2–7.7 (12H, m), 7.80 (1H, m), 7.87 (1H, m)

Preparation 56

A mixture of 2-[3-(indol-1-yl)phenylamino]-3-nitropyridine (1.0 g), acetic anhydride (0.46 g), and aluminum chloride (1.21 g) in dry methylene chloride (10 ml) was stirred at room temperature for 3 hours. The reaction mixture was treated with 1N sodium hydroxide solution and precipitated brown crystals were collected, washed with water and dried to give 2-[3-(3-acetylindol-1-yl)phenylamino]-3-nitropyridine (1.17 g).

NMR (DMSO-d$_6$, δ): 2.54 (3H, s), 7.06 (1H, dd, J=8 Hz, 6 Hz), 7.33 (2H, m), 7.45 (1H, m), 7.63 (1H, dd, J=8 Hz, 8 Hz), 7.73 (1H, m), 7.78 (1H, m), 8.09 (1H, m), 8.32 (1H, m), 8.57 (1H, m), 8.66 (1H, s)

Preparation 57

The following compounds were obtained according to a similar manner to that of Preparation 41.

(1) 3-(1-Naphthyl)-1-nitrobenzene

NMR (CDCl$_3$, δ): 7.4–7.6 (4H, m), 7.68 (1H, t, J=8 Hz), 7.77 (1H, d, J=8 Hz), 7.83 (1H, dd, J=8 Hz, 2 Hz), 7.93 (2H, m), 8.30 (1H, dd, J=8 Hz, 2 Hz), 8.39 (1H, m)

(2) 3-(3-Biphenylyl)-1-nitrobenzene

NMR (CDCl$_3$, δ): 7.35–7.75 (9H, m), 7.82 (1H, s), 7.98 (1H, d, J=8 Hz), 8.23 (1H, dd, J=8 Hz, 2 Hz), 8.50 (1H, m)

Preparation 58

To a solution of 2-methyl-4-(3-aminophenyl)-3-oxo-3,4-dihydropyrido[2,3-b]pyrazine (7.4 g) and triethylamine (5.72 ml) in dioxane was added 3,5-dichlorobenzoyl chloride (6.14 g) in dropwise. The mixture was stirred for 3 hours at room temperature. The reaction mixture was quenched by water and extracted with ethyl acetate (100 ml). The crude product was purified by chromatography to obtain 2-methyl-4-[3-(3,5-dichlorobenzoylamino)phenyl]-3-oxo-3,4-dihydropyrido[2,3-b]pyrazine (4.4 g).

NMR (CDCl$_3$, 300 MHz, δ): 9.09 (1H, br s), 8.38 (1H, m), 8.19 (1H, d, J=7 Hz), 7.80 (1H, s), 7.68 (2H, s), 7.52 (1H, d, J=6 Hz), 7.39 (1H, s), 7.35–7.23 (2H, m), 6.54 (1H, d, J=6 Hz), 2.73 (3H, s)

Preparation 59

A mixture of 3-nitrophenylhydrazine hydrochloride (8.77 g) and 1,3,5-triazine (2.50 g) in ethanol (40 ml) was stirred under reflux for 4 hours. Then the mixture was poured into aqueous sodium bicarbonate and extracted with ethyl acetate twice. The combined organic phase was washed with aqueous sodium bicarbonate and brine, dried over magnesium sulfate and concentrated. The residue was chromatographed on silica gel column (hexane-ethyl acetate, 3:7) to give 1-(3-nitrophenyl)-1H-1,2,4-triazole (2.89 g) as a solid.

NMR (CDCl$_3$, 300 MHz, δ): 7.74 (1H, t, J=8 Hz), 8.10 (1H, dt, J=8 Hz, 2 Hz), 8.18 (1H, s), 8.28 (1H, dt, J=8 Hz, 2 Hz)., 8.60 (1H, t, J=2 Hz), 8.70 (1H, s)

Preparation 60

To a solution of morpholine (5.0 ml) in dichloromethane (50 ml) was added 3-nitrobenzoyl chloride (5.05 g). The mixture was stirred at room temperature for 15 minutes, then poured into a mixture of ethyl acetate and water. The organic phase was separated, washed with dilute hydrochloric acid, sodium bicarbonate and brine, dried over magnesium sulfate and concentrated to give 4-(3-nitrophenylcarbonyl)morpholine (6.46 g).

NMR (CDCl$_3$, 300 MHz, δ): 3.3–4.0 (8H, m), 7.65 (1H, t, J=8 Hz), 7.78 (1H, dt, J=8 Hz, 2 Hz), 8.30 (2H, m)

Preparation 61

To a mixture of 4-bromopyridine hydrochloride (5.25 g) and tetrakis(triphenylphosphine)palladium(0) (0.93 g) in toluene (50 ml) was added 3M aqueous solution of sodium bicarbonate (27 ml) and a solution of dihydroxy(3-nitrophenyl)borane (5.0 g) in methanol (12 ml). The mixture was stirred at 80° C. for 1 hour and cooled. Then the mixture was poured into aqueous sodium bicarbonate and extracted with ethyl acetate twice. The combined organic phase was washed with aqueous sodium bicarbonate and brine, dried over magnesium sulfate and concentrated. The residue was chromatographed on silica gel (1%–2% methanol in chloroform) to give 4-(3-nitrophenyl)pyridine (3.46 g).

NMR (CDCl$_3$, 300 MHz, δ): 7.57 (2H, dd, J=2 Hz, 5 Hz), 7.70 (1H, t, J=8 Hz), 7.98 (1H, dt, J=8 Hz, 2 Hz), 8.32 (1H, m), 8.51 (1H, t, J=2 Hz), 8.76 (2H, d, J=5 Hz)

Preparation 62

To a mixture of 2-bromopyridine (1.91 ml) and tetrakis(triphenylphosphine)palladium(0) (0.46 g) in 1,2-dimethoxyethane (40 ml) was added 2M aqueous solution of sodium bicarbonate (20 ml) and a solution of dihydroxy(3-nitrophenyl)borane (3.67 g) in methanol (10 ml). The mixture was stirred at 80° C. for 2.5 hours and cooled. Then the mixture was poured into aqueous sodium bicarbonate and extracted with ethyl acetate twice. The combined organic phase was washed with aqueous sodium bicarbonate and brine, dried over magnesium sulfate and concentrated. The residue was chromatographed on silica gel (hexane-ethyl acetate (3:1)) to give 2-(3-nitrophenyl)pyridine (1.35 g).

NMR (CDCl$_3$, 300 MHz, δ): 7.32 (1H, m), 7.65 (1H, t, J=8 Hz), 7.83 (2H, m), 8.27 (1H, m), 8.38 (1H, d, J=8 Hz), 8.73 (1H, m), 8.87 (1H, t, J=2 Hz)

Preparation 63

To a mixture of 3-bromopyridine (2.6 ml) and tetrakis(triphenylphosphine)palladium(0) (0.93 g) in toluene (50 ml) was added 2M aqueous solution of sodium bicarbonate (27 ml) and a solution of dihydroxy(3-nitrophenyl)borane (5.0 g) in methanol (12 ml). The mixture was stirred at 80° C. for 6 hours and cooled. Then the mixture was poured into aqueous sodium bicarbonate and extracted with ethyl acetate twice. The combined organic phase was washed with aqueous sodium bicarbonate and brine, dried over magnesium sulfate and concentrated. The residue was chromatographed on silica gel (hexane-ethyl acetate (3:7)) to give 3-(3-nitrophenyl)pyridine (3.57 g).

NMR (CDCl$_3$, 300 MHz, δ): 7.46 (1H, dd, J=5 Hz, 8 Hz), 7.69 (1H, t, J=8 Hz), 7.9–8.0 (2H, m), 8.28 (1H, dt, J=8 Hz, 2 Hz), 8.47 (1H, t, J=2 Hz), 8.70 (1H, dd, J=2 Hz, 5 Hz), 8.90 (1H, d, J=2 Hz)

Preparation 64

The following compounds were obtained according to a similar manner to that of Preparation 41, 61, 62 or 63.

(1) 2-(3-Nitrophenyl)thiophene

NMR (CDCl$_3$, 300 MHz, δ): 7.13 (1H, dd, J=4 Hz, 5 Hz), 7.39 (1H, dd, J=1 Hz, 5 Hz), 7.45 (1H, dd, J=1 Hz, 4 Hz), 7.55 (1H, t, J=8 Hz), 7.91 (1H, m), 8.12 (1H, dt, J=8 Hz, 2 Hz), 8.47 (1H, t, J=2 Hz)

(2) 2-Chloro-5-(3-nitrophenyl)thiophene

NMR (CDCl$_3$, 300 MHz, δ): 6.97 (1H, d, J=4 Hz), 7.21 (1H, d, J=4 Hz), 7.57 (1H, t, J=8 Hz), 7.80 (1H, dt, J=8 Hz, 2 Hz), 8.14 (1H, dt, J=8 Hz, 2 Hz), 8.37 (1H, t, J=2 Hz)

(3) 3-(3-Nitrophenyl)thiophene

NMR (CDCl$_3$, 300 MHz, δ): 7.45–7.5 (2H, m), 7.58 (1H, m), 7.92 (1H, dt, J=8 Hz, 2 Hz), 8.14 (1H, dt, J=8 Hz, 2 Hz), 8.45 (1H, t, J=2 Hz)

(4) 1-(2-Fluorophenyl)-3-nitrobenzene

NMR (CDCl$_3$, 300 MHz, δ): 7.15–7.3 (2H, m), 7.35–7.55 (2H, m), 7.63 (1H, t, J=8 Hz), 7.90 (1H, d, J=8 Hz), 8.25 (1H, d, J=8 Hz), 8.43 (1H, s)

(5) Methyl 4-(3-nitrophenyl)benzoate

NMR (CDCl$_3$, 300 MHz, δ): 3.98 (3H, s), 7.6–7.75 (3H, m), 7.97 (1H, dt, J=8 Hz, 2 Hz), 8.18 (2H, dt, J=8 Hz, 2 Hz), 8.27 (1H, dt, J=8 Hz, 2 Hz), 8.49 (1H, t, J=2 Hz)

(6) 4-(3-Nitrophenyl)acetanilide

NMR (DMSO-d$_6$, 300 MHz, δ): 2.09 (3H, s), 7.8–7.9 (5H, m), 8.1–8.2 (2H, m), 8.40 (1H, s)

(7) 3-(6-Methoxy-2-naphthyl)aniline

NMR (DMSO-d$_6$, δ): 3.89 (3H, s), 5.16 (2H, s), 6.56 (1H, m), 6.90 (1H, m), 6.96 (1H, m), 7.12 (1H, d, J=8 Hz), 7.18 (1H, dd, J=8 Hz, 2 Hz), 7.33 (1H, m), 7.69 (1H, m), 7.88 (2H, m), 8.00 (1H, m)

(8) 3-(3-Quinolyl)aniline

NMR (CDCl$_3$, δ): 3.85 (2H, s), 6.75 (1H, dd, J=8 Hz, 2 Hz), 7.00 (1H, m), 7.10 (1H, d, J=8 Hz), 7.30 (1H, dd, J=8 Hz, 8 Hz), 7.55 (1H, dd, J=8 Hz, 8 Hz), 7.72 (1H, dd, J=8 Hz, 8 Hz), 7.85 (1H, d, J=8 Hz), 8.12 (1H, d, J=8 Hz), 8.25 (1H, d, J=2 Hz), 9.15 (1H, s)

(9) 3-(3-Cyclopentyloxy-4-methoxyphenyl)aniline

NMR (CDCl$_3$, δ): 1.60 (2H, m), 1.8–2.0 (8H, m), 3.71 (2H, s), 3.87 (3H, s), 4.84 (1H, m), 6.64 (1H, m), 6.85 (1H, m), 6.92 (2H, m), 7.09 (2H, m), 7.20 (1H, m)

(10) 3-(3-Methoxycarbonylphenyl)aniline

NMR (CDCl$_3$, δ): 3.92 (3H, s), 6.68 (1H, dd, J=8 Hz, 3 Hz), 6.93 (1H, s), 7.00 (1H, dd, J=8 Hz, 2 Hz), 7.24 (1H, dd, J=8 Hz, 3 Hz), 7.47 (1H, dd, J=8 Hz, 8 Hz), 7.73 (1H, dd, J=8 Hz, 2 Hz), 7.99 (1H, dd, J=8 Hz, 2 Hz), 8.24 (1H, dd, J=2 Hz, 2 Hz)

MASS (m/z): 228 (M+1)

(11) Methyl (E)-3-(3-aminophenyl)cinnamate

NMR (CDCl$_3$, δ): 3.77 (2H, br s), 3.81 (3H, s), 6.50 (1H, d, J=15 Hz), 6.70 (1H, dd, J=8 Hz, 2 Hz), 6.90 (1H, d, J=2 Hz), 6.98 (1H, d, J=8 Hz), 7.24 (1H, dd, J=8 Hz, 8 Hz), 7.43 (1H, dd, J=8 Hz, 8 Hz), 7.50 (1H, m), 7.58 (1H, m), 7.70 (1H, m), 7.75 (1H, d, J=15 Hz)

(12) 3-(4-Isoquinolyl)aniline

NMR (CDCl$_3$, δ): 3.80 (2H, s), 6.80 (2H, m), 6.90 (1H, d, J=8 Hz), 7.30 (1H, dd, J=8 Hz, 8 Hz), 7.63 (2H, m), 8.00 (2H, m), 8.78 (1H, s), 9.23 (1H, s)

(13) 3-(3-Acetamidophenyl)aniline

NMR (DMSO-d$_6$, δ): 2.05 (3H, s), 5.17 (2H, s), 6.54 (1H, m), 6.70 (1H, m), 6.80 (1H, m), 7.10 (1H, dd, J=8 Hz, 8 Hz), 7.20 (1H, m), 7.32 (1H, dd, J=8 Hz, 8 Hz), 7.50 (1H, m), 7.82 (1H, m)

MASS (m/z): 227 (M+1)

Preparation 65

A mixture of 4-(3-nitrophenyl)acetanilide (4.25 g) and 10% palladium on carbon (0.8 g) in ethanol (50 ml) and 1,4-dioxane (50 ml) was stirred under hydrogen (3 atm) at room temperature for 3 hours. The catalyst was removed by filtration and the solvent was evaporated. The resulting solid was collected and washed with isopropyl ether to give 4-(3-aminophenyl)acetanilide (3.40 g).

NMR (DMSO-d$_6$, 300 MHz, δ): 2.05 (3H, s), 5.11 (2H, s), 6.52 (1H, d, J=8 Hz), 6.74 (1H, d, J=8 Hz), 6.81 (1H, s), 7.07 (1H, t, J=8 Hz), 7.49 (2H, d, J=8 Hz), 7.63 (2H, d, J=8 Hz)

Preparation 66

A mixture of methyl 4-(3-nitrophenyl)benzoate (8.37 g), iron powder (7.5 g) and hydrochloric acid (35%, 22 ml) in methanol (60 ml) was stirred under reflux for 3 hours. Then the mixture was poured into aqueous sodium bicarbonate and extracted with ethyl acetate twice. The combined organic phase was washed with aqueous sodium bicarbonate and brine, dried over magnesium sulfate and concentrated. The resultant solid was collected and washed with isopropyl ether to give methyl 4-(3-aminophenyl)benzoate (5.33 g).

NMR (DMSO-d$_6$, 300 MHz, δ): 3.88 (3H, s), 5.22 (2H, s), 6.62 (1H, dt, J=8 Hz, 2 Hz), 6.84 (1H, dt, J=8 Hz, 2 Hz), 6.90 (1H, t, J=2 Hz), 7.13 (1H, t, J=8 Hz), 7.70 (2H, dt, J=8 Hz, 2 Hz), 8.01 (2H, dt, J=8 Hz, 2 Hz)

Preparation 67

The following compounds were obtained according to a similar manner to that of Preparation 3, 21, 23, 44, 45, 65 or 66.

(1) 4-(3-Aminophenylcarbonyl)morpholine

NMR (DMSO-d$_6$, 300 MHz, δ): 3.2–3.7 (8H, m), 5.23 (2H, s), 6.47 (1H, dt, J=8 Hz, 2 Hz), 6.54 (1H, t, J=2 Hz), 6.60 (1H, dt, J=8 Hz, 2 Hz), 7.06 (1H, t, J=8 Hz)

(2) 3-(2-Fluorophenyl)aniline

NMR (DMSO-d$_6$, 300 MHz, δ): 5.18 (2H, s), 6.5–6.7 (2H, m), 6.72 (1H, m), 7.10 (1H, t, J=8 Hz), 7.2–7.5 (4H, m)

(3) 1-(3-Aminophenyl)-1H-1,2,4-triazole

NMR (DMSO-d$_6$, δ): 5.48 (2H, s), 6.59 (1H, m), 6.93 (1H, m), 7.03 (1H, t, J=2 Hz), 7.17 (1H, t, J=8 Hz), 8.18 (1H, s), 9.14 (1H, s)

(4) 3-(3-Aminophenyl)thiophene

NMR (DMSO-d$_6$ 300 MHz, δ): 5.09 (2H, s), 6.50 (1H, dd, J=2 Hz, 8 Hz), 6.8–6.9 (2H, m), 7.05 (1H, t, J=8 Hz), 7.40 (1H, dd, J=2 Hz, 5 Hz), 7.60 (1H, m), 7.65 (1H, t, J=2 Hz)

(5) 2-(3-Aminophenyl)-5-chlorothiophene

NMR (DMSO-d$_6$, 300 MHz, δ): 5.24 (2H, s), 6.53 (1H, dd, J=2 Hz, 5 Hz), 6.7–6.75 (2H, m), 7.0–7.15 (2H, m), 7.21 (1H, d, J=4 Hz)

(6) 2-(3-Aminophenyl)thiophene

NMR (DMSO-d$_6$, 300 MHz, δ): 5.20 (2H, s), 6.50 (1H, m), 6.75–6.85 (2H, m), 7.0–7.15 (2H, m), 7.33 (1H, dd, J=1 Hz, 4 Hz), 7.47 (1H, dd, J=1 Hz, 5 Hz)

(7) 4-(3-Aminophenyl)pyridine

NMR (DMSO-d$_6$, 300 MHz, δ): 5.27 (2H, s), 6.67 (1H, dd, J=2 Hz, 8 Hz), 6.85–6.95 (2H, m), 7.15. (1H, t, J=8 Hz), 7.57 (2H, dd, J=2 Hz, 5 Hz), 8.59 (2H, d, J=5 Hz)

(8) 3-(3-Aminophenyl)pyridine

NMR (DMSO-d$_6$, 300 MHz, δ): 5.23 (2H, s), 6.62 (1H, m), 6.8–6.9 (2H, m), 7.13 (1H, t, J=8 Hz), 7.45 (1H, dd, J=5 Hz, 8 Hz), 7.94 (1H, dt, J=8 Hz, 2 Hz), 8.53 (1H, d, J=5 Hz), 8.78 (1H, d, J=2 Hz)

(9) 2-(3-Aminophenyl)pyridine

NMR (DMSO-d$_6$, 300 MHz, δ): 5.19 (2H, s), 6.62 (1H, m), 7.05–7.2 (2H, m), 7.25–7.35 (2H, m), 7.75–7.85 (2H, m), 8.61 (1H, m)

(10) 3-(Benzoylamino)aniline

NMR (DMSO-d$_6$, 300 MHz, δ): 5.07 (2H, s), 6.34 (1H, d, J=8 Hz), 6.86 (1H, d, J=8 Hz), 6.97 (1H, t, J=8 Hz), 7.14 (1H, s), 7.5–7.6 (3H, m), 7.95 (2H, d, J=8 Hz), 9.97 (1H, s)

(11) Methyl 1-(3-aminophenyl)indole-5-carboxylate

NMR (CDCl$_3$, δ): 3.86 (2H, s), 3.92 (3H, s), 6.70 (2H, m), 6.77 (1H, m), 6.85 (1H, d, J=8 Hz), 7.27 (1H, d, J=8 Hz), 7.35 (1H, d, J=3 Hz), 7.57 (1H, d, J=8 Hz), 7.90 (1H, d, J=8 Hz), 8.42 (1H, s)

(12) 3-(3-Aminophenylcarbamoyl)quinoline

NMR (DMSO-d$_6$, 300 MHz, δ): 5.14 (2H, s), 6.37 (1H, d, J=8 Hz), 6.9–7.05 (2H, m), 7.15 (1H, s), 7.72 (1H, t, J=8 Hz), 7.90 (1H, t, J=8 Hz), 8.1–8.2 (2H, m), 8.92 (1H, s), 9.33 (1H, d, J=2 Hz)

(13) 3-[(E)-2-(3,5-Dichlorophenyl)vinyl]aniline

NMR (DMSO-d$_6$, 300 MHz, δ): 5.13 (2H, s), 6.53 (1H, d, J=8 Hz), 6.78 (2H, m), 7.0–7.1 (2H, m), 7.31 (1H, d, J=16 Hz), 7.46 (1H, s), 7.69 (2H, s)

(14) 3-Amino-N-(3,5-dichlorophenyl)benzamide

NMR (DMSO-d$_6$, 300 MHz, δ): 5.37 (2H, s), 7.0–7.1 (2H, m), 7.17 (1H, t, J=8 Hz), 7.30 (1H, s), 7.89 (1H, d, J=2 Hz)

(15) 3-Amino-N-methyl-N-(3,5-dichlorophenyl)benzamide

NMR (DMSO-d$_6$, 300 MHz, δ): 3.32 (3H, s), 5.20 (2H, s), 6.33 (1H, d, J=8 Hz), 6.51 (1H, dd, J=2 Hz, 8 Hz), 6.59 (1H, s), 6.90 (1H, t, J=8 Hz), 7.29 (2H, s), 7.40 (1H, s)

Preparation 68

A mixture of 2-chloro-3-nitropyridine (3.20 g), methyl 3,5-diaminobenzoate (3.20 g) and potassium carbonate (4.0 g) in 1,4-dioxane (60 ml) was stirred under reflux for 4 hours. After cooling, insoluble materials were removed by filtration and the filtrate was concentrated. The residue was chromatographed on silica gel column (5% methanol in chloroform) to give 2-(3-amino-5-methoxycarbonylphenylamino)-3-nitropyridine (1.12 g).

NMR (DMSO-d$_6$, 300 MHz, δ): 3.81 (3H, s), 5.48 (2H, s), 6.95–7.0 (2H, m), 7.12 (1H, m), 7.39 (1H, s), 8.5–8.55 (2H, m), 9.86 (1H, s)

Preparation 69

A mixture of 2-chloro-3-nitropyridine (1.15 g), 2-(3-aminophenyl)pyridine (1.12 g) and potassium carbonate (1.36 g) in diglyme (15 ml) was stirred at 150° C. for 3 hours. After cooling, insoluble materials were removed by filtration and the filtrate was concentrated. The residue was chromatographed on silica gel column (hexane-ethyl acetate, 1:1) to give 3-nitro-2-[3-(2-pyridyl)phenylamino]pyridine (1.68 g)

NMR (CDCl$_3$, 300 MHz, δ): 6.85 (1H, dd, J=5 Hz, 8 Hz), 7.2–7.3 (1H, m), 7.50 (1H, t, J=8 Hz), 7.75–7.85 (4H, m), 8.23 (2H, m), 8.5–8.6 (1H, m), 8.70 (1H, d, J=5 Hz)

Preparation 70

The following compounds were obtained according to a similar manner to that of Preparation 1, 5, 27, 28, 47, 48, 49, 68 or 69.

(1) 2-[3,5-Bis(methoxycarbonyl)phenylamino]-3-nitropyridine

NMR (DMSO-d$_6$, 300 MHz, δ): 3.92 (6H, s), 7.09 (1H, dd, J=5 Hz, 8 Hz), 8.22 (1H, m), 8.5–8.6 (4H, m)

(2) 2-[3-(Morpholinocarbonyl)phenylamino]-3-nitropyridine

NMR (CDCl$_3$, 300 MHz, δ): 3.5–3.9 (8H, m), 6.90 (1H, dd, J=5 Hz, 8 Hz), 7.10 (1H, dt, J=8 Hz, 2 Hz), 7.44 (1H, t, J=8 Hz), 7.68 (1H, dt, J=8 Hz, 2 Hz), 7.89 (1H, t, J=2 Hz), 8.49 (1H, dd, J=2 Hz, 5 Hz), 8.56 (1H, dd, J=2 Hz, 8 Hz)

(3) 2-[3-(4-Acetylaminophenyl)phenylamino]-3-nitropyridine

NMR (CDCl$_3$, 300 MHz, δ): 2.21 (3H, s), 6.86 (1H, dd, J=5 Hz, 8 Hz), 7.3–7.5 (3H, m), 7.55–7.65 (5H, m), 7.84 (1H, s), 8.45–8.6 (2H, m)

(4) 2-[3-(4-Methoxycarbonylphenyl)phenylamino]-3-nitropyridine

NMR (CDCl$_3$, 300 MHz, δ): 3.96 (3H, s), 6.87 (1H, dd, J=5 Hz, 8 Hz), 7.4–7.55 (2H, m), 7.70 (3H, m), 7.92 (1H, t, J=2 Hz), 8.13 (2H, dt, J=8 Hz, 2 Hz), 8.5–8.6 (2H, m)

(5) 2-[3-(2-Fluorophenyl)phenylamino]-3-nitropyridine

NMR (CDCl$_3$, 300 MHz, δ): 6.86 (1H, dd, J=5 Hz, 8 Hz), 7.1–7.5 (6H, m), 7.70 (1H, d, J=8 Hz), 7.82 (1H, d, J=2 Hz), 7.5–7.6 (2H, m)

(6) 1-[3-[(3-Nitropyridin-2-yl)amino]phenyl]-1H-1,2,4-triazole

NMR (CDCl$_3$, 300 MHz, δ): 6.93 (1H, dd, J=5 Hz, 8 Hz), 7.4–7.55 (2H, m), 7.61 (1H, dt, J=8 Hz, 2 Hz), 8.13 (1H, s), 8.30 (1H, t, J=2 Hz), 8.55–8.65 (3H, m)

(7) 3-Nitro-2-[3-(3-thienyl)phenylamino]pyridine

NMR (CDCl$_3$, 300 MHz, δ): 6.86 (1H, dd, J=5 Hz, 8 Hz), 7.5–7.55 (5H, m), 7.61 (1H, m), 7.88 (1H, s), 8.5–8.6 (2H, m)

(8) 2-[3-(5-Chloro-2-thienyl)phenylamino]-3-nitropyridine

NMR (CDCl$_3$, 300 MHz, δ): 6.85–6.95 (2H, m), 7.12 (1H, d, J=4 Hz), 7.32 (1H, dt, J=8 Hz, 2 Hz), 7.40 (1H, t, J=8 Hz), 7.58 (1H, m), 7.87 (1H, t, J=2 Hz), 8.5–8.6 (2H, m)

(9) 3-Nitro-2-[3-(2-thienyl)phenylamino]pyridine

NMR (CDCl$_3$, 300 MHz, δ): 6.86 (1H, dd, J=5 Hz, 8 Hz), 7.10 (1H, dd, J=4 Hz, 5 Hz), 7.3–7.45 (4H, m), 7.60 (1H, m), 7.90 (1H, t, J=2 Hz), 8.5–8.6 (2H, m)

(10) 3-Nitro-2-[3-(4-pyridyl)phenylamino]pyridine

NMR (CDCl$_3$, 300 MHz, δ): 6.89 (1H, dd, J=5 Hz, 8 Hz), 7.4–7.6 (4H, m), 7.72 (1H, dt, J=8 Hz, 2 Hz), 7.99 (1H, t, J=2 Hz), 8.5–8.6 (2H, m), 8.69 (2H, d, J=5 Hz)

(11) 3-Nitro-2-[3-(3-pyridyl)phenylamino]pyridine

NMR (CDCl$_3$, 300 MHz, δ): 6.89 (1H, dd, J=5 Hz, 8 Hz), 7.35–7.45 (2H, m), 7.52 (1H, t, J=8 Hz), 7.68 (1H, dt, J=8 Hz, 2 Hz), 7.9–8.0 (2H, m), 8.5–8.6 (2H, m), 8.62 (1H, dd, J=2 Hz, 5 Hz), 8.90 (1H, d, J=2 Hz)

(12) 2-[3-(Benzoylamino)phenylamino]-3-nitropyridine

NMR (DMSO-d$_6$, 300 MHz, δ): 7.01 (1H, dd, J=5 Hz, 8 Hz), 7.35 (1H, t, J=8 Hz), 7.44 (1H, d, J=8 Hz), 7.5–7.65

(4H, m), 7.98 (2H, d, J=8 Hz), 8.11 (1H, s), 8.5–8.6 (2H, m), 9.99 (1H, s), 10.31 (1H, s)

(13) 2-[3-(6-Methoxy-2-naphthyl)phenylamino]-3-nitropyridine

NMR (DMSO-d$_6$, δ): 3.90 (3H, s), 7.01 (1H, m), 7.20 (1H, m), 7.37 (1H, m), 7.50 (1H, dd, J=8 Hz, 8 Hz), 7.57 (1H, m), 7.73 (1H, m), 7.84 (1H, m), 7.93 (2H, m), 8.04 (1H, m), 8.18 (1H, s), 8.56 (2H, m)

(14) 3-Nitro-2-(3-succinimidophenylamino)pyridine

NMR (CDCl$_3$, 300 MHz, δ): 8.56–8.47 (2H, m), 7.79 (1H, s), 7.67 (1H, d, J=9 Hz), 7.48 (1H, t, J=9 Hz), 7.10 (1H, d, J=9 Hz), 6.91–6.84 (1H, m), 2.91 (4H, s)

(15) 2-[3-(5-Methoxycarbonylindol-1-yl)phenylamino]-3-nitropyridine

NMR (CDCl$_3$, δ): 3.94 (3H, s), 6.78 (dH, d, J=3 Hz), 6.91 (1H, dd, J=8 Hz, 5 Hz), 7.28 (1H, m), 7.45 (1H, d, J=3 Hz), 7.52 (2H, m), 7.72 (1H, d, J=8 Hz), 7.95 (1H, d, J=8 Hz), 8.16 (1H, m), 8.45 (1H, s), 8.55 (2H, m)

(16) 2-[3-(3-Quinolyl)phenylamino]-3-nitropyridine

NMR (CDCl$_3$, δ): 6.89 (1H, dd, J=8 Hz, 3 Hz), 7.55 (3H, m), 7.70 (2H, m), 7.92 (1H, d, J=8 Hz), 8.07 (1H, s), 8.14 (1H, d, J=8 Hz), 8.34 (1H, d, J=3 Hz), 8.52 (mH, m), 8.57 (1H, m), 9.21 (1H, d, J=3 Hz)

(17) 2-[3-(3-Cyclopentyloxy-4-methoxyphenyl)phenylamino]-3-nitropyridine

NMR (DMSO-d$_6$, δ): 1.59 (2H, m), 1.74 (4H, m), 1.90 (2H, m), 3.79 (3H, s), 4.92 (1H, m), 7.00 (1H, dd, J=8 Hz, 5 Hz), 7.04 (1H, d, J=8 Hz), 7.20 (2H, m), 7.41 (2H, m), 7.63 (1H, m), 7.88 (1H, s), 8.53 (2H, m)

(18) 2-[3-(3-Methoxycarbonylphen yl)phenylamino]-3-nitropyridine mp: 179–181° C.

NMR (CDCl$_3$, δ): 3.95 (3H, 5), 6.87 (1H, dd, J=8 Hz, 5 Hz), 7.50 (3H, m), 7.70 (1H, m), 7.82 (1H, m), 7.89 (1H, m), 8.04 (1H, m), 8.30 (1H, m), 8.52 (2H, m)

(19) 2-[3-[(E)-3-Methoxycarbonylvinylphenyl]phenylamino]-3-nitropyridine

NMR (DMSO-d$_6$, δ): 3.74 (3H, s), 6.80 (1H, d, J=16 Hz), 7.03 (1H, dd, J=8 Hz, 5 Hz), 7.52 (3H, m), 7.76 (4H, m), 7.98 (1H, m), 8.07 (1H, m), 8.55 (2H, m)

(20) 2-[3-(4-Isoquinolyl)phenylamino]-3-nitropyridine

NMR (DSMO-d$_6$, δ): 7.01 (1H, m), 7.33 (1H, dd, J=8 Hz, 2 Hz), 7.57 (1H, dd, J=8 Hz, 8 Hz), 7.7–7.9 (4H, m), 8.03 (1H, d, J=8 Hz), 8.23 (1H, d, J=8 Hz), 8.54 (3H, m), 9.36 (1H, s)

(21) 2-[3-(3-Acetamidophenyl) phenylamino]-3-nitropyridine

NMR (CDCl$_3$, δ): 2.20 (3H, s), 6.83 (1H, dd, J=8 Hz, 5 Hz), 7.3–7.4 (4H, m), 7.45 (1H, dd, J=8 Hz, 8 Hz), 7.52 (1H, m), 7.67 (1H, m), 7.75 (1H, s), 7.83 (1H, m), 8.52 (2H, m)

(22) 3-[3-[(3-Nitropyridin-2-yl)amino]phenylcarbamoyl]-quinoline

NMR (DMSO-d$_6$, 300 MHz, δ): 7.02 (1H, dd, J=5 Hz, 8 Hz), 7.35–7.5 (2H, m), 7.62 (1H, d, J=8 Hz), 7.74 (1H, t, J=8 Hz), 7.91 (1H, t, J=8 Hz), 8.1–8.2 (3H, m), 8.55–8.6 (2H, m), 8.99 (1H, s), 9.38 (1H, d, J=2 Hz)

(23) 2-[3-[(E)-2-(3,5-Dichlorophenyl)vinyl]phenylamino]-3-nitropyridine

NMR (CDCl$_3$, 300 MHz, δ): 6.68 (1H, dd, J=5 Hz, 8 Hz) 6.99 (1H, d, J=16 Hz), 7.13 (1H, d, J=16 Hz), 7.27 (1H, m), 7.32 (1H, d, J=8 Hz), 7.35–7.45 (3H, m), 7.59 (1H, d, J=8 Hz), 7.83 (1H, s), 8.5–8.6 (2H, m)

(24) 2-[3-(3,5-Dichlorophenylcarbamoyl)phenylamino-3-nitropyridine

NMR (DMSO-d$_6$, 300 MHz, δ): 7.04 (1H, dd, J=5 Hz, 8 Hz), 7.23 (1H, s), 7.55 (1H, t, J=8 Hz), 7.72 (1H, d, J=8 Hz), 7.9–8.0 (3H, m), 8.20 (1H, m), 8.5–8.6 (2H, m)

(25) 2-[3-[N-Methyl-N-(3,5-dichlorophenyl)carbamoyl]phenylamino]-3-nirtopyridine NMR (CDCl$_3$, 300 MHz, δ): 3.49 (3H, s), 6.88 (1H, dd, J=5 Hz, 8 Hz), 7.0–7.2 (4H, m), 7.28 (1H, t, J=8 Hz), 7.56 (1H, dd, J=2 Hz, 8 Hz), 7.94 (1H, s), 7.45–7.55 (2H, m)

(26) 2-(3-Carboxyphenylamino)-3-nitropyridine

NMR (DMSO-d$_6$, δ): 7.03 (1H, dd, J=8 Hz, 5 Hz), 7.50 (1H, dd, J=8 Hz, 8 Hz), 7.71 (1H, m), 7.88 (1H, m), 8.25 (1H, m), 8.55 (2H, m)

(27) 6-Phenylthio-2-[3-(3-phenylureidophenyl]-3-nitropyridine

NMR (DMSO-d$_6$, δ): 6.60 (1H, d, J=8 Hz), 7.00 (3H, m), 7.10 (1H, m), 7.29 (2H, m), 7.4–7.7 (8H, m), 8.38 (1H, d, J=8 Hz), 8.67 (2H, m)

Preparation 71

A mixture of 2-(3-acetylamino-5-methoxycarbonylphenylamino)-3-nitropyridine (1.20 g) and 10% palladium on carbon (0.25 g) in methanol (15 ml) and 1,4-dioxane (15 ml) was stirred under hydrogen (3 atm) at room temperature for 3 hours. The catalyst was removed by filtration and the solvent was evaporated. The resulting solid was collected and washed with isopropyl ether to give 2-(3-acetylamino-5-methoxycarbonylphenylamino)-3-aminopyridine (1.10 g).

NMR (DMSO-d$_6$, 300 MHz, δ): 2.05 (3H, s), 3.82 (3H, s), 5.12 (2H, s), 6.68 (1H, dd, J=5 Hz, 8 Hz), 6.92 (1H, d, J=8 Hz), 7.52 (1H, d, J=5 Hz), 7.78 (1H, t, J=2 Hz), 7.90 (1H, m), 8.00 (1H, s), 8.21 (1H, s)

Preparation 72

The following compounds were obtained according to a similar manner to that of Preparation 3, 31, 33, 52, 53, 54 or 71.

(1) 2-[3-(4-Acetylaminophenyl)phenylamino]-3-aminopyridine

NMR (DMSO-d$_6$, 300 MHs, δ): 2.07 (3H, s), 5.09 (2H, s), 6.63 (1H, dd, J=5 Hz, 8 Hz), 6.91 (1H, dd, J=2 Hz, 8 Hz), 7.10 (1H, d, J=8 Hz), 7.29 (1H, t, J=8 Hz), 7.5–7.6 (3H, m), 7.65–7.7 (3H, m), 7.82 (2H, d, J=8 Hz)

(2) 3-Amino-2-[3-(2-pyridyl)phenylamino]pyridine

NMR (DMSO-d$_6$, 300 MHz, δ): 5.12 (2H, s), 6.64 (1H, m), 6.92 (1H, d, J=8 Hz), 7.3–7.4 (2H, m), 7.53 (2H, d, J=8 Hz), 7.85–7.95 (4H, m), 8.27 (1H, s), 8.67 (1H, d, J=5 Hz)

(3) 3-Amino-2-[3-(3-pyridyl)phenylamino]pyridine

NMR (DMSO-d$_6$, 300 MHz, δ): 5.09 (2H, s), 6.64 (1H, dd, J=5 Hz, 8 Hz), 6.93 (1H, dd, J=2 Hz, 8 Hz), 7.18 (1H, dd, J=2 Hz, 8 Hz), 7.35 (1H, t, J=8 Hz), 7.45–7.55 (2H, m), 7.72 (1H, dd, J=2 Hz, 8 Hz), 7.85–7.95 (2H, m), 8.01 (1H, dt, J=8 Hz, 2 Hz), 8.57 (1H, dd, J=2 Hz, 5 Hz), 8.83 (1H, d, J=2 Hz)

(4) 3-Amino-2-[3-(4-pyridyl)phenylamino]pyridine

NMR (DMSO-d$_6$, 300 MHz, δ): 5.10 (2H, s), 6.67 (1H, dd, J=5 Hz, 8 Hz), 6.93 (1H, dd, J=2 Hz, 8 Hz), 7.25 (1H, d, J=8 Hz), 7.38 (1H, t, J=8 Hz), 7.53 (1H, dd, J=2 Hz, 5 Hz), 7.64 (2H, d, J=5 Hz), 7.78 (1H, d, J=8 Hz), 7.91 (1H, s), 8.02 (1H, s), 8.63 (2H, d, J=5 Hz)

(5) 3-Amino-2-[3-(2-thienyl)phenylamino]pyridine

NMR (DMSO-d$_6$, 300 MHz, δ): 5.10 (2H, s), 6.66 (1H, dd, J=5 Hz, 8 Hz), 6.93 (1H, dd, J=2 Hz, 8 Hz), 7.1–7.2 (2H, m), 7.27 (1H, t, J=8 Hz), 7.42 (1H, dd, J=2 Hz, 5 Hz), 7.5–7.55 (2H, m), 7.66 (1H, d, J=8 Hz), 7.86 (1H, s), 7.91 (1H, t, J=2 Hz)

(6) 3-Amino-2-[3-(5-chloro-2-thienyl)phenylamino]pyridine

NMR (DMSO-d$_6$, 300 MHz, δ): 5.10 (2H, s), 6.67 (1H, dd, J=5 Hz, 8 Hz), 6.93 (1H, dd, J=2 Hz, 8 Hz), 7.1–7.2 (2H, m), 7.25–7.35 (2H, m), 7.54 (1H, dd, J=2 Hz, 5 Hz), 7.65 (1H, dd, J=2 Hz, 8 Hz), 7.89 (1H, d, J=2 Hz)

(7) 3-Amino-2-[3-(3-thienyl)phenylamino]pyridine

NMR (DMSO-$d_6$, 300 MHz, δ): 5.08 (2H, s), 6.63 (1H, dd, J=5 Hz, 8 Hz), 6.92 (1H, dd, J=2 Hz, 8 Hz), 7.18 (1H, d, J=8 Hz), 7.27 (1H, t, J=8 Hz), 7.47 (1H, dd, J=2 Hz, 5 Hz), 7.53 (1H, dd, J=2 Hz, 5 Hz), 7.63 (2H, m), 7.73 (1H, m), 7.79 (1H, s), 7.90 (1H, t, J=2 Hz)

(8) 1-[3-[(3-Aminopyridin-2-yl)amino]phenyl]-1H-1,2,4-triazole

NMR (DMSO-$d_6$, 300 MHz, δ): 5.13 (2H, s), 6.69 (1H, dd, J=5 Hz, 8 Hz), 6.96 (1H, dd, J=2 Hz, 8 Hz), 7.30 (1H, m), 7.39 (1H, t, J=8 Hz), 7.55 (1H, dd, J=2 Hz, 5 Hz), 7.68 (1H, dt, J=8 Hz, 2 Hz), 8.07 (1H, s), 8.19 (1H, t, J=2 Hz), 8.22 (1H, s), 9.21 (1H, s)

(9) 3-Amino-2-[3-(2-fluorophenyl)phenylamino]pyridine

NMR (DMSO-$d_6$, 300 MHz, δ): 5.10 (2H, s), 6.64 (1H, dd, J=5 Hz, 8 Hz), 6.92 (1H, dd, J=2 Hz, 8 Hz), 7.01 (1H, d, J=8 Hz), 7.25–7.55 (6H, m), 7.72 (1H, dt, J=8 Hz, 2 Hz), 7.80 (1H, d, J=2 Hz), 7.87 (1H, m)

(10) 3-Amino-2-[3-(4-methoxycarbonylphenyl)phenylamino]pyridine

NMR (DMSO-$d_6$, 300 MHz, δ): 3.89 (3H, s), 5.10 (2H, s), 6.67 (1H, dd, J=5 Hz, 8 Hz), 6.94 (1H, dd, J=2 Hz, 8 Hz), 7.20 (1H, d, J=8 Hz), 7.37 (1H, t, J=8 Hz), 7.53 (1H, dd, J=2 Hz, 5 Hz), 7.79 (3H, m), 7.91 (1H, s), 7.98 (1H, t, J=2 Hz), 8.07 (2H, d, J=8 Hz)

(11) 3-Amino-2-[3-(morpholinocarbonyl)phenylamino]pyridine

NMR (DMSO-$d_6$, 300 MHz, δ): 3.3–3.7 (8H, m), 5.09 (2H, s), 6.65 (.1H, dd, J=5 Hz, 8 Hz), 6.86 (1H, dt, J=8 Hz, 2 Hz), 6.92 (1H, dd, J=2 Hz, 8 Hz), 7.29 (1H, t, J=8 Hz), 7.51 (1H, dd, J=2 Hz, 5 Hz), 7.65 (1H, dt, J=8 Hz, 2 Hz), 7.73 (1H, t, J=2 Hz), 7.90 (1H, s)

(12) 3-Amino-2-[3,5-bis(methoxycarbonyl)phenylamino]pyridine

NMR (DMSO-$d_6$, 300 MHz, δ): 3.88 (6H, s), 5.13 (2H, s), 6.71 (1H, dd, J=5 Hz, 8 Hz), 6.97 (1H, d, J=8 Hz), 7.55 (1H, d, J=5 Hz), 7.96 (1H, s), 8.29 (1H, s), 8.52 (1H, s)

(13) 3-Amino-2-[3-methoxycarbonyl-5-(2-naphthoylamino)phenylamino]pyridine

NMR (DMSO-$d_6$, 300 MHz, δ): 3.89 (3H, s), 5.18 (2H, s), 6.70 (1H, dd, J=5, 8 Hz), 6.96 (1H, d, J=8 Hz), 7.57 (1H, m), 7.6–7.7 (2H, m), 7.95–8.15 (7H, m), 8.50 (1H, s), 8.63 (1H, s)

(14) 3-Amino-2-[3-(benzoylamino)phenylamino]pyridine

NMR (DMSO-$d_6$, 300 MHz, δ): 5.11 (2H, s), 6.64 (1H, m), 6.91 (1H, d, J=8 Hz), 7.15–7.3 (2H, m), 7.4–7.65 (5H, m), 7.79 (1H, s), 7.98 (2H, d, J=8 Hz), 8.08 (1H, s)

(15) 2-[3-(6-Methoxy-2-naphthyl)phenylamino]-3-aminopyridine

NMR (CDCl$_3$, δ): 3.45 (2H, br s), 3.93 (3H, s), 6.30 (1H, s), 6.80 (1H, dd, J=8 Hz, 5 Hz), 7.04 (1H, m), 7.16 (2H, m), 7.30 (2H, m), 7.39 (1H, m), 7.54 (1H, m), 7.71 (1H, m), 7.79 (2H, m), 7.87 (1H, m), 7.98 (1H, s)

(16) 2-[3-(5-Methoxycarbonylindol-1-yl)phenylamino]-3-aminopyridine

NMR (CDCl$_3$, δ): 3.48 (2H, br s), 3.93 (3H, s), 6.42 (1H, s), 6.73 (1H, m), 6.81 (1H, m), 7.05 (2H, m), 7.21 (1H, m), 7.42 (1H, m), 7.61 (1H, m), 7.70 (1H, m), 7.88 (1H, m), 7.91 (1H, m), 8.42 (1H, m)

(17) 2-[3-(3-Quinolyl)phenylamino]-3-aminopyridine

NMR (DMSO-$d_6$, δ): 5.12 (2H, s), 6.67 (1H, dd, J=8 Hz, 5 Hz), 6.95 (1H, d, J=8 Hz), 7.34 (1H, d, J=8 Hz), 7.42 (1H, dd, J=8 Hz, 8 Hz), 7.55 (1H, d, J=5 Hz), 7.67 (1H, dd, J=8 Hz, 8 Hz), 7.80 (2H, m), 7.95 (1H, s), 8.09 (2H, m), 8.59 (1H, m), 9.21 (1H, d, J=3 Hz)

(18) 2-[3-(3-Cyclopentyloxy-4-methoxyphenyl)phenylamino]-3-aminopyridine

NMR (CDCl$_3$, δ): 1.62 (2H, m), 1.85 (2H, m), 1.94 (4H, m), 3.45 (2H, m), 3.87 (3H, s), 4.85 (1H, m), 6.27 (1H, s), 6.79 (1H, dd, J=8 Hz, 5 Hz), 6.92 (1H, d, J=8 Hz), 7.03 (1H, d, J=8 Hz), 7.13 (3H, m), 7.23 (1H, m), 7.34 (1H, dd, J=8 Hz, 8 Hz), 7.42 (1H, m), 7.85 (1H, d, J=5 Hz)

(19) 2-[3-(3-Methoxycarbonylphenyl)phenylamino]-3-aminopyridine

NMR (CDCl$_3$, δ): 3.47 (2H, s), 3.94 (3H, s), 6.32 (1H, s), 6.79 (1H, dd, J=8 Hz, 5 Hz), 7.03 (1H, d, J=8 Hz), 7.22 (1H, m), 7.35 (2H, m), 7.49 (2H, m), 7.79 (1H, d, J=8 Hz), 7.85 (1H, m), 8.00 (1H, d, J=8 Hz), 8.28 (1H, s)

(20) 2-[3-[3-[(E)-2-Methoxycarbonylvinyl]phenyl]phenylamino]-3-aminopyridine

NMR (CDCl$_3$, δ): 3.45 (2H, br s), 3.81 (3H, s), 6.30 (1H, s), 6.50 (1H, d, J=16 Hz), 6.81 (1H, m), 7.05 (1H, m), 7.17 (1H, m), 7.30 (1H, m), 7.36 (1H, m), 7.48 (2H, m), 7.60 (1H, m), 7.72 (1H, s), 7.75 (1H, d, J=16 Hz), 7.87 (1H, d, J=3 Hz)

(21) 2-[3-(4-Isoquinolyl)phenylamino]-3-aminopyridine

NMR (CDCl$_3$, δ): 3.50 (2H, br s), 6.40 (1H, s), 6.80 (1H, m), 7.03 (1H, m), 7.10 (1H, m), 7.44 (3H, m), 7.66 (2H, m), 7.85 (1H, m), 8.05 (2H, m), 8.52 (1H, s), 9.22 (1H, s)

(22) 2-[3-(3-Acetamidophenyl)phenylamino]-3-aminopyridine

NMR (CDCl$_3$, δ): 2.13 (3H, s), 3.50 (2H, br s), 6.33 (1H, s), 6.77 (1H, dd, J=8 Hz, 5 Hz), 7.00 (1H, d, J=8 Hz), 7.12 (1H, dd, J=8 Hz, 2 Hz), 7.2–7.4 (5H, m), 7.50 (1H, m), 7.55 (1H, m), 7.61 (1H, s), 7.82 (1H, d, J=5 Hz)

(23) 2-(3-Iodophenylamino)-3-aminopyridine

NMR (DMSO-$d_6$, δ): 5.06 (2H, s), 6.66 (1H, m), 6.92 (1H, m), 7.00 (1H, dd, J=8 Hz, 8 Hz), 7.15 (1H, m), 7.51 (1H, m), 7.61 (1H, m), 7.83 (1H, s), 8.08 (1H, s)

(24) 3-[3-[(3-Aminopyridin-2-yl)amino]phenylcarbamoyl]quinoline

NMR (DMSO-$d_6$, 300 MHz, δ): 5.12 (2H, s), 6.65 (1H, dd, J=5 Hz, 8 Hz), 6.92 (1H, d, J=8 Hz), 7.2–7.35 (2H, m), 7.45 (1H, d, J=8 Hz), 7.52 (1H, d, J=5 Hz), 7.73 (1H, t, J=8 Hz), 7.81 (1H, s), 7.90 (1H, t, J=8 Hz), 8.1–8.2 (3H, m), 8.97 (1H, d, J=2 Hz), 9.37 (1H, s)

(25) 3-Amino-2-[3-[(E)-2-(3,5-dichlorophenyl)vinyl]phenylamino]pyridine

NMR (DMSO-$d_6$, 300 MHz, δ): 5.09 (2H, s), 6.64 (1H, dd, J=5 Hz, 8 Hz), 6.92 (1H, d, J=8 Hz), 7.1–7.2 (2H, m), 7.28 (1H, t, J=8 Hz), 7.4–7.6 (4H, m), 7.72 (2H, s), 7.80 (1H, s), 7.84 (1H, s)

(26) 3-Amino-2-[3-[N-methyl-N-(3,5-dichlorophenyl)carbamoyl]phenylamino]pyridine NMR (DMSO-$d_6$, 300 MHz, δ): 3.37 (3H, s), 5.08 (2H, s), 6.63 (1H, dd, J=5 Hz, 8 Hz), 6.73 (1H, d, J=8 Hz), 6.90 (1H, d, J=8 Hz), 7.13 (1H, t, J=8 Hz), 7.3–7.45 (3H, m), 7.5–7.6 (2H, m), 7.83 (2H, m)

(27) 6-Phenylthio-2-[3-(3-phenylureido)phenylamino]-aminopyridine

NMR (DMSO-$d_6$, δ): 4.50 (2H, br s), 6.5–7.6 (10H, m), 8.30 (1H, m), 8.95 (2H, m)

(28) 2-(3-Phenylsulfonylaminophenylamino)-3-aminopyridine

NMR (DMSO-$d_6$, δ): 5.07 (2H, s), 6.55 (1H, m), 6.61 (1H, m), 6.89 (1H, m), 7.02 (1H, dd, J=8 Hz, 8 Hz), 7.25 (2H, m), 7.55 (5H, m), 7.82 (2H, m)

(29) 2-(3-Methoxycarbonylphenylamino)-3-aminopyridine

NMR (DMSO-$d_6$, δ): 3.83 (3H, s), 5.30 (2H, br s), 6.68 (1H, dd, J=8 Hz, 6 Hz), 6.95 (1H, d, J=8 Hz), 7.37 (1H, dd, J=8 Hz, 8 Hz), 7.44 (1H, d, J=8 Hz), 7.51 (1H, d, J=6 Hz), 7.99 (1H, d, J=8 Hz), 8.09 (1H, s), 8.18 (1H, s)

Preparation 73

To a mixture of 2-(3-amino-5-methoxycarbonylphenylamino)-3-nitropyridine (550 mg)

and triethylamine (0.3 ml) in 1,4-dioxane (10 ml) was added 2-naphthoyl chloride (0.40 g). The mixture was stirred at room temperature for 15 minutes, then poured into a mixture of ethyl acetate and aqueous sodium bicarbonate. The organic phase containing orange solid was washed with water twice and the solid was collected to give 2-[3-methoxycarbonyl-5-(2-naphthoylamino)phenylamino]-3-nitropyridine (730 mg).

NMR (DMSO-d$_6$, 300 MHz, δ): 3.90 (3H, s), 7.05 (1H, dd, J=5 Hz, 8 Hz), 7.6–7.7 (2H, m), 8.0–8.15 (5H, m), 8.29 (1H, t, J=2 Hz), 8.47 (1H, m), 8.55–8.6 (2H, m), 8.64 (1H, s)

Preparation 74

To a mixture of 2-[3-amino-5-methoxycarbonylphenylamino]-3-nitropyridine (1.10 g), triethylamine (0.6 ml) and 4-dimethylaminopyridine (14 mg) in 1,4-dioxane (15 ml) was added acetic anhydride (0.40 ml). The mixture was stirred at room temperature for 20 hours, then poured into a mixture of ethyl acetate and aqueous sodium bicarbonate. The organic phase was separated, washed with aqueous sodium bicarbonate and brine, dried over magnesium sulfate and concentrated. The resultant solid was collected and washed with isopropyl ether to give 2-(3-acetylamino-5-methoxycarbonylphenylamino)-3-nitropyridine (1.21 g).

NMR (CDCl$_3$, 300 MHz, δ): 2.21 (3H, s), 3.93 (3H, s), 6.89 (1H, dd, J=5, 8 Hz), 7.49 (1H, s), 7.79 (1H, s), 8.01 (1H, s), 8.41 (1H, s), 8.5–8.6 (2H, m)

Preparation 75

To a mixture of 3-nitroaniline (5.95 g) and triethylamine (6.0 ml) in dichloromethane (40 ml) was added dropwise a solution of benzoyl chloride (5.0 ml) in dichloromethane (20 ml). The mixture was stirred at room temperature for 15 minutes, then poured into a mixture of ethyl acetate and water. The organic phase was separated, washed with brine, dried over magnesium sulfate and concentrated. The resultant solid was collected and washed with isopropyl ether to give 1-benzoylamino-3-nitrobenzene (9.05 g).

NMR (CDCl$_3$, 300 MHz, δ): 7.45–7.65 (4H, m), 7.90 (2H, d, J=8 Hz), 8.01 (1H, d, J=8 Hz), 8.05–8.2 (2H, m), 8.50 (1H, s)

Preparation 76

The solution of 3-nitro-2-(3-succinimidophenylamino)-pyridine (3.47 g) was hydrogenated with palladium on carbon (0.5 g) at 3 atm for 5 hours. The mixture was filtrated and evaporated to give 3-amino-2-(3-succinimidophenylamino)pyridine (2.89 g).

NMR (DMSO-d$_6$, 300 MHz, δ): 8.00 (1H, s), 7.64 (1H, dd, J=8 Hz, 1 Hz), 7.56 (1H, d, J=1 Hz), 7.50 (1H, d, J=3 Hz), 7.31 (1H, t, J=8 Hz), 6.92 (1H, d, J=7 Hz), 6.70 (1H, d, J=7 Hz), 6.66 (1H, dd, J=8 Hz, 3 Hz), 5.23 (2H, br s), 2.69 (4H, s)

Preparation 77

The following compound was synthesized from 3-nitroaniline and maleic anhydride according to a similar manner to that described in Organic Synthesis Collective Volume 5 pp944.

(Z)-3-(3-Nitrophenylcarbamoyl)acrylic acid

NMR (DMSO-d$_6$, 300 MHz, δ): 6.34 (1H, d, J=10 Hz), 6.50 (1H, d, J=10 Hz), 7.63 (1H, t, J=8 Hz), 7.92 (1H, d, J=8 Hz), 7.95 (1H, d, J=8 Hz), 8.65 (1H, s)

MASS (FAB) (m/e): 235

Preparation 78

The following compound was synthesized from (Z)-3-(3-nitrophenylcarbamoyl)acrylic acid according to a similar manner to that described in Organic Synthesis Collective Volume 5 pp944.

N-(3-Nitrophenyl)maleimide

NMR (DMSO-d$_6$, 300 MHz, δ): 7.26 (2H, s), 7.77–7.88 (2H, m),8.22–8.31 (2H, m)

Preparation 79

To a solution of N-(3-nitrophenyl)maleimide (26.3 g) in methanol-dioxane (1:1) was added suspension of palladium on carbon (2 g) in water. The reaction mixture was hydrogenated for 4 hours at 3 atm. (White crystal was precipitated.) The mixture was added 1N hydrochloric acid (ca. 300 ml) to dissolve the crude product. The mixture was filtrated and evaporated. Obtained residue was dissolved in water and basified by aqueous sodium hydrogencarbonate. Precipitate was collected by suction to give N-(3-aminophenyl)succinimide (12.6 g).

NMR (DMSO-d$_6$, 300 MHz, δ): 2.72 (4H, s), 5.25 (2H, s), 6.33 (1H, d, J=7 Hz), 6.39 (1H, d, J=1 Hz), 6.58 (1H, dd, J=7 Hz, 1 Hz), 7.07 (1H, t, J=9 Hz)

MASS (FAB) (m/e): 191 (M+1)

Preparation 80

A mixture of ethyl 4-hydroxy-3-methoxybenzoate (7.17 g), cyclopentyl bromide (4.7 ml) and potassium carbonate (7.6 g) in N,N-dimethylformamide (70 ml) was stirred at 80° C. for 3 hours. Then the mixture was poured into water and extracted with ethyl acetate twice. The combined organic solution was washed with water and brine, dried over magnesium sulfate and concentrated. The residue was chromatographed on silica gel column (hexane-ethyl acetate, 4:1) to give ethyl 4-cyclopentyloxy-3-methoxybenzoate (8.58 g) as an oil.

NMR (CDCl$_3$, 300 MHz, δ): 1.39 (3H, t, J=7 Hz), 1.55–2.10 (8H, m), 3.90 (3H, s), 4.36 (2H, q, J=7 Hz), 4.83 (1H, m), 6.88 (1H, d, J=8 Hz), 7.54 (1H, d, J=2 Hz), 7.65 (1H, dd, J=2 Hz, 8 Hz)

Preparation 81

A mixture of ethyl 4-cyclopentyloxy-3-methoxybenzoate (1.06 g) and 4N aqueous sodium hydroxide (4 ml) in ethanol (8 ml) and 1,4-dioxane (8 ml) was stirred at 80° C. for 3 hours. Then the mixture was poured into dilute hydrochloric acid and extracted with ethyl acetate. The organic solution was washed with dilute hydrochloric acid and brine, dried over magnesium sulfate and concentrated. The resultant solid was collected and washed with isopropyl ether to give 4-cyclopentyloxy-3-methoxybenzoic acid (730 mg).

NMR (CDCl$_3$, 300 MHz, δ): 1.55–2.10 (8H, m), 3.90 (3H, s), 4.87 (1H, m), 6.91 (1H, d, J=8 Hz), 7.60 (1H, d, J=2 Hz), 7.74 (1H, dd, J=2 Hz, 8 Hz)

Preparation 82

To a solution of 3-quinolinecarboxylic acid (2.50 g) in dichloromethane (50 ml) was added oxalyl chloride (2.6 ml) and three drops of N,N-dimethylformamide. After stirring at room temperature for 30 minutes, the mixture was concentrated and the residual solid was added to a mixture of 3-nitroaniline (1.60 g) and triethylamine (4.0 ml) in dichloromethane (40 ml). After stirring at room temperature for 15 minutes, the mixture was poured into aqueous sodium bicarbonate and extracted with ethyl acetate three times. The combined organic phase was washed with aqueous sodium bicarbonate and brine, dried over magnesium sulfate and concentrated. The resultant solid was collected and washed with isopropyl ether to give 3-(3-nitrophenylcarbamoyl) quinoline (2.98 g).

NMR (DMSO-$d_6$, 300 MHz, δ): 7.7–7.8 (2H, m), 7.93 (1H, t, J=8 Hz), 8.02 (1H, dd, J=2 Hz, 8 Hz), 8.15–8.3 (3H, m), 8.84 (1H, m), 9.02 (1H, d, J=2 Hz), 9.40 (1H, s)

Preparation 83

A mixture of 3-nitrostyrene (4.6 ml), 1,3-dichloro-5-iodobenzene (7.8 g), palladium(II) acetate (0.20 g), tetrabutylammonium chloride (8.4 g) and sodium bicarbonate (6.3 g) in N,N-dimethylformamide (40 ml) was stirred at 110° C. for 4 hours. Then the mixture was poured into aqueous sodium bicarbonate and extracted with ethyl acetate twice. The combined organic phase was washed with aqueous sodium bicarbonate and brine, dried over magnesium sulfate and concentrated. The resultant solid was collected and washed with isopropyl ether to give 1,3-dichloro-5-[(E)-2-(3-nitrophenyl)vinyl]benzene (7.93 g).

NMR (DMSO-$d_6$, 300 MHz, δ): 7.4–7.55 (2H, m), 7.6–7.75 (4H, m), 8.05 (1H, d, J=8 Hz), 8.15 (1H, dd, J=2 Hz, 8 Hz), 8.43 (1H, t, J=2 Hz)

Preparation 84

To a mixture of 3,5-dichloroaniline (8.1 g) and triethylamine (7.0 ml) in chloroform (100 ml) was added dropwise a solution of 3-nitrobenzoyl chloride (9.3 g) in chloroform (50 ml). The mixture was stirred at room temperature for 1 hour, then poured into aqueous sodium bicarbonate. The resultant precipitate was collected and washed with chloroform and water to give 3-nitro-N-(3,5-dichlorophenyl) benzamide (12.50 g).

NMR (DMSO-$d_6$, 300 MHz, δ): 7.38 (1H, s), 7.8–7.9 (3H, m), 8.39 (1H, d, J=8 Hz), 8.48 (1H, d, J=8 Hz), 8.80 (1H, s)

Preparation 85

A mixture of 2-[3-(3,5-dichlorophenylcarbamoyl) phenylamino]-3-nitropyridine (565 mg) and iron powder (0.4 g) in acetic acid (5 ml) and 1,4-dioxane (5 ml) was stirred at 80° C. for 3 hours. Then the mixture was poured into aqueous sodium bicarbonate and extracted with ethyl acetate twice. The combined organic phase was washed with aqueous sodium bicarbonate and brine, dried over magnesium sulfate and concentrated. The resultant solid was collected and washed with isopropyl ether to give 3-amino-2-[3-(3,5-dichlorophenylcarbamoyl)phenylamino]pyridine (284 mg).

NMR (DMSO-$d_6$, 300 MHz, δ): 5.12 (2H, s), 6.68 (1H, m), 6.93 (1H, d, J=8 Hz), 7.3–7.6 (4H, m), 7.9–8.1 (5H, m)

Prenaration 86

To a suspension of sodium hydride (60% in oil, 1.1 g) in N,N-dimethylformamide (20 ml) was added dropwise a solution of 3-nitro-N-(3,5-dichlorophenyl)benzamide (5.89 g) in N,N-dimethylformamide (40 ml). The mixture was stirred at room temperature for 1 hour, then iodomethane (3 ml) was added thereto. After stirring at room temperature for 1 hour, dilute hydrochloric acid was added to the mixture and extracted with ethyl acetate twice. The combined organic solution was washed with water and brine, dried over magnesium sulfate and concentrated. The residue was solidified with isopropyl ether to give 3-nitro-N-methyl-N-(3,5-dichlorophenyl)benzamide (4.62 g).

NMR (CDCl$_3$, 300 MHz, δ): 3.49 (3H, s), 7.00 (2H, s), 7.21 (1H, m), 7.48 (1H, t, J=8 Hz), 7.63 (1H, d, J=8 Hz), 8.15–8.25 (2H, m)

Preparation 87

A mixture of 3-amino-2-(3-biphenylylamino)pyridine (157 mg) and 4-methyl-2-oxopentanoic acid (94 mg) in ethanol (3 ml) was stirred under reflux for 2 hours. The mixture was cooled and then poured into a mixture of ethyl acetate and aqueous sodium bicarbonate. The organic phase was separated, washed with aqueous sodium bicarbonate and brine, dried over magnesium sulfate and concentrated. The residue was chromatographed on silica gel column (hexane-ethyl acetate, 3:1) to give 4-(3-biphenylyl)-2-isobutyl-3-oxo-3,4-dihydropyrido[2,3-b]pyrazine (47 mg).

NMR (CDCl$_3$, 300 MHz, δ): 1.07 (6H, d, J=7 Hz), 2.39 (1H, m), 2.90 (2H, d, J=7 Hz), 7.25–7.5 (6H, m), 7.6–7.8 (4H, m), 8.20 (1H, d, J=8 Hz), 8.43 (1H, d, J=5 Hz)

Preparation 88

The following compounds were obtained according to a similar manner to that of Preparation 87.

(1) 4-(3-Iodophenyl)-2-methyl-3-oxo-3,4-dihydropyrido[2,3-b]pyrazine

NMR (DMSO-$d_6$, δ): 2.48 (3H, s), 7.38 (3H, s), 7.78 (1H, s), 7.75 (1H, m), 8.20 (1H, m), 8.36 (1H, m)

(2) 2-Methyl-4-(3-succinimidophenyl)-3-oxo-3,4-dihydropyrido[2,3-b]pyrazine

NMR (DMSO-$d_6$, 300 MHz, δ): 2.79 (4H, s), 3.31 (3H, s), 7.30 (1H, s), 7.36–7.45 (3H, m), 7.65 (1H, t, J=8 Hz), 8.22 (1H, d, J=7 Hz), 8.37 (1H, d, J=5 Hz)

(3) 2-Isobutyl-4-[3-(2-naphthoylamino)phenyl]-3-oxo-3,4-dihydropyrido[2,3-b]pyrazine NMR (CDCl$_3$, 300 MHz, δ): 1.04 (6H, d, J=7 Hz), 2.38 (1H, m), 2.89 (2H, d, J=7 Hz), 6.85 (1H, dt, J=8 Hz, 2 Hz), 7.29 (1H, dd, J=5 Hz, 8 Hz), 7.45–7.60 (3H, m), 7.72 (1H, dd, J=2 Hz, 8 Hz), 7.8–7.9 (5H, m), 8.18 (1H, dd, J=2 Hz, 8 Hz), 8.32 (1H, s), 8.40 (1H, dd, J=2 Hz, 5 Hz), 8.52 (1H, s)

(4) 2-Methyl-4-(3-methoxycarbonylphenyl)-3-oxo-3,4-dihydropyrido[2,3-b]pyrazine

NMR (DMSO-$d_6$, 300 MHz, δ): 2.49 (3H, s), 3.86 (3H, s), 7.39 (1H, dd, J=4 Hz, 7 Hz), 7.67 (1H, d, J=7 Hz), 7.72 (1H, dd, J=6 Hz, 7 Hz), 7.97 (1H, s), 8.08 (1H, d, J=7 Hz), 8.22 (1H, d, J=6 Hz), 8.35 (1H, d, J=4 Hz)

(5) 4-(3-Biphenylyl)-2-(1-methylpropyl)-3-oxo-3,4-dihydropyrido[2,3-b]pyrazine

NMR (CDCl$_3$, 300 MHz, δ): 1.00 (3H, t, J=7 Hz), 1.34 (3H, d, J=7 Hz), 1.65 (1H, m), 1.98 (1H, m), 3.50 (1H, m), 7.25–7.45 (5H, m), 7.52 (1H, s), 7.6–7.7 (3H, m), 7.76 (1H, dd, J=2 Hz, 8 Hz), 8.20 (1H, dd, J=2 Hz, 8 Hz), 8.42 (1H, d, J=5 Hz)

(6) 2-Isobutyl-4-[3-(1H-1,2,4-triazol-1-yl)phenyl]-3-oxo-3,4-dihydropyrido[2,3-b]pyrazine NMR (CDCl$_3$, 300 MHz, δ): 1.07 (6H, d, J=7 Hz), 2.38 (1H, m), 2.90 (2H, d, J=7 Hz), 7.3–7.4 (2H, m), 7.7–7.8 (2H, m), 7.86 (1H, dd, J=2 Hz, 8 Hz), 8.10 (1H, s), 8.40 (1H, dd, J=2 Hz, 5 Hz), 8.60 (1H, s)

(7) 2-Methyl-4-[3-(1-naphthyl)phenyl]-3-oxo-3,4-dihydropyrido[2,3-b]pyrazine mp: 196–198° C.

NMR (CDCl$_3$, δ): 2.68 (3H, s), 7.30 (1H, dd, J=8 Hz, 6 Hz), 7.38 (1H, m), 7.4–7.55 (5H, m), 7.70 (2H, m), 7.88 (2H, m), 8.09 (1H, m), 8.15 (1H, d, J=8 Hz), 8.47 (1H, d, J=6 Hz)

(8) 2-Methyl-4-(3-biphenylyl)-3-oxo-3,4-dihydropyrido[2,3-b]pyrazine

NMR (CDCl$_3$, 300 MHz, δ): 2.68 (3H, s), 7.25–7.50 (6H, m), 7.59–7.68 (3H, m), 7.50 (1H, dd, J=8 Hz, 3 Hz), 8.16 (1H, dd, J=8 Hz, 3 Hz), 8.41 (1H, dd, J=7 Hz, 3 Hz)

(9) 2-Methyl-4-(3-acetamidophenyl)-3-oxo-3,4-dihydropyrido[2,3-b]pyrazine

NMR (DMSO-d$_6$, 300 MHz, δ): 2.04 (3H, s), 2.49 (3H, s), 6.98 (1H, d, J=7 Hz), 7.39 (1H, dd, J=5 Hz, 7 Hz), 7.44 (1H, dd, J=7 Hz, 7 Hz), 7.57 (1H, d, J=7 Hz), 7.65 (1H, s), 8.21 (1H, d, J=7 Hz), 8.47 (1H, d, J=5 Hz)

Preparation 89

A mixture of 3-amino-2-[(3-cyclopentyloxy-4-methoxyphenyl)amino]pyridine (180 mg) and 2-oxosuccinic acid (90 mg) in ethanol (4 ml) was stirred under reflux for 1.5 hours. The mixture was cooled and then poured into a mixture of ethyl acetate and aqueous sodium bicarbonate. The organic phase was separated, washed with aqueous sodium bicarbonate and brine, dried over magnesium sulfate and concentrated. The resultant solid was washed with ethanol to give 4-(3-cyclopentyloxy-4-methoxyphenyl)-2-methyl-3-oxo-3,4-dihydropyrido[2,3-b]pyrazine (100 mg).

NMR (CDCl$_3$, 300 MHz, δ): 1.5–1.65 (2H, m), 1.75–2.0 (6H, m), 2.67 (3H, s), 3.91 (3H, s), 4.73 (1H, m), 6.77 (1H, d, J=2 Hz), 6.82 (1H, dd, J=2 Hz, 8 Hz), 7.04 (1H, d, J=8 Hz), 7.29 (1H, m), 8.15 (1H, d, J=8 Hz), 8.46 (1H, d, J=5 Hz)

Preparation 90

The suspension of 2-methyl-4-(3-acetamidophenyl)-3-oxo-3,4-dihydropyrido[2,3-b]pyrazine (8.6 g) in 3N hydrochloric acid (50 ml) was refluxed for an hour. The mixture was made basic by sodium bicarbonate (15 g) to obtain 2-methyl-4-(3-aminophenyl)-3-oxo-3,4-dihydropyrido[2,3-b]pyrazine (7.4 g) in yellow powder.

NMR (CDCl$_3$, 300 MHz, δ): 2.64 (3H, s), 3.80 (2H, br s), 6.57 (1H, d, J=3 Hz), 6.63 (1H, d, J=7 Hz), 6.81 (1H, dd, J=7 Hz, 3 Hz), 7.25–7.30 (2H, m), 7.35 (1H, dd, J=7 Hz, 7 Hz), 8.13 (1H, d, J=7 Hz), 8.44 (1H, m)

Preparation 91

The following compound was obtained according to a similar manner to that of Preparation 73 or 74.

2-(3-Phenylsulfonylaminophenylamino)-3-nitropyridine

NMR (DMSO-d$_6$, δ): 6.83 (1H, m), 7.00 (1H, dd, J=8 Hz, 4 Hz), 7.20 (2H, m), 7.58 (4H, m), 7.82 (2H, m), 8.50 (2H, m), 9.87 (1H, s)

Preparation 92

A mixture of 2-methoxy-5-nitrophenol (4.86 g), cyclopentyl bromide (3.4 ml) and potassium carbonate (4.8 g) in N,N-dimethylformamide (50 ml) was stirred at 50° C. for 3 hours. Then the mixture was poured into a mixture of ethyl acetate and aqueous sodium bicarbonate. The organic phase was separated, washed with aqueous sodium bicarbonate and brine, dried over magnesium sulfate and concentrated. The resultant solid was collected and washed with isopropyl ether to give 3-cyclopentyloxy-4-methoxy-1-nitrobenzene (5.05 g).

NMR (CDCl$_3$, 300 MHz, δ): 1.6–2.1 (8H, m), 3.94 (3H, s), 4.86 (1H, m), 6.90 (1H, d, J=8 Hz), 7.75 (1H, d, J=2 Hz), 7.90 (1H, dd, J=2 Hz, 8 Hz)

Preparation 93

A mixture of 3-cyclopentyloxy-4-methoxy-1-nitrobenzene (5.02 g), iron powder (4.8 g) and hydrochloric acid (35%, 15 ml) in ethanol (40 ml) was stirred under reflux for 3 hours. Then the mixture was poured into aqueous sodium bicarbonate and extracted with ethyl acetate twice. The combined organic phase was washed with aqueous sodium bicarbonate and brine, dried over magnesium sulfate and concentrated to give 3-cyclopentyloxy-4-methoxyaniline (2.60 g) as an oil.

NMR (DMSO-d$_6$, 300 MHz, δ): 1.5–1.9 (8H, m), 3.59 (3H, s), 4.55–4.7 (3H, m), 6.05 (1H, m), 6.23 (1H, d, J=2 Hz), 6.61 (1H, d, J=8 Hz)

Preparation 94

A mixture of 2-chloro-3-nitropyridine (2.17 g), 3-cyclopentyloxy-4-methoxyaniline (2.58 g) and potassium carbonate (2.6 g) in 1,4-dioxane (30 ml) was stirred under reflux for 20 hours. After cooling, insoluble materials were removed by filtration and the filtrate was concentrated. The resultant solid was collected and washed with isopropyl ether to give 2-[(3-cyclopentyloxy-4-methoxyphenyl)amino]-3-nitropyridine (1.35 g) as an orange solid.

NMR (CDCl$_3$, 300 MHz, δ): 1.55–1.7 (2H, m), 1.8–2.0 (6H m), 3.86 (3H, s), 4.79 (1H, m), 6.79 (1H, dd, J=5 Hz, 8 Hz), 6.89 (1H, d, J=8 Hz), 7.09 (1H, m), 7.19 (1H, m), 8.46 (1H, d, J=5 Hz), 8.52 (1H, dd, J=2 Hz, 8 Hz)

Preparation 95

A mixture of 2-[(3-cyclopentyloxy-4-methoxyphenyl)amino]-3-nitropyridine (1.30 g) and 10% palladium on carbon (0.3 g) in ethanol (20 ml) and 1,4-dioxane (20 ml) was stirred under hydrogen (3 atm) at room temperature for 1 hours. The catalyst was removed by filtration and the solvent was evaporated. The resulting solid was collected and washed with isopropyl ether to give 3-amino-2-[(3-cyclopentyloxy-4-methoxyphenyl)amino]pyridine (992 mg).

NMR (DMSO-d$_6$, 300 MHz, δ): 1.5–1.95 (8H, m), 3.69 (3H, s), 4.70 (1H, m), 6.58 (1H, dd, J=5 Hz, 8 Hz), 6.8–6.9 (2H, m), 7.15 (1H, m), 7.31 (1H, d, J=2 Hz), 7.42 (1H, d, J=5 Hz), 7.70 (1H, s)

Preparation 96

To a mixture of 3-nitroaniline (2.07 g) and triethylamine (2.3 ml) in 1,4-dioxane (40 ml) was added 2-naphthoyl chloride (3.00 g) and the mixture was stirred at room temperature for 30 minutes. Then the mixture was poured into aqueous sodium bicarbonate and extracted with ethyl acetate three times. The combined organic phase was washed with aqueous sodium bicarbonate and brine, dried over magnesium sulfate and concentrated. The resultant solid was collected and washed with isopropyl ether to give N-(3-nitrophenyl)-2-naphthalenecarboxamide (3.02 g).

NMR (DMSO-d$_6$, 300 MHz, δ): 7.6–7.75 (3H, m), 7.95–8.15 (5H, m), 8.28 (1H, dt, J=8 Hz, 2 Hz), 8.65 (1H, s), 8.87 (1H, t, J=2 Hz)

Preparation 97

A mixture of N-(3-nitrophenyl)-2-naphthalenecarboxamide (2.94 g), iron powder (3.0 g) and hydrochloric acid (35%, 9 ml) in ethanol (30 ml) was stirred at 80° C. for 2 hours. Then the mixture was poured into aqueous sodium bicarbonate and extracted with ethyl acetate twice. The combined organic phase was washed with aqueous sodium bicarbonate and brine, dried over magnesium sulfate and concentrated. The resultant solid was collected and washed with isopropyl ether to give N-(3-aminophenyl)-2-naphthalenecarboxamide (2.17 g).

NMR (DMSO-d$_6$, 300 MHz, δ): 5.10 (2H, s), 6.34 (1H, dt, J=8 Hz, 2 Hz), 6.91 (1H, dt, J=8 Hz, 2 Hz), 6.99 (1H, t, J=8 Hz), 7.17 (1H, t, J=2 Hz), 7.6–7.7 (2H, m), 7.95–8.1 (4H, m), 8.55 (1H, s)

Preparation 98

A mixture of 2-chloro-3-nitropyridine (0.87 g), N-(3-aminophenyl)-2-naphthalenecarboxamide (1.31 g) and potassium carbonate (1.0 g) in 1,4-dioxane (20 ml) was stirred under reflux for 20 hours. After cooling, insoluble materials were removed by filtration and the filtrate was concentrated. The resultant solid was collected and washed with isopropyl ether to give 2-[3-(2-naphthoylamino)phenylamino]-3-nitropyridine (961 mg) as an orange solid.

NMR (DMSO-d$_6$, 300 MHz, δ): 7.02 (1H, dd, J=5 Hz, 8 Hz), 7.39 (1H, t, J=8 Hz), 7.47 (1H, d, J=8 Hz), 7.6–7.7 (3H, m), 8.0–8.2 (5H, m), 8.55–8.65 (3H, m)

Preparation 99

A mixture of 2-[3-(2-naphthoylamino)phenylamino]-3-nitropyridine (948 mg), iron powder (0.55 g) and hydrochloric acid (35%, 2 ml) in ethanol (8 ml) was stirred at 80° C. for 30 minutes. Then the mixture was poured into aqueous sodium bicarbonate and extracted with ethyl acetate twice. The combined organic phase was washed with aqueous sodium bicarbonate and brine, dried over magnesium sulfate and concentrated. The resultant solid was collected and washed with isopropyl ether to give 3-amino-2-[3-(2-naphthoylamino)phenylamino]pyridine (682 mg).

NMR (DMSO-d$_6$, 300 MHz, δ): 5.11 (2H, s), 6.64 (1H, dd, J=5 Hz, 8 Hz), 6.92 (1H, dd, J=2 Hz, 8 Hz), 7.2–7.3 (2H, m), 7.45 (1H, dt, J=8 Hz, 2 Hz), 7.52 (1H, dd, J=2 Hz, 5 Hz), 7.6–7.7 (2H, m), 7.80 (1H, s), 8.0–8.15 (5H, m), 8.60 (1H, s)

Preparation 100

The following compound was obtained by subjecting 2-(3-carboxyphenylamino)-3-aminopyridine to methyl esterification in the conventional manner.

2-(3-Methoxycarbonylphenylamino)-3-aminopyridine

NMR (CDC$_3$, δ): 3.95 (3H, s), 6.89 (1H, dd, J=8 Hz, 5 Hz), 7.49 (1H, dd, J=8 Hz, 8 Hz), 7.86 (1H, m), 7.92 (1H, m), 8.30 (1H, m), 8.53 (1H, m)

Preparation 101

A mixture of 3-nitrostyrene (3.98 g), 3,5-dichloropyridine (3.70 g), palladium(II) acetate (0.20 g), tetrabutylammonium chloride (7.0 g) and sodium bicarbonate (5.3 g) in N,N-dimethylformamide (35 ml) was stirred at 135° C. for 2 hours. Then the mixture was poured into aqueous sodium bicarbonate and extracted with ethyl acetate twice. The combined organic phase was washed with aqueous sodium bicarbonate and brine, dried over magnesium sulfate and concentrated. The resultant solid was collected and washed with isopropyl ether to give 3-chloro-5-[(E)-2-(3-nitrophenyl)vinyl]pyridine (3.01 g).

NMR (CDCl$_3$, 300 MHz, δ): 7.1–7.3 (2H, m), 7.59 (1H, t, J=8 Hz), 7.8–7.9 (2H, m), 8.18 (1H, m), 8.40 (1H, t, J=2 Hz), 8.51 (1H, d, J=2 Hz), 8.63 (1H, s)

Preparation 102

A mixture of 3-chloro-5-[(E)-2-(3-nitrophenyl)vinyl]pyridine (2.99 g), iron powder (2.6 g) and hydrochloric acid (35%, 8 ml) in methanol (50 ml) was stirred at 60° C. for 3 hours. Then the mixture was poured into aqueous sodium bicarbonate and extracted with ethyl acetate twice. The combined organic phase was washed with aqueous sodium bicarbonate and brine, dried over magnesium sulfate and concentrated. The resultant solid was collected and washed with isopropyl ether to give 3-[(E)-2-(3-aminophenyl)vinyl]-5-chloropyridine (1.33 g).

NMR (DMSO-d$_6$, 300 MHz, δ): 5.13 (2H, s), 6.54 (1H, d, J=8 Hz), 6.79 (2H, m), 7.0–7.15 (2H, m), 7.37 (1H, d, J=16 Hz), 8.21 (1H, s), 8.47 (1H, d, J=2 Hz), 8.70 (1H, s)

Preparation 103

The following compound was obtained according to a similar manner to that of Preparation 1, 5, 27, 28, 47, 48, 49, 68 or 69.

2-[3-(E)-2-(-Chloropyridin-3-yl)vinyl]phenylamino]-3-nitropyridine

NMR (CDCl$_3$, 300 MHz, δ): 6.88 (1H, dd, J=5 Hz, 8 Hz), 7.06 (1H, d, J=16 Hz), 7.20 (1H, d, J=16 Hz), 7.3–7.45 (2H, m), 7.61 (1H, d, J=8 Hz), 7.85 (2H, m), 8.47 (1H, s), 8.5–8.6 (3H, m)

Preparation 104

The following compound was obtained according to a similar manner to that of Preparation 3, 31, 33, 52, 53, 54 or 71.

3-Amino-2-[3-[(E)-2-(5-chloropyridin-3-yl)vinyl]phenylamino]pyridine

NMR (DMSO-d$_6$, 300 MHz, δ): 5.10 (2H, s), 6.64 (1H, dd, J=5 Hz, 8 Hz), 6.91 (1H, d, J=8 Hz), 7.1–7.3 (3H, m), 7.4–7.65 (3H, m), 7.75–7.9 (2H, m), 8.27 (1H, s), 8.48 (1H, s), 8.73 (1H, s)

EXAMPLE 1

A mixture of 4-(3-aminophenyl)-2-benzyl-3-oxo-3,4-dihydropyrido[2,3-b]pyrazine (150 mg) and 1-naphthyl isocyanate (94 mg) in dry dioxane (3 ml) was stirred at room temperature for 3 hours. The precipitates were collected and washed with isopropyl ether to give 4-[3-[3-(1-naphthyl)ureido]phenyl]-2-benzyl-3-oxo-3,4-dihydropyrido[2,3-b]pyrazine NMR (DMSO-d$_6$, δ): 4.23 (2H, s), 6.95 (1H, m), 7.15–7.7 (13H, m), 7.95 (2H, t, J=7 Hz), 8.11 (1H, d, J=8 Hz), 8.25 (1H, dd, J=1.5 Hz, 8 Hz), 8.41 (1H, dd, J=1.5 Hz, 5 Hz), 8.83 (1H, s), 9.25 (1H, s)

EXAMPLE 2

A mixture of 3-amino-2-[(m-tolyl)amino]pyridine (299 mg) and phenylpyruvic acid (246 mg) in ethanol (5 ml) was refluxed for 2 hours. The mixture was cooled and the precipitates were collected and washed with ethanol to give 2-benzyl-3-oxo-4-(m-tolyl)-3,4-dihydropyrido[2,3-b]pyrazine (264 mg).

NMR (CDCl$_3$, δ): 2.42 (3H, s), 4.31 (2H, s), 7.05 (2H, d, J=8 Hz), 7.2–7.55 (8H, m), 8.18 (1H, dd, J=1.5 Hz, 8 Hz), 8.41 (1H, dd, J=1.5 Hz, 5 Hz)

EXAMPLE 3

The following compounds were obtained according to a similar manner to that of Example 2.
(1) 2-Benzyl-3-oxo-4-(pyridin-3-yl)-3,4-dihydropyrido[2,3-b]pyrazine NMR CDCl$_3$, δ): 4.32 (2H, s), 7.15–7.4 (4H, m), 7.45–7.6 (3H, m), 7.68 (1H, dt, J=8 Hz, 1.5 Hz), 8.21 (1H, dd, J=1.5

Hz, 8 Hz), 8.37 (1H, dd, J=1.5 Hz, 5 Hz), 8.57 (1H, d, J=1.5 Hz), 8.73 (1H, dd, J=1.5 Hz, 5 Hz)

(2) 2-Benzyl-3-oxo-4-(pyridin-2-yl)-3,4-dihydropyrido[2,3-b]pyrazine

NMR CDCl$_3$, δ): 4.30 (2H, s), 7.2–7.55 (8H, m), 7.97 (1H, dt, J=1.5 Hz, 8 Hz), 8.19 (1H, dd, J=1.5 Hz, 8 Hz), 8.36 (1H, dd, J=1.5 Hz, 5 Hz), 8.75 (1H, m)

(3) 2-Benzyl-4-(1-naphthyl)-3-oxo-3,4-dihydropyrido[2,3-b]pyrazine

NMR (CDCl$_3$, δ): 4.36 (2H, d, J=5 Hz), 7.1–7.55 (10H, m), 7.64 (1H, t, J=8 Hz), 7.9–8.1 (2H, m), 8.15–8.35 (2H, m)

(4) 4-(3-Acetamidophenyl)-2-benzyl-3-oxo-3,4-dihydropyrido[2,3-b]pyrazine

NMR (DMSO-d$_6$, δ): 2.05 (3H, s), 4.21 (2H, s), 6.99 (1H, dt, J=8 Hz, 1 Hz), 7.15–7.5 (7H, m), 7.58 (2H, d, J=8 Hz), 8.23 (1H, dd, J=1.5 Hz, 8 Hz), 8.38 (1H, dd, J=1.5 Hz, 5 Hz), 10.13 (1H, s)

(5) 2-Benzyl-4-(3-ethoxycarbonylphenyl)-3-oxo-3,4-dihydropyrido[2,3-b]pyrazine

NMR (CDCl$_3$, δ): 1.37 (3H, t, J=7 Hz), 4.25–4.45 (4H, m), 7.15–7.55 (7H, m), 7.65 (1H, t, J=8 Hz), 7.95 (1H, s), 8.20 (2H, dd, J=1.5 Hz, 8 Hz), 8.38 (1H, dd, J=1.5 Hz, 5 Hz)

(6) 2-Benzyl-4-(4-methoxycarbonylphenyl)-3-oxo-3,4-dihydropyrido[2,3-b]pyrazine

NMR (CDCl$_3$, δ): 3.96 (3H, s), 4.31 (2H, s), 7.2–7.55 (8H, m), 8.15–8.3 (3H, m), 8.38 (1H, dd, J=1.5 Hz, 5 Hz)

(7) 2-Benzyl-4-(4-methoxycarbonylmethylphenyl)-3-oxo-3,4-dihydropyrido[2,3-b]pyrazine NMR (CDCl$_3$, δ): 3.70 (2H, s), 3.72 (3H, s), 4.30 (2H, s), 7.15–7.4 (6H, m), 7.48 (4H, m), 8.18 (1H, dd, J=1.5 Hz, 8 Hz), 8.39 (1H, dd, J=1.5 Hz, 5 Hz)

(8) 2-Benzyl-4-(3-methoxycarbonylmethylphenyl)-3-oxo-3,4-dihydropyrido[2,3-b]pyrazine NMR (CDCl$_3$, δ): 3.69 (5H, s), 4.31 (2H, s), 7.15–7.6 (10H, m), 8.18 (1H, dd, J=1.5 Hz, 8 Hz), 8.40 (1H, dd, J=1.5 Hz, 5 Hz)

(9) 4-(4-Acetylphenyl)-2-benzyl-3-oxo-3,4-dihydropyrido[2,3-b]pyrazine

NMR (CDCl$_3$, δ): 2.67 (3H, s), 4.32 (2H, s), 7.2–7.55 (8H, m), 8.1–8.25 (3H, m), 8.38 (1H, dd, J=1.5 Hz, 5 Hz)

(10) 4-(3-Acetylphenyl)-2-benzyl-3-oxo-3,4-dihydropyrido[2,3-b]pyrazine

NMR (CDCl$_3$, δ): 2.61 (3H, s), 4.32 (2H, s), 7.2–7.35 (4H, m), 7.45–7.55 (3H, m), 7.68 (1H, t, J=8 Hz), 7.86 (1H, s), 8.09 (1H, dt, J=8 Hz, 1.5 Hz), 8.20 (1H, dd, J=1.5 Hz, 8 Hz), 8.37 (1H, dd, J=1.5 Hz, 5 Hz)

(11) 2-Benzyl-4-(3-fluorophenyl)-3-oxo-3,4-dihydropyrido[2,3-b]pyrazine

NMR (CDCl$_3$, δ): 4.31 (2H, s), 6.95–7.1 (2H, m), 7.15–7.4 (5H, m), 7.45–7.65 (3H, m), 8.20 (1H, dd, J=1.5 Hz, 8 Hz), 8.40 (1H, dd, J=1.5 Hz, 5 Hz)

(12) 2-Benzyl-4-(3-hydroxyphenyl)-3-oxo-3,4-dihydropyrido[2,3-b]pyrazine

NMR (DMSO-d$_6$, δ): 4.21 (2H, s), 6.72 (2H, d, J=8 Hz), 6.88 (1H, m), 7.2–7.45 (6H, m), 8.22 (1H, dd, J=1.5 Hz, 8 Hz), 8.40 (1H, dd, J=1.5 Hz, 5 Hz), 9.71 (1H, s)

(13) 2-Benzyl-4-(4-methoxyphenyl)-3-oxo-3,4-dihydropyrido[2,3-b]pyrazine

NMR (CDCl$_3$, δ): 3.87 (3H, s), 4.31 (2H, s), 7.0–7.4 (8H, m), 7.51 (2H, d, J=8 Hz), 8.18 (1H, dd, J=1.5 Hz, 8 Hz), 8.41 (1H, dd, J=1.5 Hz, 5 Hz)

(14) 2-Benzyl-4-(3-methoxyphenyl)-3-oxo-3,4-dihydropyrido[2,3-b]pyrazine

NMR (CDCl$_3$, δ): 3.81 (3H, s), 4.31 (2H, s), 6.75–6.9 (2H, m), 7.05 (1H, m), 7.2–7.55 (7H, m), 8.18 (1H, dd, J=1.5 Hz, 8 Hz), 8.42 (1H, dd, J=1.5 Hz, 5 Hz)

EXAMPLE 4

A mixture of 2-benzyl-4-(3-hydroxyphenyl-3-oxo-3,4-dihydropyrido[2,3-b]pyrazine (135 mg), acetic anhydride (84 mg), triethylamine (83 mg) and 4-dimethylaminopyridine (5 mg) in dichlormethane (2 ml) was stirred at room temperature for 1 hour. The mixture was poured into ethyl acetate and washed with water and brine, dried over magnesium sulfate and concentrated. The solids were collected and washed with isopropyl ether to give 4-(3-acetoxyphenyl)-2-benzyl-3-oxo-3,4-dihydropyrido[2,3-b]pyrazine (90 mg)

NMR (CDCl$_3$, δ): 2.28 (3H, s), 4.30 (2H, s), 7.05–7.35 (7H, m), 7.45–7.6 (3H, m), 8.18 (1H, dd, J=1.5 Hz, 8 Hz), 8.40 (1H, dd, J=1.5 Hz, 5 Hz)

EXAMPLE 5

1N aqueous solution of sodium hydroxide (2 ml) was added to a solution of 2-benzyl-4-(3-methoxycarbonylmethylphenyl)-3-oxo-3,4-dihydropyrido[2,3-b]pyrazine (213 mg) in methanol (4 ml) and 1,4-dioxane (2 ml). After stirred at room temperature for 1 hour, the mixture was acidified with dilute hydrochloric acid and extracted with ethyl acetate. The organic phase was washed with water and brine, dried over magnesium sulfate and concentrated to give 2-benzyl-4-(3-carboxymethylphenyl)-3-oxo-3,4-dihydropyrido[2,3-b]pyrazine (163 mg) as powder.

NMR (DMSO-d$_6$, δ): 3.64 (2H, s), 4.21 (2H, s), 7.15–7.65 (10H, m), 8.24 (1H, dd, J=1.5 Hz, 8 Hz), 8.38 (1H, dd, J=1.5 Hz, 5 Hz)

EXAMPLE 6

The following compounds were obtained according to a similar manner to that of Example 5.

(1) 2-Benzyl-4-(3-carboxyphenyl)-3-oxo-3,4-dihydropyrido[2,3-b]pyrazine

NMR (DMSO-d$_6$, δ): 4.22 (2H, s), 7.15–7.75 (8H, m), 7.92 (1H, s), 8.05 (1H, dt, J=8 Hz, 1.5 Hz), 8.24 (1H, dd, J=1.5 Hz, 8 Hz), 8.38 (1H, dd, J=1.5 Hz, 5 Hz)

(2) 2-Benzyl-4-(4-carboxyphenyl)-3-oxo-3,4-dihydropyrido[2,3-b]pyrazine

NMR (DMSO-d$_6$, δ): 4.22 (2H, s), 7.2–7.6 (8H, m), 8.10 (2H, d, J=9 Hz), 8.26 (1H, dd, J=1.5 Hz, 8 Hz), 8.38 (1H, dd, J=1.5 Hz, 5 Hz)

(3) 2-Benzyl-4-(4-carboxymethylphenyl)-3-oxo-3,4-dihydropyrido[2,3-b]pyrazine

NMR (DMSO-d$_6$, δ): 3.68 (2H, s), 4.21 (2H, s), 7.15–7.5 (10H, m), 8.23 (1H, dd, J=1.5 Hz, 8 Hz), 8.39 (1H, dd, J=1.5 Hz, 5 Hz)

EXAMPLE 7

A mixture of 2-benzyl-4-(3-carboxyphenyl)-3-oxo-3,4-dihydropyrido[2,3-b]pyrazine (143 mg), ethylamine hydrochloride (39 mg), 1-ethyl-3-(3-dimethylaminopropyl) carbodiimide hydrochloride (92 mg) and triethylamine (49 mg) in dichloromethane (2 ml) and N,N-dimethylformamide (1 ml) was stirred at room temperature for 3 hours. The mixture was poured into ethyl acetate and washed with water and brine, dried over magnesium sulfate and concentrated. The residue was subjected to preparative thin layer chromatography (hexane-ethyl acetate, 1:4) to afford 2-benzyl-4-(3-ethylcarbamoylphenyl)-3-oxo-3,4-dihydropyrido[2,3-b]pyrazine (16 mg) as powder.

NMR (CDCl$_3$, δ): 1.22 (3H, t, J=7 Hz), 3.48 (2H, m), 4.30 (2H, s), 6.14 (1H, br s), 7.2–7.45 (5H, m), 7.48 (2H, d, J=7 Hz), 7.6–7.7 (2H, m), 7.90 (1H, d, J=8 Hz), 8.19 (1H, d, J=8 Hz), 8.37 (1H, m)

EXAMPLE 8

The following compound was obtained according to a similar manner to that of Example 7.

2-Benzyl-4-(3-methylcarbamoylphenyl)-3-oxo-3,4-dihydropyrido[2,3-b]pyrazine

NMR (CDCl$_3$, δ): 2.98 (3H, d, J=7 Hz), 4.31 (2H, s), 6.22 (1H, br s), 7.2–7.55 (8H, m), 7.6–7.8 (2H, m), 7.88 (1H, d, J=8 Hz), 8.20 (1H, d, J=8 Hz), 8.37 (1H, m)

EXAMPLE 9

A mixture of 2-benzyl-4-(3-carboxyphenyl)-3-oxo-3,4-dihydropyrido[2,3-b]pyrazine (50 mg), 1-iodopropane (48 mg) and potassium carbonate (58 mg) in N,N-dimethylformamide (1 ml) was stirred at room temperature for 2 hours. The mixture was poured into ethyl acetate and washed with water and brine, dried over magnesium sulfate and concentrated. The residue was subjected to preparative thin layer chromatography (hexane-ethyl acetate, 1:1) to afford 2-benzyl-3-oxo-4-(3-propyloxycarbonylphenyl)-3,4-dihydropyrido[2,3-b]pyrazine (18 mg) as powder.

NMR (CDCl$_3$, δ): 0.99 (3H, t, J=7 Hz), 1.77 (2H, m), 4.2–4.35 (4H, m), 7.15–7.55 (7H, m), 7.66 (1H, t, J=8 Hz), 7.95 (1H, s), 8.19 (2H, dt, J=1.5 Hz, 8 Hz), 8.38 (1H, dt, J=1.5 Hz, 5 Hz)

EXAMPLE 10

A mixture of 2-benzyl-4-(3-carboxyphenyl)-3-oxo-3,4-dihydropyrido[2,3-b]pyrazine (166 mg), diphenylphosphoryl azide (128 mg) and triethylamine (47 mg) in ethanol (3 ml) was refluxed for 4 hours. The mixture was poured into ethyl acetate and washed with water and brine, dried over magnesium sulfate and concentrated. The residue was subjected to silica gel column chromatography (hexane-ethyl acetate, 1:1) to afford 2-benzyl-4-(3-ethoxycarbonylaminophenyl)-3-oxo-3,4-dihydropyrido[2,3-b]pyrazine (35 mg) as powder.

NMR (CDCl$_3$, δ): 1.27 (3H, t, J=7 Hz), 4.18 (2H, q, J=7 Hz), 4.30 (2H, s), 6.82 (1H, s), 6.94 (1H, dt, J=8 Hz, 1.5 Hz), 7.15–7.55 (9H, m), 8.18 (1H, dd, J=1.5 Hz, 8 Hz), 8.39 (1H, dd, J=1.5 Hz, 5 Hz)

EXAMPLE 11

A mixture of 4-(3-acetamidophenyl)-2-benzyl-3-oxo-3,4-dihydropyrido[2,3-b]pyrazine (6.03 g) in 3N hydrochloric acid (150 ml) was refluxed for 1 hour. Sodium bicarbonate was added thereto until the mixture was alkaline. The mixture was extracted with ethyl acetate and the organic solution was washed with water and brine, dried over magnesium sulfate and concentrated to give the solids. The solids were collected and washed with ethanol to give 4-(3-aminophenyl)-2-benzyl-3-oxo-3,4-dihydropyrido[2,3-b]pyrazine (5.05 g).

NMR (DMSO-d$_6$, δ): 4.20 (2H, s), 5.27 (2H, s), 6.39 (2H, d, J=8 Hz), 6.66 (1H, d, J=8 Hz), 7.1–7.45 (7H, m), 8.22 (1H, dd, J=1.5 Hz, 8 Hz), 8.41 (1H, dd, J=1.5 Hz, 5 Hz)

EXAMPLE 12

The following compounds were obtained according to a similar manner to that of Example 1.
(1) 4-[3-(3-Ethylureido)phenyl]-2-benzyl-3-oxo-3,4-dihydropyrido[2,3-b]pyrazine NMR (DMSO-d$_6$, δ): 1.03 (3H, t, J=7 Hz), 3.08 (2H, m), 4.20 (2H, s), 6.16 (1H, t, J=6 Hz), 6.82 (1H, m), 7.2–7.45 (9H, m), 8.22 (1H, d, J=8 Hz), 8.38 (1H, d, J=5 Hz), 8.60 (1H, s)
(2) 4-[3-(3-Phenylureido)phenyl]-2-benzyl-3-oxo-3,4-dihydropyrido[2,3-b]pyrazine NMR (DMSO-d$_6$, δ): 4.22 (2H, s), 6.9–7.0 (2H, m), 7.2–7.55 (13H, m), 8.23 (1H, dd, J=1.5 Hz, 8 Hz), 8.40 (1H, dd, J=1.5 Hz, 5 Hz), 8.72 (1H, s), 8.87 (1H, s)

EXAMPLE 13

To a solution of 4-(3-aminophenyl)-2-benzyl-3-oxo-3,4-dihydropyrido[2,3-b]pyrazine (200 mg) in acetic acid (2 ml) and water (2 ml) was added solution of potassium cyanate (99 mg) in water (1 ml). The mixture was stirred at room temperature for 2 hours and concentrated. The residue was dissolved in ethyl acetate and washed with an aqueous sodium bicarbonate solution, and brine, dried over magnesium sulfate and concentrated. The residue was subjected to silica gel column chromatography (4% methanol in chloroform) to afford 2-benzyl-3-oxo-4-(3-ureidophenyl)-3,4-dihydropyrido[2,3-b]pyrazine (78 mg) as solid.

NMR (DMSO-d$_6$, δ) 4.21 (2H, s), 5.92 (2H, s), 6.84 (1H, m), 7.15–7.5 (9H, m), 8.22 (1H, dd, J=1.5 Hz, 8 Hz), 8.39 (1H, dd, J=1.5 Hz, 5 Hz), 8.72 (1H, s)

EXAMPLE 14

A mixture of 4-(3-aminophenyl)-2-benzyl-3-oxo-3,4-dihydropyrido[2,3-b]pyrazine (150 mg), phenylisothiocyanate (79 mg) in 1,4-dioxane (2 ml) was stirred at 80° C. for 4 hours. The precipitates were collected and washed with isopropyl ether to give 2-benzyl-3-oxo-4-[3-(3-(phenyl)thioureido)phenyl]-3,4-dihydropyrido[2,3-b]pyrazine (113 mg).

NMR (DMSO-d$_6$, δ): 4.22 (2H, s), 7.05–7.55 (14H, m), 7.74 (1H, d, J=8 Hz), 8.24 (1H, dd, J=1.5 Hz, 8 Hz), 8.41 (1H, dd, J=1.5 Hz, 5 Hz), 9.86 (1H, s), 9.93 (1H, s)

EXAMPLE 15

The following compounds were obtained according to a similar manner to that of Example 1.
(1) 2-Benzyl-3-oxo-4-[3-(3-phenylsulfonylureido)phenyl]-3,4-dihydropyrido[2,3-b]pyrazine NMR (DMSO-d$_6$, 200 MHz, δ): 4.19 (2H, s), 6.98 (1H, m), 7.15–7.5 (9H, m), 7.55–7.75 (3H, m), 7.95 (2H, dd, J=1.5 Hz, 8 Hz), 8.21 (1H, dd, J=1.5 Hz, 8 Hz), 8.36 (1H, m), 9.09 (1H, s)
(2) 2-Benzyl-3-oxo-4-[3-(3-benzylureido)phenyl]-3,4-dihydropyrido[2,3-b]pyrazine NMR (DMSO-d$_6$, 200 MHz, δ): 4.21 (2H, s), 4.28 (1H, d, J=6 Hz), 6.70 (1H, t, J=6 Hz), 6.85 (1H, m), 7.15–7.5 (14H, m), 8.22 (1H, dd, J=1.5 Hz, 8 Hz), 8.39 (1H, dd, J=1.5 Hz, 5 Hz), 8.78 (1H, s)
(3) 2-Benzyl-3-oxo-4-[3-[3-(4-nitrophenyl)ureido]phenyl]-3,4-dihydropyrido[2,3-b]pyrazine NMR (DMSO-d$_6$, 200 MHz, δ): 4.22 (2H, s), 6.99 (1H, m), 7.2–7.6 (9H, m), 7.68 (2H, d, J=9 Hz), 8.15–8.3 (3H, m), 8.40 (1H, dd, J=1.5 Hz, 5 Hz), 9.23 (1H, s), 9.50 (1H, s)
(4) 2-Benzyl-3-oxo-4-[3-[3-(3-nitrophenyl)ureido]phenyl]-3,4-dihydropyrido[2,3-b]pyrazine NMR (DMSO-d$_6$, 200 MHz, δ) 4.23 (2H, s), 6.98 (1H, m), 7.2–7.9 (12H, m), 8.25 (1H, dd, J=1.5 Hz, 8 Hz), 8.40 (1H, dd, J=1.5 Hz, 5 Hz), 8.58 (1H, t, J=1.5 Hz), 9.07 (1H, s), 9.30 (1H, s)
(5) 2-Benzyl-3-oxo-4-[3-[3-(2-nitrophenyl)ureido]phenyl]-3,4-dihydropyrido[2,3-b]pyrazine NMR (DMSO-d$_6$, 200 MHz, δ): 4.22 (2H, s), 6.99 (1H, m), 7.15–7.6 (11H, m), 7.68 (1H, dt, J=1.5 Hz, 8 Hz), 8.09 (1H, dd, J=1.5 Hz, 8 Hz), 8.2–8.3 (2H, m), 8.40 (1H, dd, J=1.5 Hz, 5 Hz), 9.63 (1H, s), 10.05 (1H, s)
(6) 2-Benzyl-3-oxo-4-[3-[3-(4-methoxyphenyl)ureido]phenyl]-3,4-dihydropyrido[2,3-b]pyrazine NMR (DMSO-d$_6$, 200 MHz, δ): 3.71 (3H, s), 4.22 (2H, s), 6.8–6.95 (3H, m), 7.2–7.6 (11H, m), 8.24 (1H, dd, J=1.5 Hz, 8 Hz), 8.40 (1H, dd, J=1.5 Hz, 5 Hz), 8.52 (1H, s), 8.78 (1H, s)

(7) 2-Benzyl-3-oxo-4-[3-[3-(3-methoxyphenyl)ureido]phenyl]-3,4-dihydropyrido[2,3-b]pyrazine NMR (DMSO-$d_6$, 200 MHz, δ): 3.71 (3H, s), 4.22 (2H, s), 6.55 (1H, dd, J=1.5 Hz, 8 Hz), 6.85–7.00 (2H, m), 7.1–7.5 (10H, m), 7.55 (1H, s), 8.24 (1H, dd, J=1.5 Hz, 8 Hz), 8.40 (1H, dd, J=1.5 Hz, 8 Hz), 8.73 (1H, s), 8.86 (1H, s)

(8) 2-Benzyl-3-oxo-4-[3-[3-(2-methoxyphenyl)ureido]phenyl]-3,4-dihydropyrido[2,3-b]pyrazine NMR (DMSO-$d_6$, 200 MHz, δ): 3.88 (3H, s), 4.22 (2H, s), 6.8–7.1 (4H, m), 7.2–7.6 (1H, m), 8.08 (1H, dd, J=1.5 Hz, 8 Hz), 8.2–8.3 (2H, m), 8.39 (1H, dd, J=1.5 Hz, 5 Hz), 9.51 (1H, s)

(9) 2-Benzyl-3-oxo-4-[3-[3-(3-methylthiophenyl)ureido]phenyl]-3,4-dihydropyrido[2,3-b]pyrazine NMR (DMSO-$d_6$, 300 MHz, δ): 2.44 (3H, s), 4.22 (2H, s), 6.8–7.0 (2H, m), 7.1–7.6 (12H, m), 8.23 (1H, d), 8.40 (1H, d, J=5 Hz), 8.78 (1H, s), 8.89 (1H, s)

(10) 2-Benzyl-3-oxo-4-[3-[3-(4-trifluoromethylphenyl)ureido]phenyl]-3,4-dihydropyrido[2,3-b]pyrazine NMR (DMSO-$d_6$, 200 MHz, δ): 4.22 (2H, s), 6.97 (1H, m), 7.2–7.7 (13H, m), 8.24 (1H, dd, J=1.5 Hz, 8 Hz), 8.40 (1H, dd, J=1.5 Hz, 5 Hz), 9.01 (1H, s), 9.17 (1H, s)

(11) 2-Benzyl-3-oxo-4-[3-[3-(3,4-dichlorophenyl)ureido]phenyl]-3,4-dihydropyrido[2,3-b]pyrazine NMR (DMSO-$d_6$, 200 MHz, δ): 4.22 (2H, s), 6.97 (1H, m), 7.2–7.6 (11H, m), 7.88 (1H, d, J=3 Hz), 8.25 (1H, dd, J=1.5 Hz, 8 Hz), 8.40 (1H, dd, J=1.5 Hz, 5 Hz), 9.03 (1H, s), 9.07 (1H, s)

(12) 2-Benzyl-3-oxo-4-[3-(3-phenyl-1-methylureido)phenyl]3,4-dihydropyrido[2,3-b]pyrazine NMR (DMSO-$d_6$, 200 MHz, δ): 3.34 (3H, s), 4.22 (2H, s), 6.98 (1H, t, J=8 Hz), 7.15–7.65 (14H, m), 8.24 (1H, dd, J=1.5 Hz, 8 Hz), 8.32 (1H, s), 8.41 (1H, dd, J=1.5 Hz, 5 Hz)

EXAMPLE 16

The following compounds were obtained according to a similar manner to that of Example 2.

(1) 2-(4-Nitrophenyl)-3-oxo-4-phenyl-3,4-dihydropyrido[2,3-b]pyrazine

NMR (DMSO-$d_6$, 200 MHz, δ): 7.38–7.63 (6H, m), 8.35–8.54 (6H, m)

(2) 2-Benzyl-3-oxo-4-[3-(N-methylacetamido)phenyl]-3,4-dihydropyrido[2,3-b]pyrazine NMR (DMSO-$d_6$, 200 MHz, δ): 1.88 (3H, s), 3.20 (3H, s), 4.22 (2H, s), 7.15–7.65 (10H, m), 8.24 (1H, dd, J=1.5 Hz, 8 Hz), 8.40 (1H, dd, J=1.5 Hz, 5 Hz)

(3) 2-(3-Indolyl)-3-oxo-4-phenyl-3,4-dihydropyrido[2,3-b]pyrazine

NMR (DMSO-$d_6$, 200 MHz, δ): 6.62 (1H, dd, J=7 Hz, 9 Hz), 6.82 (1H, d, J=7 Hz), 6.88 (1H, dd, J=1 Hz, 9 Hz), 7.16–7.34 (3H, m), 7.34–7.75 (6H, m), 8.32 (1H, m), 8.90 (1H, m)

(4) 2-(3-Indolylmethyl)-3-oxo-4-phenyl-3,4-dihydropyrido[2,3-b]pyrazine

NMR (DMSO-$d_6$, 200 MHz, δ): 4.31 (2H, s), 7.12–6.93 (2H, m), 7.27 (1H, d, J=1 Hz), 7.28–7.40 (4H, m), 7.45–7.61 (3H, m), 7.67 (1H, d, J=10 Hz), 8.22 (1H, dd, J=1 Hz, 10 Hz), 8.36 (1H, dd, J=1 Hz, 5 Hz)

(5) 2-Phenethyl-3-oxo-4-phenyl-3,4-dihydropyrido[2,3-b]pyrazine

NMR (DMSO-$d_6$, 200 MHz, δ): 3.05–3.23 (4H, m), 7.15–7.60 (11H, m), 8.28 (1H, dd, J=1 Hz, 8 Hz), 8.39 (1H, dd, J=1 Hz, 5 Hz)

(6) 2-(3-Phenylpropyl)-3-oxo-4-phenyl-3,4-dihydropyrido[2,3-b]pyrazine

NMR (CDCl$_3$, 300 MHz, δ): 2.21 (2H, quint, J=7 Hz), 2.82 (2H, t, J=7 Hz), 3.06 (2H, t, J=7 Hz), 7.15–7.35 (8H, m), 7.49–7.63 (3H, m), 8.16 (1H, d, J=7 Hz), 8.41 (1H, dd, J=1 Hz, 7 Hz)

(7) 2-(2-Nitrobenzyl)-3-oxo-4-phenyl-3,4-dihydropyrido[2,3-b]pyrazine

NMR (DMSO-$d_6$, 200 MHz, δ): 4.63 (2H, s), 7.28–7.40 (3H, m), 7.48–7.80 (6H, m), 8.01 (1H, dd, J=1 Hz, 10 Hz), 8.12 (1H, dd, J=1 Hz, 10 Hz), 8.38 (1H, dd, J=1 Hz, 5 Hz)

(8) 2-Benzyl-3-oxo-4-phenyl-3,4-dihydropyrido[2,3-b]pyrazine

NMR (CDCl$_3$, 200 MHz, δ): 4.31 (2H, s), 7.20–7.38 (6H, m), 7.42–7.62 (5H, m), 8.18 (1H, dd, J=1 Hz, 8 Hz), 8.40 (1H, dd, J=1 Hz, 5 Hz)

(9) 2-Benzyl-3-oxo-4-(3-methoxycarbonylphenyl)-3,4-dihydropyrido[2,3-b]pyrazine

NMR (CDCl$_3$, 200 MHz, δ): 3.90 (3H, s), 4.32 (2H, s), 4.22–7.37 (4H, m), 7.45–7.53 (3H, m), 7.66 (1H, dd, J=9 Hz, 9 Hz), 7.95 (1H, dd, J=1 Hz, 1 Hz), 8.16–8.22 (2H, m), 8.38 (1H, dd, J=1 Hz, 5 Hz)

(10) 2-(4-Hydroxybenzyl)-3-oxo-4-(3-methoxycarbonylphenyl)-3,4-dihydropyrido[2,3-b]pyrazine NMR (DMSO-$d_6$, 200 MHz, δ): 3.87 (3H, s), 3.90 (2H, s), 6.70 (2H, d, J=8 Hz), 7.17 (2H, d, J=8 Hz), 7.39 (1H, dd, J=5 Hz, 9 Hz), 7.75–7.61 (2H, m), 7.98 (1H, m), 8.08 (1H, m), 8.24 (1H, dd, J=1 Hz, 9 Hz), 8.37 (1H, dd, J=1 Hz, 5 Hz), 9.27 (1H, br s)

(11) 3-Oxo-2-phenyl-4-[3-[3-(2-methoxyphenyl)ureido]phenyl]-3,4-dihydropyrido[2,3-b]pyrazine NMR (DMSO-$d_6$, δ): 3.87 (3H, s), 6.9–7.1 (4H, m), 7.3 (2H, m), 7.4–7.6 (6H, m), 7.65 (1H, s), 8.1 (1H, m), 8.3 (2H, m), 8.4 (1H, m), 9.55 (1H, s)

(12) 2-(2-Carboxyethyl)-3-oxo-4-[3-[3-(2-methoxyphenyl)ureido]phenyl]-3,4-dihydropyrido[2,3-b]pyrazine mp: 143–153° C. (dec.)

NMR (DMSO-$d_6$, δ): 2.78 (2H, t, J=7 Hz), 3.11 (2H, t, J=7 Hz), 3.88 (3H, s), 6.8–7.05 (4H, m), 7.45 (3H, m), 7.59 (1H, s), 8.10 (1H, d, J=7 Hz), 8.25 (1H, d, J=7 Hz), 8.29 (1H, s), 8.40 (1H, d, J=3 Hz), 9.53 (1H, s)

(13) 2-(4-Hydroxyphenylmethyl)-3-oxo-4-[3-[3-(2-methoxyphenyl)ureido]phenyl]-3,4-dihydropyrido[2,3-b]pyrazine mp: 220–221° C.

NMR (DMSO-$d_6$, δ): 3.88 (3H, s), 4.10 (2H, s), 6.70 (2H, d, J=8 Hz), 6.8–7.1 (4H, m), 7.18 (2H, d, J=8 Hz), 7.43 (3H, m), 7.55 (1H, s), 8.08 (1H, d, J=7 Hz), 8.25 (2H, m), 8.40 (1H, m), 9.26 (1H, s), 9.50 (1H, s)

(14) 2-(2-Nitrophenylmethyl)-3-oxo-4-[3-[3-(2-methoxyphenyl)ureido]phenyl]-3,4-dihydropyrido[2,3-b]pyrazine mp: 200–208° C. (dec.)

NMR (DMSO-$d_6$, δ): 3.90 (3H, s), 4.63 (2H, s), 6.8–7.1 (4H, m), 7.3–7.5 (3H, m), 7.6–7.7 (4H, m), 8.02 (1H, d, J=7 Hz), 8.10 (2H, m), 8.30 (1H, s), 8.40 (1H, m), 9.55 (1H, s)

(15) 4-(3-Acetamidophenyl)-2-(2-carboxyethyl)-3-oxo-3,4-dihydropyrido[2,3-b]pyrazine mp: 264–269° C. (dec.)

NMR (DMSO-$d_6$, δ): 2.05 (3H, s), 3.77 (2H, t, J=7 Hz), 3.09 (2H, t, J=7 Hz), 7.00 (1H, d, J=7 Hz), 7.4 (3H, m), 7.60 (1H, d, J=7 Hz), 7.64 (1H, s), 8.21 (1H, d, J=7 Hz), 8.38 (1H, d, J=3 Hz)

(16) 4-(3-Acetamidophenyl)-2-benzyl-6-ethoxy-3-oxo-3,4-dihydropyrido[2,3-b]pyrazine mp: 212–214° C.

NMR (DMSO-$d_6$, δ): 1.25 (3H, t, J=7 Hz), 2.08 (3H, s), 4.15 (5H, m), 6.70 (1H, d, J=8 Hz), 7.05 (3H, m), 7.20 (3H, m), 7.47 (1H, dd, J=8 Hz, 8 Hz), 7.61 (1H, m), 7.75 (1H, s), 7.98 (1H, d, J=8 Hz)

(17) 2-Benzyl-3-oxo-4-[3-((E)-2-methoxycarbonylvinyl)phenyl]-3,4-dihydropyrido[2,3-b]pyrazine NMR (CDCl$_3$, 300 MHz, δ): 3.78 (3H, s), 4.31 (2H, s), 6.43 (1H, d, J=16 Hz), 7.2–7.35 (5H, m), 7.42 (1H, s), 7.50

(2H, d, J=8 Hz), 7.55–7.75 (3H, m), 8.19 (1H, dd, J=1.5 Hz, 8 Hz), 8.38 (1H, dd, J=1.5 Hz, 5 Hz)

(18) 2-Benzyl-3-oxo-4-[3-((E)-2-cyanovinyl)phenyl]-3,4-dihydropyrido[2,3-b]pyrazine NMR (CDCl$_3$, 300 MHz, δ): 4.30 (2H, S), 6.88 (1H, J=16 Hz), 7.2–7.65 (11H, m), 8.20 (1H, dd, J=1.5 Hz, 8 Hz), 8.38 (1H, dd, J=1.5 Hz, 5 Hz)

(19) 4-[3-((E)-2-Benzoylvinyl)phenyl]-3-oxo-2-benzyl-3,4-dihydropyrido[2,3-b]pyrazine NMR (CDCl$_3$, 300 MHz, δ): 4.32 (2H, s), 7.2–7.35 (5H, m), 7.45–7.65 (8H, m), 7.77 (1H, d, J=8 Hz), 7.82 (1H, d, J=16 Hz), 7.98 (2H, dd, J=1.5 Hz, 8 Hz), 8.20 (1H, dd, J=1.5 Hz, 8 Hz), 8.39 (1H, dd, J=1.5 Hz, 5 Hz)

(20) 2-Benzyl-3-oxo-4-[3-[2-(2-naphthyl)ethyl]phenyl]-3,4-dihydropyrido[2,3-b]pyrazine NMR (DMSO-d$_6$, 300 MHz, δ): 2.95–3.15 (4H, m), 4.12 (2H, s), 7.17 (1H, d, J=8 Hz), 7.2–7.5 (12H, m), 7.76 (3H, m), 8.23 (1H, d, J=8 Hz), 8.38 (1H, d, J=5 Hz)

(21) 2-Benzyl-4-[3-[(E)-2-(2-naphthyl)vinyl]phenyl]-3,4-dihydropyrido[2,3-b]pyrazine NMR (DMSO-d$_6$, 300 MHz, δ): 4.24 (2H, s), 7.2–7.6 (12H, m), 7.67 (1H, s), 7.75 (1H, d, J=8 Hz), 7.85–7.95 (4H, m), 7.99 (1H, s), 8.27 (1H, dd, J=1.5 Hz, 8 Hz), 8.42 (1H, dd, J=1.5 Hz, 5 Hz)

(22) 2-Benzyl-3-oxo-4-(3-phenethylphenyl)-3,4-dihydropyrido[2,3-b]pyrazine

NMR (DMSO-d$_6$, 300 MHz, δ): 4.22 (2H, s), 7.1–7.5 (15H, m), 8.23 (1H, d, J=8 Hz), 8.39 (1H, d, J=5 Hz)

(23) 2-Benzyl-3-oxo-4-((E)-3-styrylphenyl)-3,4-dihydropyrido[2,3-b]pyrazine

NMR (DMSO-d$_6$, 300 MHs, δ): 4.22 (2H, s), 7.2–7.45 (12H, m), 7.5–7.65 (4H, m), 7.68 (1H, dd, J=1 Hz, 8 Hz), 8.25 (1H, d, J=8 Hz), 8.39 (1H, d, J=5 Hz)

(24) 2-Benzyl-3-oxo-4-[3-(3-indolizinylcarbonyl)phenyl]-3,4-dihydropyrido[2,3-b]pyrazine NMR (CDCl$_3$, 300 MHz, δ): 4.35 (2H, s), 6.54 (1H, d, J=5 Hz), 6.95 (1H, m), 7.15–7.35 (5H, m), 7.45–7.6 (5H, m), 7.65–7.75 (2H, m), 7.97 (1H, d, J=8 Hz), 8.19 (1H, d, J=8 Hz), 8.42 (1H, d, J=5 Hz), 9.96 (1H, d, J=7 Hz)

(25) 2-Benzyl-3-oxo-4-[3-(4-methoxybenzoyl)phenyl]-3,4-dihydropyrido[2,3-b]pyrazine NMR (CDCl$_3$, 300 MHz, δ): 3.98 (3H, s), 4.41 (2H, s), 7.05 (2H, d, J=8 Hz), 7.3–7.45 (4H, m), 7.55–7.65 (3H, m), 7.75–7.85 (2H, m), 7.95–8.05 (3H, m), 8.28 (1H, d, J=8 Hz), 8.49 (1H, d, J=5 Hz)

(26) 2-Benzyl-3-oxo-4-[3-(imidazol-4-yl)phenyl]-3,4-dihydropyrido[2,3-b]pyrazine NMR (DMSO-d$_6$, 300 MHz, δ): 4.22 (2H, s), 7.12 (1H, d, J=8 Hz), 7.15–7.8 (10H, m), 7.88 (1H, d, J=8 Hz), 8.24 (1H, d, J=8 Hz), 8.38 (1H, d, J=5 Hz), 12.19 (1H, br s)

(27) 2-Benzyl-3-oxo-4-[3-[2-(pyridin-3-yl)thiazol-4-yl]phenyl]-3,4-dihydropyrido[2,3-b]pyrazine NMR (DMSO-d$_6$, 300 MHz, δ): 4.23 (2H, s), 7.2–7.45 (7H, m), 7.55 (1H, dd, J=5 Hz, 8 Hz), 7.66 (1H, t, J=8 Hz), 8.07 (1H, t, J=1.5 Hz), 8.18 (1H, d, J=8 Hz), 8.26 (1H, d, J=8 Hz), 8.3–8.4 (3H, m), 8.68 (1H, d, J=5 Hz), 9.20 (1H, d, J=1.5 Hz)

(28) 4-[3-(2-Aminothiazol-4-yl)phenyl]-3-oxo-2-benzyl-3,4-dihydropyrido[2,3-b]pyrazine NMR (DMSO-d$_6$, 300 MHz, δ): 4.22 (2H, s), 7.04 (3H, s), 7.2–7.45 (7H, m), 7.52 (1H, t, J=8 Hz), 7.72 (1H, s), 7.89 (1H, d, J=8 Hz), 8.23 (1H, d, J=8 Hz), 8.38 (1H, d, J=5 Hz)

(29) 2-Benzyl-3-oxo-4-[3-(4-phenylpyrimidin-2-yl)oxyphenyl]-3,4-dihydropyrido[2,3-b]pyrazine NMR (DMSO-d$_6$, 300 MHz, δ): 4.21 (2H, s), 7.15–7.65 (13H, m), 7.87 (1H, d, J=5 Hz), 8.13 (2H, d, J=8 Hz), 8.23 (1H, d, J=8 Hz), 8.44 (1H, d, J=5 Hz), 8.72 (1H, d, J=5 Hz)

(30) 2-Benzyl-3-oxo-4-[3-(pyrimidin-2-yl)oxyphenyl]-3,4-dihydropyrido[2,3-b]pyrazine NMR (DMSO-d$_6$, 300 MHz, δ): 4.21 (2H, s), 7.15–7.5 (10H, m), 7.58 (1H, t, J=8 Hz), 8.23 (1H, d, J=8 Hz), 8.42 (1H, d, J=5 Hz), 8.67 (2H, d, J=5 Hz)

(31) 2-Benzyl-3-oxo-4-[3-(pyrimidin-2-yl)aminophenyl]-3,4-dihydropyrido[2,3-b]pyrazine NMR (DMSO-d$_6$, 300 MHz, δ): 4.23 (2H, s), 6.8–6.95 (2H, m), 7.2–7.5 (7H, m), 7.77 (1H, s), 7.83 (1H, d, J=8 Hz), 8.24 (1H, d, J=8 Hz), 8.40 (1H, d, J=5 Hz), 8.47 (2H, d, J=5 Hz), 9.84 (1H, s)

(32) 2-Benzyl-3-oxo-4-[3-(4-methylthiazol-2-yl)aminophenyl]-3,4-dihydropyrido[2,3-b]pyrazine NMR (DMSO-d$_6$, 300 MHz, δ): 2.17 (3H, s), 4.21 (2H, s), 6.46 (1H, s), 6.86 (1H, d, J=8 Hz), 7.2–7.5 (8H, m), 7.75 (1H, m), 8.23 (1H, d, J=8 Hz), 8.39 (1H, d, J=5 Hz)

(33) 2-Benzyl-3-oxo-4-[3-(4-phenylthiazol-2-yl)aminophenyl]-3,4-dihydropyrido[2,3-b]pyrazine NMR (DMSO-d$_6$, 300 MHz, δ): 4.23 (2H, s), 6.94 (1H, d, J=8 Hz), 7.2–7.6 (12H, m), 7.83 (2H, d, J=8 Hz), 7.94 (1H, d, J=8 Hz), 8.26 (1H, d, J=8 Hz), 8.42 (1H, d, J=5 Hz)

(34) 2-Benzyl-3-oxo-4-(3-biphenylyl)-3,4-dihydropyrido[2,3-b]pyrazine

NMR (CDCl$_3$, 300 MHz, δ): 4.33 (2H, s), 7.2–7.8 (15H, m), 8.20 (1H, dd, J=1.5 Hz, 8 Hz), 8.41 (1H, dd, J=1.5 Hz, 5 Hz)

(35) 2-Benzyl-3-oxo-4-(3-cyanophenyl)-3,4-dihydropyrido[2,3-b]pyrazine

NMR (CDCl$_3$, 300 MHz, δ): 4.30 (2H, s), 7.2–7.35 (4H, m), 7.45–7.85 (6H, m), 8.21 (1H, dd, J=1.5 Hz, 8 Hz), 8.37 (1H, dd, J=1.5 Hz, 5 Hz)

(36) 2-Benzyl-3-oxo-4-(3-chlorophenyl)-3,4-dihydropyrido[2,3-b]pyrazine

NMR (DMSO-d$_6$, 300 MH, δ): 4.22 (2H, s), 7.12 (1H, d, J=8 Hz), 7.2–7.75 (8H, m), 7.88 (1H, s), 8.23 (1H, d, J=8 Hz), 8.38 (1H, d, J=5 Hz)

(37) 2-Benzyl-3-oxo-4-(3-nitrophenyl)-3,4-dihydropyrido[2,3-b]pyrazine

NMR (CDCl$_3$, 300 MHz, δ): 4.32 (2H, s), 7.2–7.4 (4H, m), 7.48 (2H, d, J=7 Hz), 7.64 (1H, d, J=8 Hz), 7.76 (1H, t, J=8 Hz), 8.2–8.3 (1H, m), 8.35–8.45 (1H, m)

EXAMPLE 17

The following compound was obtained according to a similar manner to that of Example 11.

2-Benzyl-3-oxo-4-(3-methylaminophenyl)-3,4-dihydropyrido[2,3-b]pyrazine

NMR (DMSO-d$_6$, 200 MHz, δ): 2.67 (3H, d, J=5 Hz), 4.21 (2H, s), 5.85 (1H, q, J=5 Hz), 6.4–6.5 (2H, m), 6.62 (1H, d, J=8 Hz), 7.15–7.45 (7H, m), 8.22 (1H, dd, J=1.5 Hz, 8 Hz), 8.40 (1H, dd, J=1.5 Hz, 5 Hz)

EXAMPLE 18

The following compounds were obtained according to a similar manner to that of Example 14.

(1) 2-Benzyl-3-oxo-4-[3-[3-benzoyl(thioureido)]phenyl]-3,4-dihydropyrido[2,3-b]pyrazine NMR (DMSO-d$_6$, 200 MHz, δ): 4.23 (2H, s), 7.2–7.8 (13H, m), 7.9–8.05 (3H, m), 8.25 (1H, dd, J=1.5 Hz, 8 Hz), 8.42 (1H, dd, J=1.5 Hz, 5 Hz)

(2) 2-Benzyl-3-oxo-4-[3-[3-(1-naphthyl)(thioureido)]phenyl]-3,4-dihydropyrido[2,3-b]pyrazine NMR (DMSO-d$_6$, 200 MHz, δ): 4.21 (2H, s), 7.05–7.55 (13H, m), 7.75–8.05 (4H, m), 8.23 (1H, dd, J=1.5 Hz, 8 Hz), 8.39 (1H, dd, J=1.5 Hz, 5 Hz), 9.90 (1H, s), 9.97 (1H, s)

EXAMPLE 19

A mixture of 1-naphthylacetic acid (82 mg), oxalyl chloride (0.02 ml) and catalytic amount of N,N- dimethylformamide in dichloromethane (2 ml) was stirred at room temperature for 30 minutes. The above solution was added to a mixture of 4-(3-aminophenyl)-3-oxo-2-benzyl-3,4-dihydropyrido[2,3-b]pyrazine (131 mg) and triethylamine (0.085 ml) in dichloromethane (2 ml). The mixture was stirred at room temperature for 30 minutes, then poured into a mixture of ethyl acetate add water. The organic phase was washed with aqueous sodium bicarbonate solution and brine, dried over magnesium sulfate and concentrated. The residue was crystallized with ethanol to give 2-benzyl-3-oxo-4-[3-[(1-naphthyl)acetylamino]phenyl]-3,4-dihydropyrido[2,3-b]pyrazine (123 mg).

NMR (DMSO-$d_6$, 200 MHz, δ): 4.16 (2H, s), 4.19 (2H, s), 7.01 (1H, d, J=8 Hz), 7.2–7.7 (13H, m), 7.8–8.0 (2H, m), 8.12 (1H, m), 8.21 (1H, dd, J=1.5 Hz, 8 Hz), 8.37 (1H, dd, J=1.5 Hz, 5 Hz)

EXAMPLE 20

To a mixture of 4-(3-aminophenyl)-3-oxo-2-benzyl-3,4-dihydropyrido[2,3-b]pyrazine (150 mg), benzylsulfonyl chloride (96 mg) and pyridine (0.04 ml) in 1,4-dioxane (3 ml) was stirred at 80° C. for 2 hours. The mixture was poured into a mixture of ethyl acetate and water. The organic phase was washed with water and brine, dried over magnesium sulfate, concentrated, and subjected to silica gel column chromatography (hexane-ethyl acetate 1:1) to afford 4-(3-benzylsulfonylaminophenyl)-3-oxo-2-benzyl-3,4-dihydropyrido[2,3-b]pyrazine (49 mg) as a solid.

NMR (DMSO-$d_6$, 300 MHz, δ): 4.23 (2H, s), 4.51 (2H, s), 7.0–7.7 (15H, m), 8.25 (1H, dd, J=1.5 Hz, 8 Hz), 8.40 (1H, dd, J=1.5 Hz, 5 Hz)

EXAMPLE 21

To a mixture of 4-(3-aminophenyl)-3-oxo-2-benzyl-3,4-dihydropyrido[2,3-b]pyrazine (131 mg) and triethylamine (0.067 ml) in dichloromethane (3 ml) was added benzoyl chloride (0.056 ml). The mixture was stirred at room temperature for 30 minutes, then poured into a mixture of ethyl acetate and aqueous sodium bicarbonate solution. The organic phase was separated, washed with brine, dried over magnesium sulfate and concentrated. The residue was crystallized from isopropyl ether to give 4-(3-benzoylaminophenyl)-3-oxo-2-benzyl-3,4-dihydropyrido[2,3-b]pyrazine (110 mg).

NMR (DMSO-$d_6$, 300 MHz, δ): 4.22 (2H, s), 7.08 (1H, d, J=8 Hz), 7.2–7.65 (10H, m), 7.75–7.85 (2H, m), 7.96 (2H, d, J=8 Hz), 8.25 (1H, d, J=8 Hz), 8.40 (1H, m)

EXAMPLE 22

The following compounds were obtained according to similar manners to those of Examples 19, 20 and 21.

(1) 2-Benzyl-3-oxo-4-[(3-cinnamoylamino)phenyl]-3,4-dihydropyrido[2,3-b]pyrazine NMR (DMSO-$d_6$, 300 MHz, δ): 4.22 (2H, s), 6.85 (1H, d, J=16 Hz), 7.05 (1H, d, J=8 Hz), 7.2–7.8 (15H, m), 8.25 (1H, d, J=8 Hz), 8.40 (1H, d, J=5 Hz)

(2) 2-Benzyl-3-oxo-4-[3-(4-isobutylcinnamoylamino)phenyl]-3,4-dihydropyrido[2,3-b]pyrazine NMR (DMSO-$d_6$, 300 MHz, δ): 0.88 (6H, d, J=7 Hz), 1.86 (1H, m), 2.48 (2H, d, J=7 Hz), 4.22 (2H, s), 6.78 (1H, d, J=16 Hz), 7.03 (1H, d, J=8 Hz), 7.2–7.6 (12H, m), 7.7–7.8 (2H, m), 8.25 (1H, d, J=8 Hz), 8.40 (1H, d, J=5 Hz)

(3) 2-Benzyl-3-oxo-4-[3-(3,4-dimethoxybenzoylamino)phenyl]-3,4-dihydropyrido[2,3-b]pyrazine NMR (DMSO-$d_6$, 300 MHz, δ): 3.83 (6H, s), 4.22 (2H, s), 7.0–7.1 (2H, m), 7.2–7.55 (8H, m), 7.62 (1H, d, J=8 Hz), 7.72 (1H, s), 8.87 (1H, d, J=8 Hz), 8.25 (1H, d, J=8 Hz), 8.40 (1H, d, J=5 Hz)

(4) 2-Benzyl-3-oxo-4-[3-(diphenylacetylamino)phenyl]-3,4-dihydropyrido[2,3-b]pyrazine NMR (DMSO-$d_6$, 300 MHz, δ): 4.20 (2H, s), 5.18 (1H, s), 7.02 (1H, d, J=8 Hz), 7.2–7.5 (17H, m), 7.62 (1H, d, J=8 Hz), 7.69 (1H, t, J=1.5 Hz), 8.22 (1H, d, J=8 Hz), 8.36 (1H, d, J=5 Hz)

(5) 2-Benzyl-3-oxo-4-[3-((E)-3-phenyl-2-methylpropenoylamino)phenyl]-3,4-dihydropyrido[2,3-b]pyrazine NMR (DMSO-$d_6$, 300 MHz, δ): 2.10 (3H, s), 4.22 (2H, s), 7.05 (1H, d, J=8 Hz), 7.2–7.55 (12H, m), 7.7–7.8 (3H, m), 8.25 (1H, d, J=8 Hz), 8.40 (1H, d, J=5 Hz)

(6) 2-Benzyl-3-oxo-4-[3-(3,4-dichlorobenzoylamino)phenyl]-3,4-dihydropyrido[2,3-b]pyrazine NMR (DMSO-$d_6$, 300 MHz, δ): 4.22 (2H, s), 7.11 (1H, d, J=8 Hz), 7.2–7.45 (6H, m), 7.54 (1H, t, J=8 Hz), 7.75–7.85 (3H, m), 7.92 (1H, dd, J=1.5 Hz, 8 Hz), 8.2–8.3 (2H, m), 8.40 (1H, d, J=5 Hz)

(7) 2-Benzyl-3-oxo-4-[3-(cyclohexylideneacetylamino)phenyl]-3,4-dihydropyrido[2,3-b]pyrazine NMR (DMSO-$d_6$, 200 MHz, δ): 1.45–1.7 (6H, m), 2.1–2.25 (2H, m), 2.75–2.9 (2H, m), 4.22 (2H, s), 5.81 (1H, s), 6.98 (1H, d, J=8 Hz), 7.15–7.5 (7H, m), 7.59 (1H, d, J=8 Hz), 7.71 (1H, t, J=1.5 Hz), 8.23 (1H, dd, J=1.5 Hz, 8 Hz), 8.39 (1H, dd, J=1.5 Hz, 5 Hz), 10.07 (1H, s)

(8) 2-Benzyl-3-oxo-4-[3-(3,4-methylenedioxybenzoylamino)phenyl]-3,4-dihydropyrido[2,3-b]pyrazine NMR (DMSO-$d_6$, 300 MHz, δ): 4.30 (2H, s), 6.01 (2H, s), 6.78 (1H, d, J=8 Hz), 6.86 (1H, d, J=8 Hz), 7.1–7.35 (5H, m), 7.4–7.5 (3H, m), 7.6–7.7 (2H, m), 8.15–8.25 (2H, m), 8.40 (1H, m)

(9) 2-Benzyl-3-oxo-4-[3-(2-thienylcarbonylamino)phenyl]-3,4-dihydropyrido[2,3-b]pyrazine NMR (DMSO-$d_6$, 300 MHz, δ): 4.22 (2H, s), 7.06 (1H, d, J=8 Hz), 7.15–7.45 (7H, m), 7.54 (1H, t, J=8 Hz), 7.68 (1H, m), 7.75–7.9 (2H, m), 8.04 (1H, t, J=1.5 Hz), 8.25 (1H, d, J=8 Hz), 8.40 (1H, d, J=5 Hz), 10.42 (1H, s)

(10) 2-Benzyl-3-oxo-4-[3-(2,4-hexadienoylamino)phenyl]-3,4-dihydropyrido[2,3-b]pyrazine NMR (CDCl$_3$, 300 MHz, δ): 1.81 (3H, d, J=6 Hz), 4.32 (2H, s), 5.60 (1H, d, J=16 Hz), 5.95–6.1 (2H, m), 6.83 (1H, d, J=8 Hz), 7.1–7.55 (10H, m), 8.22 (1H, dd, J=1.5 Hz, 8 Hz), 8.40 (1H, dd, J=1.5 Hz, 5 Hz)

(11) 4-[3-[3-(Benzoylamino)benzoylamino]phenyl]-3-oxo-2-benzyl-3,4-dihydropyrido[2,3-b]pyrazine NMR (DMSO-$d_6$, 300 MHz, δ): 4.22 (2H, s), 7.08 (1H, dt, J=8 Hz, 1.5 Hz), 7.2–7.65 (11H, m), 7.69 (1H, dt, J=8 Hz, 1.5 Hz), 7.8–7.9 (2H, m), 7.95–8.05 (3H, m), 8.24 (1H, dd, J=1.5 Hz, 8 Hz), 8.31 (1H, t, J=1.5 Hz), 8.41 (1H, dd, J=1.5 Hz, 5 Hz)

(12) 2-Benzyl-3-oxo-4-[3-[3-[(pyrimidin-2-yl)oxy]benzoylamino]phenyl]-3,4-dihydropyrido[2,3-b]pyrazine NMR (CDCl$_3$, 300 MHz, δ): 4.24 (2H, s), 6.78 (1H, d, J=8 Hz), 6.98 (1H, t, J=5 Hz), 7.0–7.1 (1H, m), 7.17 (2H, t, J=8 Hz), 7.25–7.5 (7H, m), 7.6–7.7 (2H, m), 7.77 (1H, d, J=8 Hz), 8.19 (1H, d, J=8 Hz), 8.41 (1H, m), 8.45–8.55 (3H, m)

(13) 2-Benzyl-3-oxo-4-[3-[3-[(3-nitropyridin-2-yl)amino]benzoylamino]phenyl]-3,4-dihydropyrido[2,3-b]pyrazine NMR (CDCl$_3$, 300 MHz, δ): 4.28 (2H, s), 6.8–6.9 (2H, m), 7.05–7.8 (13H, m), 8.15–8.25 (2H, m), 8.35–8.55 (3H, m), 10.14 (1H, s)

(14) 2-Benzyl-3-oxo-4-[3-(4-biphenylylcarbonylamino)phenyl]-3,4-dihydropyrido[2,3-b]pyrazine NMR (DMSO-$d_6$, 300 MHz, δ): 4.23 (2H, s), 7.08 (1H, d, J=8 Hz), 7.2–7.6 (10H, m), 7.77 (2H, d, J=8 Hz), 7.8–7.9

(4H, m), 8.07 (2H, d, J=8 Hz), 8.25 (1H, d, J=8 Hz), 8.41 (1H, d, J=5 Hz)

(15) 2-Benzyl-3-oxo-4-(3-cyclohexylcarbonylaminophenyl)-3,4-dihydropyrido[2,3-b]pyrazine NMR (DMSO-$d_6$, 300 MHz, δ): 1.1–1.5 (5H, m), 1.6–1.9 (5H, m), 2.32 (1H, m), 4.21 (2H, s), 6.98 (1H, d, J=8 Hz), 7.2–7.5 (7H, m), 7.59 (1H, d, J=8 Hz), 7.67 (1H, t, J=1.5 Hz), 8.23 (1H, d, J=8 Hz), 8.38 (1H, m)

(16) 2-Benzyl-3-oxo-4-[3-(3-phenylpropionylamino)phenyl]-3,4-dihydropyrido[2,3-b]pyrazine NMR (DMSO-$d_6$, 300 MHz, δ): 2.64 (2H, t, J=7 Hz), 2.89 (2H, t, J=7 Hz), 4.20 (2H, s), 6.98 (1H, d, J=8 Hz), 7.1–7.7 (14H, m), 8.23 (1H, d, J=8 Hz), 8.38 (1H, d, J=5 Hz)

(17) 2-Benzyl-3-oxo-4-[3-(4-propylbenzoylamino)phenyl]-3,4-dihydropyrido[2,3-b]pyrazine NMR (DMSO-$d_6$, 300 MHz, δ): 0.90 (3H, t, J=7 Hz), 1.62 (2H, m), 2.62 (2H, t, J=7 Hz), 4.22 (2H, s), 7.07 (1H, d, J=8 Hz), 7.2–7.6 (9H, m), 7.75–7.9 (4H, m), 8.25 (1H, d, J=8 Hz), 8.40 (1H, d, J=5 Hz)

(18) 2-Benzyl-3-oxo-4-[3-(4-chlorobenzoylamino)phenyl]-3,4-dihydropyrido[2,3-b]pyrazine NMR (DMSO-$d_6$, 300 MHz, δ): 4.22 (2H, s), 7.08 (1H, d, J=8 Hz), 7.2–7.45 (6H, m), 7.52 (1H, t, J=8 Hz), 7.62 (2H, d, J=8 Hz), 7.75–7.85 (2H, m), 7.98 (2H, d, J=8 Hz), 8.24 (1H, d, J=8 Hz), 8.39 (1H, d, J=5 Hz)

(19) 2-Benzyl-3-oxo-4-[3-(3-nitrobenzoylamino)phenyl]-3,4-dihydropyrido[2,3-b]pyrazine NMR (DMSO-$d_6$, 300 MHz, δ): 4.22 (2H, s), 7.13 (1H, d, J=8 Hz), 7.2–7.45 (7H, m), 7.57 (1H, t, J=8 Hz), 7.75–7.9 (3H, m), 8.27 (1H, d, J=8 Hz), 8.35–8.5 (3H, m), 8.80 (1H, s)

(20) 2-Benzyl-3-oxo-4-[3-(4-nitrobenzoylamino)phenyl]-3,4-dihydropyrido[2,3-b]pyrazine NMR (DMSO-$d_6$, 300 MHz, δ): 4.22 (2H, s), 7.12 (1H, d, J=8 Hz), 7.2–7.45 (6H, m), 7.55 (1H, t, J=8 Hz), 8.35–8.45 (2H, m), 8.18 (2H, d, J=8 Hz), 8.25 (1H, d, J=8 Hz), 8.35–8.45 (3H, m)

(21) 2-Benzyl-3-oxo-4-[3-(2-naphthoylamino)phenyl]-3,4-dihydropyrido[2,3-b]pyrazine NMR (DMSO-$d_6$, 300 MHz, δ): 4.24 (2H, s), 7.11 (1H, d, J=8 Hz), 7.2–7.75 (9H, m), 7.8–8.2 (6H, m), 8.27 (1H, d, J=8 Hz), 8.42 (1H, d, J=5 Hz), 8.60 (1H, s)

(22) 2-Benzyl-3-oxo-4-[3-(1-naphthoylamino)phenyl]-3,4-dihydropyrido[2,3-b]pyrazine NMR (DMSO-$d_6$, 300 MHz, δ): 4.24 (2H, s), 7.11 (1H, d, J=8 Hz), 7.2–7.7 (10H, m), 7.75–7.85 (2H, m), 7.92 (1H, s), 8.0–8.3 (4H, m), 8.43 (1H, d, J=5 Hz)

(23) 2-Benzyl-3-oxo-4-(3-isonicotinoylaminophenyl)-3,4-dihydropyrido[2,3-b]pyrazine NMR (DMSO-$d_6$, 300 MHz, δ): 4.22 (2H, s), 7.12 (1H, d, J=8 Hz), 7.2–7.45 (6H, m), 7.55 (1H, t, J=8 Hz), 7.75–7.9 (4H, m), 8.25 (1H, d, J=8 Hz), 8.40 (1H, m), 8.78 (2H, d, J=5 Hz)

(24) 2-Benzyl-3-oxo-4-(3-nicotinoylaminophenyl)-3,4-dihydropyrido[2,3-b]pyrazine NMR (DMSO-$d_6$, 300 MHz, δ): 4.22 (2H, s), 7.11 (1H, d, J=8 Hz), 7.2–7.6 (8H, m), 7.75–7.9 (2H, m), 8.2–8.35 (2H, m), 8.40 (1H, d, J=5 Hz), 8.77 (1H, d, J=5 Hz), 9.10 (1H, s)

(25) 2-Benzyl-3-oxo-4-[3-(N-methyl-N-benzoylamino)phenyl]-3,4-dihydropyrido[2,3-b]pyrazine NMR (CDCl$_3$, 300 MHz, δ): 3.52 (3H, s), 4.28 (2H, s), 6.98 (1H, t, J=1.5 Hz), 7.06 (1H, dd, J=1.5 Hz, 8 Hz), 7.1–7.5 (13H, m), 8.15 (1H, dd, J=1.5 Hz, 8 Hz), 8.27 (1H, dd, J=1.5 Hz, 5 Hz)

EXAMPLE 23

To a stirred solution of 4-[3-[3-(2-methoxyphenyl)ureido]phenyl]-3-oxo-2-(2-carboxyethyl)-3,4-dihydropyrido[2,3-b]pyrazine (2.30 g) and N-hydroxysuccinimide (1.15 g) was added 1-ethyl-3-(3-dimethylaminopropyl)carbodiimide (1.20 g) and the resulting mixture was stirred for 24 hours. The reaction mixture was concentrated, diluted with ethyl acetate, washed with a saturated sodium bicarbonate solution, water and brine, and dried over magnesium sulfate. After evaporation of the solvent, the residue was triturated with ether to give 4-[3-[3-(2-methoxyphenyl)ureido]phenyl]-3-oxo-2-[2-succinimidooxycarbonylethyl]-3,4-dihydropyrido[2,3-b]pyrazine (2.35 g) as a solid.

mp: 235–237° C.

NMR (DMSO-$d_6$, δ): 1.79 (2H, m), 1.94 (2H, m), 2.78 (2H, t, J=7 Hz), 3.12 (2H, t, J=7 Hz), 3.30 (2H, t, J=7 Hz), 3.54 (2H, t, J=7 Hz), 3.88 (3H, s), 6.8–7.05 (4H, m), 7.4 (3H, m), 7.58 (1H, s), 8.09 (1H, d, J=7 Hz), 8.20 (1H, d, J=7 Hz), 8.29 (1H, s), 8.40 (1H, m), 9.53 (1H, s)

EXAMPLE 24

To a solution of 2-[2-succinimidooxycarbonylethyl]-4-[3-[3-(2-methoxyphenyl)ureido]phenyl]-3-oxo-3,4-dihydropyrido[2,3-b]pyrazine (0.28 g) in dioxane was added a solution of dimethylamine hydrochloride (81 mg) in water and triethylamine (101 mg). The mixture was stirred for 18 hours, diluted with ethyl acetate, washed with water. After removal of the solvents, crude residue was crystallized from ethanol to give 2-[2-(N,N-dimethylcarbamoyl)ethyl]-3-oxo-4-[3-[3-(2-methoxyphenyl)ureido]phenyl]-3,4-dihydropyrido[2,3-b]pyrazine.

mp: 242–245° C.

NMR (DMSO-$d_6$, δ): 2.85 (3H, s), 2.87 (2H, m), 3.06 (3H, s), 3.10 (2H, m), 3.88 (3H, s), 6.8–7.05 (4H, m), 7.40 (3H, m), 7.58 (1H, s), 8.09 (1H, d, J=7 Hz), 8.22 (1H, d, J=7 Hz), 8.28 (1H, s), 8.39 (1H, m), 9.53 (1H, s)

EXAMPLE 25

The following compound was obtained according to a similar manner to that of Example 24.

4-[3-[3-(2-Methoxyphenyl)ureido]phenyl]-3-oxo-2-[2-(1-pyrrolidinylcarbamoyl)ethyl]-3,4-dihydropyrido[2,3-b]pyrazine NMR (DMSO-$d_6$, δ): 0.98 (1H, m), 1.28 (2H, m), 1.57 (1H, m), 2.00 (1H, m), 2.39 (2H, m), 2.75 (3H, m), 3.25 (1H, m), 3.45 (1H, m), 3.88 (3H, s), 6.75 (1H, m), 6.90 (3H, m), 7.02 (1H, d, J=7 Hz), 7.18 (1H, m, J=7 Hz), 7.29 (1H, m), 7.40 (1H, dd, J=7 Hz, 7 Hz), 7.50 (2H, m), 7.60 (1H, m), 8.08 (1H, d, J=7 Hz), 8.23 (1H, s), 9.46 (1H, s)

EXAMPLE 26

A mixture of 2-benzyl-3-oxo-4-(3-carboxyphenyl)-3,4-dihydropyrido[2,3-b]pyrazine (357 mg), triethylamine (0.14 ml) and diphenylphosphoryl azide (0.216 ml) in benzene (5 ml) was refluxed for 15 minutes. 3-Aminopyridine (113 mg) was then added to the mixture and the reflux was continued for 5 hours. The reaction mixture was poured into a mixture of ethyl acetate and aqueous sodium bicarbonate solution. The organic phase was separated, washed with brine, dried over magnesium sulfate and concentrated. The resultant solid was collected and washed with methanol to give 2-benzyl-3-oxo-4-[3-[3-(3-pyridyl)ureido]phenyl]-3,4-dihydropyrido[2,3-b]pyrazine (168 mg).

NMR (DMSO-$d_6$, 200 MHz, δ): 4.22 (2H, s), 6.96 (1H, m), 7.2–7.6 (10H, m), 7.92 (1H, m), 8.15–8.3 (2H, m), 8.41 (1H, dd, J=1.5 Hz, 5 Hz), 8.60 (1H, d, J=1.5 Hz), 8.91 (1H, s), 9.02 (1H, s)

EXAMPLE 27

A mixture of 2-benzyl-3-oxo-4-(3-carboxyphenyl)-3,4-dihydropyrido[2,3-b]pyrazine (214 mg), triethylamine (0.084 ml) and diphenylphosphoryl azide (0.129 ml) in toluene (4 ml) was refluxed for 30 minutes. 2-Aminopyridine (113 mg) was then added to the mixture and reflux was continued for 1 hour. The reaction mixture was poured into a mixture of ethyl acetate and water. The organic phase was separated, washed with brine, dried over magnesium sulfate, concentrated and subjected to silica gel column chromatography (hexane-ethyl acetate, 1:3) to afford 2-benzyl-3-oxo-4-[3-[3-(2-pyridyl)ureido]phenyl]-3,4-dihydropyrido[2,3-b]pyrazine (48 mg) as a solid.

NMR (DMSO-$d_6$, 200 MHz, δ): 4.22 (2H, s), 6.95–7.05 (2H, m), 7.2–7.8 (12H, m), 8.2–8.3 (2H, m), 8.41 (1H, dd, J=1.5 Hz, 5 Hz), 9.56 (1H, s)

EXAMPLE 28

The following compounds were obtained according to similar manners to those of Example 26 and 27.

(1) 2-Benzyl-3-oxo-4-[3-[3-(4-pyridyl)ureido]phenyl]-3,4-dihydropyrido[2,3-b]pyrazine NMR (DMSO-$d_6$, 200 MHz, δ): 4.22 (2H, s), 6.98 (1H, m), 7.2–7.6 (11H, m), 8.24 (1H, dd, J=1.5 Hz, 8 Hz), 8.3–8.45 (3H, m), 9.09 (1H, s) 9.18 (1H, s)

(2) 2-Benzyl-3-oxo-4-[3-(3-phenyl-3-methylureido)phenyl]-3,4-dihydropyrido[2,3-b]pyrazine NMR (DMSO-$d_6$, 200 MHz, δ): 3.27 (3H, s), 4.20 (2H, s), 6.90 (1H, d, J=8 Hz), 7.15–7.45 (13H, m), 7.57 (1H, d, J=8 Hz), 8.23 (1H, dd, J=1.5 Hz, 8 Hz), 8.32 (1H, s), 8.40 (1H, dd, J=1.5 Hz, 5 Hz)

(3) 2-Benzyl-3-oxo-4-(3-[3-(o-tolyl)ureido]phenyl]-3,4-dihydropyrido[2,3-b]pyrazine NMR (DMSO-$d_6$, 200 MHz, δ): 2.25 (3H, s), 4.22 (2H, s), 6.85–7.0 (2H, m), 7.05–7.5 (11H, m), 7.55 (1H, s), 7.78 (1H, d, J=8 Hz), 7.98 (1H, s), 8.24 (1H, dd, J=1.5 Hz, 8 Hz), 8.40 (1H, dd, J=1.5 Hz, 5 Hz), 9.21 (1H, s)

(4) 2-Benzyl-3-oxo-4-[3-[3-(2,6-xylyl)ureido]phenyl]-3,4-dihydropyrido[2,3-b]pyrazine NMR (DMSO-$d_6$, 200 MHz, δ): 2.20 (6H, s), 4.21 (2H, s), 6.88 (1H, dt, J=8 Hz, 1.5 Hz), 7.06 (3H, s), 7.15–7.55 (9H, m), 7.79 (1H, s), 8.23 (1H, dd, J=1.5 Hz, 8 Hz), 8.40 (1H, dd, J=1.5 Hz, 5 Hz), 8.96 (1H, s)

(5) 2-Benzyl-3-oxo-4-[3-[3-(2-biphenylyl)ureido]phenyl]-3,4-dihydropyrido[2,3-b]pyrazine NMR (DMSO-$d_6$, 200 MHz, δ): 4.22 (2H, s), 6.90 (1H, m), 7.1–7.6 (17H, m), 7.72 (1H, s), 7.88 (1H, d, J=8 Hz), 8.23 (1H, dd, J=1.5 Hz, 8 Hz), 8.40 (1H, dd, J=1.5 Hz, 5 Hz), 9.22 (1H, s)

(6) 2-Benzyl-3-oxo-4-[3-[3-(2-methoxycarbonylphenyl)ureido]phenyl]-3,4-dihydropyrido[2,3-b]pyrazine NMR (DMSO-$d_6$, 200 MHz, δ): 3.90 (3H, s), 4.22 (2H, s), 6.97 (1H, d, J=8 Hz), 7.08 (1H, t, J=8 Hz), 7.2–7.65 (9H, m), 7.95 (1H, dd, J=1.5 Hz, 8 Hz), 8.25 (1H, dd, J=1.5 Hz, 8 Hz), 8.32 (1H, d, J=8 Hz), 8.41 (1H, dd, J=1.5 Hz, 5 Hz), 10.08 (2H, s)

(7) 2-Benzyl-3-oxo-4-[3-[3-(2-thiazolyl)ureido]phenyl]-3,4-dihydropyrido[2,3-b]pyrazine NMR (DMSO-$d_6$, 200 MHz, δ): 4.22 (2H, s), 7.00 (1H, m), 7.11 (1H, d, J=4 Hz), 7.2–7.5 (10H, m), 7.59 (1H, s), 8.24 (1H, dd, J=1.5 Hz, 8 Hz), 8.40 (1H, dd, J=1.5 Hz, 5 Hz), 9.17 (1H, s)

(8) 2-Benzyl-3-oxo-4-[3-(3-cyclohexylureido)phenyl]-3,4-dihydropyrido[2,3-b]pyrazine NMR (DMSO-$d_6$, 200 MHz, δ): 1.05–1.9 (10H, m), 3.3–3.55 (1H, m), 4.22 (2H, s), 6.14 (1H, d, J=8 Hz), 6.82 (1H, m), 7.2–7.5 (9H, m), 8.23 (1H, dd, J=1.5 Hz, 8 Hz), 8.39 (1H, dd, J=1.5 Hz, 5 Hz), 8.49 (1H, s)

(9) 2-Benzyl-3-oxo-4-[3-(indolin-1-yl)carbonylaminophenyl]-3,4-dihydropyrido[2,3-b]pyrazine NMR (DMSO-$d_6$, 300 MHz, δ): 3.17 (2H, d, J=8 Hz), 4.12 (2H, d, J=8 Hz), 4.22 (2H, s), 6.85–7.75 (13H, m), 7.84 (1H, d, J=8 Hz), 8.25 (1H, d, J-8 Hz), 8.41 (1H, m), 8.71 (1H, s)

(10) 2-Benzyl-3-oxo-4-[3-(1,2,3,4-tetrahydroquinolin-1-yl)carbonylaminophenyl]-3,4-dihydropyrido[2,3-b]pyrazine NMR (DMSO-$d_6$, 300 MHz, δ): 1.89 (2H, m), 2.73 (2H, t, J=7 Hz), 3.70 (2H, t, J=7 Hz), 4.21 (2H, s), 6.9–7.6 (14H, m), 8.23 (1H, d, J=8 Hz), 8.40 (1H, m), 9.05 (1H, s)

(11) 2-Benzyl-3-oxo-4-[3-[3-(2-carboxyphenyl)ureido]phenyl-[3,4-dihydropyrido[2,3-b]pyrazine NMR (DMSO-$d_6$, 200 MHz, δ): 4.22 (2H, s), 6.75–6.95 (2H, m), 7.15–7.65 (9H, m), 7.98 (1H, dd, J=1.5 Hz, 8 Hz), 8.1–8.3 (2H, m), 8.40 (1H, dd, J=1.5 Hz, 5 Hz), 9.68 (1H, s)

(12) 2-Benzyl-3-oxo-4-[3-[3-[4-(N,N-dimethylamino)phenyl]ureido]phenyl]-3,4-dihydropyrido[2,3-b]pyrazine NMR (DMSO-$d_6$, 300 MHz, δ): 2.82 (6H, s), 4.21 (2H, s), 6.67 (2H, d, J=8 Hz), 6.88 (1H, d, J=5 Hz), 7.2–7.45 (11H, m), 7.50 (1H, s), 8.23 (1H, d, J=8 Hz), 8.33 (1H, s), 8.39 (1H, d, J=5 Hz), 8.69 (1H, s)

EXAMPLE 29

A mixture of 2-benzyl-3-oxo-4-(3-carboxymethylphenyl)-3,4-dihydropyrido[2,3-b]pyrazine (250 mg), oxalyl chloride (0.07 ml) and catalytic amount of N,N-dimethylformamide in dichloromethane (3 ml) was stirred at 0° C. for 10 minutes. The above solution was added to a mixture of aniline (0.065 ml) and triethylamine (0.135 ml) in dichloromethane (3 ml). The mixture was stirred at room temperature for 2 hours, then poured into a mixture of ethyl acetate and water. The organic phase was washed with aqueous sodium bicarbonate and brine, dried over magnesium sulfate and concentrated. The resultant solid was collected and washed with methanol to give 2-benzyl-3-oxo-4-(3-anilinocarbonylmethyl)-3,4-dihydropyrido[2,3-b]pyrazine (112 mg).

NMR (DMSO-$d_6$, 200 MHz, δ): 3.71 (2H, s), 4.21 (2H, s), 7.0–7.65 (13H, m), 7.87 (2H, d, J=8 Hz), 8.23 (1H, dd, J=1.5 Hz, 8 Hz), 8.38 (1H, dd, J=1.5 Hz, 5 Hz), 10.21 (1H, s)

EXAMPLE 30

The following compound was obtained according to a similar manner to that of Example 29.

4-[3-(1-naphthyl)carbamoylmethylphenyl]-2-benzyl-3-oxo-3,4-dihydropyrido[2,3-b]pyrazine NMR (DMSO-$d_6$, 200 MHz, δ): 3.89 (2H, s), 4.22 (2H, s), 7.1–7.8 (15H, m), 7.9–8.1 (2H, m), 8.25 (1H, dd, J=1.5 Hz, 8 Hz), 8.38 (1H, dd, J=1.5 Hz, 5 Hz), 10.18 (1H, s)

EXAMPLE 31

A mixture of 2-benzyl-3-oxo-4-(3-carboxyphenyl)-3,4-dihydropyrido[2,3-b]pyrazine (186 mg) and 1,1'-carbonyldiimidazole (130 mg) in tetrahydrofuran (4 ml) was stirred at room temperature for 3 hours. Aniline (0.075 ml) was then added to the mixture and stirring was continued for 24 hours. The reaction mixture was poured into a mixture of ethyl acetate and aqueous sodium bicarbonate solution. The organic phase was washed with brine, dried over magnesium sulfate, concentrated, and subjected to silica gel column chromatography (chloroform-methanol, 40:1) to afford 2-benzyl-3-oxo-4-(3-anilinocarbonylphenyl)-3,4-dihydropyrido[2,3-b]pyrazine (103 mg) as a solid.

NMR (DMSO-d$_6$, 300 MHz, δ): 4.23 (2H, s), 7.10 (1H, t, J=8 Hz), 7.2–7.45 (8H, m), 7.60 (1H, d, J=8 Hz), 7.65–7.8 (3H, m), 7.93 (1H, t, J=1.5 Hz), 8.10 (1H, d, J=8 Hz), 8.27 (1H, d, J=8 Hz), 8.39 (1H, m)

EXAMPLE 32

A mixture of 2-quinolinecarboxylic acid (520 mg) and 1,1'-carbonyldiimidazole (243 mg) in tetrahydrofuran (5 ml) was stirred at room temperature for 1.5 hours. A solution of 4-(3-aminophenyl)-3-oxo-2-benzyl-3,4-dihydropyrido[2,3-b]pyrazine (493 mg) in 1,4-dioxane (5 ml) was added to the mixture and stirring was continued for 5 days. The reaction mixture was poured into a mixture of ethyl acetate and an aqueous sodium bicarbonate solution. The organic phase was washed with brine, dried over magnesium sulfate, concentrated, and subjected to silica gel column chromatography (hexane-ethyl acetate, 1:1) to afford 2-benzyl-3-oxo-4-[3-(quinolin-2-yl) carbonylaminophenyl]-3,4-dihydropyrido[2,3-b]pyrazine (87 mg) as a solid.

NMR (DMSO-d$_6$, 300 MHz, δ): 4.24 (2H, s), 7.14 (1H, d, J=8 Hz), 7.2–7.45 (6H, m), 7.57 (1H, t, J=8 Hz), 7.76 (1H, t, J=8 Hz), 7.85–8.15 (4H, m), 8.2–8.3 (3H, m), 8.42 (1H, d, J=5 Hz), 8.63 (1H, d, J=8 Hz), 10.93 (1H, s)

EXAMPLE 33

To a suspension of 2-(2-carboxyethyl)-3-oxo-4-[3-[3-(2-methoxyphenyl)ureido]phenyl]-3,4-dihydropyrido[2,3-b]pyrazine (0.15 g) in ethanol (9 ml) was added conc. sulfonic acid (0.9 ml) and the mixture was refluxed for 30 minutes. After cooling, the reaction mixture was neutralized and ethanol was evaporated. Crystalline materials formed were collected, washed with water and dried to give 2-(2-ethoxycarbonylethyl)-3-oxo-4-[3-[3-(2-methoxyphenyl)ureido]phenyl]-3,4-dihydropyrido[2,3-b]pyrazine (0.12 g).

mp: 175° C.

NMR (DMSO-d$_6$, δ): 1.20 (3H, t, J=7 Hz), 2.82 (2H, t, J=7 Hz), 3.15 (2H, t, J=7 Hz), 3.89 (3H, s), 4.10 (2H, q, J=7 Hz), 6.8–7.05 (4H, m), 7.4 (3H, m), 7.60 (1H, s), 8.10 (1H, d, J=7 Hz), 8.20 (1H, d, J=7 Hz), 8.30 (1H, s), 8.40 (1H, m), 9.52 (1H, s)

EXAMPLE 34

The following compounds were obtained according to a similar manner to that of Example 33.

(1) 4-[3-[3-(2-Methoxyphenyl)ureido]phenyl]-3-oxo-2-(2-propyloxycarbonylethyl)-3,4-dihydropyrido[2,3-b]pyrazine mp: 161–163° C.

NMR (DMSO-d$_6$, δ): 0.88 (3H, t, J=7 Hz), 1.60 (2H, m), 2.84 (2H, t, J=7 Hz), 3.13 (2H, t, J=7 Hz), 3.88 (3H, s), 4.01 (2H, t, J=7 Hz), 6.8–7.05 (4H, m), 7.4 (3H, m), 7.58 (1H, s), 8.09 (1H, d, J=7 Hz), 8.18 (1H, d, J=7 Hz), 8.28 (1H, s), 8.40 (1H, d, J=3 Hz), 9.52 (1H, s)

(2) 2-(2-Methoxycarbonylethyl)-3-oxo-4-[3-[3-(2-methoxyphenyl)ureido]phenyl]-3,4-dihydropyrido[2,3-b]pyrazine mp: 194–196° C.

NMR (DMSO-d$_6$, δ): 2.86 (2H, t, J=7 Hz), 3.15 (2H, t, J=7 Hz), 3.65 (3H, s), 3.89 (3H, s), 6.85–7.1 (4H, m), 7.45 (3H, m), 7.60 (1H, s), 8.10 (1H, d, J=7 Hz), 8.21 (1H, d, J=7 Hz), 8.29 (1H, s), 8.40 (1H, d, J=3 Hz), 9.52 (1H, s)

EXAMPLE 35

To a stirred suspension of 2-(2-carboxyethyl)-3-oxo-4-[3-[3-(2-methoxyphenyl)ureido]phenyl]-3,4-dihydropyrido[2,3-b]pyrazine (115 mg) and 1-hydroxybenzotriazole (40 mg) in dry dioxane (10 ml) was added 1-ethyl-3-(3-dimethylaminopropyl)carbodiimide (47 mg) and N-methylpiperazine (30 mg). The mixture was stirred at room temperature for 4 hours, diluted with ethyl acetate, washed with water. After evaporation of the solvents, crude residue was crystallized from ethanol to give 4-[3-[3-(2-methoxyphenyl)ureido]phenyl]-2-[2-(4-methylpiperazin-1-yl)carbonylethyl]-3-oxo-3,4-dihydropyrido[2,3-b]pyrazine.

mp: 195–197° C.

NMR (DMSO-d$_6$, δ): 2.20 (3H, s), 2.24 (2H, m), 2.36 (2H, m), 2.85 (2H, t, J=7 Hz), 3.12 (2H, t, J=7 Hz), 3.48 (2H, m), 3.55 (2H, m), 3.88 (3H, s), 6.8–7.05 (4H, m), 7.4 (3H, m), 7.60 (1H, s), 8.10 (1H, d, J=7 Hz), 8.21 (1H, d, J=7 Hz), 8.28 (1H, s), 8.40 (1H, m), 9.53 (1H, s)

EXAMPLE 36

The following compound was obtained according to a similar manner to that of Example 35.

4-[3-[3-(2-Methoxyphenyl)ureido]phenyl]-3-oxo-2-[2-[(2S)-2-methoxycarbonylpyrrolidin-1-yl]carbonylethyl]-3,4-dihydropyrido[2,3-b]pyrazine mp: 209–212° C.

NMR (DMSO-d$_6$, δ): 1.86 (1H, m), 1.97 (1H, m), 2.18 (1H, m), 2.83 (1H, m), 3.10 (2H, m), 3.58 (3H, s), 3.18 (2H, m), 3.87 (3H, s), 4.31 (1H, m), 6.8–7.05 (4H, m), 7.42 (3H, m), 7.59 (1H, s), 8.08 (1H, d, J=7 Hz), 8.23 (1H, d, J=7 Hz), 8.28 (1H, s), 8.39 (1H, m), 9.53 (1H, s)

EXAMPLE 37

The mixture of 2-(2-nitrobenzyl)-3-oxo-4-phenyl-3,4-dihydropyrido[2,3-b]pyrazine (1.39 g), iron (2.17 g) and acetic acid (1.16 g) in ethanol (15 ml) was refluxed for 3 hours. The reaction mixture was cooled and filtered. To the filtrate was added saturated sodium hydrogencarbonate solution, and extracted with ethyl acetate. The organic layer was dried and evaporated. The crude product was purified by silica column chromatography to obtain 2-(2-aminobenzyl)-3-oxo-4-phenyl-3,4-dihydropyrido[2,3-b]pyrazine (120 mg).

NMR (CDCl$_3$, 200 MHz, δ): 4.21 (2H, s), 4.21 (2H, br s), 6.64 (1H, dd, J=1 Hz, 7 Hz), 6.73 (1H, dd, J=1 Hz, 7 Hz), 7.04 (1H, ddd, J=1 Hz, 7 Hz and 7 Hz), 7.18–7.35 (3H, m), 7.35–7.60 (4H, m), 8.14 (1H, dd, J=1 Hz, 10 Hz), 8.37 (1H, dd, J=1 Hz, 5 Hz)

EXAMPLE 38

To a mixture of 4-(3-aminophenyl)-2-(3-pyridylmethyl)-3-oxo-3,4-dihydropyrido[2,3-b]pyrazine (180 mg) and triethylamine (0.10 ml) in 1,4-dioxane (4 ml) was added 3,5-dichlorobenzoylchloride (126 mg). The mixture was stirred at room temperature for 10 minutes, then poured into a mixture of ethyl acetate and aqueous sodium bicarbonate. The organic phase was separated, washed with aqueous sodium bicarbonate and brine, dried over magnesium sulfate and concentrated. The residue was chromatographed on silica gel column (ethyl acetate) and crystallized from ethanol to give 4-[3-(3,5-dichlorobenzoylamino)phenyl]-2-(3-pyridylmethyl)-3-oxo-3,4-dihydropyrido[2,3-b]pyrazine (163 mg).

NMR (DMSO-d$_6$, 300 MHz, δ): 4.27 (2H, s), 7.12 (1H, d, J=8 Hz), 7.3–7.45 (2H, m), 7.56 (1H, t, J=8 Hz), 7.75–7.85 (3H, m), 7.88 (1H, t, J=2 Hz), (2H, d, J=2 Hz), 8.21 (1H, dd, J=2, 8 Hz), 8.41 (1H, d, J=5 Hz), 8.48 (1H, d, J=5 Hz), 8.60 (1H, d, J=2 Hz)

EXAMPLE 39

To a mixture of 4-(3-aminophenyl)-2-(3-pyridylmethyl)-3-oxo-3,4-dihydropyrido[2,3-b]pyrazine (480 mg) and triethylamine (0.23 ml) in dichloromethane (7 ml) was added 2-naphthoyl chloride (291 mg). The mixture was stirred at room temperature for 20 minutes, then poured into a mixture of ethyl acetate and aqueous sodium bicarbonate. The organic phase was separated, washed with aqueous sodium bicarbonate and brine, dried over magnesium sulfate and concentrated. The residue was crystallized from ethanol to give 4-[3-(2-naphthoylamino)phenyl]-2-(3-pyridylmethyl)-3-oxo-3,4-dihydropyrido[2,3-b]pyrazine (280 mg).

NMR (CDCl$_3$, 300 MHz, δ): 4.31 (2H, s), 6.91 (1H, d, J=8 Hz), 7.2–7.35 (2H, m), 7.45–7.6 (3H, m), 7.72 (1H, dd, J=2, 8 Hz), 7.75–7.9 (6H, m), 8.18 (1H, d), 8.31 (1H, s), 8.4–8.5 (3H, m), 8.71 (1H, m)

EXAMPLE 40

To a solution of 4-(3-aminophenyl)-2-(3-pyridylmethyl)-3-oxo-3,4-dihydropyrido[2,3-b]pyrazine (329 mg) in chloroform (5 ml) was added 3,5-dichlorobenzoylchloride (220 mg). The mixture was stirred at room temperature for 15 minutes and concentrated. The residue was crystallized from methanol to give 4-[3-(3,5-dichlorobenzoylamino)phenyl]-2-(3-pyridylmethyl)-3-oxo-3,4-dihydropyrido[2,3-b] pyrazinehydrochloride (370 mg).

NMR (DMSO-d$_6$, 300 MHz, δ): 4.49 (2H, s), 7.11 (1H, d, J=8 Hz), 7.40 (1H, dd, J=5, 8 Hz), 7.57 (1H, t, J=8 Hz), 7.80 (1H, d, J=8 Hz), 7.89 (2H, m), 8.0–8.05 (3H, m), 8.17 (1H, dd, J=2, 5 Hz), 8.42 (1H, d, J=5 Hz), 8.53 (1H, d, J=8 Hz), 8.83 (1H, d, J=5 Hz), 8.92 (1H, s)

EXAMPLE 41

The following compounds were obtained according to a similar manner to that of Example 19, 20, 21, 38, 39 or 40.

(1) 4-[3-(2-Chlorobenzoylamino)phenyl]-2-(3-pyridylmethyl)-3-oxo-3,4-dihydropyrido[2,3-b]pyrazine NMR (CDCl$_3$, 300 MHz, δ): 4.30 (2H, s), 7.04 (1H, d, J=8 Hz), 7.2–7.45 (5H, m), 7.5–7.65 (2H, m), 7.70 (1H, dd, J=2, 8 Hz), 7.75–7.9 (2H, m), 8.15–8.25 (2H, m), 8.42 (1H, d, J=5 Hz), 8.48 (1H, d, J=5 Hz), 8.70 (1H, s)

(2) 4-[3-(3-Bromobenzoylamino)phenyl]-2-(3-pyridylmethyl)-3-oxo-3,4-dihydropyrido[2,3-b]pyrazine NMR (CDCl$_3$, 300 MHz, δ): 4.32 (2H, s), 6.80 (1H, d, J=8 Hz), 7.19 (1H, dd, J=5 Hz, 8 Hz), 7.25–7.35 (2H, m), 7.41 (1H, t, J=8 Hz), 7.60 (1H, d, J=8 Hz), 7.65–7.8 (4H, m), 7.90 (1H, t, J=2 Hz), 8.20 (1H, d, J=8 Hz), 8.4–8.45 (2H, m), 8.49 (1H, s), 8.70 (1H, d, J=2 Hz)

(3) 4-[3-[3-(2-Pyrimidinyloxy)benzoylamino]phenyl]-2-(3-pyridylmethyl)-3-oxo-3,4-dihydropyrido[2,3-b]pyrazine NMR (DMSO-d$_6$, 300 MHz, δ): 4.25 (2H, s), 7.10 (1H, d, J=8 Hz), 7.3–7.65 (6H, m), 7.75–7.9 (5H, m), 8.21 (1H, d, J=8 Hz), 8.40 (1H, d, J=5 Hz), 8.47 (1H, m), 8.60 (1H, s), 8.68 (2H, d, J=5 Hz)

(4) 4-[3-[4-[(E)-2-Methoxycarbonylvinyl]benzoylamino]phenyl]-2-(3-pyridylmethyl)-3-oxo-3,4-dihydropyrido[2,3-b]pyrazine NMR (CDCl$_3$, 300 MHz, δ): 3.80 (3H, s), 4.30 (2H, s), 6.48 (1H, d, J=16 Hz), 6.89 (1H, d, J=8 Hz), 7.2–7.35 (2H, m), 7.4–7.55 (3H, m), 7.6–7.7 (2H, m), 7.75–7.85 (4H, m), 8.18 (1H, d, J=8 Hz), 8.34 (1H, s), 8.41 (1H, dd, J=2, 5 Hz), 8.48 (1H, d, J=5 Hz), 8.72 (1H, d, J=2 Hz)

(5) 4-[3-[(E)-Cinnamoylamino]phenyl]-2-(3-pyridylmethyl)-3-oxo-3,4-dihydropyrido[2,3-b]pyrazine NMR (CDCl$_3$, 300 MHz, δ): 4.32 (2H, s), 6.38 (1H, d, J=16 Hz), 6.90 (1H, d, J=8 Hz), 7.2–7.45 (8H, m), 7.5–7.7 (3H, m), 8.20 (1H, d, J=8 Hz), 8.35 (1H, d, J=8 Hz), 8.4–8.5 (2H, m), 8.73 (1H, s)

(6) 4-[3-[(E)-3-(2-Chlorophenyl)propenoylamino]phenyl]-2-(3-pyridylmethyl)-3-oxo-3,4-dihydropyrido[2,3-b]pyrazine NMR (CDCl$_3$, 300 MHz, δ): 4.32(2H, s), 6.38 (1H, d, J=16 Hz), 7.15–7.5 (8H, m), 7.75 (1H, s), 7.83 (1H, d, J=8 Hz), 7.98 (1H, d, J=16 Hz), 8.21 (1H, d, J=8 Hz), 8.4–8.5 (3H, m), 8.72 (1H, s)

(7) 4-[3-[(E)-3-(2,6-Dichlorophenyl)propenoylamino]phenyl]-2-(3-pyridylmethyl)-3-oxo-3,4-dihydropyrido[2,3-b]pyrazine NMR (CDCl$_3$, 300 MHz, δ): 4.32 (2H, s), 6.49 (1H, d, J=16 Hz), 6.91 (1H, d, J=8 Hz), 7.1–7.2 (2H, m), 7.25–7.45 (5H, m), 7.7–7.85 (3H, m), 8.21 (1H, d, J=8 Hz), 8.4–8.5 (2H, m), 8.71 (1H, s), 8.80 (1H, s)

(8) 4-[3-[(E)-3-(4-Methoxycarbonylphenyl)propenoylamino]phenyl]-2-(3-pyridylmethyl)-3-oxo-3,4-dihydropyrido[2,3-b]pyrazine NMR (CDC13, 300 MHz, δ): 3.90 (3H, s), 4.32 (2H, s), 6.43 (1H, d, J=16 Hz), 6.89 (1H, d, J=8 Hz), 7.2–7.5 (5H, m), 7.55–7.7 (3H, m), 7.82 (1H, d, J=8 Hz), 7.97 (2H, d, J=8 Hz), 8.21 (1H, dd, J=2 Hz, 8 Hz), 7.4–7.5 (3H, m), 8.74 (1H, d, J=2 Hz)

(9) 4-[3-(3,4-Methylenedioxybenzoylamino)phenyl]-2-(3-pyridylmethyl)-3-oxo-3,4-dihydropyrido[2,3-b]pyrazine NMR (CDCl$_3$, 300 MHz, δ): 4.31 (2H, s), 6.02 (2H, s), 6.79 (1H, d, J=8 Hz), 6.93 (1H, d, J=8 Hz), 7.2–7.35 (4H, m), 7.48 (1H, t, J=8 Hz), 7.60 (1H, d, J=8 Hz), 7.75–7.85 (2H, m), 8.10 (1H, s), 8.17 (1H, d, J=8 Hz), 8.41 (1H, d, J=5 Hz), 8.48 (1H, d, J=5 Hz), 8.71 (1H, s)

(10) 4-[3-[(Benzofuran-2-yl)carbonylamino]phenyl]-2-(3-pyridylmethyl)-3-oxo-3,4-dihydropyrido[2,3-b]pyrazine NMR (CDCl$_3$, 300 MHz, δ): 4.32 (2H, s), 7.05 (1H, d, J=8 Hz), 7.2–7.6 (7H, m), 7.69 (1H, d, J=8 Hz), 7.75–7.85 (3H, m), 8.19 (1H, d, J=8 Hz), 8.43 (1H, m), 8.5–8.6 (2H, m), 8.72 (1H, s)

(11) 4-[3-[(1-Methylindol-2-yl)carbonylamino]phenyl]-2-(3-pyridylmethyl)-3-oxo-3,4-dihydropyrido[2,3-b]pyrazine NMR (CDCl$_3$, 300 MHz, δ): 4.03 (3H, s), 4.31 (2H, s), 6.95–7.05 (2H, m), 7.1–7.4 (5H, m), 7.54 (1H, t, J=8 Hz), 7.61 (2H, d, J=8 Hz), 7.8–7.85 (2H, m), 8.19 (1H, d, J=8 Hz), 8.23 (1H, s), 8.43 (1H, d, J=5 Hz), 8.49 (1H, d, J=5 Hz), 8.72 (1H, s)

(12) 4-[3-[(Benzo[b]thiophen-2-yl)carbonylamino]phenyl]-2-(3-pyridylmethyl)-3-oxo-3,4-dihydropyrido[2,3-b]pyrazine NMR (CDCl$_3$, 300 MHz, δ): 4.31 (2H, s), 6.92 (1H, d, J=8 Hz), 7.2–7.55 (5H, m), 7.65 (1H, d, J=8 Hz), 7.7–7.9 (4H, m), 8.18 (1H, d, J=8 Hz), 8.32 (1H, s), 8.4–8.55 (2H, m), 8.73 (1H, s)

(13) 4-[3-[(6-Methoxycarbonyl-2-naphthoyl)amino]phenyl]-2-(3-pyridylmethyl)-3-oxo-3,4-dihydropyrido[2,3-b]pyrazine NMR (CDCl$_3$, 300 MHz, δ): 4.00 (3H, s), 4.22 (2H, s), 6.93 (1H, d, J=8 Hz), 7.2–7.35 (2H, m), 7.51 (1H, t, J=8 Hz), 7.7–8.0 (2H, m), 8.11 (1H, d, J=8 Hz), 8.19 (1H, d, J=8 Hz), 8.32 (1H, s), 8.4–8.55 (3H, m), 8.60 (1H, s), 8.72 (1H, s)

(14) 4-[3-[(6-Acetoxy-2-naphthoyl)amino]phenyl]-2-(3-pyridylmethyl)-3-oxo-3,4-dihydropyrido[2,3-b]pyrazine NMR (DMSO-d$_6$, 300 MHz, δ): 2.35 (3H, s), 4.28 (2H, S), 7.11 (1H, d, J=8 Hz), 7.3–7.5 (3H, m), 7.57 (1H, t, J=8 Hz), 7.75–7.9 (4H, m), 8.14 (1H, d, J=8 Hz), 8.22 (1H, d, J=8 Hz), 8.42 (1H, d, J=5 Hz), 8.48 (1H, d, J=5 Hz), 8.6–8.65 (2H, m)

(15) 4-[3-[(3-Methoxycarbonyl-5-nitrobenzoyl)amino]phenyl]-2-(3-pyridylmethyl)-3-oxo-3,4-dihydropyrido[2,3-b]pyrazine NMR (DMSO-d$_6$, 300 MHz, δ): 3.98 (3H, s), 4.28 (2H, s), 7.17 (1H, dd, J=2 Hz, 8 Hz), 7.3–7.45 (2H, m), 7.59 (1H, t, J=8 Hz), 7.75–7.85 (2H, m), 7.89 (1H, d, J=8 Hz), 8.21 (1H, d, J=8 Hz), 8.4–8.5 (2H, m), 8.60 (1H, d, J=2 Hz), 8.78 (1H, s), 8.92 (1H, s), 9.05 (1H, s)

(16) 4-[3-(3,5-Dinitrobenzoylamino)phenyl]-2-(3-pyridylmethyl)-3-oxo-3,4-dihydropyrido[2,3-b]pyrazine NMR (CDCl$_3$, 300 MHz, δ): 4.31 (2H, s), 6.70 (1H, d, J=8 Hz), 6.93 (1H, dd, J=5 Hz, 8 Hz), 7.25–7.35 (2H, m), 7.43 (1H, dd, J=5 Hz, 8 Hz), 7.67 (1H, d, J=8 Hz), 8.0–8.1 (2H, m), 8.32 (1H, d, J=8 Hz), 8.50 (2H, m), 8.99 (2H, d, J=2 Hz), 9.07 (1H, t, J=2 Hz), 9.63 (1H, s)

(17) 4-[3-(3,5-Dimethoxybenzoylamino)phenyl]-2-(3-pyridylmethyl)-3-oxo-3,4-dihydropyrido[2,3-b]pyrazine NMR (DMSO-d$_6$, 300 MHz, δ): 3.80 (6H, s), 4.27 (2H, s), 6.71 (1H, m), 7.10 (3H, m), 7.3–7.45 (2H, m), 7.53 (1H, t, J=8 Hz), 7.75–7.9 (3H, m), 8.21 (1H, d, J=8 Hz), 8.40 (1H, d, J=5 Hz), 8.47 (1H, d, J=5 Hz), 8.59 (1H, s)

(18) 4-[3-(3,5-Dibromobenzoylamino)phenyl]-2-(3-pyridylmethyl)-3-oxo-3,4-dihydropyrido[2,3-b]pyrazine.hydrochloride NMR (DMSO-d$_6$, 300 MHz, δ): 4.49 (2H, s), 7.11 (2H, d, J=8 Hz), 7.41 (1H, dd, J=5 Hz, 8 Hz), 7.57 (1H, t, J=8 Hz), 7.80 (1H, d, J=8 Hz), 7.89 (1H, s), 8.0–8.2 (5H, m), 8.42 (1H, d, J=5 Hz), 8.55 (1H, d, J=8 Hz), 8.83 (1H, d, J=5 Hz), 8.93 (1H, d, J=2 Hz)

(19) 4-[3-[3,5-Bis(trifluoromethyl)benzoylamino]phenyl]-2-(3-pyridylmethyl)-3-oxo-3,4-dihydropyrido[2,3-b]pyrazine.hydrochloride NMR (DMSO-d$_6$, 300 MHz, δ): 4.49 (2H, s), 7.13 (1H, d), 7.42 (1H, dd, J=5 Hz, 8 Hz), 7.60 (1H, t, J=8 Hz), 7.8–7.9 (2H, m), 8.01 (1H, dd, J=5 Hz, 8 Hz), 8.18 (1H, d, J=8 Hz), 8.39 (1H, s), 8.43 (1H, d, J=5 Hz), 8.53 (1H, dd, J=2 Hz, 8 Hz), 8.62 (2H, s), 8.83 (1H, d, J=5 Hz), 8.83 (1H, s)

(20) 4-[2-Fluoro-5-(2-naphthoylamino)phenyl]-2-(3-pyridylmethyl)-3-oxo-3,4-dihydropyrido[2,3-b]pyrazine mp: 264–268° C.

NMR (CDCl$_3$-CD$_3$OD=1:1, 5) 4.37 (2H, s), 7.3–7.45 (3H, m), 7.6 (3H, m), 7.85–8.05 (7H, m), 8.25 (1H, d, J=8 Hz), 8.45 (3H, m), 8.64 (1H, s)

(21) 2-Benzyl-4-(3-cyclohexylcarbonylaminophenyl)-3-oxo-3,4-dihydropyrido[2,3-b]pyrazine NMR (DMSO-d6, 300 MHz, δ): 1.1–1.5 (5H, m), 1.6–1.9 (5H, m), 2.33 (1H, m), 4.21 (2H, s), 6.98 (1H, d, J=8 Hz), 7.2–7.5 (7H, m), 7.59 (1H, d, J=8 Hz), 7.68 (1H, s), 8.23 (1H, d, J=8 Hz), 8.39 (1H, m)

EXAMPLE 42

A mixture of 3-amino-2-[3-[(E)-2-(4-pyridyl)vinyl]phenylamino]pyridine (575 mg) and 3-(3-pyridyl)pyruvic acid (0.37 g) in ethanol (10.ml) was stirred under reflux for 1.5 hours. After evaporation of the solvent, the residue was chromatographed on silica gel column (chloroform-methanol, 9:1) and crystallized from ethanol to give 2-(3-pyridylmethyl)-4-[3-[(E)-2-(4-pyridyl)vinyl]phenyl]-3-oxo-3,4-dihydropyrido[2,3-b]pyrazine (395 mg).

NMR (DMSO-d$_6$, 300 MHz, δ): 4.28 (2H, s), 7.25–7.45 (4H, m), 7.5–7.7 (7H, m), 7.78 (2H, m), 8.23 (1H, dd, J=2 Hz, 5 Hz), 8.41 (1H, m), 8.48 (1H, d, J=5 Hz), 8.55 (2H, d, J=5 Hz),8.60 (1H, d, J=2 Hz)

EXAMPLE 43

A mixture of 2-[3-(2-naphthyl)phenylamino]-3-aminopyridine and 3-(3-pyridyl)pyruvic acid in ethanol was stirred under reflux for 40 hours. After evaporation of the solvent, crude residue was chromatographed on silica gel to give 4-[3-(2-naphthyl)phenyl]-2-(3-pyridylmethyl)-3-oxo-3,4-dihydropyrido[2,3-b]pyrazine. Crystallization from ether and recrystallization with methanol afforded colorless crystals.

mp: 155–156° C.

NMR (CDCl$_3$, δ): 4.34 (2H, s), 7.30 (3H, m), 7.48 (2H, m), 7.62 (1H, s), 7.71 (1H, dd, J=8 Hz, 8 Hz), 7.74 (1H, dd, J=8 Hz, 2 Hz), 7.88 (4H, m), 8.08 (1H, s), 8.19 (1H, d, J=8 Hz), 8.45 (1H, d, J=5 Hz), 8.51 (1H, d, J=4 Hz), 8.75 (1H, s)

MASS (m/z): 441 (M+1)

EXAMPLE 44

A mixture of 2-(3-acetamidophenylamino)-3-aminopyridine (1.0 g) and 3-(3-pyridyl)pyruvic acid (0.82 g) in ethanol (50 ml) was stirred under reflux for 6 hours. After evaporation of the solvent, crude residue was chromatographed on silica gel and crystallized from ethyl acetate to give 4-(3-acetamidophenyl)-2-(3-pyridylmethyl)-3-oxo-3,4-dihydropyrido[2,3-b]pyrazine (1.04 g).

NMR (CDCl$_3$, δ): 2.00 (3H, s), 4.31 (2H, s), 6.95 (1H, m), 7.25 (1H, dd, J=8 Hz, 5 Hz), 7.33 (1H, dd, J=8 Hz, 5 Hz), 7.45 (2H, m), 7.60 (1H, s), 7.81 (1H, m), 7.98 (1H, s), 8.20 (1H, dd, J=8 Hz, 1 Hz), 8.44 (1H, dd, J=5 Hz, 1 Hz), 8.48 (1H, m), 8.72 (1H, s)

MASS (m/z): 372 (M+1)

EXAMPLE 45

The following compounds were obtained according to a similar manner to that of Example 2, 42, 43 or 44.

(1) 2-(3-Pyridylmethyl)-4-[3-[(E)-2-(2-quinolyl)vinyl]phenyl]-3-oxo-3,4-dihydropyrido[2,3-b]pyrazine NMR (DMSO-d$_6$, 300 MHz, δ): 4.29 (2H, s), 7.3–7.65 (6H, m), 7.7–8.0 (8H, m), 8.23 (1H, d, J=8 Hz), 8.38 (1H, d, J=8 Hz), 8.4–8.5 (2H, m), 8.61 (1H, d)

(2) 2-(3-Pyridylmethyl)-4-[3-[(E)-2-(4-quinolyl)vinyl]phenyl-3-oxo-3,4-dihydropyrido[2,3-b]pyrazine NMR (DMSO-d$_6$, 300 MHz, δ): 4.30 (2H, s), 7.3–7.45 (3H, m), 7.6–7.95 (8H, m), 8.04 (1H, d, J=8 Hz), 8.13 (1H, d, J=16 Hz), 8.25 (1H, d, J=8 Hz), 8.4–8.55 (3H, m), 8.61 (1H, s), 8.90 (1H, d, J=5 Hz)

(3) 2-(3-Pyridylmethyl)-4-[3-[(E)-2-(5-pyrimidinyl)vinyl]phenyl]-3-oxo-3,4-dihydropyrido[2,3-b]pyrazine NMR (DMSO-d$_6$, 300 MHz, δ): 4.28 (2H, s), 7.25–7.45 (4H, m), 7.55–7.65 (3H, m), 7.7–7.85 (2H, m), 8.22 (1H, d, J=8 Hz), 8.41 (1H, d, J=5 Hz), 8.48 (1H, m), 8.60 (1H, d, J=2 Hz), 9.05 (2H, s), 9.08 (1H, s)

(4) 2-(3-Pyridylmethyl)-4-[3-[(E)-2-(2-pyridyl)vinyl]phenyl]-3-oxo-3,4-dihydropyrido 2,3-b]pyrazine NMR (DMSO-d$_6$, 300 MHz, δ): 4.27 (2H, s), 7.25–7.85 (12H, m), 8.23 (1H, d, J=8 Hz), 8.41 (1H, d, J=5 Hz), 8.48 (1H, d, J=5 Hz), 8.55–8.65 (2H, m)

(5) 2-(3-Pyridylmethyl)-4-[3-[(E)-2-(3-pyridyl)vinyl]phenyl]-3-oxo-3,4-dihydropyrido[2,3-b]pyrazine NMR (DMSO-d$_6$, 300 MHz, δ): 4.28 (2H, s), 7.25–7.8 (10H, m), 8.05 (1H, d, J=8 Hz), 8.22 (1H, d, J=8 Hz), 8.41 (1H, d, J=5 Hz), 8.48 (2H, m), 8.60 (1H, s), 8.77 (1H, s)

(6) 2-Benzyl-4-[3-[3-(2-methoxyphenyl)ureido]phenyl]-3-oxo-3,4-dihydropyrido[2,3-b]pyrazine mp: 238–239° C.

NMR (DMSO-d$_6$, δ): 6.46 (1H, m), 7.06 (1H, m), 7.25 (1H, m), 7.31 (1H, m), 7.56 (1H, m), 7.78 (1H, m), 8.03 (1H, m), 8.56 (2H, m)

(7) 2-Benzyl-4-[3-(2-cyanopyrrol-1-yl)phenyl]-3-oxo-3,4-dihydropyrido[2,3-b]pyrazine mp: 165–166° C.

NMR (DMSO-d$_6$, δ): 4.22 (2H, s), 6.46 (1H, m), 7.2–7.45 (7H, m), 7.52 (2H, m), 7.65–7.8 (3H, m), 8.26 (1H, m), 8.42 (1H, m)

MASS (m/z): 404 (M+1)

(8) 2-Benzyl-4-[3-(benzothiazol-2-yl)phenyl]-3-oxo-3,4-dihydropyrido[2,3-b]pyrazine mp: 197–198° C.

NMR (DMSO-d$_6$, δ): 4.23 (2H, s), 7.2–7.6 (9H, m), 7.77 (1H, dd, J=8 Hz, 8 Hz), 8.05 (1H, d, J=8 Hz), 8.15–8.3 (4H, m), 8.40 (1H, m)

(9) 2-Benzyl-4-(3-benzoylphenyl)-3-oxo-3,4-dihydropyrido[2,3-b]pyrazine mp: 154–155° C.

NMR (CDCl$_3$, δ): 4.30 (2H, s), 7.2–7.35 (4H, m), 7.45–7.6 (6H, m), 7.70 (1H, dd, J=8 Hz, 8 Hz), 7.74 (1H, m), 7.85 (2H, m), 7.96 (1H, m), 8.20 (1H, dd, J=8 Hz, 2 Hz), 8.40 (1H, dd, J=5 Hz, 2 Hz)

(10) 2-Benzyl-4-(3-trifluoromethylphenyl)-3-oxo-3,4-dihydropyrido[2,3-b]pyrazine mp: 125–127° C.

NMR (CDCl$_3$, δ): 4.30 (2H, s), 7.2–7.35 (4H, m), 7.48 (3H, m), 7.55 (1H, s), 7.68 (1H, s), 7.75 (1H, m), 8.20 (1H, dd, J=8 Hz, 2 Hz), 8.38 (1H, dd, J=5 Hz, 2 Hz)

(11) 2-Benzyl-4-[3-(3-acetylindol-1-yl)phenyl]-3-oxo-3,4-dihydropyrido[2,3-b]pyrazine mp: 157–159° C.

NMR (DMSO-d$_6$, δ): 2.50 (3H, s), 4.35 (2H, s), 7.10 (2H, m), 7.22 (3H, m), 7.32 (3H, m), 7.50 (1H, m), 7.61 (1H, m), 7.75–7.90 (3H, m), 8.12 (1H, m), 8.29 (2H, m), 8.60 (1H, s)

(12) 4-(3-Methoxycarbonylphenyl)-2-(3-pyridylmethyl)-3-oxo-3,4-dihydropyrido[2,3-b]pyrazine mp: 208–210° C.

NMR (CDCl$_3$, δ): 3.91 (3H, s), 4.32 (2H, s), 7.28 (2H, m), 7.49 (1H, m), 7.68 (1H, dd, J=8 Hz, 8 Hz), 7.81 (1H, m), 7.97 (1H, m), 8.20 (1H, m), 8.40 (1H, m), 8.50 (1H, m), 8.72 (1H, m)

(13) 4-[3-(1-Pyrrolyl)phenyl]-2-(3-pyridylmethyl)-3-oxo-3,4-dihydropyrido[2,3-b]pyrazine mp: 128–130° C.

NMR (CDCl$_3$, δ): 4.27 (2H, s), 6.36 (2H, m), 7.03 (2H, m), 7.12 (1H, m), 7.18 (1H, dd, J=8 Hz, 5 Hz), 7.25 (1H, m), 7.30 (1H, dd, J=8 Hz, 5 Hz), 7.50 (1H, m), 7.56 (1H, m), 7.60 (1H, dd, J=8 Hz, 8 Hz), 8.10 (1H, dd, J=8 Hz, 1 Hz), 8.31 (1H, m), 8.35 (1H, dd, J=5 Hz, 1 Hz), 8.46 (1H, m)

(14) 4-(3-Trifluoromethylphenyl)-2-(3-pyridylmethyl)-3-oxo-3,4-dihydropyrido[2,3-b]pyrazine mp: 88–90° C.

NMR (CDCl$_3$, δ): 4.22 (2H, m), 7.18 (1H, m), 7.30 (1H, m), 7.48 (3H, m), 7.69 (1H, m), 7.80 (1H, m), 8.27 (1H, m), 8.35 (1H, m), 8.47 (1H, m)

(15) 4-(5-Acetamido-2-fluorophenyl)-2-(3-pyridylmethyl)-3-oxo-3,4-dihydropyrido[2,3-b]pyrazine mp: 212–214° C.

NMR (DMSO-d$_6$, δ): 2.03 (3H, s), 4.27 (2H, s), 7.40 (3H, m), 7.61 (1H, m), 7.79 (2H, m), 8.23 (1H, dd, J=8 Hz, 2 Hz), 8.43 (1H, dd, J=5 Hz, 2 Hz), 8.47 (1H, m), 8.59 (1H, m)

(16) 4-(3-Benzoylphenyl)-2-(3-pyridylmethyl)-3-oxo-3,4-dihydropyrido[2,3-b]pyrazine mp: 142–143° C.

NMR (CDCl$_3$, δ): 4.26 (2H, s), 7.17 (1H, dd, J=8 Hz, 5 Hz), 7.30 (1H, dd, J=8 Hz, 5 Hz), 7.50 (4H, m), 7.60 (1H, m), 7.68 (1H, dd, J=8 Hz, 8 Hz), 7.75 (1H, m), 7.80 (2H, m), 7.96 (1H, m), 8.10 (1H, dd, J=8 Hz, 2 Hz), 8.29 (1H, m), 8.35 (1H, dd, J=5 Hz, 2 Hz), 8.44 (1H, m)

(17) 4-[3-(3-Acetylindol-1-yl)phenyl]-2-(3-pyridylmethyl)-3-oxo-3,4-dihydropyrido[2,3-b]pyrazine mp: 153–156° C.

NMR (CDCl$_3$, δ): 2.56 (3H, s), 4.33 (2H, s), 7.25–7.45 (5H, m), 7.50 (1H, m), 7.60 (1H, m), 7.70 (1H, m), 7.80 (2H, m), 8.00 (1H, s), 8.20 (1H, d, J=8 Hz), 8.45 (2H, m), 8.51 (1H, m), 8.73 (1H, m)

(18) 4-[3-(1-Indolyl)phenyl]-2-(3-pyridylmethyl)-3-oxo-3,4-dihydropyrido[2,3-b]pyrazine mp: 166–168° C.

NMR (DMSO-d$_6$, δ): 4.28 (2H, s), 6.73 (1H, d, J=3 Hz), 7.1–7.25 (2H, m), 7.3–7.45 (3H, m), 7.6–7.8 (7H, m), 8.22 (1H, dd, J=8 Hz, 2 Hz), 8.46 (2H, m), 8.60 (1H, br s)

(19) 4-[3-(1-Naphthyl)phenyl]-2-(3-pyridylmethyl)-3-oxo-3,4-dihydropyrido[2,3-b]pyrazine mp: 162–165° C.

NMR (CDCl$_3$, δ): 4.31 (2H, s), 7.2–7.6 (8H, m), 7.70 (2H, m), 7.85 (3H, m), 8.07 (1H, d, J=8 Hz), 8.17 (1H, d, J=8 Hz), 8.50 (2H, m), 8.72 (1H, s)

(20) 4-[3-(3-Biphenylyl)phenyl]-2-(3-pyridylmethyl)-3-oxo-3,4-dihydropyrido[2,3-b]pyrazine NMR (CDCl$_3$, δ): 4.32 (2H, s), 7.2–7.7 (12H, m), 7.80 (3H, m), 8.18 (1H, m), 8.44 (1H, m), 8.50 (1H, m), 8.72 (1H, m)

EXAMPLE 46

A solution of 4-(3-acetamidophenyl)-2-(3-pyridylmethyl)-3-oxo-3,4-dihydropyrido[2,3-b]pyrazine (0.9 g) in 4N hydrochloric acid (22 ml) was stirred under reflux for 90 minutes, and cooled. The reaction mixture was neutralized with solid sodium bicarbonate and precipitated white crystals were collected, washed with water and dried to give 4-(3-aminophenyl)-2-(3-pyridylmethyl)-3-oxo-3,4-dihydropyrido[2,3-b]pyrazine (0.73 g).

mp: 168–170° C.

NMR (CDCl$_3$, δ): 3.81 (2H, s), 4.30 (2H, s), 6.53 (1H, m), 6.62 (1H, dd, J=8 Hz, 2 Hz), 6.80 (1H, dd, J=8 Hz, 2 Hz), 7.27 (2H, m), 7.35 (1H, dd, J=8 Hz, 8 Hz), 7.83 (1H, m), 8.17 (1H, dd, J=8 Hz, 1 Hz), 8.48 (1H, m), 8.50 (1H, m), 8.72 (1H, m)

EXAMPLE 47

The following compound was obtained according to a similar manner to that of Example 11 or 46.

4-(5-Amino-2-fluorophenyl)-2-(3-pyridylmethyl)-3-oxo-3,4-dihydropyrido[2,3-b]pyrazine mp: 177–179° C.

NMR (DMSO-d$_6$, δ): 4.26 (2H, s), 5.18 (2H, s), 6.53 (1H, dd, J=7 Hz, 4 Hz), 6.68 (1H, m), 7.08 (1H, dd, J=8 Hz, 8 Hz), 7.36 (1H, dd, J=8 Hz, 5 Hz), 7.42 (1H, dd, J=8 Hz, 5 Hz), 7.77 (1H, m), 8.21 (1H, dd, J=8 Hz, 2 Hz), 8.47 (2H, m), 8.59 (1H, m)

EXAMPLE 48

Treatment of 4-[3-(2-naphthoylamino)phenyl]-2-(3-pyridylmethyl)-3-oxo-3,4-dihydropyrido [2,3-b]pyrazine (3.84 g) with methanolic hydrogen chloride afforded 4-[3-(2-naphthoylamino)phenyl]-2-(3-pyridylmethyl)-3-oxo-3,4-dihydropyrido[2,3-b]pyrazinehydrochloride (2.80 g) as pale yellow solid.

NMR (DMSO-d$_6$, 300 MHz, δ): 4.50 (2H, s), 7.10 (1H, d, J=8 Hz), 7.42 (1H, dd, J=5 Hz, 8 Hz), 7.55–7.7 (3H, m), 7.88 (1H, d, J=8 Hz), 7.95–8.15 (7H, m), 8.45 (1H, m), 8.56 (1H, d, J=8 Hz), 8.62 (1H, s), 8.83 (JH, d, J=5 Hz), 8.95 (1H, s)

EXAMPLE 49

The following compound was obtained according to a similar manner to that of Example 48.

4-[3-(3-Biphenylyl)phenyl]-2-(3-pyridylmethyl)-3-oxo-3,4-dihydropyrido [2,3-b]pyrazine.hydrochloride mp: 202–205° C.

NMR (DMSO-d$_6$, δ): 4.53 (2H, s), 7.35 (1H, dd, J=8 Hz, 6 Hz), 7.40 (1H, d, J=8 Hz), 7.49 (2H, m), 7.62 (2H, d, J=8 Hz), 7.75 (5H, m), 7.92 (1H, dd, J=8 Hz, 6 Hz), 8.00 (2H, m), 8.07 (1H, m), 8.11 (1H, d, J=8 Hz), 8.29 (1H, d, J=6 Hz), 8.40 (1H, d, J=8 Hz), 8.78 (1H, d, J=6 Hz), 8.82 (1H, s)

EXAMPLE 50

The following compounds were obtained according to a similar manner to that of Example 1.

(1) 4-[2-Fluoro-5-[3-(2-fluorophenyl)ureido]phenyl]-2-(3-pyridylmethyl)-3-oxo-3,4-dihydropyrido[2,3-b]pyrazine mp: 146–149° C.

NMR (DMSO-d$_6$, δ): 4.28 (2H, s), 7.01 (1H, m), 7.11 (1H, m), 7.22 (1H, dd, J=13 Hz, 8 Hz), 7.36 (2H, m), 7.44 (1H, m), 7.50 (1H, m), 7.70 (1H, m), 7.79 (1H, d, J=8 Hz), 8.09 (1H, dd, J=8 Hz, 8 Hz), 8.23 (1H, d, J=8 Hz), 8.44 (2H, m), 8.58 (2H, m), 9.26 (1H, s)

(2) 4-[2-Fluoro-5-[3-(2-methoxyphenyl)ureido]phenyl]-2-(3-pyridylmethyl)-3-oxo-3,4-dihydropyrido[2,3-b]pyrazine mp: 152–155° C.

NMR (DMSO-d$_6$, δ): 3.87 (3H, s), 4.28 (2H, s), 6.87 (1H, m), 6.94 (1H, m), 7.02 (1H, m), 7.3–7.44 (4H, m), 8.09 (1H, m), 8.23 (2H, m), 8.45 (2H, m), 8.60 (1H, s), 9.53 (1H, s)

(3) 4-[3-[3-(2-Nitrophenyl)ureido]phenyl]-2-(3-pyridylmethyl)-3-oxo-3,4-dihydropyrido[2,3-b]pyrazine mp: 188–189° C.

NMR (DMSO-d$_6$, δ): 4.25 (2H, s), 6.98 (1H, m), 7.20 (1H, dd, J=8 Hz, 8 Hz), 7.37 (2H, m), 7.48 (2H, m), 7.57 (1H, s), 7.69 (1H, dd, J=8 Hz, 8 Hz), 7.78 (1H, m), 8.08 (1H, dd, J=8 Hz, 1 Hz), 8.19 (1H, dd, J=8 Hz, 1 Hz), 8.24 (1H, d, J=8 Hz), 8.40 (1H, dd, J=5 Hz, 1 Hz), 8.45 (1H, dd, J=5 Hz, 1 Hz), 8.59 (1H, d, J=1 Hz), 9.61 (1H, s)

(4) 4-[3-[3-(2-Methoxyphenyl)ureido]phenyl]-2-(3-pyridylmethyl)-3-oxo-3,4-dihydropyrido[2,3-b]pyrazine mp: 163–169° C.

NMR (CDCl$_3$, δ): 3.45 (3H, s), 4.38 (2H, s), 6.77 (2H, m), 6.92 (2H, m), 7.02 (1H, m), 7.16 (1H, s), 7.23 (1H, m), 7.30 (1H, m), 7.37 (1H, dd, J=8 Hz, 5 Hz), 7.66 (1H, s), 7.87 (1H, m), 7.94 (1H, s), 8.09 (1H, dd, J=8 Hz, 3 Hz), 8.25 (1H, dd, J=8 Hz, 1 Hz), 8.49 (2H, m), 8.76 (1H, m)

EXAMPLE 51

A mixture of 3-amino-2-[3-(3-pyridyl)phenylamino]pyridine (150 mg) and 3-phenylpyruvic acid (113 mg) in ethanol (4 ml) was stirred under reflux for 2 hours. The mixture was cooled and then poured into a mixture of ethyl acetate and aqueous sodium bicarbonate. The organic phase was separated, washed with aqueous sodium bicarbonate and brine, dried over magnesium sulfate and concentrated. The residue was crystallized from ethanol to give 2-benzyl-4-[3-(3-pyridyl)phenyl]-3-oxo-3,4-dihydropyrido[2,3-b]pyrazine (127 mg).

NMR (CDCl$_3$, 300 MHz, δ): 4.32 (2H, s), 7.2–7.4 (6H, m), 7.45–7.55 (3H, m), 7.65–7.8 (2H, m), 7.89(1H, dt, J=8 Hz, 2 Hz), 8.21 (1H, dd, J=2 Hz, 8 Hz), 8.41 (1H, dd, J=2 Hz, 5 Hz), 8.59 (1H, dd, J=2 Hz, 5 Hz), 8.87 (1H, s, J=2 Hz)

EXAMPLE 52

A mixture of 2-[3-acetylamino-5-methoxycarbonylphenylamino]-3-aminopyridine (1.07 g) and 3-(3-pyridyl)pyruvic acid (0.65 g) in methanol (15 ml) was stirred under reflux for 5 hours. The precipitate was collected and washed with methanol to give 4-(3-acetylamino-5-methoxycarbonylphenyl)-2-(3-pyridylmethyl)-3-oxo-3,4-dihydropyrido[2,3-b]pyrazine (1.08 g).

NMR (DMSO-d$_6$, 300 MHz, δ): 2.09 (3H, s), 3.87 (3H, s), 4.24 (2H, s), 7.8–7.95 (2H, m), 7.63 (1H, s), 7.78 (1H, d, J=8 Hz), 7.90 (1H, s), 8.20 (1H, d, J=8 Hz), 8.26 (1H, s), 8.38 (1H, d, J=5 Hz), 8.47 (1H, m), 8.59 (1H, s)

EXAMPLE 53

A mixture of 3-amino-2-[3-methoxycarbonyl-5-(2-naphthoylamino)phenylamino]pyridine (180 mg) and 3-phenylpyruvic acid (86 mg) in methanol (4 ml) was stirred under reflux for 4 hours. The precipitate was collected and washed with methanol to give 2-benzyl-4-[3-methoxycarbonyl-5-(2-naphthoylamino)phenyl]-3-oxo-3,4-dihydropyrido[2,3-b]pyrazine (169 mg).

NMR (CDCl$_3$, 300 MHz, δ): 3.81 (3H, s), 4.32 (2H, 5), 7.15–7.35 (4H, m), 7.45–7.65 (5H, m), 7.8–7.9 (4H, m), 8.15–8.3 (3H, m), 8.33 (1H, s), 8.39 (1H, d, J=5 Hz), 8.56 (1H, s)

EXAMPLE 54

The following compounds were obtained according to a similar manner to that of Example 2, 42, 43, 44, 51, 52 or 53.

(1) 4-[3-[(E)-2-Phenylvinyl]phenyl]-2-(3-pyridylmethyl)-3-oxo-3,4-dihydropyrido[2,3-b]pyrazine NMR (CDCl$_3$, 300 MHz, δ): 4.32 (2H, s), 7.1–7.7 (13H, m), 7.93 (1H, d, J=8 Hz), 8.20 (1H, dd, J=2 Hz, 8 Hz), 8.45 (1H, dd, J=2 Hz, 5 Hz), 8.52 (1H, dd, J=2, 5 Hz), 8.72 (1H, s)

(2) 4-[3-[(E)-2-(2-Naphthyl)vinyl]phenyl]-2-(3-pyridylmethyl)-3-oxo-3,4-dihydropyrido[2,3-b]pyrazine NMR (CDCl$_3$, 300 MHz, δ): 4.33 (2H, s), 7.1–7.35 (5H, m), 7.4–7.5 (3H, m), 7.59 (1H, t, J=8 Hz), 7.70 (2H, m), 7.75–7.9 (5H, m), 8.20 (1H, d, J=8 Hz), 8.45 (1H, d, J=5 Hz), 8.52 (1H, dd, J=2 Hz, 5 Hz), 8.73 (1H, s)

(3) 2-Benzyl-4-[3-(2-pyridyl)phenyl]-3-oxo-3,4-dihydropyrido[2,3-b]pyrazine

NMR (CDCl$_3$, 300 MHz, δ): 4.31 (2H, s), 7.2–7.35 (6H, m), 7.50 (2H, d, J=8 Hz), 7.6–7.8 (3H, m), 7.94 (1H, m), 8.1–8.25 (2H, m), 8.40 (1H, m), 8.65 (1H, d, J=5 Hz)

(4) 2-(3-Pyridylmethyl)-4-[3-(2-pyridyl)phenyl]-3-oxo-3,4-dihydropyrido[2,3-b]pyrazine NMR (CDCl$_3$, 300 MHz, δ): 4.31 (2H, s), 7.2–7.35 (4H, m), 7.65–7.85 (4H, m), 7.97 (1H, t, J=2 Hz), 8.17 (2H, m), 8.41 (1H, dd, J=2 Hz, 5 Hz), 8.50 (1H, dd, J=2 Hz, 5 Hz), 8.67 (1H, m), 8.73 (1H, d, J=2 Hz)

(5) 2-(3-Pyridylmethyl)-4-[3-(3-pyridyl)phenyl]-3-oxo-3,4-dihydropyrido[2,3-b]pyrazine NMR (CDCl$_3$, 300 MHz, δ): 4.32 (2H, s), 7.2–7.4 (4H, m), 7.50 (1H, t, J=2 Hz), 7.65–7.8 (2H, m), 7.83 (1H, dt, J=8 Hz, 2 Hz), 7.90 (1H, dt, J=8 Hz, 2 Hz), 8.20 (1H, dd, J=2 Hz, 8 Hz), 8.43 (1H, dd, J=2 Hz, 5 Hz), 8.52 (1H, dd, J=2 Hz, 5 Hz), 8.60 (1H, dd, J=2 Hz, 5 Hz), 8.73 (1H, d, J=2 Hz), 8.88 (1H, d, J=2 Hz)

(6) 2-Benzyl-4-[3-(4-pyridyl)phenyl]-3-oxo-3,4-dihydropyrido[2,3-b]pyrazine

NMR (CDCl$_3$, 300 MHz, δ): 4.32 (2H, s), 7.2–7.4 (5H, m), 7.45–7.55 (5H, m), 7.70 (1H, t, J=8 Hz), 7.78 (1H, dt, J=8 Hz, 2 Hz), 8.21 (1H, dd, J=2 Hz, 8 Hz), 8.40 (1H, dd, J=2 Hz, 5 Hz), 8.65 (2H, dd, J=2 Hz, 5 Hz)

(7) 2-Benzyl-4-[3-(2-thienyl)phenyl]-3-oxo-3,4-dihydropyrido[2,3-b]pyrazine

NMR (CDCl$_3$, 300 MHz, δ): 4.32 (2H, s), 7.07 (1H, m), 7.15–7.35 (7H, m), 7.45–7.6 (4H, m), 7.73 (1H, d, J=8 Hz), 8.20 (1H, d, J=8 Hz), 8.41 (1H, m)

(8) 2-(3-Pyridylmethyl)-4-[3-(2-thienyl)phenyl]-3-oxo-3,4-dihydropyrido[2,3-b]pyrazine NMR (CDCl₃, 300 MHz, δ): 4.32 (2H, s), 7.07 (1H, dd, J=5 Hz, 8 Hz), 7.18 (1H, m), 7.2–7.35 (4H, m), 7.49 (1H, t, J=2 Hz), 7.59 (1H, t, J=8 Hz), 7.75 (1H, dt, J=8 Hz, 2 Hz), 7.82 (1H, dt, J=8 Hz, 2 Hz), 8.19 (1H, dd, J=2 Hz, 8 Hz), 8.43 (1H, dd, J=2 Hz, 5 Hz), 8.51 (1H, dd, J=2 Hz, 5 Hz), 8.73 (1H, d, J=2 Hz)

(9) 4-[3-(5-Chloro-2-thienyl)phenyl]-2-benzyl-3-oxo-3,4-dihydropyrido[2,3-b]pyrazine NMR (CDCl₃, 300 MHz, δ): 4.32 (2H, s), 6.88 (1H, d, J=4 Hz), 7.08 (1H, d, J=4 Hz), 7.15–7.4 (6H, m), 7.45–7.65 (4H, m), 8.20 (1H, dd, J=2 Hz, 8 Hz), 8.40 (1H, m)

(10) 4-[3-(5-Chloro-2-thienyl)phenyl]-2-(3-pyridylmethyl)-3-oxo-3,4-dihydropyrido[2,3-b]pyrazine NMR (CDC13, 300 MHz, δ): 4.32 (2H, s), 6.89 (1H, d, J=4 Hz), 7.09 (1H, d, J=4 Hz), 7.15–7.45 (4H, m), 7.55–7.7 (2H, m), 7.83 (1H, dd, J=2 Hz, 8 Hz), 8.20 (1H, dd, J=2 Hz, 8 Hz), 8.43 (1H, dd, J=2 Hz, 5 Hz), 8.52 (1H, dd, J=2 Hz, 5 Hz), 8.73 (1H, s)

(11) 2-Benzyl-4-[3-(3-thienyl)phenyl]-3-oxo-3,4-dihydropyrido[2,3-b]pyrazine

NMR (CDCl₃, 300 MHz, δ): 4.31 (2H, s), 7.15–7.4 (7H, m), 7.45–7.55 (4H, m), 7.59 (1H, t, J=8 Hz)

(12) 2-(3-Pyridylmethyl)-4-[3-(3-thienyl)phenyl]-3-oxo-3,4-dihydropyrido[2,3-b]pyrazine NMR (CDCl₃, 300 MHz, δ): 4.31 (2H, s), 7.15–7.4 (5H, m), 7.46 (2H, m), 7.60 (1H, t, J=8 Hz), 7.73 (1H, d, J=8 Hz), 7.82 (1H, dt, J=8 Hz, 2 Hz), 8.18 (1H, dd, J=2 Hz, 8 Hz), 8.42 (1H, dd, J=2 Hz, 5 Hz), 8.51 (1H, dd, J=2 Hz, 5 Hz), 8.72 (1H, s)

(13) 2-Benzyl-4-[3-(1H-1,2,4-triazol-1-yl)phenyl]-3-oxo-3,4-dihydropyrido[2,3-b]pyrazine NMR (DMSO-d₆, 300 MHz, δ): 4.22 (2H, s), 7.2–7.5 (7H, m), 7.74 (1H, t, J=8 Hz), 7.95 (1H, t, J=2 Hz), 8.02 (1H, dt, J=8 Hz, 2 Hz), 8.27 (2H, m), 8.40 (1H, dd, J=2 Hz, 5 Hz), 9.30 (1H, s)

(14) 2-(3-Pyridylmethyl)-4-[3-(1H-1,2,4-triazol-1-yl)phenyl]-3-oxo-3,4-dihydropyrido[2,3-b]pyrazine NMR (DMSO-d₆, 300 MHz, δ): 4.27 (2H, s), 7.35–7.5 (3H, m), 7.7–7.8 (2H, m), 7.96 (1H, t, J=2 Hz), 8.03 (1H, dt, J=8 Hz, 2 Hz), 8.2–8.3 (2H, m), 8.41 (1H, dd, J=2 Hz, 5 Hz), 8.47 (1H, dd, J=2 Hz, 5 Hz), 8.60 (1H, dd, J=2 Hz, 5 Hz), 9.31 (1H, s)

(15) 2-Benzyl-4-[3-(2-fluorophenyl)phenyl]-3-oxo-3,4-dihydropyrido[2,3-b]pyrazine NMR (CDCl₃, 300 MHz, δ): 4.32 (2H, s), 7.1–7.35 (8H, m), 7.45–7.55 (4H, m), 7.6–7.75 (2H, m), 8.19 (1H, dd, J=2 Hz, 8 Hz), 8.42 (1H, dd, J=2 Hz, 5 Hz)

(16) 4-[3-(2-Fluorophenyl)phenyl]-2-(3-pyridylmethyl)-3-oxo-3,4-dihydropyrido[2,3-b]pyrazine NMR (CDCl₃, 300 MHz, δ): 4.32 (2H, s), 7.1–7.35 (6H, m), 7.45–7.55 (2H, m), 7.66 (1H, t, J=8 Hz), 7.72 (1H, m), 7.83 (1H, dt, J=8 Hz, 2 Hz), 8.18 (1H, dd, J=2 Hz, 8 Hz), 8.44 (1H, dd, J=2 Hz, 5 Hz), 8.51 (1H, dd, J=2 Hz, 5 Hz), 8.72 (1H, d, J=2 Hz)

(17) 2-Benzyl-4-[3-(4-methoxycarbonylphenyl)phenyl]-3-oxo-3,4-dihydropyrido[2,3-b]pyrazine NMR (CDCl₃, 300 MHz, δ): 3.94 (3H, s), 4.33 (2H, s), 7.2–7.35 (5H, m), 7.51 (2H, m), 7.65–7.7 (3H, m), 7.77 (1H, dt, J=8 Hz, 2 Hz), 8.10 (2H, dt, J=8 Hz, 2 Hz), 8.21 (1H, dd, J=2 Hz, 8 Hz), 8.41 (1H, dd, J=2 Hz, 5 Hz)

(18) 4-[3-(4-Acetylaminophenyl)phenyl]-2-benzyl-3-oxo-3,4-dihydropyrido[2,3-b]pyrazine NMR (CDCl₃, 300 MHz, δ): 2.10 (3H, s), 4.33 (2H, s), 7.2–7.35 (5H, m), 7.4–7.7 (10H, m), 8.22 (1H, dd, J=2 Hz, 8 Hz), 8.42 (1H, dd, J=2 Hz, 5 Hz)

(19) 4-[3-(4-Acetylaminophenyl)phenyl]-2-(3-pyridylmethyl)-3-oxo-3,4-dihydropyrido[2,3-b]pyrazine NMR (CDCl₃, 300 MHz, δ): 2.13 (3H, s), 4.33 (2H, s), 7.2–7.35 (3H, m), 7.4–7.7 (8H, m), 7.83 (1H, d, J=8 Hz), 8.20 (1H, d, J=8 Hz), 8.45 (1H, m), 8.51 (1H, m), 8.73 (1H, s)

(20) 2-Benzyl-4-(3-morpholinocarbonylphenyl)-3-oxo-3,4-dihydropyrido[2,3-b]pyrazine NMR (DMSO-d₆, 300 MHz, δ): 3.3–3.7 (8H, m), 4.22 (2H, s), 7.2–7.65 (10H, m), 8.24 (1H, dd, J=2 Hz, 8 Hz), 8.39 (1H, dd, J=2 Hz, 5 Hz)

(21) 2-Benzyl-4-[3,5-bis(methoxycarbonyl)phenyl]-3-oxo-3,4-dihydropyrido[2,3-b]pyrazine NMR (CDCl₃, 300 MHz, δ): 3.93 (6H, s), 4.31 (2H, s), 7.2–7.35 (4H, m), 7.48 (2H, d, J=8 Hz), 8.14 (2H, s), 8.20 (1H, d, J=8 Hz), 8.34 (1H, m), 8.81 (1H, s)

(22) 4-[3,5-Bis(methoxycarbonyl)phenyl]-2-(3-pyridylmethyl)-3-oxo-3,4-dihydropyrido[2,3-b]pyrazine NMR (CDCl₃, 300 MHz, δ): 3.94 (6H, s), 4.31 (2H, s), 7.2–7.35 (2H, m), 7.80 (1H, d, J=8 Hz), 8.15–8.25 (3H, m), 8.38 (1H, d, J=5 Hz), 8.52 (1H, d, J=5 Hz), 8.72 (1H, s), 8.83 (1H, t, J=2 Hz)

(23) 4-[3-Methoxycarbonyl-5-(2-naphthoylamino)phenyl]-2-(3-pyridylmethyl)-3-oxo-3,4-dihydropyrido[2,3-b]pyrazine NMR (DMSO-d₆, 300 MHz, δ): 3.90 (3H, s), 4.28 (2H, s), 7.8–7.95 (2H, m), 7.6–7.7 (2H, m), 7.75 (1H, d, J=2 Hz), 7.79 (1H, d, J=8 Hz), 8.0–8.15 (4H, m), 8.2–8.25 (2H, m), 8.40 (1H, d, J=5 Hz), 8.48 (1H, d, J=5 Hz), 8.57 (1H, t, J=2 Hz), 8.61 (1H, d, J=2 Hz), 8.65 (1H, s)

(24) 4-[3-(6-Methoxy-2-naphthyl)phenyl]-2-(3-pyridylmethyl)-3-oxo-3,4-dihydropyrido[2,3-b]pyrazine mp: 228–231° C.

NMR (DMSO-d₆, δ): 3.89 (3H, s), 4.29 (2H, s), 7.20 (1H, m), 7.38 (4H, m), 7.67 (1H, dd, J=8 Hz, 8 Hz), 7.82 (3H, m), 7.91 (3H, m), 8.20 (2H, m), 8.42 (1H, m), 8.47 (1H, m), 8.61 (1H, m)

(25) 4-[3-(5-Methoxycarbonylindol-1-yl)phenyl]-2-(3-pyridylmethyl)-3-oxo-3,4-dihydropyrido[2,3-b]pyrazine mp: 193–197° C.

NMR (DMSO-d₆, δ): 3.86 (3H, s), 4.27 (2H, s), 6.90 (1H, d, J=3 Hz), 7.35 (1H, m), 7.43 (1H, m), 7.47 (1H, m), 7.69 (1H, d, J=8 Hz), 7.75–7.85 (6H, m), 8.23 (1H, d, J=8 Hz), 8.38 (1H, s), 8.47 (1H, m), 8.61 (1H, m)

(26) 4-[3-(3-Quinolyl)phenyl]-2-(3-pyridylmethyl)-3-oxo-3,4-dihydropyrido[2,3-b]pyrazine mp: 237° C.

NMR (DMSO-d₆, δ): 4.28 (2H, s), 7.37 (1H, dd, J=8 Hz, 5 Hz), 7.42 (1H, dd, J=8 Hz, 5 Hz), 7.47 (1H, d, J=8 Hz), 7.65 (1H, dd, J=8 Hz, 8 Hz), 7.75 (1H, m), 7.79 (2H, m), 7.97 (1H, m), 8.05 (3H, m), 8.24 (1H, m), 8.43 (1H, m), 8.48 (1H, m), 8.62 (1H, m), 8.71 (1H, d, J=3 Hz), 9.28 (1H, s)

(27) 4-[3-(3-Cyclopentyloxy-4-methoxyphenyl)phenyl]-2-(3-pyridylmethyl)-3-oxo-3,4-dihydropyrido[2,3-b]pyrazine mp: 109–111° C.

NMR CDCl₃, δ): 1.60 (2H, m), 1.85 (2H, m), 1.90 (4H, m), 3.87 (3H, s), 4.33 (2H, s), 4.82 (1H, m), 6.91 (1H, d, J=8 Hz), 7.13 (2H, m), 7.20 (1H, m), 7.27 (1H, m), 7.31 (1H, m), 7.41 (1H, m), 7.63 (1H, dd, J=8 Hz, 8 Hz), 7.69 (1H, m), 7.84 (1H, m), 8.19 (1H, m), 8.45 (1H, d, J=5 Hz), 8.51 (1H, m), 8.74 (1H, m)

(28) 4-[3-(3-Methoxycarbonylphenyl)phenyl]-2-(3-pyridylmethyl)-3-oxo-3,4-dihydropyrido[2,3-b]pyrazine mp: 179–181° C.

NMR (CDCl₃, δ): 3.92 (3H, s), 4.32 (2H, s), 7.30 (3H, m), 7.52 (2H, m), 7.69 (1H, dd, J=8 Hz, 8 Hz), 7.80 (3H, m), 8.03 (1H, d, J=8 Hz), 8.19 (1H, d, J=8 Hz), 8.30 (1H, s), 8.44 (1H, m), 8.51 (1H, m), 8.74 (1H, m)

MASS (m/z): 449 (M+1)

(29) 4-[3-[(E)-2-Methoxycarbonylvinyl]phenyl]-2-(3-pyridylmethyl)-3-oxo-3,4-dihydropyrido[2,3-b]pyrazine mp: 180–181° C.

NMR (DMSO-d$_6$, δ): 3.71 (3H, s), 4.27 (2H, s), 6.77 (1H, d, J=16 Hz), 7.40 (3H, m), 7.53 (1H, dd, J=8 Hz, 8 Hz), 7.66 (1H, dd, J=8 Hz, 8 Hz), 7.7–7.85 (5H, m), 7.92 (1H, d, J=8 Hz), 8.07 (1H, s), 8.22 (1H, d, J=8 Hz), 8.41 (1H, m), 8.48 (1H, m), 8.61 (1H, m)

(30) 4-[3-(4-Isoquinolyl)phenyl]-2-(3-pyridylmethyl)-3-oxo-3,4-dihydropyrido[2,3-b]pyrazine mp: 157–163° C.

NMR (CDCl$_3$, δ): 4.33 (2H, s), 7.23 (1H, m), 7.32 (1H, m), 7.40 (1H, m), 7.45 (1H, m), 7.60–7.85 (5H, m), 8.04 (1H, d, J=8 Hz), 8.09 (1H, d, J=8 Hz), 8.20 (1H, d, J=8 Hz), 8.50 (2H, m), 8.58 (1H, s), 8.73 (1H, m), 9.25 (1H, s)

(31) 4-[3-(3-Acetamidophenyl)phenyl]-2-(3-pyridylmethyl)-3-oxo-3,4-dihydropyrido[2,3-b]pyrazine mp: 188–194° C.

NMR (CDCl$_3$, δ): 2.13 (3H, s), 4.32 (2H, s), 7.2–7.35 (5H, m), 7.45 (2H, m), 7.55 (1H, s), 7.62 (1H, dd, J=8 Hz, 8 Hz), 7.70 (2H, m), 7.82 (1H, m), 8.18 (1H, d, J=8 Hz), 8.41 (1H, m), 8.49 (1H, d, J=5 Hz), 8.73 (1H, s)

MASS (m/z): 448 (M+1)

EXAMPLE 55

A mixture of 2-benzyl-4-[3-(4-methoxycarbonylphenyl)phenyl]-3-oxo-3,4-dihydropyrido[2,3-b]pyrazine (150 mg) and lithium bromide (0.30 g) in N,N-dimethylformamide (3 ml) was stirred under reflux for 4 hours. The mixture was cooled and poured into dilute hydrochloric acid with stirring. The resultant precipitate was collected and washed with water to give 2-benzyl-4-[3-(4-carboxyphenyl)phenyl]-3-oxo-3,4-dihydropyrido[2,3-b]pyrazine (119 mg).

NMR (CDCl$_3$, 300 MHz, δ): 4.32 (2H, s), 7.2–7.35 (5H, m), 7.5–7.6 (3H, m), 7.65–7.85 (4H, m), 8.14 (2H, d, J=8 Hz), 8.22 (1H, dd, J=2 Hz, 8 Hz), 8.42 (1H, dd, J=2 Hz, 5 Hz)

EXAMPLE 56

A suspension of 4-[3-(4-acetylaminophenyl)phenyl]-2-benzyl-3-oxo-3,4-dihydropyrido[2,3-b]pyrazine (963 mg) in 3N hydrochloric acid (25 ml) was stirred under reflux for 3 hours. Then the mixture was poured into ice-water and alkalinized with sodium bicarbonate. The resultant solid was collected and washed with water to give 4-[3-(4-aminophenyl)phenyl]-2-benzyl-3-oxo-3,4-dihydropyrido[2,3-b]pyrazine (577 mg).

NMR (DMSO-d$_6$, 300 MHz, δ): 4.32 (2H, s), 5.28 (2H, s), 6.63 (2H, d, J=8 Hz), 7.15–7.45 (9H, m), 7.52 (2H, m), 7.67 (1H, d, J=8 Hz), 8.23 (1H, dd, J=2 Hz, 8 Hz), 8.40 (1H, dd, J=2 Hz, 5 Hz)

EXAMPLE 57

To a mixture of 4-[3-(4-aminophenyl)phenyl]-2-benzyl-3-oxo-3,4-dihydropyrido[2,3-b]pyrazine (94 mg) and triethylamine (0.04 ml) in dichloromethane (3 ml) was added methanesulfonyl chloride (0.04 ml). The mixture was stirred at room temperature for 30 minutes, then poured into a mixture of ethyl acetate and aqueous sodium bicarbonate. The organic phase was separated, washed with aqueous sodium bicarbonate and brine, dried over magnesium sulfate and concentrated. The residue was chromatographed on silica gel column (35% ethyl acetate in hexane) and crystallized from ethanol to give 2-benzyl-4-[3-(4-methylsulfonylaminophenyl)phenyl]-3-oxo-3,4-dihydropyrido[2,3-b]pyrazine (53 mg).

NMR (CDCl3, 300 MHz, δ): 3.00 (3H, s), 4.33 (2H, s), 6.77 (1H, s), 7.2–7.35 (7H, m), 7.42 (1H, m), 7.45–7.55 (4H, m), 7.6–7.7 (2H, m), 8.21 (1H, dd, J=2 Hz, 8 Hz), 8.41 (1H, dd, J=2 Hz, 5 Hz)

EXAMPLE 58

To a mixture of 4-[3-(4-aminophenyl)phenyl]-2-benzyl-3-oxo-3,4-dihydropyrido[2,3-b]pyrazine (95 mg) and triethylamine (0.05 ml) in dichloromethane (3 ml) was added benzoyl chloride (0.03 ml). The mixture was stirred at room temperature for 20 minutes, then poured into a mixture of ethyl acetate and aqueous sodium bicarbonate. The organic phase was separated, washed with aqueous sodium bicarbonate and brine, dried over magnesium sulfate and concentrated. The residue was crystallized from methanol to give 4-[3-(4-benzoylaminophenyl)phenyl]-2-benzyl-3-oxo-3,4-dihydropyrido[2,3-b]pyrazine (73 mg).

NMR (CDCl$_3$, 300 MHz, δ): 4.32 (2H, s), 7.1–7.35 (5H, m), 7.4–7.75 (12H, m), 7.85 (2H, d, J=8 Hz), 7.99 (1H, d), 8.20 (1H, d, J=8 Hz), 8.41 (1H, m)

EXAMPLE 59

A mixture of 2-benzyl-4-(3-carboxyphenyl)-3-oxo-3,4-dihydropyrido[2,3-b]pyrazine (339 mg), diphenylphosphoryl azide (0.21 ml) and triethylamine (0.14 ml) in benzene (5 ml) was stirred under reflux for 30 minutes. Then 4-aminomorpholine (0.11 ml) was added to the mixture and reflux was continued additional 3 hours. The mixture was poured into a mixture of ethyl acetate and aqueous sodium bicarbonate. The organic phase was separated, washed with aqueous sodium bicarbonate and brine, dried over magnesium sulfate and concentrated. The residue was chromatographed on silica gel column (3% methanol in chloroform) to give 2-benzyl-4-[3-(3-morpholinoureido)phenyl]-3-oxo-3,4-dihydropyrido[2,3-b]pyrazine (138 mg).

NMR (CDCl$_3$, 300 MHz, δ): 2.65 (2H, br s), 3.0 (2H, br s), 3.65 (2H, br s), 3.9 (2H, br s), 4.31 (2H, s), 5.48 (1H, s), 6.93 (!H, dt, J=8 Hz, 2 Hz), 7.2–7.35 (4H, m), 7.40 (1H, t, J=2 Hz), 7.45–7.55 (3H, m), 7.71 (1H, dd, J=2 Hz, 8 Hz), 8.19 (2H, dt, J=8 Hz, 2 Hz), 7.40 (1H, dd, J=2 Hz, 5 Hz)

EXAMPLE 60

A mixture of 4-(3-aminophenyl)-2-benzyl-3-oxo-3,4-dihydropyrido[2,3-b]pyrazine (339 mg), triethylamine (0.18 ml), 4-dimethylaminopyridine (5 mg) and morpholinocarbonyl chloride (0.15 ml) in 1,4-dioxane (4 ml) was stirred at 80° C. for 2 hours. Then the mixture was poured into a mixture of ethyl acetate and aqueous sodium bicarbonate. The organic phase was separated, washed with aqueous sodium bicarbonate and brine, dried over magnesium sulfate and concentrated. The residue was chromatographed on silica gel column (ethyl acetate) to give 2-benzyl-4-[3-(morpholinocarbonylamino)phenyl]-3-oxo-3,4-dihydropyrido[2,3-b]pyrazine (242 mg).

NMR (DMSO-d$_6$, 300 MHz, δ): 3.42 (4H, m), 3.60 (4H, m), 4.21 (2H, s), 6.90 (1H, d, J=8 Hz), 7.2–7.45 (8H, m), 7.55 (1H, d, J=8 Hz), 8.23 (1H, dd, J=2 Hz, 8 Hz), 8.40 (1H, dd, J=2 Hz, 5 Hz), 8.72 (1H, s)

EXAMPLE 61

A mixture of 4-(3-acetylamino-5-methoxycarbonylphenyl)-2-(3-pyridylmethyl)-3-oxo-3,4-dihydropyrido[2,3-b]pyrazine (847 mg) and hydrochloric acid (35%, 1 ml) in methanol (10 ml) was stirred under reflux for 2 hours. After cooling, the resultant precipitate was collected and washed with methanol to give 4-(3-amino-5-methoxycarbonylphenyl)-2-(3-pyridylmethyl)-3-oxo-3,4-dihydropyrido[2,3-b]pyrazinedihydrochloride (612 mg).

NMR (CD$_3$OD, 300 MHz, δ): 3.96 (3H, s), 4.59 (2H, s), 7.42 (1H, dd, J=5 Hz, 8 Hz), 7.67 (1H, s), 8.02 (1H, s), 8.1–8.2 (3H, m), 8.38 (1H, d, J=5 Hz), 8.73 (1H, d, J=8 Hz), 8.82 (1H, d, J=5 Hz), 8.99 (1H, s)

EXAMPLE 62

To a mixture of 4-(3-aminophenyl)-2-benzyl-3-oxo-3,4-dihydropyrido[2,3-b]pyrazine (150 mg) and triethylamine (0.1 ml) in dichloromethane (4 ml) was added 2-furoyl chloride (0.05 ml). The mixture was stirred at room temperature for 20 minutes, then poured into a mixture of ethyl acetate and aqueous sodium bicarbonate. The organic phase was separated, washed with aqueous sodium bicarbonate and brine, dried over magnesium sulfate and concentrated. The residue was crystallized from ethanol to give 2-benzyl-4-[3-(2-furoylamino)phenyl]-3-oxo-3,4-dihydropyrido[2,3-b]pyrazine (145 mg).

NMR (CDCl$_3$, 300 MHz, δ): 6.52 (1H, m), 7.00 (1H, d, J=8 Hz), 7.15–7.35 (5H, m), 7.45–7.6 (4H, m), 7.7–7.8 (2H, m), 8.15–8.25 (2H, m), 8.41 (1H, m)

EXAMPLE 63

To a mixture of 4-(3-aminophenyl)-2-benzyl-3-oxo-3,4-dihydropyrido[2,3-b]pyrazine (150 mg) and triethylamine (0.16 ml) in dichloromethane (3 ml) was added 3-[(E)-3-pyridyl]acryloyl chloridehydrochloride (140 mg). The mixture was stirred at room temperature for 30 minutes, then poured into a mixture of ethyl acetate and aqueous sodium bicarbonate. The organic phase was separated, washed with aqueous sodium bicarbonate and brine, dried over magnesium sulfate and concentrated. The residue was crystallized from methanol to give 2-benzyl-4-[3-[(E)-3-(3-pyridyl)acryloylamino]phenyl]-3-oxo-3,4-dihydropyrido[2,3-b]pyrazine (138 mg).

NMR (CDCl$_3$, 300 MHz, δ): 4.32 (2H, s), 6.35 (1H, d, J=16 Hz), 6.84 (1H, d, J=8 Hz), 7.05 (1H, t, J=8 Hz), 7.15–7.6 (9H, m), 7.71 (1H, d, J=8 Hz), 8.28 (1H, d, J=8 Hz), 8.43 (1H, d, J=5 Hz), 8.53 (1H, d, J=5 Hz), 8.62 (1H, s), 8.69 (1H, s)

EXAMPLE 64

To a mixture of 4-(3-aminophenyl)-2-benzyl-3-oxo-3,4-dihydropyrido[2,3-b]pyrazine (150 mg) and triethylamine (0.1 ml) in dichloromethane (4 ml) was added methoxyglyoxyloyl chloride (0.05 ml). The mixture was stirred at room temperature for 20 minutes, then poured into a mixture of ethyl acetate and aqueous sodium bicarbonate. The organic phase was separated, washed with aqueous sodium bicarbonate and brine, dried over magnesium sulfate and concentrated. The resultant solid was collected and washed with methanol to give 2-benzyl-4-[3-(methoxyglyoxyloylamino)phenyl]-3-oxo-3,4-dihydropyrido[2,3-b]pyrazine (163 mg).

NMR (DMSO-d$_6$, 300 MHz, δ): 3.86 (3H, s), 4.21 (2H, s), 7.13 (1H, d, J=8 Hz), 7.2–7.45 (6H, m), 7.53 (1H, t, J=8 Hz), 7.75–7.85 (2H, m), 8.24 (2H, d, J=8 Hz), 8.39 (1H, d, J=5 Hz)

EXAMPLE 65

To a mixture of 4-(3-aminophenyl)-2-benzyl-3-oxo-3,4-dihydropyrido[2,3-b]pyrazine (192 mg) and triethylamine (0.12 ml) in 1,4-dioxane (4 ml) was added isopropyl chloroformate (0.10 ml). The mixture was stirred at room temperature for 30 minutes, then poured into aqueous sodium bicarbonate and extracted with ethyl acetate twice. The combined organic phase was washed with aqueous sodium bicarbonate and brine, dried over magnesium sulfate and concentrated. The resultant solid was collected and washed with methanol to give 2-benzyl-4-(3-isopropoxycarbonylaminophenyl)-3-oxo-3,4-dihydropyrido[2,3-b]pyrazine (167 mg).

NMR (DMSO-d$_6$, 300 MHz, δ): 1.23 (6H, d, J=8 Hz), 4.21 (2H, s), 4.87 (1H, m), 6.93 (1H, dt, J=8 Hz, 2 Hz), 7.2–7.5 (9H, m), 8.23 (1H, dd, J=2 Hz, 8 Hz), 8.39 (1H, dd, J=2 Hz, 5 Hz), 9.77 (1H, s)

EXAMPLE 66

The following compounds were obtained according to a similar manner to that of Example 19, 20, 21, 38, 39, 40, 60, 62, 63, 64 or 65.

(1) 4-[3-(4-Acetoxybenzoylamino)phenyl]-2-benzyl-3-oxo-3,4-dihydropyrido[2,3-b]pyrazine NMR (CDCl$_3$, 300 MHz, δ): 2.30 (3H, s), 4.30 (2H, s), 6.83 (1H, m), 7.08 (2H, d, J=8 Hz), 7.1–7.35 (4H, m), 7.4–7.5 (3H, m), 7.61 (1H, s), 7.70 (1H, d, J=8 Hz), 7.79 (2H, d, J=8 Hz), 8.20 (1H, d, J=8 Hz), 8.27 (1H, s), 8.40 (1H, m)

(2) 4-[3-[3,5-Bis(methoxycarbonyl)benzoylamino]phenyl]-2-(3-pyridylmethyl)-3-oxo-3,4-dihydropyrido[2,3-b]pyrazine.hydrochloride NMR (DMSO-d$_6$, 300 MHz, δ): 3.95 (6H, s), 4.49 (2H, s), 7.13 (1H, d, J=8 Hz), 7.42 (1H, dd, J=5 Hz, 8 Hz), 7.59 (1H, t, J=8 Hz), 7.8–7.9 (2H, m), 8.01 (1H, dd, J=5 Hz, 8 Hz), 8.19 (1H, d, J=8 Hz), 8.44 (1H, t, J=2 Hz), 8.52 (1H, d, J=8 Hz), 8.64 (1H, d, J=2 Hz), 8.75–8.85 (3H, m), 8.93 (1H, s)

(3) 4-[3-(3,5-Diethoxybenzoylamino)phenyl]-2-(3-pyridylmethyl)-3-oxo-3,4-dihydropyrido[2,3-b]pyrazine NMR (DMSO-d$_6$, 300 MHz, δ): 1.33 (6H, t, J=7 Hz), 4.09 (4H, q, J=7 Hz), 4.27 (2H, s), 6.69 (1H, d, j=2 Hz), 7.05–7.1 (3H, m), 7.3–7.45 (3H, m), 7.53 (1H, t, J=8 Hz), 7.75–7.85 (3H, m), 8.21 (1H, d, J=8 Hz), 8.40 (1H, d, J=5 Hz), 8.47 (1H, d, J=5 Hz), 8.60 (1H, s)

(4) 4-[3-(3,5-Diisopropoxybenzoylamino)phenyl]-2-(3-pyridylmethyl)-3-oxo-3,4-dihydropyrido[2,3-b]pyrazine NMR (DMSO-d$_6$, 300 MHz, δ): 1.29 (12H, d, J=7 Hz), 4.28 (2H, s), 4.69 (2H, m), 6.66 (1H, t, J=2 Hz), 7.0–7.1 (3H, m), 7.35–7.45 (2H, m), 7.52 (1H, t, J=8 Hz), 7.75–7.85 (3H, m), 8.21 (1H, d, J=8 Hz), 8.41 (1H, m), 8.48 (1H, d, J=5 Hz), 8.60 (1H, d, J=2 Hz)

(5) 4-[3-(3,5-Di-tert-butylbenzoylamino)phenyl]-2-(3-pyridylmethyl)-3-oxo-3,4-dihydropyrido[2,3-b]pyrazine.hydrochloride NMR (DMSO-d$_6$, 300 MHz, δ): 1.32 (18H, s), 4.49 (2H, s), 7.09 (1H, d, J=8 Hz), 7.42 (1H, dd, J=5 Hz, 8 Hz), 7.5–7.65 (2H, m), 7.77 (2H, s), 7.8–7.9 (2H, m), 8.01 (1H, dd, J=5 Hz, 8 Hz), 8.18 (1H, d, J=8 Hz), 8.44 (1H, m), 8.52 (1H, d, J=8 Hz), 8.83 (1H, d, J=5 Hz), 8.92 (1H, s)

(6) 4-[3-[(2,6-Dichloropyridin-4-ylcarbonylamino]phenyl]-2-(3-pyridylmethyl)-3-oxo-3,4-dihydropyrido[2,3-b]pyrazine.hydrochloride NMR (DMSO-d$_6$, 300 MHz, δ): 4.48 (2H, s), 7.14 (1H, d, J=8 Hz), 7.41 (1H, dd, J=5 Hz, 8 Hz), 7.60 (1H, t, J=8 Hz), 7.80 (1H, d, J=8 Hz), 7.79 (1H, s), 8.0–8.1 (3H, m), 8.18 (1H, d, J=8 Hz), 8.42 (1H, d, J=5 Hz), 8.52 (1H, d, J=8 Hz), 8.82 (1H, d, J=5 Hz), 8.92 (1H, s)

(7) 2-Benzyl-4-[3-[(E)-3-(4-pyridyl)acryloylamino]phenyl]-3-oxo-3,4-dihydropyrido[2,3-b]pyrazine NMR (DMSO-d$_6$, 300 MHz, δ): 4.27 (2H, s), 7.0–7.1 (2H, m), 7.35–7.45 (2H, m), 7.5–7.6 (4H, m), 7.7–7.8 (3H, m), 8.21 (1H, d, J=8 Hz), 8.41 (1H, d, J=5 Hz), 8.48 (1H, d, J=5 Hz), 8.60 (1H, d, J=2 Hz), 8.65 (2H, d, J=5 Hz)

(8) 4-[3-(3,4-Dichlorobenzoylamino)phenyl]-2-(3-pyridylmethyl)-3-oxo-3,4-dihydropyrido[2,3-b]pyrazine NMR (CDCl₃, 300 MHz, δ): 4.32 (2H, s), 6.79 (1H, d, J=8 Hz), 7.17 (1H, dd, J=5 Hz, 8 Hz), 7.3–7.5 (3H, m), 7.6–7.7 (3H, m), 7.88 (1H, d, J=2 Hz), 8.22 (1H, d, J=8 Hz), 8.35–8.45 (2H, m), 8.62 (1H, s), 8.69 (1H, s)

(9) 4-[3-(3,5-Dimethylbenzoylamino)phenyl]-2-(3-pyridylmethyl)-3-oxo-3,4-dihydropyrido[2,3-b]pyrazine NMR (CDCl₃, 300 MHz, δ): 2.36 (6H, s), 4.31 (2H, s), 7.01 (1H, d, J=8 Hz), 7.18 (1H, s), 7.2–7.35 (2H, m), 7.41 (2H, s), 7.55 (1H, t, J=8 Hz), 7.70 (1H, d, J=8 Hz), 7.75–7.85 (2H, m), 7.99 (1H, s), 8.19 (1H, d, J=8 Hz), 8.4–8.5 (2H, m), 8.72 (1H, s)

EXAMPLE 67

A mixture of 3-amino-2-(3-biphenylylamino)pyridine (196 mg) and 3-(4-hydroxyphenyl)pyruvic acid (162 mg) in ethanol (5 ml) was stirred under reflux for 2 hours. The mixture was cooled and then poured into a mixture of ethyl acetate and aqueous sodium bicarbonate. The organic phase was separated, washed with aqueous sodium bicarbonate and brine, dried over magnesium sulfate and concentrated. The residue was crystallized from methanol to give 4-(3-biphenylyl)-2-(4-hydroxybenzyl)-3-oxo-3,4-dihydropyrido[2,3-b]pyrazine (186 mg).

NMR (DMSO-d₆, 300 MHz, δ): 4.11 (2H, s), 6.70 (2H, dt, J=8 Hz, 2 Hz), 7.18 (2H, d, J=8 Hz), 7.3–7.5 (5H, m), 7.6–7.75 (4H, m), 7.81 (1H, d, J=8 Hz), 8.26 (1H, d, J=8 Hz), 8.40 (1H, d, J=5 Hz), 9.26 (1H, s)

EXAMPLE 68

The following compounds were obtained according to a similar manner to that of Example 2, 42, 43, 44, 51, 52, 53 or 67.

(1) 4-(3-Biphenylyl)-2-(3-pyridylmethyl)-3-oxo-3,4-dihydropyrido[2,3-b]pyrazine

NMR (CDCl₃, 300 MHz, δ): 4.32 (2H, s), 7.2–7.5 (7H, m), 7.6–7.7 (3H, m), 7.75 (1H, dt, J=8 Hz, 2 Hz), 7.83 (1H, dt, 8 Hz, 2 Hz), 8.19 (1H, dd, J=2 Hz, 8 Hz), 8.44 (1H, dd, J=2 Hz, 5 Hz), 8.51 (1H, dd, J=2 Hz, 5 Hz), 8.73 (1H, d, J=2 Hz)

(2) 4-[3-(3-Indolizinylcarbonyl)phenyl]-2-(3-pyridylmethyl)-3-oxo-3,4-dihydropyrido[2,3-b]pyrazine NMR (DMSO-d₆, 300 MHz, δ): 4.28 (2H, s), 6.71 (1H, d, J=5 Hz), 7.13 (1H, dt, J=2 Hz, 8 Hz), 7.3–7.5 (4H, m), 7.61 (1H, m), 7.7–7.85 (4H, m), 7.90 (1H, dt, J=8 Hz, 2 Hz), 8.22 (1H, dd, J=2 Hz, 8 Hz), 8.45 (2H, m), 8.60 (1H, d, J=2 Hz), 9.87 (1H, d, J=8 Hz)

(3) 4-(3-Benzoylaminophenyl)-2-(3-pyridylmethyl)-3-oxo-3,4-dihydropyrido[2,3-b]pyrazine NMR (DMSO-d₆, 300 MHz, δ): 4.27 (2H, s), 7.09 (1H, d, J=8 Hz), 7.35–7.45 (2H, m), 7.5–7.65 (4H, m), 7.75–7.9 (3H, m), 7.96 (2H, d, J=8 Hz), 8.21 (1H, dd, J=2 Hz, 8 Hz), 8.42 (1H, dd, J=2 Hz, 5 Hz), 8.48 (1H, dd, J=2 Hz, 8 Hz), 8.60 (1H, d, J=2 Hz)

(4) 4-(3-Biphenylyl)-2-phenyl-3-oxo-3,4-dihydropyrido[2,3-b]pyrazine

NMR (CDCl₃, 300 MHz, δ): 7.3–7.8 (13H, m), 8.30 (1H, dd, J=2 Hz, 8 Hz), 8.40 (2H, m), 8.48 (1H, dd, J=2 Hz, 5 Hz)

(5) 2-(3-Pyridylmethyl)-4-[3-[(quinolin-3-yl)carbonylamino]phenyl]-3-oxo-3,4-dihydropyrido[2,3-b]pyrazine NMR (DMSO-d₆, 300 MHz, δ): 4.29 (2H, s), 7.14 (1H, d, J=8 Hz), 7.35–7.45 (2H, m), 7.59 (1H, t, J=8 Hz), 7.7–7.95 (5H, m), 8.1–8.25 (3H, m), 8.4–8.5 (2H, m), 8.61 (1H, s), 8.98 (1H, d, J=2 Hz), 9.37 (1H, d, J=2 Hz)

(6) 4-[3-(N-Methyl-N-acetylamino)phenyl]-2-(3-pyridylmethyl)-3-oxo-3,4-dihydropyrido[2,3-b]pyrazine NMR (DMSO-d₆, 300 MHz, δ): 3.20 (3H, s), 4.27 (2H, s), 7.3–7.5 (4H, m), 7.61 (1H, t, J=8 Hz), 7.79 (1H, d, J=8 Hz), 8.21 (1H, m), 8.40 (1H, d, J=5 Hz), 8.47 (1H, d, J=5 Hz), 8.60 (1H, s)

(7) 4-[3-[(E)-2-(3,5-Dichlorophenyl)vinyl]phenyl]-2-(3-pyridylmethyl)-3-oxo-3,4-dihydropyrido[2,3-b]pyrazine NMR (CDCl₃, 300 MHz, δ): 4.32 (2H, s), 6.97 (1H, d, J=16 Hz), 7.1–7.4 (8H, m), 7.55–7.65 (2H, m), 7.83 (1H, d, J=8 Hz), 8.20 (1H, d, J=8 Hz), 8.43 (1H, m), 8.52 (1H, m), 8.73 (1H, s)

(8) 2-(3-Pyridylmethyl)-4-[3-(3,5-dichlorophenylcarbamoyl)phenyl]-3-oxo-3,4-dihydropyrido[2,3-b]pyrazine NMR (DMSO-d₆, 300 MHz, δ): 4.27 (2H, s), 7.3–7.45 (3H, m), 7.64 (1H, d, J=8 Hz), 7.7–7.85 (2H, m), 7.9–8.0 (3H, m), 8.10 (1H, d, J=8 Hz), 8.23 (1H, d, J=8 Hz), 8.4–8.5 (2H, m), 8.60 (1H, s)

(9) 2-(3-Pyridylmethyl)-4-[3-[N-methyl-N-(3,5-dichlorophenyl)carbamoyl]phenyl]-3-oxo-3,4-dihydropyrido[2,3-b]pyrazine NMR (CDCl₃, 300 MHz, δ): 3.45 (3H, s), 4.48 (2H, s), 6.99 (2H, s), 7.18 (1H, m), 7.2–7.3 (3H, m), 7.45–7.55 (2H, m), 7.80 (1H, dd, J=2 Hz, 8 Hz), 8.13 (1H, m), 8.32 (1H, m), 8.51 (1H, m), 8.70 (1H, d, J=2 Hz)

(10) 2-Benzyl-4-[3-[(E)-2-(4-pyridyl)vinyl]phenyl]-3-oxo-3,4-dihydropyrido[2,3-b]pyrazine NMR (CDCl₃, 300 MHz, δ): 4.31 (2H, s), 7.01 (1H, d, J=16 Hz), 7.2–7.35 (8H, m), 7.4–7.7 (5H, m), 8.20 (1H, m), 8.40 (1H, d, J=5 Hz), 8.58 (2H, d, J=5 Hz)

(11) 2-Benzyl-4-(3-cyclopentyloxy-4-methoxyphenyl)-3-oxo-3,4-dihydropyrido[2,3-b]pyrazine NMR (CDCl₃, 300 MHz, δ): 1.5–1.65 (2H, m), 1.75–2.0 (6H, m), 3.89 (3H, s), 4.31 (2H, s), 4.70 (1H, m), 6.72 (1H, d, J=2 Hz), 6.79 (1H, dd, J=2 Hz), 7.01 (1H, d, J=8 Hz), 7.2–7.32 (4H, m), 7.50 (1H, d, J=8 Hz), 8.18 (1H, d, J=8 Hz), 8.43 (1H, d, J=5 Hz)

(12) 4-[3-[3-(2-Methoxyphenyl)ureido]phenyl]-2-phenyl-3-oxo-3,4-dihydropyrido[2,3-b]pyrazine NMR (DMSO-d₆, δ): 3.88 (3H, s), 6.55 (1H, m), 6.95 (5H, m), 7.25 (2H, m), 7.50 (5H, m), 8.30 (4H, m), 9.55 (1H, s)

(13) 2-Benzyl-4-(3-phenylsulfonylaminophenyl)-3-oxo-3,4-dihydropyrido[2,3-b]pyrazine mp: 199–211° C.

NMR (DMSO-d₆, δ): 4.20 (2H, s), 6.98 (1H, d, J=8 Hz), 7.13 (2H, m), 7.30 (7H, m), 7.55 (2H, m), 7.62 (1H, m), 7.79 (2H, m), 8.20 (1H, d, J=8 Hz), 8.35 (1H, m)

(14) 2-Benzyl-6-phenylthio-4-[3-(3-phenylureido)phenyl]-3-oxo-3,4-dihydropyrido[2,3-b]pyrazine mp: 183–185° C.

NMR (DMSO-d₆, δ): 4.20 (2H, s), 6.9–7.05 (19H, m), 7.62 (1H, s), 7.98 (1H, d, J=8 Hz), 8.80 (1H, s), 8.93 (1H, s)

(15) 2-Benzyl-4-[3-(pyrrol-1-yl)phenyl]-3-oxo-3,4-dihydropyrido[2,3-b]pyrazine mp: 169–170° C.

(16) 2-(4-Hydroxybenzyl)-4-[3-(pyrrol-1-yl)phenyl]-3-oxo-3,4-dihydropyrido[2,3-b]pyrazine mp: 263° C.

NMR (DMSO-d₆, δ): 4.08 (2H, s), 6.26 (2H, m), 6.70 (2H, d, J=8 Hz), 7.18 (2H, d, J=8 Hz), 7.21 (1H, m), 7.40 (3H, m), 7.61 (1H, dd, J=8 Hz, 8 Hz), 7.67 (1H, m), 7.73 (1H, m), 8.26 (1H, dd, J=8 Hz, 2 Hz), 8.40 (1H, dd, J=5 Hz, 2 Hz), 9.25 (1H, s)

(17) 2-Benzyl-4-[3-(2-methoxycarbonylpyrrol-1-yl)phenyl]-3-oxo-3,4-dihydropyrido[2,3-b]pyrazine mp: 190–191° C.

NMR (DMSO-d$_6$, δ): 3.72 (3H, s), 4.23 (2H, s), 6.65 (1H, m), 7.24 (1H, m), 7.3–7.45 (6H, m), 7.50 (1H, m), 7.67 (1H, dd, J=8 Hz, 8 Hz), 7.85 (2H, m), 8.03 (1H, m), 8.27 (1H, m), 8.41 (1H, m)

EXAMPLE 69

To a mixture of 4-(3-biphenylyl)-2-(4-hydroxybenzyl)-3-oxo-3,4-dihydropyrido[2,3-b]pyrazine (76 mg), triethylamine (0.05 ml) and 4-dimethylaminopyridine (3 mg) in 1,4-dioxane (2 ml) was added acetic anhydride (0.035 ml). The mixture was stirred at room temperature for 1 hour, then poured into a mixture of ethyl acetate and aqueous sodium bicarbonate. The organic phase was separated, washed with aqueous sodium bicarbonate and brine, dried over magnesium sulfate and concentrated to give 2-(4-acetoxybenzyl)-4-(3-biphenylyl)-3-oxo-3,4-dihydropyrido[2,3-b]pyrazine (58 mg).

NMR (CDCl$_3$, 300 MHz, δ): 4.31 (2H, s), 7.03 (2H, d, J=8 Hz), 7.25–7.8 (12H, m), 8.20 (1H, d, J=8 Hz), 8.43 (1H, d, J=5 Hz)

EXAMPLE 70

A mixture of cyclopentanol (0.08 ml) and triphosgene (87 mg) in 1,2-dichloroethane (2 ml) was stirred at room temperature for 20 hours. Then the mixture was added to a mixture of 4-(3-aminophenyl)-2-benzyl-3-oxo-3,4-dihydropyrido[2,3-b]pyrazine (193 mg) and triethylamine (0.25 ml) in 1,4-dioxane (3 ml). The mixture was stirred at room temperature for 1 hour, then poured into aqueous sodium bicarbonate and extracted with ethyl acetate twice. The combined organic phase was washed with aqueous sodium bicarbonate and brine, dried over magnesium sulfate and concentrated. The residue was chromatographed on silica gel column (chloroform-methanol, 40:1) to give 2-benzyl-4-(3-cyclopentyloxycarbonylaminophenyl)-3-oxo-3,4-dihydropyrido[2,3-b]pyrazine (41 mg).

NMR (CDCl$_3$, 300 MHz, δ): 1.55–1.95 (8H, m), 4.31 (2H, s), 5.17 (1H, m), 6.73 (1H, s), 6.94 (1H, m), 7.2–7.5 (8H, m), 8.19 (1H, dd, J=2 Hz, 8 Hz), 8.42 (1H, dd, J=2 Hz, 5 Hz)

EXAMPLE 71

To a mixture of 4-[3-(4-acetoxybenzoylamino)phenyl]-2-benzyl-3-oxo-3,4-dihydropyrido[2,3-b]pyrazine (147 mg) in methanol (3 ml) and 1,4-dioxane (3 ml) was added a solution of potassium carbonate (83 mg) in water (0.5 ml). The mixture was stirred at room temperature for 1.5 hours, then poured into a mixture of ethyl acetate and water. The organic phase was separated, washed with brine, dried over magnesium sulfate and concentrated. The residue was crystallized from ethanol to give 2-benzyl-4-[3-(4-hydroxybenzoylamino)phenyl]-3-oxo-3,4-dihydropyrido[2,3-b]pyrazine (53 mg).

NMR (DMSO-d$_6$, 300 MHz, δ): 4.22 (2H, s), 6.87 (2H, d, J=8 Hz), 7.04 (1H, m), 7.2–7.45 (7H, m), 7.50 (1H, t, J=8 Hz), 7.75–7.9 (4H, m), 8.23 (1H, m), 8.40 (1H, d, J=5 Hz)

EXAMPLE 72

The following compound was obtained by reacting 4-[3-(3-aminophenyl)phenyl]-2-(3-pyridylmethyl)-3-oxo-3,4-dihydropyrido[2,3-b]pyrazine with methyl isocyanate according to a similar manner to that of Example 1.

4-[3-[3-(3-Methylureido)phenyl]phenyl]-2-(3-pyridylmethyl)-3-oxo-3,4-dihydropyrido[2,3-b]pyrazine mp: 248–252° C.

NMR (DMSO-d$_6$, δ): 2.63 (3H, d, J=6 Hz), 4.28 (2H, s), 6.01 (1H, q, J=6 Hz), 7.20 (1H, d, J=8 Hz), 7.3–7.43 (5H, m), 7.60 (1H, m), 7.64 (1H, d, J=8 Hz), 7.76 (3H, m), 8.20 (1H, m), 8.41 (1H, d, J=5 Hz), 8.47 (1H, m), 8.59 (1H, s), 8.62 (1H, s)

EXAMPLE 73

The following compound was obtained by reacting 4-[3-(3-aminophenyl)phenyl]-2-(3-pyridylmethyl)-3-oxo-3,4-dihydropyrido[2,3-b]pyrazine with ethylisocyanate according to a similar manner to that of Example 1.

4-[3-[3-(3-Ethylureido)phenyl]phenyl]-2-(3-pyridylmethyl)-3-oxo-3,4-dihydropyrido[2,3-b]pyrazine mp: 257–258° C.

NMR (DMSO-d$_6$, δ): 1.04 (3H, t, J=7 Hz), 3.08 (2H, m), 4.26 (2H, s), 6.11 (1H, t, J=7 Hz), 7.20 (1H, m), 7.3–7.43 (5H, m), 7.61 (1H, m), 7.64 (1H, d, J=8 Hz), 7.75 (3H, m), 8.20 (1H, m), 8.40 (1H, d, J=5 Hz), 8.46 (1H, d, J=5 Hz), 8.53 (1H, s), 8.60 (1H, s)

EXAMPLE 74

The following compound was obtained by reacting 4-[3-(3-aminophenyl)phenyl]-2-(3-pyridylmethyl)-3-oxo-3,4-dihydropyrido[2,3-b]pyrazine with phenylisocyanate according to a similar manner to that of Example 1.

4-[3-[3-(3-Phenylureido)phenyl]phenyl]-2-(3-pyridylmethyl)-3-oxo-3,4-dihydropyrido[2,3-b]pyrazine mp: 234° C.

NMR (DMSO-d$_6$, δ): 4.28 (2H, s), 6.97 (1H, dd, J=8 Hz, 8 Hz), 7.28 (3H, m), 7.40 (7H, m), 7.66 (2H, m), 7.80 (3H, m), 8.20 (1H, m), 8.40 (1H, m), 8.47 (1H, m), 8.60 (1H, s), 8.70 (1H, s), 8.80 (1H, s)

EXAMPLE 75

The following compound was obtained according to a similar manner to that of Example 56.

4-[3-(3-Aminophenyl)phenyl]-2-(3-pyridylmethyl)-3-oxo-3,4-dihydropyrido[2,3-b]pyrazine mp: 202–204° C.

NMR (CDCl$_3$, δ): 3.73 (2H, s), 4.32 (2H, s), 6.15 (1H, m), 6.90 (1H, m), 6.98 (1H, d, J=8 Hz), 7.25 (4H, m), 7.44 (1H, s), 7.62 (1H, dd, J=8 Hz, 8 Hz), 7.70 (1H, d, J=8 Hz), 7.82 (1H, d, J=8 Hz), 8.18 (1H, d, J=8 Hz), 8.43 (1H, d, J=5 Hz), 8.50 (1H, m), 8.72 (1H, s)

EXAMPLE 76

The following compounds were obtained according to a similar manner to that of Example 57 or 58.

(1) 4-[3-[3-N,N-Bis(methylsulfonyl)amino]phenyl]phenyl]-2-(3-pyridylmethyl)-3-oxo-3,4-dihydropyrido[2,3-b]pyrazine mp: 240–246° C.

NMR (DMSO-d$_6$, δ): 3.55 (6H, s), 4.28 (2H, s), 7.40 (3H, m), 7.53 (1H, m), 7.60 (1H, dd, J=8 Hz, 8 Hz), 7.69 (1H, dd, J=8 Hz, 8 Hz), 7.79 (3H, m), 7.85 (1H, m), 7.90 (1H, m), 8.23 (1H, d, J=8 Hz), 8.41 (1H, m), 8.48 (1H, m), 8.60 (1H, m)

(2) 4-[3-[3-(2-Naphthoylamino)phenyl]phenyl]-2-(3-pyridylmethyl)-3-oxo-3,4-dihydropyrido[2,3-b]pyrazine mp: 202–210° C.

NMR (DMSO-d$_6$, δ): 4.28 (2H, s), 7.38 (3H, m), 7.46 (2H, m), 7.65 (4H, m), 7.80 (2H, m), 7.90 (1H, m), 8.05 (4H, m), 8.16 (1H, s), 8.22 (1H, d, J=8 Hz), 8.44 (2H, m), 8.60 (2H, s)

(3) 4-[3-[3-[(Benzo[b]thiophen-2-yl)carbonylamino]phenyl]phenyl]-2-(3-pyridylmethyl)-3-oxo-3,4-dihydropyrido[2,3-b]pyrazine mp: 216–218° C.

NMR (DMSO-d$_6$, δ): 4.27 (2H, s), 7.40 (3H, m), 7.48 (4H, m), 7.69 (2H, m), 7.81 (3H, m), 8.01 (1H, m), 8.07 (1H, d, J=8 Hz), 8.12 (1H, s), 8.22 (1H, d, J=8 Hz), 8.37 (1H, s), 8.41 (1H, d, J=4 Hz), 8.48 (1H, d, J=4 Hz), 8.60 (1H, s)

(4) 4-[3-[3-(2-Quinoxalinylcarbonylamino)phenyl]phenyl]-2-(3-pyridylmethyl)-3-oxo-3,4-dihydropyrido[2,3-b]pyrazine mp: 206–209° C.

NMR (DMSO-d$_6$, δ): 4.26 (2H, s), 7.40 (3H, m), 7.52 (2H, m), 7.68 (1H, m), 7.72 (1H, m), 7.80 (1H, m), 7.85 (1H, m), 8.02 (3H, m), 8.22 (2H, m), 8.30 (2H, m), 8.42 (1H, m), 8.46 (1H, m), 8.60 (1H, s), 9.57 (1H, s)

(5) 4-[3-(3-Propionylaminophenyl)phenyl]-2-(3-pyridylmethyl)-3-oxo-3,4-dihydropyrido[2,3-b]pyrazine mp: 223–224° C.

NMR (DMSO-d$_6$, δ): 1.08 (3H, t, J=7 Hz), 2.31 (2H, q, J=7 Hz), 4.26 (2H, s), 7.35 (5H, m), 7.62 (3H, m), 7.76 (2H, m), 7.95 (1H, s), 8.20 (1H, m), 8.41 (1H, m), 8.47 (1H, m), 8.59 (1H, s)

(6) 4-[3-[3-[(E)-3-(4-Pyridyl)acryloylamino]phenyl]phenyl]-2-(3-pyridylmethyl)-3-oxo-3,4-dihydropyrido[2,3-b]pyrazine mp: 185–191° C.

NMR (DMSO-d$_6$, δ): 4.27 (2H, s), 7.03 (1H, d, J=16 Hz), 7.40 (5H, m), 7.57 (3H, m), 7.75 (5H, m), 8.01 (1H, s), 8.21 (1H, m), 8.41 (1H, m), 8.47 (1H, m), 8.62 (3H, m)

EXAMPLE 77

The following compounds were obtained according to similar manners to those of Example 57 or 58, and Example 48.

(1) 4-[3-[3-(3,5-Dichlorophenylsulfonylamino)phenyl]phenyl]-2-(3-pyridylmethyl)-3-oxo-3,4-dihydropyrid[2,3-b]pyrazinehydrochloride mp: 185–195° C.

NMR (DMSO-d$_6$, δ) 4.48 (2H, s), 7.10 (1H, m), 7.40 (4H, m), 7.50 (2H, m), 7.6–7.8 (5H, m), 7.98 (1H, m), 8.18 (1H, m), 8.42 (1H, m), 8.50 (1H, m), 8.81 (1H, m), 8.90 (1H, s)

(2) 4-[3-(3-Benzoylaminophenyl)phenyl]-2-(3-pyridylmethyl)-3-oxo-3,4-dihydropyrido[2,3-b]pyrazine.hydrochloride mp: 210° C. (dec.)

NMR (DMSO-d$_6$, δ): 4.47 (2H, s), 7.35–7.75 (10H, m), 7.80 (2H, m), 7.97 (3H, m), 8.18 (2H, m), 8.45 (2H, m), 8.80 (1H, d, J=5 Hz, 8.90 (1H, s)

MASS: 510 (M+1)

(3) 4-[3-[3-[(E)-3-Ethoxycarbonylacryloylamino]phenyl]phenyl]-2-(3-pyridylmethyl)-3-oxo-3,4-dihydropyrid[2,3-b]pyrazine mp: 130–160° C. (dec.)

NMR (DMSO-d$_6$, δ): 1.25 (3H, t, J=7 Hz), 4.21 (2H, q, J=7 Hz), 4.49 (2H, s), 6.70 (1H, d, J=14 Hz), 7.24 (1H, d, J=14 Hz), 7.35–7.5 (4H, m), 7.62 (2H, m), 7.69 (1H, dd, J=8 Hz, 8 Hz), 7.78 (1H, m), 8.00 (1H, m), 8.10 (1H, s), 8.17 (1H, d, J=8 Hz), 8.43 (1H, d, J=5 Hz), 8.51 (1H, m), 8.82 (1H, m), 8.92 (1H, s)

(4) 4-[3-(3-Ethoxycarbonylaminophenyl)phenyl]-2-(3-pyridylmethyl)-3-oxo-3,4-dihydropyrido[2,3-b]pyrazine.hydrochloride mp: 168–183° C.

NMR (DMSO-d$_6$, δ): 1.23 (3H, t, J=7 Hz), 4.12 (2H, q, J=7 Hz), 4.45 (2H, s), 7.28 (1H, m), 7.40 (4H, m), 7.58 (1H, m), 7.66 (1H, dd, J=8 Hz, 8 Hz), 7.74 (1H, m), 7.84 (1H, m), 7.96 (1H, dd, J=8 Hz, 6 Hz), 8.17 (1H, d, J=8 Hz), 8.42 (1H, m), 8.47 (1H, m), 8.79 (1H, m), 8.89 (1H, s), 9.72 (1H, s)

(5) 4-[3-[3-(Cyclopropylcarbonylamino)phenyl]phenyl]-2-(3-pyridylmethyl)-3-oxo-3,4-dihydropyrido[2,3-b]pyrazine.hydrochloride mp: 265–274° C.

NMR (DMSO-d$_6$, δ): 0.77 (4H, d, J=7 Hz), 1.83 (1H, m), 4.48 (2H, s), 7.3–7.45 (4H, m), 7.55 (1H, m), 7.60 (1H, m), 7.68 (1H, dd, J=8 Hz, 8 Hz), 7.75 (1H, m), 8.00 (2H, m), 8.18 (1H, d, J=8 Hz), 8.43 (1H, m), 8.51 (1H, m), 8.83 (1H, m), 8.92 (1H, s)

(6) 4-[3-(3-Pyruvoylaminophenyl)phenyl]-2-(3-pyridylmethyl)-3-oxo-3,4-dihydropyrido[2,3-b]pyrazine.hydrochloride mp: 202–206° C. (dec.)

NMR (DMSO-d$_6$, δ): 3.84 (3H, s), 4.48 (2H, s), 7.38 (1H, dd, J=8 Hz, 2 Hz), 7.41 (1H, dd, J=8 Hz, 5 Hz), 7.48 (2H, m), 7.63 (1H, m), 7.70 (1H, dd, J=8 Hz, 8 Hz), 7.79 (2H, m), 8.00 (1H, dd, J=8 Hz, 5 Hz), 8.10 (1H, s), 8.18 (1H, dd, J=8 Hz, 2 Hz), 8.44 (1H, d, J=5 Hz), 8.49 (1H, dd, J=8 Hz, 2 Hz), 8.82 (1H, d, J=5 Hz), 8.91 (1H, s)

(7) 4-[3-[3-(3-Ethoxycarbonylpropanoylamino)phenyl]phenyl]-2-(3-pyridylmethyl)-3-oxo-3,4-dihydropyrido[2,3-b]pyrazine.hydrochloride mp: 104–158° C. (dec.)

NMR (DMSO-d$_6$, δ): 1.17 (3H, t, J=7 Hz), 2.59 (4H, m), 4.03 (2H, q, J=7 Hz), 4.48 (2H, s), 7.3–7.43 (4H, m), 7.53 (1H, m), 7.60 (1H, m), 7.68 (1H, dd, J=8 Hz, 8 Hz), 7.75 (1H, m), 7.96 (1H, m), 8.00 (1H, m), 8.19 (1H, m), 8.43 (1H, m), 8.47 (1H, m), 8.80 (1H, m), 8.90 (1H, s)

(8) 4-[3-(3-Phenoxycarbonylaminophenyl)phenyl]-2-(3-pyridylmethyl)-3-oxo-3,4-dihydropyrido[2,3-b]-pyrazine.hydrochloride mp: 188–197° C.

NMR (DMSO-d$_6$, δ): 4.47 (2H, s), 7.2–7.3 (3H, m), 7.3–7.5 (7H, m), 7.60 (1H, s), 7.68 (1H, dd, J=8 Hz, 8 Hz), 7.78 (1H, m), 7.91 (1H, m), 7.98 (1H, m), 8.17 (1H, m), 8.43 (1H, m), 8.47 (1H, m), 8.80 (1H, m), 8.90 (1H, s)

(9) 4-[3-[(E)-3-Cinnamoylaminophenyl]phenyl]-2-(3-pyridylmethyl)-3-oxo-3,4-dihydropyrido[2,3-b]pyrazine.hydrochloride mp: 181–191° C.

NMR (DMSO-d$_6$, δ): 4.50 (2H, s), 6.90 (1H, d, J=16 Hz), 7.43 (7H, m), 7.56 (1H, m), 7.62 (3H, m), 7.70 (2H, m), 7.79 (1H, m), 8.00 (1H, dd, J=8 Hz, 5 Hz), 8.12 (1H, m), 8.19 (1H, d, J=8 Hz), 8.45 (1H, m), 8.50 (1H, m), 8.82 (1H, d, J=5 Hz), 8.92 (1H, s)

(10) 4-[3-(3,5-Difluorobenzoylamino)phenyl]-2-(3-pyridylmethyl)-3-oxo-3,4-dihydropyrido[2,3-b]pyrazine NMR (CDCl$_3$, 300 MHz, δ): 4.31 (2H, s), 6.85 (1H, d, J=8 Hz), 6.9–7.0 (1H, m), 7.21 (1H, dd, J=5 Hz, 8 Hz), 7.3–7.5 (4H, m), 7.62 (1H, d, J=8 Hz), 7.71 (1H, s), 7.79 (1H, d, J=8 Hz), 8.20 (1H, d, J=8 Hz), 8.42 (2H, m), 8.57 (1H, s), 8.70 (1H, s)

(11) 4-[3-[(E)-3-(4-Nitrophenyl)propenoylamino]phenyl]-2-(3-pyridylmethyl)-3-oxo-3,4-dihydropyrido[2,3-b]pyrazine NMR (DMSO-d$_6$, 300 MHz, δ): 4.27 (2H, s), 7.0–7.1 (2H, m), 7.35–7.45 (2H, m), 7.53 (1H, t, J=8 Hz), 7.65–7.8 (4H, m), 7.90 (2H, d, J=8 Hz), 8.21 (1H, d, J=8 Hz), 8.30 (2H, d, J=8 Hz), 8.40 (1H, d, J=5 Hz), 8.48 (1H, d, J=5 Hz), 8.60 (1H, d, J=2 Hz)

(12) 4-[3-(3,5-Dichlorophenylsulfonylamino)phenyl]-2-(3-pyridylmethyl)-3-oxo-3,4-dihydropyrido[2,3-b]pyrazine.hydrochloride mp: 228–238° C.

NMR (DMSO-d$_6$, δ): 4.40 (2H, s), 6.80 (1H, m), 7.08 (1H, m), 7.17 (1H, m), 7.23 (1H, m), 7.40 (3H, m), 7.74 (1H, m), 7.88 (1H, m), 7.99 (1H, m), 8.05 (1H, m), 8.38 (2H, m), 8.75 (1H, m), 8.84 (1H, m)

(13) 4-(3-Phenoxycarbonylaminophenyl)-2-(3-pyridylmethyl)-3-oxo-3,4-dihydropyrido[2,3-b]pyrazine mp: 227–232° C.

NMR (DMSO-$d_6$, δ): 4.45 (2H, s), 7.01 (1H, m), 7.22 (3H, m), 7.40 (3H, m), 7.53 (3H, m), 8.00 (1H, m), 8.13 (1H, m), 8.41 (1H, m), 8.51 (1H, m), 8.82 (1H, m), 8.90 (1H, m)

EXAMPLE 78

The solution of 2-methyl-4-(3-succinimidophenyl)-3-oxo-3,4-dihydropyrido[2,3-b]pyrazine (18.4 g), N-bromosuccinimide (12.7 g) and benzoylperoxide (1.6 g) were refluxed for 4 hours. The mixture was evaporated and purified by chromatography (chloroform) to obtain 2-bromomethyl-4-(3-succinimidophenyl)-3-oxo-3,4-dihydropyrido[2,3-b]pyrazine (15.6 g) as yellow crystals.

NMR (CDCl$_3$, 300 MHz, δ): 2.89 (4H, s), 4.67 (2H, s), 7.33 (1H, dd, J=7 Hz, 4 Hz), 7.36 (1H, dd, J=7 Hz, 1 Hz), 7.43 (1H, t, J=1 Hz), 7.59 (1H, dd, J=7 Hz, 1 Hz), 7.69 (1H, t, J=7 Hz), 8.22 (1H, d, J=7 Hz), 8.48 (1H, d, J=4 Hz)

MASS (FAB) (m/e): 413, 415

EXAMPLE 79

To a solution of 2-bromomethyl-3-succinimidophenyl-3-oxo-3,4-dihydropyrido[2,3-b]pyrazine (990 mg) in acetonitrile (10 ml) was added 1-acetylimidazole (528 mg). The solution was refluxed for an hour. The mixture was evaporated. The residue was dissolved in 4N-hydrochloric acid (15 ml), and the solution was heated at 110° C. for 2 hours. The solution was evaporated. To the residue was added triethylamine (5 ml) and methanol (10 ml). The mixture was evaporated. The residue was purified by column chromatography to obtain 2-(1-imidazolylmethyl)-4-(3-aminophenyl)-3-oxo-3,4-dihydropyrido[2,3-b]pyrazine (410 mg) as yellow powder.

NMR (DMSO-$d_6$, 300 MHz, δ): 5.32 (2H, br s), 5.44 (2H, s), 6.38–6.46 (2H, m), 6.68 (1H, d, J=7 Hz), 6.95 (1H, s), 7.18 (1H, dd, J=7 Hz, 7 Hz), 7.22 (1H, s), 7.35–7.41 (1H, m), 7.72 (1H, s), 8.13 (1H, d, J=7 Hz), 8.43 (1H, d, J=5 Hz)

MASS (FAB) (m/e): 319

EXAMPLE 80

The solution of 2-(1-imidazolylmethyl)-4-(3-aminophenyl)-3-oxo-3,4-dihydropyrido[2,3-b]pyrazine (1.07 g), 2-naphthoyl chloride (705 mg) and triethylamine (0.94 ml) in dioxane-dimethyl sulfoxide (10 ml) (2:1) was stirred for 18 hours. To the mixture was added water. The mixture was extracted by ethyl acetate (100 ml) and organic layer was dried by magnesium sulfate and evaporated. The crude product was chromatographed to obtain 2-(1-imidazoylmethyl)-4-[3-(2-naphthoylamino)phenyl]-3-oxo-3,4-dihydropyrido[2,3-b]pyrazine (360 mg) as yellow powder.

NMR (DMSO-$d_6$, 300 MHz, δ): 5.47 (2H, s), 6.96 (1H, s), 7.11 (1H, d, J=7 Hz), 7.24 (1H, s), 7.38–7.43 (1H, m), 7.55–7.69 (3H, m), 7.72 (1H, s), 7.88 (1H, d, J=7 Hz), 7.94 (1H, s), 7.96–8.11 (4H, m), 8.19 (1H, d, J=7 Hz), 8.45 (1H, m), 8.59 (1H, s)

EXAMPLE 81

A solution of 4-[3-(3-aminophenyl)phenyl]-2-(3-pyridylmethyl)-3-oxo-3,4-dihydropyrido[2,3-b]pyrazine (100 mg) and phthalic anhydride (48 mg) in dioxane (3 ml) was stirred overnight at room temperature. The reaction mixture was diluted with water, and precipitated crystals were collected to give 4-[3-[3-(2-carboxybenzoylamino)phenyl]phenyl]-2-(3-pyridylmethyl)-3-oxo-3,4-dihydropyrido[2,3-b]pyrazine (110 mg).

mp: 150° C. (dec.)

NMR (DMSO-$d_6$, δ): 4.26 (2H, s), 7.40 (5H, m), 7.55 (2H, m), 7.65 (4H, m), 7.75 (2H, m), 7.88 (1H, d, J=8 Hz), 8.05 (1H, s), 8.20 (1H, d, J=8 Hz), 8.40 (1H, d, J=5 Hz), 8.46 (1H, br s), 8.60 (1H, br s)

MASS: 554 (M+1)

EXAMPLE 82

The following compounds were obtained according to a similar manner to that of Example 81.

(1) 4-[3-[3-(3-Carboxypropanoylamino)phenyl]phenyl]-2-(3-pyridylmethyl)-3-oxo-3,4-dihydropyrido[2,3-b]pyrazine mp: 193–199° C.

NMR (DMSO-$d_6$, δ): 2.55 (4H, m), 4.27 (2H, s), 7.40 (5H, m), 7.55 (1H, m), 7.64 (2H, m), 7.77 (2H, m), 7.94 (1H, m), 8.21 (1H, m), 8.40 (1H, m), 8.45 (1H, m), 8.60 (1H, s)

(2) 4-[3-[3-[(Z)-3-Carboxy-3-phenylacryloylamino]phenyl]phenyl]-2-(3-pyridylmethyl)-3-oxo-3,4-dihydropyrido[2,3-b]pyrazine mp: 189–198° C. (dec.)

NMR (DMSO-$d_6$, δ): 4.25 (2H, s), 6.43 (1H, s), 7.40 (8H, m), 7.65 (5H, m), 7.78 (2H, m), 8.01 (1H, m), 8.20 (1H, m), 8.40 (1H, m), 8.47 (1H, m), 8.60 (1H, m)

EXAMPLE 83

To a solution of 4-[3-(3-aminophenyl)phenyl]-2-(3-pyridylmethyl)-3-oxo-3,4-dihydropyrido[2,3-b]pyrazine (200 mg) in dioxane (6 ml) was added trifluoroacetic anhydride (48 mg) and the mixture was stirred at room temperature for 2 hours. The reaction mixture was diluted with water and sodium bicarbonate solution and precipitated crystals were collected to give 4-[3-(3-trifluoroacetylaminophenyl)phenyl]-2-(3-pyridylmethyl)-3-oxo-3,4-dihydropyrido[2,3-b]pyrazine (0.25 g).

mp: 138–144° C.

NMR (DMSO-$d_6$, δ): 4.25 (2H, s), 7.39 (3H, m), 7.53 (2H, m), 7.69 (3H, m), 7.80 (2H, m), 7.97 (1H, m), 8.21 (1H, m), 8.40 (1H, m), 8.47 (1H, m), 8.60 (1H, m)

MASS: 502 (M+1)

EXAMPLE 84

To a solution of 4-cyclopentyloxy-3-methoxybenzoic acid (118 mg) in dichloromethane (2 ml) was added oxalyl chloride (0.09 ml) and 1 drop of N,N-dimethylformamide. After stirring at room temperature for 30 minutes, the mixture was concentrated and the residue was dissolved in dichloromethane (2 ml). The above solution was added to a mixture of 4-(3-aminophenyl)-2-benzyl-3-oxo-3,4-dihydropyrido[2,3-b]pyrazine (137 mg) and triethylamine (0.105 ml) in dichloromethane (3 ml). The mixture was stirred at room temperature for 30 minutes, then poured into a mixture of ethyl acetate and aqueous sodium bicarbonate. The organic phase was separated, washed with aqueous sodium bicarbonate and brine, dried over magnesium sulfate and concentrated. The residue was crystallized from methanol to give 2-benzyl-4-[3-(4-cyclopentyloxy-3-methoxybenzoylamino)phenyl]-3-oxo-3,4-dihydropyrido[2,3-b]pyrazine (139 mg).

NMR (CDCl$_3$, 300 MHz, δ): 1.5–2.0 (8H, m), 3.84 (3H, s), 4.30 (2H, s), 4.78 (1H, m), 6.74 (1H, d, J=8 Hz), 6.88

(1H, d, J=8 Hz), 7.15–7.3 (4H, m), 7.35–7.5 (4H, m), 7.62 (1H, t, J=2 Hz), 7.71 (1H, d, J=8 Hz), 8.12 (1H, s), 8.19 (1H, dd, J=2 Hz, 8 Hz), 8.40 (1H, dd, J=2 Hz, 5 Hz)

EXAMPLE 85

A mixture of 4-[3-(6-acetoxy-2-naphthoylamino)phenyl]-2-(3-pyridylmethyl)-3-oxo-3,4-dihydropyrido[2,3-b]pyrazine (840 mg) in 3N hydrochloric acid (25 ml) was stirred at room temperature for 2 hours. Then the mixture was concentrated and poured into a mixture of ethyl acetate and aqueous sodium bicarbonate. The organic phase was separated, washed with aqueous sodium bicarbonate and brine, dried over magnesium sulfate and concentrated. The residue was crystallized from ethanol to give 4-[3-(6-hydroxy-2-naphthoylamino)phenyl]-2-(3-pyridylmethyl)-3-oxo-3,4-dihydropyrido[2,3-b]pyrazine (127 mg).

NMR (DMSO-$d_6$, 300 MHz, $\delta$): 4.28 (2H, s), 7.10 (1H, d, J=8 Hz), 7.20 (2H, m), 7.35–7.45 (2H, m), 7.55 (1H, t, J=8 Hz), 7.75–8.0 (6H, m), 8.22 (1H, d, J=8 Hz), 8.4–8.55 (3H, m), 8.62 (1H, s)

EXAMPLE 86

A solution of 4-[3-(N-methyl-N-acetylamino)phenyl]-2-(3-pyridylmethyl)-3-oxo-3,4-dihydropyrido[2,3-b]pyrazine (2.02 g) in 3N hydrochloric acid (20 ml) was stirred under reflux for 2 hours. Then the mixture was poured into ice-water and alkalinized with sodium bicarbonate. The resultant solid was collected and washed with water and recrystallized from ethanol to give 4-[3-(methylamino) phenyl]-2-(3-pyridylmethyl)-3-oxo-3,4-dihydropyrido[2,3-b]pyrazine (1.06 g).

NMR (DMSO-$d_6$, 300 MHz, $\delta$): 2.67 (3H, d, J=6 Hz), 4.24 (2H, s), 5.86 (1H, m), 6.43 (2H, m), 6.64 (1H, d, J=8 Hz), 7.22 (1H, t, J=8 Hz), 7.38 (2H, m), 7.78 (1H, d, J=8 Hz), 8.18 (1H, d, J=8 Hz), 8.4–8.5 (2H, m), 8.60 (1H, s)

EXAMPLE 87

To a solution of 4-[3-(methylamino)phenyl]-2-(3-pyridylmethyl)-3-oxo-3,4-dihydropyrido[2,3-b]pyrazine (200 mg) in chloroform (5 ml) was added 3-[(E)-4-methoxycarbonylphenyl]propenoyl chloride (137 mg). The mixture was stirred at room temperature for 15 minutes and concentrated. The residue was crystallized from methanol to give 4-[3-[N-methyl-N-[(E)-4-methoxycarbonylcinnamoyl] amino]phenyl]-2-(3-pyridylmethyl)-3-oxo-3,4-dihydropyrido[2,3-b]pyrazine hydrochloride (114 mg).

NMR (CDCl$_3$, 300 MHz, $\delta$): 3.50 (3H, s), 3.92 (3H, s), 4.49 (2H, s), 6.72 (1H, d, J=16 Hz), 7.17 (1H, t, J=2 Hz), 7.25–7.4 (2H, m), 7.4–7.55 (3H, m), 7.65–7.75 (2H, m), 7.88 (1H, dd, J=5 Hz, 8 Hz), 7.99 (2H, d, J=8 Hz), 8.18 (1H, m), 8.37 (1H, m), 8.49 (1H, d, J=8 Hz), 8.68 (1H, d, J=5 Hz), 8.87 (1H, s)

EXAMPLE 88

The following compounds were obtained according to a similar manner to that of Example 79.
(1) 4-[3-(1-Naphthyl)phenyl]-2-(1-imidazolylmethyl)-3-oxo-3,4-dihydropyrido[2,3-b]pyrazine
  mp: 180–185° C.
  NMR CDCl$_3$, $\delta$): 5.41 (2H, s), 7.10 (1H, s), 7.15 (1H, s), 7.35 (2H, m), 7.50 (5H, m), 7.72 (3H, m), 7.90 (2H, m), 8.07 (1H, m), 8.19 (1H, d, J=8 Hz), 8.53 (1H, m)
  MASS: 430 (M+1)
(2) 2-(1-Imidazolylmethyl)-4-[3-(3,5-dichlorobenzoylamino)phenyl]-3-oxo-3,4-dihydropyrido[2,3-b]pyrazine
  NMR (CDCl$_3$, 300 MHz, $\delta$): 5.41 (2H, s), 6.84 (1H, d, J=7 Hz), 7.00 (1H, s), 7.09 (1H, s), 7.34 (1H, dd, J=7 Hz, 5 Hz), 7.40–7.47 (2H, m), 7.64–7.74 (5H, m), 8.17 (1H, d, J=7 Hz), 8.45 (1H, m), 8.90 (1H, s)
(3) 2-(1-Imidazolylmethyl)-4-(3-biphenylyl)-3-oxo-3,4-dihydropyrido[2,3-b]pyrazine
  NMR (CDCl$_3$, 300 MHz, $\delta$): 5.40 (2H, s), 7.10 (1H, s), 7.14 (1H, s), 7.20–7.50 (5H, m), 7.57–7.78 (6H, m), 8.17 (1H, dd, J=8 Hz, 3 Hz), 8.47 (1H, m)

EXAMPLE 89

The following compound was synthesized from 1-amino-1H-1,3,5-triazole and 2-bromomethyl-4-(3-methoxycarbonylphenyl)-3-oxo-3,4-dihydropyrido[2,3-b]pyrazine according to a similar manner to that disclosed in Journal of Organic Chemistry 54, 731 (1989).

2-(1-1H-1,2,4-Triazolylmethyl)-4-(3-methoxycarbonylphenyl)-3-oxo-3,4-dihydropyrido[2,3-b]pyrazine NMR (DMSO-$d_6$, 300 MHz, $\delta$): 3.88 (3H, s), 5.66 (2H, s), 7.41 (1H, dd, J=8 Hz, 7 Hz), 7.68 (1H, d, J=9 Hz), 7.73 (1H, dd, J=9 Hz, 9 Hz), 8.01 (1H, s), 8.05 (1H, s), 8.10 (1H, d, J=8 Hz), 8.17 (1H, d, J=8 Hz), 8.42 (1H, d, J=7 Hz), 8.63 (1H, s)

EXAMPLE 90

The following compound was synthesized from 1-amino-1H-1,3,4-triazole and 2-bromomethyl-4-(3-methoxycarbonylphenyl)-3-oxo-3,4-dihydropyrido[2,3-b]pyrazine according to a similar manner to that disclosed in Journal of Organic Chemistry 54, 731 (1989).

2-(-1H-1,2,4-Triazolylmethyl)-4-(3-methoxycarbonylphenyl)-3-oxo-3,4-dihydropyrido[2,3-b]pyrazine NMR (DMSO-$d_6$, 300 MHz, $\delta$): 3.88 (3H, s), 5.66 (2H, s), 7.41 (1H, dd, J=8 Hz, 7 Hz), 7.68 (1H, d, J=9 Hz), 7.73 (1H, dd, J=9 Hz, 9 Hz), 8.01 (1H, s), 8.05 (1H, s), 8.10 (1H, d, J=8 Hz), 8.17 (1H, d, J=8 Hz), 8.42 (1H, d, J=7 Hz), 8.63 (1H, s)

EXAMPLE 91

The following compound was obtained according to a similar manner to that of Example 78.

2-Bromomethyl-4-[3-(1-naphthyl)phenyl]-3-oxo-3,4-dihydropyrido[2,3-b]pyrazine

NMR (CDCl$_3$, $\delta$): 4.70 (2H, s), 7.35 (1H, dd, J=8 Hz, 6 Hz), 7.41 (1H, m), 7.45–7.55 (5H, m), 7.70 (2H, m), 7.90 (2H, m), 8.07 (1H, m), 8.23 (1H, m), 8.54 (1H, d, J=6 Hz)

EXAMPLE 92

The following compound was obtained according to a similar manner to that of Example 35.

2-[2-(Pyrrolidinylcarbonyl)ethyl]-4-[3-[3-(2-methoxycarbonylphenyl)ureido]phenyl]-3-oxo-3,4-dihydropyrido[2,3-b]pyrazine mp: 235–237° C.

NMR (DMSO-$d_6$, $\delta$): 1.80 (2H, m), 1.94 (2H, m), 2.77 (2H, t, J=7 Hz), 3.10 (2H, t, J=7 Hz), 3.30 (2H, t, J=7 Hz), 3.53 (2H, t, J=7 Hz), 3.87 (3H, s), 6.8–7.05 (4H, m), 7.40 (3H, m), 7.59 (1H, m), 8.08 (1H, d, J=8 Hz), 8.20 (1H, d, J=8 Hz), 8.29 (1H, s), 8.38 (1H, m), 9.51 (1H, s)

EXAMPLE 93

The following compounds were obtained according to a similar manner to that of Example 26, 27 or 59.

(1) 2-Benzyl-4-[3-[3-(2-biphenylyl)ureido]phenyl]-3-oxo-3,4-dihydropyrido[2,3-b]pyrazine NMR (DMSO-d$_6$, 200 MHz, δ): 4.21 (2H, s), 6.90 (1H, m), 7.1–7.6 (17H, m), 7.72 (1H, s), 7.89 (1H, d, J=8 Hz), 8.23 (1H, dd, J=2 Hz, 8 Hz), 8.40 (1H, dd, J=2 Hz, 5 Hz), 9.21 (1H, s)

(2) 2-Benzyl-4-[3-[3-(5-quinolyl)ureido]phenyl]-3-oxo-3,4-dihydropyrido[2,3-b]pyrazine NMR (DMSO-d$_6$, 200 MHz, δ): 4.22 (2H, s), 6.97 (1H, d, J=8 Hz), 7.2–7.7 (10H, m), 7.82 (1H, d, J=8 Hz), 7.96 (1H, d, J=6 Hz), 8.24 (2H, d, J=8 Hz), 8.40 (1H, d, J=5 Hz), 8.59 (1H, d, J=6 Hz), 8.98 (1H, s), 9.30 (1H, m)

EXAMPLE 94

To a solution of 2-benzyl-4-(3-carboxyphenyl)-3-oxo-3,4-dihydropyrido[2,3-b]pyrazine (41 mg) in dichloromethane (2 ml) was added oxalyl chloride (0.02 ml) and 1 drop of N,N-dimethylformamide. After stirring at room temperature for 15 minutes, ammonia solution (28%, 1 ml) was added to the mixture and stirred at room temperature for 15 minutes. The mixture was poured into a mixture of ethyl acetate and aqueous sodium bicarbonate. The organic phase was separated, washed with aqueous sodium bicarbonate and brine, dried over magnesium sulfate and concentrated. The resultant solid was collected and washed with isopropyl ether to give 2-benzyl-4-(3-carbamoylphenyl)-3-oxo-3,4-dihydropyrido[2,3-b]pyrazine (139 mg).

NMR (DMSO-d$_6$, 200 MHz, δ): 4.21 (2H, s), 7.15–7.7 (9H, m), 7.82 (1H, s), 7.95–8.1 (2H, m), 8.25 (1H, dd, J=2 Hz, 8 Hz), 8.40 (1H, dd, J=2 Hz, 5 Hz)

EXAMPLE 95

A mixture of 2-benzyl-4-(3-carboxyphenyl)-3-oxo-3,4-dihydropyrido[2,3-b]pyrazine (200 mg), benzyl bromide (144 mg) and potassium carbonate (155 mg) in N,N-dimethylformamide (2 ml) was stirred at room temperature for 1 hour. Then the mixture was poured into a mixture of ethyl acetate and aqueous sodium bicarbonate. The organic phase was separated, washed with aqueous sodium bicarbonate and brine, dried over magnesium sulfate and concentrated. The resultant solid was collected and washed with isopropyl ether to give 2-benzyl-4-(3-benzyloxycarbonylphenyl)-3-oxo-3,4-dihydropyrido[2,3-b]pyrazine (206 mg).

NMR (CDCl$_3$, 200 MHz, δ): 4.30 (2H, s), 5.37 (2H, s), 7.2–7.5 (12H, m), 7.66 (1H, t, J=8 Hz), 7.98 (1H, t, J=2 Hz), 8.21 (2H, dt, J=2 Hz, 8 Hz), 8.38 (1H, dd, J=2 Hz, 5 Hz)

EXAMPLE 96

A mixture of 4-(3-aminophenyl)-2-benzyl-3-oxo-3,4-dihydropyrido[2,3-b]pyrazine (105 mg), propionic anhydride (0.045 ml), pyridine (0.029 ml) and 4-dimethylaminopyridine (1 mg) in dichloromethane (2 ml) was stirred at room temperature for 2 hours. Then the mixture was poured into a mixture of ethyl acetate and aqueous sodium bicarbonate. The organic phase was separated, washed with aqueous sodium bicarbonte and brine, dried over magnesium sulfate and concentrated. The residue was crystallized from ethanol to give 2-benzyl-4-(3-propionylaminophenyl)-3-oxo-3,4-dihydropyrido[2,3-b]pyrazine (90 mg)

NMR (DMSO-d$_6$, 300 MHz, δ): 1.07 (3H, t, J=7 Hz), 2.32 (2H, q, J=7 Hz), 4.21 (2H, s), 6.99 (1H, d, J=8 Hz), 7.2–7.5 (7H, m), 7.55–7.65 (2H, m), 8.23 (1H, d, J=8 Hz), 8.39 (1H, m)

EXAMPLE 97

A mixture of 2-benzyl-4-[3-[3-(2-nitrophenyl)ureido]phenyl]-3-oxo-3,4-dihydropyrido[2,3-b]pyrazine (120 mg) and 10% palladium on carbon (40 mg) in methanol (2 ml) and 1,4-dioxane (2 ml) was stirred under hydrogen (3 atm) at room temperature for 4 hours. The catalyst was removed by filtration and the solvent was evaporated. The residue was crystallized from methanol to give 4-[3-[3-(2-aminophenyl)ureido]phenyl]-2-benzyl-3-oxo-3,4-dihydropyrido[2,3-b]pyrazine (97 mg).

NMR (DMSO-d$_6$, 200 MHz, δ): 4.21 (2H, s), 4.80 (2H, s), 6.57 (1H, dt, J=2 Hz, 8 Hz), 6.7–6.95 (3H, m), 7.2–7.55 (10H, m), 7.79 (1H, s), 8.24 (1H, dd, J=2 Hz, 8 Hz), 8.40 (1H, dd, J=2 Hz, 5 Hz), 8.96 (1H, s)

EXAMPLE 98

A mixture of 3-amino-2-(3-biphenylylamino)pyridine (196 mg) and 3-(2-nitrophenyl)pyruvic acid (188 mg) in ethanol (5 ml) was stirred under reflux for 1 hour. The mixture was cooled and then poured into a mixture of ethyl acetate and aqueous sodium bicarbonate. The organic phase was separated, washed with aqueous sodium bicarbonate and brine, dried over magnesium sulfate and concentrated. The residue was crystallized from methanol to give 4-(3-biphenylyl)-2-(2-nitrobenzyl)-3-oxo-3,4-dihydropyrido[2,3-b]pyrazine (140 mg).

NMR (CDCl$_3$, 300 MHz, δ): 4.80 (2H, s), 7.22 (1H, dd, J=5 Hz, 8 Hz), 7.3–7.55 (7H, m), 7.6–7.7 (4H, m), 7.78 (1H, dt, J=8 Hz, 2 Hz), 7.99 (1H, dd, J=2 Hz, 8 Hz), 8.14 (1H, dd, J=2 Hz, 8 Hz), 8.40 (1H, dd, J=2 Hz, 5 Hz)

EXAMPLE 99

A mixture of 4-(3-methoxycarbonylphenyl)-2-methyl-3-oxo-3,4-dihydropyrido[2,3-b]pyrazine (5.02 g), N-bromosuccinimide (4.0 g) and benzoyl peroxide (0.50 g) in chloroform (60 ml) was stirred under reflux for 2 hours. The mixture was concentrated and chromatographed on silica gel column (1% methanol in chloroform) to give 2-bromomethyl-4-(3-methoxycarbonylphenyl)-3-oxo-3,4-dihydropyrido[2,3-b]pyrazine (4.75 g).

NMR (CDCl$_3$, 300 MHz, δ): 3.91 (3H, s), 4.19 (2H, s), 7.37 (1H, dd, J=5 Hz, 8 Hz), 7.53 (1H, m), 7.69 (1H, t, J=8 Hz), 8.01 (1H, s), 8.2–8.3 (2H, m), 8.46 (1H, d, J=5 Hz)

EXAMPLE 100

A mixture of 2-bromomethyl-4-(3-methoxycarbonylphenyl)-3-oxo-3,4-dihydropyrido[2,3-b]pyrazine (1.22 g) and 2-methylimidazole (1.35 g) in N,N-dimethylformamide (10 ml) was stirred at 80° C. for 1 hour. Then the mixture was poured into aqueous sodium bicarbonate and extracted with ethyl acetate twice. The combined organic solution was washed with aqueous sodium bicarbonate and brine, dried over magnesium sulfate and concentrated. The residue was chromatographed on silica gel column (5% methanol in chloroform) to give 4-(3-methoxycarbonylphenyl)-2-[(2-methylimidazol-1-yl)methyl]-3-oxo-3,4-dihydropyrido[2,3-b]pyrazine (15 4 mg).

NMR (CDCl$_3$, 300 MHz, δ): 2.49 (3H, s), 3.91 (3H, s), 5.32 (2H, s), 6.96 (1H, s), 7.02 (1H, s), 7.33 (1H, dd, J=5 Hz, 8 Hz), 7.50 (1H, d, J=8 Hz), 7.69 (1H, t, J=8 Hz), 7.99 (1H, s), 8.15–8.25 (2H, m), 8.44 (1H, d, J=5 Hz)

EXAMPLE 101

A mixture of 3-amino-2-[(3-biphenylyl)amino]pyridine (350 mg) and 2-ketoglutaric acid (235 mg) in ethanol (5 ml)

was stirred under reflux for 1 hour. After evaporation of the solvent, the residue was chromatographed on silica gel column (2.5%–3% methanol in chloroform) to give 4-(3-biphenylyl)-2-(2-carboxyethyl)-3-oxo-3,4-dihydropyrido[2,3-b]pyrazine (222 mg).

NMR (DMSO-$d_6$, 300 MHz, δ): 2.78 (2H, t, J=7 Hz), 3.12 (2H, t, J=7 Hz), 7.3–7.5 (5H, m), 7.6–7.75 (4H, m), 7.81 (1H, m), 8.23 (1H, dd, J=2 Hz, 8 Hz), 8.40 (1H, dd, J=2 Hz, 5 Hz)

EXAMPLE 102

A mixture of 4-(3-biphenylyl)-2-(2-carboxyethyl)-3-oxo-3,4-dihydropyrido[2,3-b]pyrazine. (80 mg), iodomethane (0.04 ml) and potassium carbonate (90 mg) in N,N-dimethylformamide (2 ml) was stirred at room temperature for 1 hour. Then the mixture was poured into a mixture of ethyl acetate and aqueous sodium bicarbonte. The organic phase was separated, washed with aqueous sodium bicarbonate and brine, dried over magnesium sulfate and concentrated. The residue was crystallized from methanol to give 4-(3-biphenylyl)-2-(2-methoxycarbonylethyl)-3-oxo-3,4-dihydropyrido[2,3-b]pyrazine (71 mg).

NMR (DMSO-$d_6$, 300 MHz, δ), 2.86 (2H, t, J=7 Hz), 3.17 (2H, t, J=7 Hz), 3.63 (3H, s), 7.3–7.5 (5H, m), 7.6–7.75 (4H, m), 7.82 (1H, m), 8.22 (1H, dd, J=2 Hz, 8 Hz), 8.40 (1H, dd, J=2 Hz, 5 Hz)

EXAMPLE 103

A mixture of 4-(3-methoxycarbonylphenyl)-2-(3-pyridylmethyl)-3-oxo-3,4-dihydropyrido[2,3-b]pyrazine (0.29 g) and 4N hydrochloric acid (18 ml) was stirred under reflux for 2 hours. After evaporation of the solvent, crude residue was chromatographed on silica gel (29 g, chloroform-methanol 9:1 as eluent) and crystallized from methanol to afford 4-(3-carboxyphenyl)-2-(3-pyridylmethyl)-3-oxo-3,4-dihydropyrido[2,3-b]pyrazine.hydrochloride as colorless crystal (0.29 g)

mp: 260–265° C.

NMR (DMSO-$d_6$, δ): 4.25 (2H, s), 7.39 (2H, m), 7.61 (1H, m), 7.69 (1H, dd, J=8 Hz, 8 Hz), 7.78 (1H, m), 7.94 (1H, s), 8.05 (1H, m), 8.20 (1H, d, J=8 Hz), 8.38 (1H, m), 8.48 (1H, m), 8.60 (1H, m)

EXAMPLE 104

To a solution of 2-(bromomethyl)-4-(3-succinimidophenyl)-3-oxo-3,4-dihydropyrido[2,3-b]pyrazine (420 mg) in acetonitrile (4 ml) was added 1-acetylimidazole (179 mg). The solution was refluxed for an hour. The mixture was evaporated. The residue was dissolved in water, and to the solution was added sodium carbonate. The mixture was extracted by ethyl acetate. The organic layer was evaporated. The residue was purified by column chromatography to obtain 2-(1-imidazolylmethyl)-4-(3-succinimidophenyl)-3-oxo-3,4-dihydropyrido[2,3-b]pyrazine (105 mg) as yellow powder.

NMR (DMSO-$d_6$, 300 MHz, δ): 2.79 (4H, s), 5.44 (2H, s), 6.94 (1H, s), 7.22 (1H, s), 7.32–7.46 (4H, m), 7.68 (1H, d, J=8 Hz), 7.72 (1H, s), 8.16 (1H, d, J=8 Hz), 8.42 (1H, d, J=7 Hz)

MASS (FAB) (m/e): 401

EXAMPLE 105

The mixture of 2-(3-pyridylmethyl)-4-(3-biphenylyl)-3-oxo-3,4-dihydropyrido[2,3-b]pyrazine (100 mg) and m-chloroperbenzoic acid (44.2 mg) in methylene chloride (10 ml) was stirred for 3 hours at 0° C. The mixture was washed with aqueous sodium hydrogencarbonate and extracted by chloroform (50 ml). The organic layer was evaporated and chromatographed to obtain 2-[(3-pyridyl-N-oxide)methyl]-4-(3-biphenylyl)-3-oxo-3,4-dihydropyrido[2,3-b]pyrazine (25 mg).

NMR (CDCl$_3$, 300 MHz, δ): 4.28 (2H, s), 7.20–7.48 (8H, m), 7.59–7.68 (3H, m), 7.74 (1H, d, J=9 Hz), 8.12 (1H, d, J=8 Hz), 8.18 (1H, dd,, J=8 Hz, 3 Hz), 8.36 (1H, s), 8.45 (1H, dd, J=7 Hz, 3 Hz)

MASS (FAB) (m/e): 407

EXAMPLE 106

To a solution of 2-(3-pyridylmethyl)-4-[3-(3,5-dichlorobenzoylamino)phenyl]-3-oxo-3,4-dihydropyrido[2,3-b]pyrazine (200 mg) in methylene chloride (50 ml) was added m-chloroperbenzoic acid (96.1 mg) at 0° C. The mixture was stirred for 2 hours at 0° C. The reaction mixture was allowed to warm to room temperature and stirred for an additional 5 hours. A 10% solution of sodium sulfate (20 ml) was added to the reaction mixture. The mixture was extracted by chloroform. The organic layer was dried and evaporated. The crude mixture was purified by chromatography to obtain 2-[(3-pyridyl-N-oxide)methyl]-4-[3-(3,5-dichlorobenzoylamino)phenyl]-3-oxo-3,4-dihydropyrido[2,3-b]pyrazine as yellow crystals.

NMR (DMSO-$d_6$, 300 MHz, δ): 4.21 (2H, s), 7.12 (1H, d, J=7 Hz), 7.34–7.44 (3H, m), 7.56 (1H, dd, J=7 Hz, 7 Hz), 7.77–7.86 (2H, m), 7.88 (1H, m), 7.98 (1H, s), 7.99 (1H, s), 8.14 (1H, d, J=7 Hz), 8.24 (1H, d, J=7 Hz), 8.26 (1H, s), 8.41 (1H, d, J=5 Hz)

MASS (FAB) (m/e): 518, 520

EXAMPLE 107

The mixture of 2-methyl-4-(3-biphenylyl)-3-oxo-3,4-dihydropyrido[ 2,3-b]pyrazine (17 g), N-bromosuccinimide (10.6 g) and 2,2'-azobis(4-methoxy-2,4-dimethylvaleronitrile (167 mg) in benzene (200 ml) was refluxed for 2 hours. The mixture was washed with water and evaporated. The crude products was purified by column chromatography to obtain 2-bromomethyl-4-(3-biphenylyl)-3-oxo-3,4-dihydropyrido[2,3-b]pyrazine (5 g).

NMR (CDCl$_3$, 300 MHz, δ): 4.70 (2H, s), 7.28–7.52 (6H, m), 7.59–7.69 (3H, m), 7.50 (1H, dd, J=8 Hz, 3 Hz), 8.23 (1H, dd, J=8 Hz, 3 Hz), 8.48 (1H, dd, J=7 Hz, 3 Hz)

EXAMPLE 108

To a solution of 2-bromomethyl-4-(3-biphenylyl)-3-oxo-3,4-dihydropyrido[2,3-b]pyrazine (200 mg) in acetonitrile was added triethylamine (0.14 ml) and morphorine (0.089 ml). The reaction mixture was stirred for 5 hours at 60° C. The mixture was poured into water and extracted by ethyl acetate. The organic layer was evaporated. The crude product was purified by chromatography (SiO$_2$) to obtain 2-(1-morpholinomethyl)-4-(3-biphenylyl)-3-oxo-3,4-dihydropyrido[2,3-b]pyrazine (110 mg) as yellow powder.

NMR (CDCl$_3$, 300 MHz, δ): 2.77 (4H, s), 3.82 (4H, s), 3.91 (2H, 5), 7.23–7.78 (10H, m), 8.28 (1H, d, J=8 Hz), 8.44 (1H, m)

EXAMPLE 109

The mixture of 2-methyl-4-[3-(3,5-dichlorobenzoylamino) phenyl]-3-oxo-3,4-dihydropyrido[2, 3-b]pyrazine (4.4 g), N-bromosuccinimide (2.39 g) and benzoylperoxide in chloroform (40 ml) was refluxed for 3 hours. The mixture was washed with water and extracted by chloroform (80 ml), and evaporated. The crude product was purified by chromatography to obtain 2-bromomethyl-4-[3-(3,5-dichlorobenzoylamino)phenyl]-3-oxo-3,4-dihydropyrido[2,3-b]pyrazine (1.4 g).

NMR (CDCl$_3$, 300 MHz, δ): 4.69 (2H, s), 6.93 (1H, d, J=6 Hz), 7.35 (1H, dd, J=7 Hz, 5 Hz), 7.43–7.50 (2H, m), 7.62 (1H, m), 7.74 (1H, d, J=7 Hz), 7.99 (1H, s), 8.12. (1H, s), 8.24 (1H, d, J=7 Hz), 8.37 (1H, s), 8.49 (1H, d, J=5 Hz)

EXAMPLE 110

The solution of 2-bromomethyl-4-[3-(3,5-dichlorobenzoylamino)phenyl]-3-oxo-3,4-dihydropyrido[2,3-b]pyrazine (105 mg) and 2-methylimidazole (171 mg) in N,N-dimethylformamide (10 ml) was stirred for 3 hours at 70° C. and 1 hour at 80° C. The mixture was poured into aqueous sodium hydrogencarbonate and extracted by ethyl acetate (100 ml). The organic layer was evaporated and chromatographed to obtain .2-[(2-methylimidazol-1-yl)methyl]-4-[3-(3,5-dichlorobenzoylamino)phenyl]-3-oxo-3,4-dihydropyrido[2,3-b]pyrazine (50 mg) in brown powder form.

NMR (CDCl$_3$, 300 MHz, δ): 2.47 (3H, s), 5.37 (2H, s), 6.82 (1H, d, J=6 Hz), 6.91 (1H, s), 6.99 (1H, s), 7.34 (1H, dd, J=7 Hz, 5 Hz), 7.41–7.48 (2H, m), 7.56 (1H, d, J=7 Hz), 7.69–7.71 (2H, m), 7.87 (1H, s), 8.18 (1H, d, J=7 Hz), 8.46 (1H, d, J=4 Hz), 8.88 (1H, s)

EXAMPLE 111

The solution of 2-bromomethyl-4-[3-(3,5-dichlorobenzoylamino)phenyl]-3-oxo-3,4-dihydropyrido[2,3-b]pyrazine (285 mg) and 2-phenylimidazole (734 mg) in N,N-dimethylformamide (30 ml) was stirred for 3 hours at 80° C. The mixture was poured into aqueous sodium hydrogencarbonate (150 ml) and extracted by ethyl acetate (150 mg). The organic layer was evaporated and chromatographed to obtain 2-[(2-phenylimidazol-1-yl)methyl]-4-[3-(3,5-dichlorobenzoylamino)phenyl]-3-oxo-3,4-dihydropyrido[2,3-b]pyrazine (52 mg) in brown powder form.

NMR (CDCl$_3$, 300 MHz, δ): 5.53 (2H, s), 6.82 (1H, d, J=7 Hz), 7.10 (1H, s), 7.17 (1H, s), 7.28–7.55 (7H, m), 7.59–7.66 (4H, m), 7.72 (1H, m), 8.17 (1H, dd, J=7 Hz, 3 Hz), 8.44–8.50 (2H, m)

EXAMPLE 112

The following compound was obtained according to a similar manner to that of 2, 42, 43, 44, 51, 53 or 67.

4-[3-[(E)-2-(5-Chloropyridin-3-yl)vinyl]phenyl]-2-(3-pyridylmethyl)-3-oxo-3,4-dihydropyrido[2,3-b]pyrazine NMR (DMSO-d$_6$, 300 MHz, δ): 4.27 (2H, s), 7.25–7.45 (4H, m), 7.5–7.65 (3H, m), 7.71 (1H, d, J=8 Hz), 7.79 (1H, d, J=8 Hz), 8.22 (2H, m), 8.35–8.5 (3H, m), 8.60 (1H, s), 8.70 (1H, s)

EXAMPLE 113

The following compound was obtained by reacting 2-benzyl-4-[3-(1-pyrrolyl)phenyl]-3-oxo-3,4-dihydropyrido[2,3-b]pyrazine with N-bromosuccinimide in a conventional manner.

2-Benzyl-4-[3-(2,5-dibromopyrrol-1-yl)phenyl]-3-oxo-3,4-dihydropyrido[2,3-b]pyrazine mp: 90° C. (dec.)

NMR (DMSO-d$_6$, δ): 4.22 (2H, s), 6.46 (2H, s), 7.23 (1H, m), 7.3–7.5 (7H, m), 7.55 (1H, m), 7.72 (1H, dd, J=8 Hz, 8 Hz), 8.23 (1H, m), 8.41 (1H, m)

MASS: 537 (M$^+$)

EXAMPLE 114

The following compounds can be obtained according to a similar manner to that of example 57 or 58.

(1) 4-[3-[3-[(e)-3-(3-pyridyl)acryloylamino]phenyl]phenyl]-2-(3-pyridylmethyl)-3-oxo-3,4-dihydropyrido[2,3-b]pyrazine (2) 4-[3-[3-[(e)-3-(2-pyridyl)acryloylamino]phenyl]phenyl]-2-(3-pyridylmethyl)-3-oxo-3,4-dihydropyrido[2,3-b]pyrazine

What is claimed is:

1. A compound of the formula:

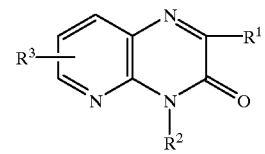

wherein

R$^1$ is aryl which may have suitable substituent(s), ar(lower)alkyl which may have suitable substituent(s), halo(lower)alkyl, carboxyethyl, protected carboxy(lower)alkyl, acyl(lower)alkyl, a heterocyclic group which may have suitable substituent(s) or a heterocyclic(lower)alkyl group which may have suitable substituent(s), R$^2$ is aryl which may have suitable substituent(s) or a heterocyclic group, and R$^3$ is hydrogen, lower alkoxy or arylthio, and a pharmaceutically acceptable salt thereof, provided that when R$^1$ is phenyl, halophenyl, trihalo (lower)alkyl, carboxyethyl, piperidyl, morpholinyl, piperazinyl, or alkylpiperazinyle, then R$^2$ is not substituted phenyl, piperidyl, morpholinyl, piperazinyl, or alkylpiperazinyl.

2. A compound of claim 1, wherein

R$^1$ is phenyl having 1 to 3 suitable substituent(s) as set forth in claim 1; phenyl(lower)alkyl which may have 1 to 3 suitable substituent(s); halo(lower)alkyl which may have one or two suitable substituent(s); carboxyethyl; heterocyclicoxycarbonyl(lower)alkyl which may have 1 to 3 suitable substituent(s); heterocycliccarbonyl(lower)alkyl which may have 1 to 3 substituent(s) selected from the group consisting of protected carboxy and lower alkyl; indolyl; or indolyl(lower)alkyl, pyridyl(lower)alkyl, imidazolyl(lower)alkyl, morpholinyl(lower)alkyl or triazolyl(lower)alkyl, each of which may have 1 to 3 suitable substituent(s);

R$^2$ is phenyl or naphthyl, each of which may have 1 to 3 suitable substituent(s), or pyridyl, and R$^3$ is hydrogen, lower alkoxy or phenylthio.

3. A compound of claim 2, wherein

R$^1$ is phenyl having one or two nitro; phenyl(lower)alkyl which may have one or two substituent(s) selected from the group consisting of nitro, amino, protected amino, hydroxy and protected hydroxy; halo(lower)alkyl; carboxyethyl; esterified carboxy(lower)alkyl; carbamoyl (lower)alkyl which may have one or two substituent(s) selected from the group consisting of lower alkyl and heterocyclic group; pyrrolidinyloxycarbonyl(lower) alkyl which may have one or two oxo; pyrrolidinylcarbonyl(lower)alkyl 20 or piperazinylcarbonyl(lower)alkyl, each of which may have one or two substituent(s) selected from the group consisting of esterified carboxy and lower alkyl; indolyl; or indolyl(lower)alkyl, pyridyl(lower)alkyl, imidazolyl(lower)alkyl, morpholinyl(lower)alkyl or triazolyl(lower)alkyl, each of which may have one or two substituent(s) selected from the group consisting of lower alkyl, N-oxide and aryl;

$R^2$ is phenyl or naphthyl, each of which may have one or two substituent(s) selected from the group consisting of lower alkyl; halogen; mono (or di or tri)halo(lower) alkyl; hydroxy; protected hydroxy; carboxy; protected carboxy; carboxy(lower)alkyl; protected carboxy (lower)alkyl; lower alkoxy; cyano; nitro; amino; acylamino; lower alkylamino; N-acyl-N-lower alkylamino; heterocyclicamino which may have 1 to 3 substituent(s) selected from the group consisting of lower alkyl and aryl; acyl; acyl(lower)alkyl; aryl which may have 1 to 3 substituent(s) selected from the group consisting of carboxy(lower)alkenyl, protected carboxy (lower)alkenyl, aryl, lower alkoxy, cyclo(lower) alkyloxy, halogen, carboxy, protected carboxy, amino, acylamino, diacylamino and acyl; ar(lower)alkyl; ar(lower)alkenyl which may have 1 to 3 halogen; acyl(lower)alkenyl; protected carboxy(lower)alkenyl; cyano(lower)alkenyl; heterocyclic(lower)alkenyl which may have 1 to 3 halogen; heterocyclic group which may have 1 to 3 substituent(s) selected from the group consisting of halogen, cyano, carboxy, protected carboxy, oxo, acyl, amino, protected amino and heterocyclic group; and heterocyclicoxy which may have 1 to 3 aryl, or pyridyl.

4. A compound of claim 3, wherein $R^1$ is phenyl having nitro; phenyl(lower)alkyl which may have nitro, amino, acylamino, hydroxy or acyloxy; halo(lower)alkyl; carboxyethyl; lower alkoxycarbonyl (lower)alkyl; carbamoyl(lower)alkyl which may have one or two substituent(s) selected from the group consisting of lower alkyl and pyrrolidinyl; pyrrolidinyloxycarbonyl(lower)alkyl which may have one or two oxo; pyrrolidinylcarbonyl(lower)alkyl or piperazinylcarbonyl(lower)alkyl, each of which may have lower alkoxycarbonyl or lower alkyl; indolyl; or indolyl(lower)alkyl, pyridyl(lower)alkyl, imidazolyl (lower)alkyl, morpholinyl(lower)alkyl or triazolyl (lower)alkyl, each of which may have lower alkyl, N-oxide or phenyl;

$R^2$ is phenyl or naphthyl, each of which may have one or two substituent(s) selected from the group consisting of lower alkyl; halogen; trihalo(lower)alkyl; hydroxy; acyloxy; carboxy; esterified carboxy; carboxy(lower) alkyl; esterified carboxy(lower)alkyl; lower alkoxy; cyano; nitro; amino; lower alkanoylamino; aryloxycarbonylamino; lower alkoxycarbonylamino; lower alkoxyglyoxyloylamino; cyclo(lower)alkylcarbonylamino; cyclo(lower)alkyloxycarbonylamino; cyclo(lower) alkylidene(lower)alkanoylamino; aroylamino which may have 1 to 3 substituent(s) selected from the group consisting of lower alkyl, halogen, lower alkoxy, carboxy, protected carboxy, nitro, hydroxy, protected hydroxy, mono (or di or tri)halo(lower)alkyl, cyclo (lower)alkyloxy, aryl, carboxy(lower)alkenyl, protected carboxy(lower)alkenyl, amino, protected amino, heterocyclicoxy, and heterocyclicamino which may have nitro; arylsulfonylamino which may have one or two halogen; ar(lower)alkylsulfonylamino; cyclo (lower)alkylcarbonylamino; [mono(or di)ar(lower) alkanoyl]amino; lower alkadienoylamino; heterocycliccarbonylamino which may have 1 to 3 substituent (s) selected from the group consisting of lower alkyl and halogen; ar(lower)alkenoylamino which may have 1 to 3 substituent(s) selected from the group consisting of lower alkyl, halogen, carboxy, protected carboxy and nitro; heterocyclic(lower)alkenoylamino; carbamoylamino which may have one or two substituent(s) selected from the group consisting of lower alkyl; [aryl which may have 1 to 3 substituent(s) selected from the group consisting of nitro, amino, protected amino, lower alkoxy, lower alkylthio, lower alkyl, aryl, carboxy, protected carboxy, di(lower)alkylamino, mono (or di or tri)halo(lower)alkyl and halogen]; arylsulfonyl; ar(lower)alkyl; cyclo(lower)alkyl; and heterocyclic group; thiocarbamoylamino which may have one or two substituent(s) selected from the group consisting of aryl and acyl; lower alkylamino; N-lower alkanoyl-N-lower alkylamino; N-aroyl-N-lower alkylamino; N-arylcarbamoyl-N-lower alkylamino; N-protected carboxyar(lower)alkenoyl-N-lower alkylamino; thiazolylamino or pyrimidinylamino, each of which may have one or two substituent(s) selected from the group consisting of lower alkyl and phenyl; lower alkanoyl; carbamoyl which may have one or two substituent(s) selected from the group consisting of lower alkyl and aryl which may have one or two halogen; aroyl which may have lower alkoxy or heterocycliccarbonyl; carbamoyl(lower)alkyl which may have one or two aryl; phenyl or naphthyl, each of which may have one or two substituent(s) selected from the group consisting of carboxy(lower)alkenyl, esterified carboxy(lower)alkenyl, phenyl, lower alkoxy, cyclo (lower)alkyloxy, halogen, carboxy, esterified carboxy, amino, lower alkanoylamino, aroylamino which may have protected carboxy or carboxy, lower alkylsulfonylamino, mono (or di or tri)halo(lower) alkanoylamino, lower alkoxycarbonylamino, aryloxycarbonylamino, carboxy(lower)alkanoylamino, protected carboxy(lower)alkanoylamino, carboxy (lower)alkenoylamino, protected carboxy(lower) alkenoylamino, cyclo(lower)alkylcarbonylamino, lower alkylglyoxyloylamino, arylsulfonylamino which may have one or two halogen, ar(lower)alkenoylamino which may have protected carboxy or carboxy, heterocyclic(lower)alkenoylamino, heterocycliccarbonylamino, carbamoylamino which may have one or two substituent(s) selected from the group consisting of lower alkyl and aryl, bis(lower alkylsulfonyl)amino, and carbamoyl which may have one or two substituent(s) selected from the group consisting of lower alkyl and aryl; phenyl(lower)alkyl; naphthyl(lower)alkyl; phenyl(lower)alkenyl or naphthyl(lower)alkenyl, each of which may have one or two halogen; aroyl(lower)alkenyl; esterified carboxy (lower)alkenyl; cyano(lower)alkenyl; pyridyl(lower) alkenyl which may have one or two halogen; pyrimidinyl(lower)alkenyl; quinolyl(lower)alkenyl; pyridyl, thienyl, pyrrolyl, pyrrolidinyl, indolyl, quinolyl, isoquinolyl, imidazolyl, thiazolyl, benzothiazolyl or triazolyl, each of which may have one or two substituent(s) selected from the group consisting of halogen, cyano, carboxy, esterified carboxy, oxo, lower alkanoyl, amino, acylamino and pyridyl; and pyrimidinyloxy which may have one or two phenyl; or pyridyl.

5. A compound of claim 4, wherein $R^1$ is phenyl having nitro; phenyl(lower)alkyl which may have nitro, amino, acylamino, hydroxy or lower alkanoyloxy; halo(lower)alkyl; carboxyethyl, lower alkoxycarbonyl(lower)alkyl; carbamoyl(lower)alkyl which may have one or two substituent(s) selected from the group consisting of lower alkyl and pyrrolidinyl; pyrrolidinyloxycarbonyl(lower)alkyl which may have two oxo; pyrrolidinylcarbonyl(lower)alkyl which may have lower alkoxycarbonyl; piperazinylcarbonyl (lower)alkyl which may have lower alkyl; indolyl; indolyl(lower)alkyl; pyridyl(lower)alkyl which may have N-oxide; imidazolyl(lower)alkyl which may have lower alkyl or phenyl; morpholinyl(lower)alkyl; or triazolyl(lower)alkyl;

$R^2$ is phenyl or naphthyl, each of which may have one or two substituent(s) selected from the group consisting of lower alkyl; halogen; trihalo(lower)alkyl; hydroxy; lower alkanoyloxy; carboxy; lower alkoxycarbonyl; phenyl(lower)alkoxycarbonyl; carboxy(lower)alkyl; lower alkoxycarbonyl(lower)alkyl; lower alkoxy; cyano; nitro; amino; lower alkanoylamino; phenoxycarbonylamino; lower alkoxycarbonylamino; lower alkoxyglyoxyloylamino; cyclo(lower)alkylcarbonylamino; cyclo(lower)alkyloxycarbonylamino; cyclo(lower)alkylidene (lower)alkanoylamino; benzoylamino or naphthoylamino, each of which may have one or two substituent(s) selected from the group consisting of lower alkyl, halogen, lower alkoxy, carboxy, esterified carboxy, nitro, hydroxy, acyloxy, trihalo(lower)alkyl, cyclo(lower)alkyloxy, phenyl, carboxy(lower)alkenyl, esterified carboxy(lower)alkenyl, amino, aroylamino, pyrimidinyloxy, and pyridylamino which may have nitro; phenylsulfonylamino which may have one or two halogen; phenyl(lower)alkylsulfonylamino; cyclo (lower)alkylcarbonylamino; [mono (or di)phenyl (lower)alkanoyl]amino; [naphthyl(lower)alkanoyl] amino; lower alkadienoylamino; furylcarbonylamino, pyridylcarbonylamino, thienylcarbonylamino, indolylcarbonylamino, indolinylcarbonylamino, quinolylcarbonylamino, tetrahydroquinolylcarbonylamino, benzofurylcarbonylamino, benzothienylcarbonylamino, methylenedioxybenzoylamino or morpholinylcarbonylamino, each of which may have one or two substituent(s) selected from the group consisting of lower alkyl and halogen; phenyl (lower)alkenoylamino which may have one or two substituent(s) selected from the group consisting of lower alkyl, halogen, carboxy, esterified carboxy and nitro; pyridyl(lower)alkenoylamino; carbamoylamino which may have one or two substituent(s) selected from the group consisting of lower alkyl; [phenyl or naphthyl, each of which may have one or two substituent(s) selected from the group consisting of nitro, amino, acylamino, lower alkoxy, lower alkylthio, lower alkyl, phenyl, carboxy, esterified carboxy, di(lower)alkylamino, trihalo(lower)alkyl and halogen]; phenylsulfonyl; phenyl(lower)alkyl; cyclo(lower)alkyl; thiazolyl; pyridyl; quinolyl; and morpholinyl; thiocarbamoylamino which may have phenyl, naphthyl or aroyl; lower alkylamino; N-lower alkanoyl-N-lower alkylamino; N-benzoyl-N-lower alkylamino; N-phenylcarbamoyl-N-lower alkylamino; N-[esterified carboxyphenyl](lower)alkenoyl-N-lower alkylamino; thiazolylamino or pyrimidinylamino each of which may have lower alkyl or phenyl; lower alkanoyl; carbamoyl which may have lower alkyl, or phenyl which may have one or two halogen; benzoyl which may have lower alkoxy; morpholinylcarbonyl; indolizinylcarbonyl; carbamoyl(lower)alkyl which may have phenyl or naphthyl; phenyl or naphthyl, each of which may have one or two substituent(s) selected from the group consisting of carboxy(lower)alkenyl, lower alkoxycarbonyl(lower)alkenyl, phenyl, lower alkoxy, cyclo(lower)alkyloxy, halogen, carboxy, lower alkoxycarbonyl, amino, lower alkanoylamino, benzoylamino which may have esterified carboxy or carboxy, lower alkylsulfonylamino, trihalo(lower) alkanoylamino, lower alkoxycarbonylamino, phenoxycarbonylamino, carboxy(lower) alkanoylamino, esterified carboxy(lower) alkanoylamino, carboxy(lower)alkenoylamino, esterified carboxy(lower)alkenoylamino, cyclo(lower) alkylcarbonylamino, lower alkylglyoxyloylamino, phenylsulfonylamino which may have one or two halogen, phenyl(lower)alkenoylamino which may have esterified carboxy or carboxy, pyridyl(lower) alkenoylamino, quinoxalinylcarbonylamino, benzothienylcarbonylamino, carbamoylamino which may have one or two substituent(s) selected from the group consisting of lower alkyl and phenyl, bis(lower alkylsulfonyl)amino, and carbamoyl which may have one or two substituent(s) selected from the group consisting of lower alkyl, phenyl and naphthyl; phenyl (lower)alkyl; naphthyl(lower)alkyl; phenyl(lower) alkenyl or naphthyl(lower)alkenyl, each of which may have one or two halogen; benzoyl(lower)alkenyl; lower alkoxycarbonyl(lower)alkenyl; cyano(lower)alkenyl; pyridyl(lower)alkenyl which may have halogen; pyrimidinyl(lower)alkenyl; quinolyl(lower)alkenyl; pyridyl, thienyl, pyrrolyl, pyrrolidinyl, indolyl, quinolyl, isoquinolyl, imidazolyl, thiazolyl, benzothiazolyl or triazolyl, each of which may have one or two substituent(s) selected from the group consisting of halogen, cyano, carboxy, lower alkoxycarbonyl, oxo, lower alkanoyl, amino, acylamino and pyridyl; and pyrimidinyloxy which may have phenyl; or pyridyl.

6. A compound of claim 5, wherein $R^1$ is nitrophenyl, phenyl(lower)alkyl, nitrophenyl(lower) alkyl, aminophenyl(lower)alkyl, hydroxyphenyl (lower)alkyl, lower alkanoyloxyphenyl(lower)alkyl, halo(lower)alkyl, carboxyethyl, lower alkoxycarbonyl (lower)alkyl, [pyrrolidinylcarbamoyl](lower)alkyl, [N,N-di(lower)alkylcarbamoyl](lower)alkyl, pyrrolidinylcarbonyl(lower)alkyl, [dioxopyrrolidinyloxycarbonyl](lower)alkyl, [lower alkoxycarbonylpyrrolidinylcarbonyl](lower)alkyl, [lower alkylpiperazinylcarbonyl](lower)alkyl, indolyl, indolyl(lower)alkyl, pyridyl(lower)alkyl which may have N-oxide, imidazolyl(lower)alkyl which may have lower alkyl or phenyl, triazolyl(lower) alkyl or morpholinyl(lower)alkyl, $R^2$ is phenyl or naphthyl, each of which may have one or two substituent(s) selected from the group consisting of lower alkyl; halogen; trihalo(lower)alkyl; hydroxy; lower alkanoyloxy; carboxy; lower alkoxycarbonyl; phenyl(lower)alkoxycarbonyl; carboxy(lower)alkyl; lower alkoxycarbonyl(lower)alkyl; lower alkoxy;

cyano; nitro; amino; lower alkanoylamino; phenoxycarbonylamino; lower alkoxycarbonylamino; lower alkoxyglyoxyloylamino; cyclo(lower)alkylcarbonylamino; cyclo(lower)alkyloxycarbonylamino; cyclo(lower)alkylidene(lower)alkanoylamino; benzoylamino which may have one or two substituent(s) selected from the group consisting of lower alkyl, halogen, lower alkoxy, carboxy, lower alkoxycarbonyl, nitro, hydroxy, lower alkanoyloxy, trihalo(lower)alkyl, cyclo(lower)alkyloxy, phenyl, carboxy(lower)alkenyl, lower alkoxycarbonyl(lower)alkenyl, amino, benzoylamino, pyrimidinyloxy, and pyridylamino which may have nitro; phenylsulfonylamino which may have one or two halogen; naphthoylamino which may have hydroxy, lower alkanoyloxy or lower alkoxycarbonyl; phenyl(lower)alkylsulfonylamino; cyclo(lower)alkylcarbonylamino; [mono(or di)phenyl(lower)alkanoyl]amino; [naphthyl(lower)alkanoyl]amino; lower alkadienoylamino; furylcarbonylamino; pyridylcarbonylamino which may have one or two halogen; thienylcarbonylamino; indolylcarbonylamino which may have lower alkyl; indolinylcarbonylamino; quinolylcarbonylamino; tetrahydroquinolylcarbonylamino; benzofurylcarbonylamino; benzothienylcarbonylamino; methylenedioxybenzoylamino; morpholinylcarbonylamino; phenyl(lower)alkenoylamino which may have lower alkyl, halogen, carboxy, lower alkoxycarbonyl or nitro; pyridyl(lower)alkenoylamino; carbamoylamino which may have one or two substituent(s) selected from the group consisting of lower alkyl; [phenyl which may have one or two substituent(s) selected from the group consisting of nitro, amino, acylamino, lower alkoxy, lower alkylthio, lower alkyl, phenyl, carboxy, lower alkoxycarbonyl, di(lower)alkylamino, trihalo(lower)alkyl; naphthyl and halogen]; naphthyl; phenylsulfonyl; phenyl(lower)alkyl; cyclo(lower)alkyl; thiazolyl; pyridyl; quinolyl; and morpholinyl; thiocarbamoylamino which may have phenyl, naphthyl, or benzoyl; lower alkylamino; N-lower alkanoyl-N-lower alkylamino; N-benzoyl-N-lower alkylamino; N-phenylcarbamoyl-N-loweralkylamino; N-[lower alkoxycarbonylphenyl](lower)alkenoyl-N-lower alkylamino; thiazolylamino which may have lower alkyl or phenyl; pyrimidinylamino; lower alkanoyl; carbamoyl which may have lower alkyl or phenyl which may have one or two halogen; benzoyl which may have lower alkoxy; morpholinylcarbonyl; indolizinylcarbonyl; carbamoyl(lower)alkyl which may have phenyl or naphthyl; phenyl which may have one or two substituent(s) selected from the group consisting of carboxy(lower)alkenyl, lower alkoxycarbonyl(lower)alkenyl, phenyl, lower alkoxy, cyclo(lower)alkyloxy, halogen, carboxy, lower alkoxycarbonyl, amino, lower alkanoylamino, benzoylamino which may have esterified carboxy or carboxy, mono- or di-lower alkylsulfonylamino, trihalo(lower)alkanoylamino, lower alkoxycarbonylamino, phenoxycarbonylamino, carboxy(lower)alkanoylamino, lower alkoxycarbonyl(lower)alkanoylamino, carboxy(lower)alkenoylamino, lower alkoxycarbonyl(lower)alkenoylamino, cyclo(lower)alkylcarbamoylamino, lower alkylglyoxyoylamino, phenylsulfonylamino which may have one or two halogen, phenyl(lower)alkenoylamino which may have esterified carboxy or carboxy, pyridyl(lower)alkenoylamino, quinoxalinylcarbonylamino, benzothienylcarbonylamino, carbamoylamino which may have one or two substituent(s) selected from the group consisting of lower alkyl and phenyl, bis(lower alkylsulfonyl)amino, carbamoyl which may have one or two substituent(s) selected from the group consisting of lower alkyl, phenyl and naphthyl; phenyl(lower)alkyl; naphthyl(lower)alkyl; phenyl(lower)alkenyl which may have two halogen; naphthyl(lower)alkenyl; benzoyl(lower)alkenyl; lower alkoxycarbonyl(lower)alkenyl; cyano(lower)alkenyl; pyridyl(lower)alkenyl which may have halogen; pyrimidinyl(lower)alkenyl; quinolyl(lower)alkenyl; pyridyl; thienyl which may have halogen; pyrrolyl which may have one or two substituent(s) selected from the group consisting of halogen, cyano and lower alkoxycarbonyl; pyrrolidinyl which may have oxo; indolyl which may have lower alkoxycarbonyl or lower alkanoyl; quinolyl; isoquinolyl; imidazolyl; thiazolyl which may have amino, acylamino or pyridyl; benzothiazolyl; triazolyl; and pyrimidinyloxy which may have phenyl; or pyridyl.

7. A compound of claim 6, wherein $R^2$ is lower alkylphenyl, trihalo(lower)alkylphenyl, hydroxyphenyl, lower alkanoyloxyphenyl, carboxyphenyl, lower alkoxycarbonylphenyl, [phenyl(lower)alkoxycarbonyl]phenyl, [carboxy(lower)alkyl]phenyl, [lower alkoxycarbonyl(lower)alkyl]phenyl, lower alkoxyphenyl, cyanophenyl, nitrophenyl, aminophenyl, [lower alkanoylamino]phenyl, [phenoxycarbonylamino]phenyl, [lower alkoxycarbonylamino]phenyl, [lower alkoxyglyoxyloylamino]phenyl, [cyclo(lower)alkyloxycarbonylamino]phenyl, [cyclo(lower)alkylcarbonylamino]phenyl, [cyclo(lower)alkylidene(lower)alkanoylamino]phenyl, [benzoylamino]phenyl, [mono (or di)(lower alkyl)benzoylamino]phenyl, [mono (or di)halobenzoylamino]phenyl, [di(lower alkoxy)benzoylamino]phenyl, [bis(lower alkoxycarbonyl)benzoylamino]phenyl, [mono (or di)nitrobenzoylamino]phenyl, [hydroxybenzoylamino]phenyl, [lower alkanoyloxybenzoylamino]phenyl, [bis[trihalo(lower)alkyl]benzoylamino]phenyl, phenyl having benzoylamino substituted with lower alkoxycarbonyl and nitro, phenyl having benzoylamino substituted with lower alkoxy and cyclo(lower)alkyloxy, [phenylbenzoylamino]phenyl, [[lower alkoxycarbonyl(lower)alkenyl]benzoylamino]-phenyl, [[benzoylamino]benzoylamino]phenyl, [pyrimidinyloxybenzoylamino]phenyl, [[nitropyridylamino]benzoylamino]phenyl, [naphthoylamino]phenyl, [hydroxynaphthoylamino]phenyl, [[lower alkanoyloxynaphthoyl]amino]phenyl, [[lower alkoxycarbonylnaphthoyl]amino]phenyl, [phenylsulfonylamino]phenyl, [dihalophenylsulfonylamino]phenyl, [phenyl(lower)alkylsulfonylamino]phenyl, [cyclo(lower)alkylcarbonylamino]phenyl, [mono (or di)phenyl(lower)alkanoylamino]phenyl, [naphthyl(lower)alkanoylamino]phenyl, [lower alkadienoylamino]phenyl, [furylcarbonylamino]phenyl, [pyridylcarbonylamino]phenyl, [dihalopyridylcarbonylamino]phenyl, [thienylcarbonylamino]phenyl, [indolinylcarbonylamino]phenyl, [quinolylcarbonylamino]phenyl, [tetrahydroquinolylcarbonylamino]phenyl, [benzofurylcarbonylamino]phenyl, [lower alkylindolylcarbonylamino]phenyl,

[benzothienylcarbonylamino]phenyl, [methylenedioxybenzoylamino]phenyl, [morpholinylcarbonylamino]phenyl, [phenyl(lower)alkenoylamino]phenyl, [[lower alkylphenyl(lower)alkenoyl]amino]phenyl, [[mono (or di)halophenyl(lower)alkenoyl]amino]phenyl, [[lower alkoxycarbonylphenyl(lower)alkenoyl]amino]-phenyl, [[nitrophenyl(lower)alkenoyl]amino]phenyl, [pyridyl(lower)alkenoylamino]phenyl, ureidophenyl, [lower alkylureido]phenyl, [phenylureido]phenyl, [[aminophenyl]ureido]phenyl, [[halophenyl]ureido]phenyl, [[nitrophenyl]ureido]phenyl, [[lower alkoxyphenyl]ureido]phenyl, [[lower alkylthiophenyl]ureido]phenyl, [[mono (or di)(lower alkyl)phenyl]ureido]phenyl, [biphenylylureido]phenyl, [[carboxyphenyl]ureido]phenyl, [[lower alkoxycarbonylphenyl]ureido]phenyl, [[di(lower)alkylaminophenyl]ureido]phenyl, [[trihalo(lower)alkylphenyl]ureido]phenyl, [[dihalophenyl]ureido]phenyl, [naphthylureido]phenyl, [phenylsulfonylureido]phenyl, [phenyl(lower)alkylureido]phenyl, [cyclo(lower)alkylureido)phenyl, [thiazolylureido]phenyl, [pyridylureido]phenyl, [quinolylureido]phenyl, [morpholinylureido]phenyl, [N-phenyl-N-lower alkylureido]phenyl, [phenyl(thioureido)]phenyl, [naphthyl(thioureido)]phenyl, [benzoyl(thioureido)]phenyl, [lower alkylamino]phenyl, [N-lower alkanoyl-N-lower alkylamino]phenyl, [N-benzoyl-N-lower alkylamino]phenyl, [N-phenylcarbamoyl-N-lower alkylamino]phenyl, [N-lower alkoxycarbonylphenyl(lower)alkenoyl-N-lower alkylamino]phenyl, [lower alkylthiazolylamino]phenyl, [phenylthiazolylamino]phenyl, [pyrimidinylamino]phenyl, lower alkanoylphenyl, carbamoylphenyl, [lower alkylcarbamoyl]phenyl, [phenylcarbamoyl]phenyl, [dihalophenylcarbamoyl]phenyl, [N-dihalophenyl-N-lower alkylcarbamoyl]phenyl, benzoylphenyl, [lower alkoxybenzoyl]phenyl, morpholinylcarbonylphenyl, indolizinylcarbonylphenyl, [phenylcarbamoyl(lower)alkyl]phenyl, [naphthylcarbamoyl(lower)alkyl]phenyl, phenylphenyl, [[lower alkoxycarbonyl(lower)alkenyl]phenyl]phenyl, biphenylylphenyl, phenyl having phenyl substituted with lower alkoxy and cyclo(lower)alkyloxy, [halophenyl]phenyl, [carboxyphenyl]phenyl, [lower alkoxycarbonylphenyl]phenyl, [aminophenyl]phenyl, [[lower alkanoylamino]phenyl]phenyl, [[benzoylamino]phenyl]phenyl, [[carboxybenzoylamino]phenyl]phenyl, [[mono (or bis)(lower alkylsulfonyl)amino]phenyl]-phenyl, [[trihalo(lower)alkanoylamino]phenyl]phenyl, [[lower alkoxycarbonylamino]phenyl]phenyl, [[phenoxycarbonylamino]phenyl]phenyl, [[carboxy(lower)alkanoylamino]phenyl]phenyl, [[lower alkoxycarbonyl(lower)alkanoylamino]phenyl]-phenyl, [[lower alkoxycarbonyl(lower)alkenoylamino]-phenyl]phenyl, [[cyclo(lower)alkylcarbonylamino]-phenyl]phenyl, [[lower alkylglyoxyloylamino]-phenyl]phenyl, [[dihalophenylsulfonylamino]-phenyl]phenyl, [[phenyl(lower)alkenoylamino]phenyl]phenyl, phenylphenyl substituted with (lower)alkenoylamino having phenyl and carboxy, [[pyridyl(lower)alkenoylamino]phenyl]phenyl, [[[halopyridyl(lower)alkenoyl]amino]phenyl]phenyl, [[quinoxalinylcarbonylamino]phenyl]phenyl, [[benzothienylcarbonylamino]phenyl]phenyl, [[lower alkylcarbamoylamino]phenyl]phenyl, [[phenylcarbamoylamino]phenyl]phenyl, [[naphthylcarbamoyl]phenyl]phenyl, naphthylphenyl, [lower alkoxynaphthyl]phenyl, [phenyl(lower)alkyl]phenyl, [naphthyl(lower)alkyl]phenyl, [phenyl(lower)alkenyl]phenyl, [dihalophenyl(lower)alkenyl]phenyl, [naphthyl(lower)alkenyl]phenyl, [benzoyl(lower)alkenyl]phenyl, [lower alkoxycarbonyl(lower)alkenyl]phenyl, [cyano(lower)alkenyl]phenyl, [pyridyl(lower)alkenyl]phenyl, [pyrimidinyl(lower)alkenyl]phenyl, [quinolyl(lower)alkenyl]phenyl, pyridylphenyl, thienylphenyl, [halothienyl]phenyl, pyrrolylphenyl, [dihalopyrrolyl]phenyl, [cyanopyrrolyl]phenyl, [lower alkoxycarbonylpyrrolyl]phenyl, [dioxopyrrolidinyl]phenyl, indolylphenyl, [lower alkoxycarbonylindolyl]phenyl, [lower alkanoylindolyl]phenyl, quinolylphenyl, isoquinolylphenyl, imidazolylphenyl, [aminothiazolyl]phenyl, [pyridylthiazolyl]phenyl, benzothiazolylphenyl, triazolylphenyl, pyrimidinyloxyphenyl, [phenylpyrimidinyloxy]phenyl, phenyl having halogen and amino, phenyl having halogen and (halophenyl)ureido, phenyl having halogen and (lower alkoxyphenyl)ureido, phenyl having halogen and lower alkanoylamino, bis(lower alkoxycarbonyl)phenyl, phenyl having lower alkoxycarbonyl and amino, phenyl having lower alkoxycarbonyl and lower alkanoylamino, phenyl having lower alkoxycarbonyl and naphthoylamino, phenyl having halogen and naphthoylamino, phenyl having cyclo(lower)alkyloxy and lower alkoxy, naphthyl or pyridyl.

8. A compound of claim 7, wherein $R^1$ is pyridyl(lower)alkyl, $R^2$ is [(dihalobenzoyl)amino]phenyl, [bis(lower alkoxycarbonyl)benzoylamino]phenyl, (naphthoylamino)phenyl, [(lower alkanoyloxynaphthoyl)amino]phenyl, [pyridyl(lower)alkenyl]phenyl, [[halopyridyl](lower)alkenyl]phenyl, [quinolyl(lower)alkenyl]phenyl, naphthylphenyl or [[[pyridyl(lower)alkenoyl]amino]phenyl]phenyl and $R^3$ is hydrogen.

9. A compound of claim 8, which is selected from the group consisting of
(1) 2-(3-pyridylmethyl)-4-[3-(3,5-dibromobenzoylamino)phenyl]-3-oxo-3,4-dihydropyrido[2,3-b]pyrazine, or its hydrochloride,
(2) 2-(3-pyridylmethyl)-4-[3-(3,5-dichlorobenzoylamino)phenyl]-3-oxo-3,4-dihydropyrido[2,3-b]pyrazine, or its hydrochloride,
(3) 2-(3-pyridylmethyl)-4-[3-[3,5-bis(methoxycarbonyl)benzoylamino]phenyl]-3-oxo-3,4-dihydropyrido[2,3-b]pyrazine, or its hydrochloride,
(4) 2-(3-pyridylmethyl)-4-[3-[(E)-2-(4-quinolyl)vinyl]phenyl]-3-oxo-3,4-dihydropyrido[2,3-b]pyrazine,
(5) 2-(3-pyridylmethyl)-4-[3-(2-naphthoylamino)phenyl]-3-oxo-3,4-dihydropyrido[2,3-b]pyrazine, or its hydrochloride,
(6) 2-(3-pyridylmethyl)-4-[3-[(6-acetoxy-2-naphthoyl)amino]phenyl]-3-oxo-3,4 -dihydropyrido[2,3-b]pyrazine,
(7) 2-(3-pyridylmethyl)-4-[3-[(E)-2-(3-pyridyl)vinyl]phenyl]-3-oxo-3,4-dihydropyrido[2,3-b]pyrazine,
(8) 2-(3-pyridylmethyl)-4-[3-[(E)-2-(4-pyridyl)vinyl]phenyl]-3-oxo-3,4-dihydropyrido[2,3-b]pyrazine,
(9) 2-(3-pyridylmethyl)-4-[3-[(E)-2-(5-chloropyridin-3-yl)vinyl]phenyl]-3-oxo-3,4-dihydropyrido[2,3-b]pyrazine,
(10) 2-(3-pyridylmethyl)-4-[3-(2-naphthyl)phenyl]-3-oxo-3,4-dihydropyrido[2,3-b]pyrazine and
(11) 2-(3-pyridylmethyl)-4-[3-[(E)-3-(4-pyridyl)acryloylamino]phenyl]phenyl]-3-oxo-3,4-dihydropyrido[2,3-b]pyrazine.

10. A compound of claim 7, wherein
R$^1$ is imidazolyl(lower)alkyl,
R$^2$ is (naphthoylamino)phenyl, and
R$^3$ is hydrogen.

11. A compound of claim 10, which is 2-(1-imidazolylmethyl)-4-[3-(2-naphthoylamino)phenyl]-3-oxo-3,4-dihydropyrido[2,3-b]pyrazine.

12. A compound of the formula:

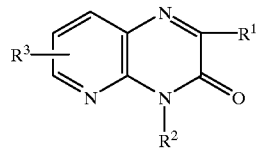

wherein
R$^1$ is aryl which may have suitable substituent(s), ar(lower)alkyl which may have suitable substituent(s), halo(lower)alkyl, carboxyethyl; protected carboxy (lower)alkyl, acyl(lower)alkyl, heterocyclic group or heterocyclic(lower)alkyl which may have suitable substituent(s),
R$^2$ is aryl which may have suitable substituent(s) or heterocyclic group, and
R$^3$ is hydrogen, lower alkoxy or arylthio,
provided that
when R$^1$ is phenyl, halophenyl, trihalo(lower)alkyl, carboxyethyl, piperidine ring, morpholine ring, or an optionally alkyl substituted piperazine ring,
and R$^3$ is hydrogen, lower alkoxy, or thiophenoxy,
then R$^2$ is not phenyl substituted by lower alkyl, by lower alkoxy, by halogen, by carboxy, by lower alkoxycarbonyl, by carboxy(lower)alkyl or by amino substituents of the following formula:

wherein R$^{10}$ and R$^{11}$, may be the same or different, each represent hydrogen, phenyl, halophenyl or alkyl, the alkyl optionally being substituted by alkoxy or by a mono- or di-alkyl or unsubstituted amino group; or R$^{10}$ and R$^{11}$, together with the nitrogen atom to which they are attached, form a piperidine, morpholine or an optionally alkyl substituted piperazine ring,
and a pharmaceutically acceptable salt thereof.

13. A compound of claim 12, wherein
R$^1$ is phenyl which may have 1 to 3 suitable substituent(s); phenyl(lower)alkyl which may have 1 to 3 suitable substituent(s); halo(lower)alkyl; carboxyethyl, protected carboxy(lower)alkyl; carbamoyl(lower)alkyl which may have one or two suitable substituent(s); heterocyclicoxycarbonyl(lower)alkyl which may have 1 to 3 suitable substituent(s); heterocycliccarbonyl (lower)alkyl which may have 1 to 3 substituent(s) selected from the group consisting of protected carboxy and lower alkyl; indolyl; or indolyl(lower)alkyl, pyridyl(lower)alkyl, imidazolyl(lower)alkyl, morpholinyl(lower)alkyl or triazolyl(lower)alkyl, each of which may have 1 to 3 suitable substituent(s);
R$^2$ is phenyl or naphthyl, each of which may have 1 to 3 suitable substituent(s), or pyridyl, and R$^3$ is hydrogen, lower alkoxy or phenylthio,
provided that
when R$^1$ is phenyl, halophenyl, trihalo(lower)alkyl, or carboxyethyl,
and R$^3$ is hydrogen, lower alkoxy, or thiophenoxy,
then R$^2$ is not phenyl substituted by lower alkyl, by lower alkoxy, by halogen, by carboxy, by lower alkoxycarbonyl, by carboxy(lower)alkyl or by amino substituents of the following formula:

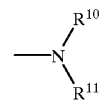

wherein R$^{10}$ and R$^{11}$, may be the same or different, each represent hydrogen, phenyl, halophenyl or alkyl, the alkyl optionally being substituted by alkoxy or by a mono- or di-alkyl or unsubstituted amino group; or R$^{10}$ and R$^{11}$, together with the nitrogen atom to which they are attached, form a piperidine, morpholine or an optionally alkyl substituted piperazine ring.

14. A compound of claim 13, wherein
R$^1$ is phenyl which may have one or two nitro; phenyl (lower)alkyl which may have one or two substituent(s) selected from the group consisting of nitro, amino, protected amino, hydroxy and protected hydroxy; halo (lower)alkyl; carboxyethyl, esterified carboxy(lower) alkyl; carbamoyl(lower)alkyl which may have one or two substituent(s) selected from the group consisting of lower alkyl and heterocyclic group; pyrrolidinyloxycarbonyl(lower)alkyl which may have one or two oxo; pyrrolidinylcarbonyl(lower)alkyl or piperazinylcarbonyl(lower)alkyl, each of which may have one or two substituent(s) selected from the group consisting of esterified carboxy and lower alkyl; indolyl; or indolyl(lower)alkyl, pyridyl(lower)alkyl, imidazolyl(lower)alkyl, morpholinyl(lower)alkyl or triazolyl(lower)alkyl, each of which may have one or two substituent(s) selected from the group consisting of lower alkyl, N-oxide and aryl;
R$^2$ is phenyl or naphthyl, each of which may have one or two substituent(s) selected from the group consisting of lower alkyl; halogen; mono(or di or tri)halo(lower) alkyl; hydroxy; protected hydroxy; carboxy; protected carboxy; carboxy(lower)alkyl; protected carboxy (lower)alkyl; lower alkoxy; cyano; nitro; amino; acylamino; lower alkylamino; N-acyl-N-lower alkylamino; heterocyclicamino which may have 1 to 3 substituent(s) selected from the group consisting of lower alkyl and aryl; acyl; acyl(lower)alkyl; aryl which may have 1 to 3 substituent(s) selected from the group consisting of carboxy(lower)alkenyl, protected carboxy (lower)alkenyl, aryl, lower alkoxy, cyclo(lower) alkyloxy, halogen, carboxy, protected carboxy, amino, acylamino, diacylamino and acyl; ar(lower)alkyl; ar(lower)alkenyl which may have 1 to 3 halogen; acyl(lower)alkenyl; protected carboxy(lower)alkenyl; cyano(lower)alkenyl; heterocyclic(lower)alkenyl which may have 1 to 3 halogen; heterocyclic group which may have 1 to 3 substituent(s) selected from the group consisting of halogen, cyano, carboxy, protected carboxy, oxo, acyl, amino, protected amino and heterocyclic group; and heterocyclicoxy which may have 1 to 3 aryl, or pyridyl, provided that when $R^1$ is phenyl, halophenyl, trihalo(lower)alkyl, or carboxyethyl, and $R^3$ is hydrogen, lower alkoxy, or thiophenoxy, then $R^2$ is not phenyl substituted by lower alkyl, by lower alkoxy, by halogen, by carboxy, by lower alkoxycarbonyl, by carboxy(lower)alkyl, by amino, by mono- or di-(lower)alkylamino, by piperidine, by morpholinje or by piperazine.

15. A compound of claim 14, wherein $R^1$ is phenyl which may have nitro; phenyl(lower)alkyl which may have nitro, amino, acylamino, hydroxy or acyloxy; halo(lower)alkyl; carboxyethyl, lower alkoxycarbonyl(lower)alkyl; carbamoyl(lower)alkyl which may have one or two substituent(s) selected from the group consisting of lower alkyl and pyrrolidinyl; pyrrolidinyloxycarbonyl(lower)alkyl which may have one or two oxo; pyrrolidinylcarbonyl(lower)alkyl or piperazinylcarbonyl(lower)alkyl, each of which may have lower alkoxycarbonyl or lower alkyl; indolyl; or indolyl(lower)alkyl, pyridyl(lower)alkyl, imidazolyl (lower)alkyl, morpholinyl(lower)alkyl or triazolyl (lower)alkyl, each of which may have lower alkyl, N-oxide or phenyl;

$R^2$ is phenyl or naphthyl, each of which may have one or two substituent(s) selected from the group consisting of lower alkyl; halogen; trihalo(lower)alkyl; hydroxy; acyloxy; carboxy; esterified carboxy; carboxy(lower) alkyl; esterified carboxy(lower)alkyl; lower alkoxy; cyano; nitro; amino; lower alkanoylamino; aryloxycarbonylamino; lower alkoxycarbonylamino; lower alkoxyglyoxyloylamino; cyclo(lower)alkylcarbonylamino; cyclo(lower)alkyloxycarbonylamino; cyclo(lower)alkylidene(lower)alkanoylamino; aroylamino which may have 1 to 3 substituent(s) selected from the group consisting of lower alkyl, halogen, lower alkoxy, carboxy, protected carboxy, nitro, hydroxy, protected hydroxy, mono(or di or tri)halo(lower)alkyl, cyclo (lower)alkyloxy, aryl, carboxy(lower)alkenyl, protected carboxy(lower)alkenyl, amino, protected amino, heterocyclicoxy, and heterocyclicamino which may have nitro; arylsulfonylamino which may have one or two halogen; ar(lower)alkylsulfonylamino; cyclo (lower)alkylcarbonylamino; [mono(or di)ar(lower) alkanoyl]amino; lower alkadienoylamino; heterocycliccarbonylamino which may have 1 to 3 substituent (s) selected from the group consisting of lower alkyl and halogen; ar(lower)alkenoylamino which may have 1 to 3 substituent(s) selected from the group consisting of lower alkyl, halogen, carboxy, protected carboxy and nitro; heterocyclic(lower)alkenoylamino, carbamoylamino which may have one or two substituent(s) selected from the group consisting of lower alkyl, [aryl which may have 1 to 3 substituent(s) selected from the group consisting of nitro, amino, protected amino, lower alkoxy, lower alkylthio, lower alkyl, aryl, carboxy, protected carboxy, di(lower)alkylamino, mono(or di or tri)halo(lower)alkyl and halogen], arylsulfonyl, ar(lower)alkyl, cyclo(lower)alkyl, and heterocyclic group; thiocarbamoylamino which may have one or two substituent(s) selected from the group consisting of aryl and acyl; lower alkylamino; N-lower alkanoyl-N-lower alkylamino; N-aroyl-N-lower alkylamino; N-arylcarbamoyl-N-lower alkylamino; N-protected carboxyar(lower)alkenoyl-N-lower alkylamino; thiazolylamino or pyrimidinylamino, each of which may have one or two substituent(s) selected from the group consisting of lower alkyl and phenyl; lower alkanoyl; carbamoyl which may have one or two substituent(s) selected from the group consisting of lower alkyl and aryl which may have one or two halogen; aroyl which may have lower alkoxy or heterocycliccarbonyl; carbamoyl(lower)alkyl which may have one or two aryl; phenyl or naphthyl, each of which may have one or two substituent(s) selected from the group consisting of carboxy(lower)alkenyl, esterified carboxy(lower)alkenyl, phenyl, lower alkoxy, cyclo (lower)alkyloxy, halogen, carboxy, esterified carboxy, amino, lower alkanoylamino, aroylamino which may have protected carboxy or carboxy, lower alkylsulfonylamino, mono(o r di or tri)halo(lower) alkanoylamino, lower alkoxycarbonylamino, aryloxycarbonylamino, carboxy(lower)alkanoyl amino, p rotected carboxy(lower)alkanoylamino, carboxy(lower)alkenoyl ami no, protected carboxy (lower)alkenoylamino, cyclo(lower) alkylcarbonylamino, lowe r alkylglyoxyloylamino, arylsulfonylamino which may have one or two halogen, ar(lower)alkenoylamino which may have protected carboxy or carboxy, heterocyclic(lower)alkenoylamino, heterocycliccarbonylamino, carbamoylamino which may have one or two substituent(s) selected from the group consisting of lower alkyl and aryl, bis(lower alkylsulfonyl)amino, and carbamoyl which may have one or two substituent(s) selected from the group consisting of lower alkyl and aryl; phenyl(lower)alkyl; naphthyl(lower)alkyl; phenyl(lower)alkenyl or naphthyl(lower)alkenyl, each of which may h ave one or two halogen; aroyl(lower)alkenyl; esterified carboxy (lower)alkenyl; cyano(lower)alkenyl; pyridyl(lower) alkenyl which may have one or tw o halogen; pyrimidinyl(lower)alkenyl; quinolyl(lower)alkenyl; pyridyl, thienyl, pyrrolyl, pyrrolidinyl, indolyl, quinolyl, isoquinolyl, imidazolyl, thiazolyl, benzothiazolyl or triazolyl, each of which may have one or two substituent(s) selected from the group consisting of halogen, cyano, carboxy, esterified carboxy, oxo, lower alkanoyl, amino, acylamino and pyridyl; and pyrimidinyloxy which may have one or two phenyl; or pyridyl, provided that when $R^1$ is phenyl, trihalo(lower)alkyl, or carboxyethyl, then $R^2$ is not phenyl substituted by lower alkyl, by lower alkoxy, by halogen, by carboxy, by lower alkoxycarbonyl, by carboxy(lower)alkyl, by amino, or by mono(lower)alkylamino.

16. A compound of claim 15, wherein $R^1$ is phenyl which may have nitro; phenyl(lower)alkyl which may have nitro, amino, acylamino, hydroxy or lower alkanoyloxy; halo(lower)alkyl; carboxyethyl, lower alkoxycarbonyl(lower)alkyl; carbamoyl(lower) alkyl which may have one or two substituent(s) selected from the group consisting of lower alkyl and pyrrolidinyl; pyrrolidinyloxycarbonyl(lower)alkyl which may have two oxo; pyrrolidinylcarbonyl(lower) alkyl which may have lower alkoxycarbonyl; piperazinylcarbonyl(lower)alkyl which may have lower alkyl; indolyl; indolyl(lower)alkyl; pyridyl (lower)alkyl which may have N-oxide; imidazolyl (lower)alkyl which may have lower alkyl or phenyl; morpholinyl(lower)alkyl; or triazolyl(lower)alkyl;

$R^2$ is phenyl or naphthyl, each of which may have one or two substituent(s) selected from the group consisting of lower alkyl; halogen; trihalo(lower)alkyl; hydroxy; lower alkanoyloxy; carboxy; lower alkoxycarbonyl; phenyl(lower)alkoxycarbonyl; carboxy(lower)alkyl; lower alkoxycarbonyl(lower)alkyl; lower alkoxy; cyano; nitro; amino; lower alkanoylamino; phenoxycarbonylamino; lower alkoxycarbonylamino; lower alkoxyglyoxyloylamino; cyclo(lower)alkylcarbonylamino; cyclo(lower)alkyloxycarbonylamino; cyclo(lower)alkylidene(lower)alkanoylamino; benzoylamino or naphthoylamino, each of which may have one or two substituent(s) selected from the group consisting of lower alkyl, halogen, lower alkoxy, carboxy, esterified carboxy, nitro, hydroxy, acyloxy, trihalo(lower)alkyl, cyclo(lower)alkyloxy, phenyl, carboxy(lower)alkenyl, esterified carboxy(lower)alkenyl, amino, aroylamino, pyrimidinyloxy, and pyridylamino which may have nitro; phenylsulfonylamino which may have one or two halogen; phenyl(lower)alkylsulfonylamino; cyclo(lower)alkylcarbonylamino; [mono(or di)phenyl(lower)alkanoyl]amino; [naphthyl(lower)alkanoyl]amino; lower alkadienoylamino; furylcarbonylamino, pyridylcarbonylamino, thienylcarbonylamino, indolylcarbonylamino, indolinylcarbonylamino, quinolylcarbonylamino, tetrahydroquinolylcarbonylamino, benzofurylcarbonylamino, benzothienylcarbonylamino, methylenedioxybenzoylamino or morpholinylcarbonylamino, each of which may have one or two substituent(s) selected from the group consisting of lower alkyl and halogen; phenyl(lower)alkenoylamino which may have one or two substituent(s) selected from the group consisting of lower alkyl, halogen, carboxy, esterified carboxy and nitro; pyridyl(lower)alkenoylamino; carbamoylamino which may have one or two substituent(s) selected from the group consisting of lower alkyl, [phenyl or naphthyl, each of which may have one or two substituent(s) selected from the group consisting of nitro, amino, acylamino, lower alkoxy, lower alkylthio, lower alkyl, phenyl, carboxy, esterified carboxy, di(lower)alkylamino, trihalo(lower)alkyl and halogen], phenylsulfonyl, phenyl(lower)alkyl, cyclo(lower)alkyl, thiazolyl, pyridyl, quinolyl, and morpholinyl; thiocarbamoylamino which may have phenyl, naphthyl or aroyl; lower alkylamino; N-lower alkanoyl-N-lower alkylamino; N-benzoyl-N-lower alkylamino; N-phenylcarbamoyl-N-lower alkylamino; N-[esterified carboxyphenyl](lower)alkenoyl-N-lower alkylamino; thiazolylamino or pyrimidinylamino each of which may have lower alkyl or phenyl; lower alkanoyl; carbamoyl which may have lower alkyl, or phenyl which may have one or two halogen; benzoyl which may have lower alkoxy; morpholinylcarbonyl; indolizinylcarbonyl; carbamoyl(lower)alkyl which may have phenyl or naphthyl; phenyl or naphthyl, each of which may have one or two substituent(s) selected from the group consisting of carboxy(lower)alkenyl, lower alkoxycarbonyl(lower)alkenyl, phenyl, lower alkoxy, cyclo(lower)alkyloxy, halogen, carboxy, lower alkoxycarbonyl, amino, lower alkanoylamino, benzoylamino which may have esterified carboxy or carboxy, lower alkylsulfonylamino, trihalo(lower)alkanoylamino, lower alkoxycarbonylamino, phenoxycarbonylamino, carboxy(lower)alkanoylamino, esterified carboxy(lower)alkanoylamino, carboxy(lower)alkenoylamino, esterified carboxy(lower)alkenoylamino, cyclo(lower)alkylcarbonylamino, lower alkylglyoxyloylamino, phenylsulfonylamino which may have one or two halogen, phenyl(lower)alkenoylamino which may have esterified carboxy or carboxy, pyridyl(lower)alkenoylamino, quinoxalinylcarbonylamino, benzothienylcarbonylamino, carbamoylamino which may have one or two substituent(s) selected from the group consisting of lower alkyl and phenyl, bis(lower alkylsulfonyl)amino, and carbamoyl which may have one or two substituent(s) selected from the group consisting of lower alkyl, phenyl and naphthyl; phenyl(lower)alkyl; naphthyl(lower)alkyl; phenyl(lower)alkenyl or naphthyl(lower)alkenyl, each of which may have one or two halogen; benzoyl(lower)alkenyl; lower alkoxycarbonyl(lower)alkenyl; cyano(lower)alkenyl; pyridyl(lower)alkenyl which may have halogen; pyrimidinyl(lower)alkenyl; quinolyl(lower)alkenyl; pyridyl, thienyl, pyrrolyl, pyrrolidinyl, indolyl, quinolyl, isoquinolyl, imidazolyl, thiazolyl, benzothiazolyl or triazolyl, each of which may have one or two substituent(s) selected from the group consisting of halogen, cyano, carboxy, lower alkoxycarbonyl, oxo, lower alkanoyl, amino, acylamino and pyridyl; and pyrimidinyloxy which may have phenyl; or pyridyl, provided that when $R^1$ is phenyl, trihalo(lower)alkyl, or carboxyethyl, then $R^2$ is not phenyl substituted by lower alkyl, by lower alkoxy, by halogen, by carboxy, by lower alkoxycarbonyl, by carboxy(lower)alkyl, by amino, or by mono(lower)alkylamino.

17. A compound of claim 16, wherein $R^1$ is phenyl, nitrophenyl, phenyl(lower)alkyl, nitrophenyl(lower)alkyl, aminophenyl(lower)alkyl, hydroxyphenyl(lower)alkyl, lower alkanoyloxyphenyl(lower)alkyl, halo(lower)alkyl, carboxyethyl, lower alkoxycarbonyl(lower)alkyl, [pyrrolidinylcarbamoyl](lower)alkyl, [N,N-di(lower)alkylcarbamoyl](lower)alkyl, pyrrolidinylcarbonyl(lower)alkyl, [dioxopyrrolidinyloxycarbonyl](lower)alkyl, [lower alkoxycarbonylpyrrolidinylcarbonyl](lower)alkyl, [lower alkylpiperazinylcarbonyl](lower)alkyl, indolyl, indolyl(lower)alkyl, pyridyl(lower)alkyl which may have N-oxide, imidazolyl(lower)alkyl which may have lower alkyl or phenyl, triazolyl(lower)alkyl, morpholinyl(lower)alkyl, $R^2$ is phenyl or naphthyl, each of which may have one or two substituent(s) selected from the group consisting of lower alkyl; halogen; trihalo(lower)alkyl; hydroxy; lower alkanoyloxy; carboxy; lower alkoxycarbonyl; phenyl(lower)alkoxycarbonyl; carboxy(lower)alkyl; lower alkoxycarbonyl(lower)alkyl; lower alkoxy; cyano; nitro; amino; lower alkanoylamino; phenoxycarbonylamino; lower alkoxycarbonylamino; lower alkoxyglyoxyloylamino; cyclo(lower)alkylcarbonylamino; cyclo(lower)alkyloxycarbonylamino; cyclo(lower)alkylidene(lower)alkanoylamino; benzoylamino which may have one or two substituent(s) selected from the group consisting of lower alkyl, halogen, lower alkoxy, carboxy, lower alkoxycarbonyl, nitro, hydroxy, lower alkanoyloxy, trihalo(lower)alkyl, cyclo(lower)alkyloxy, phenyl, carboxy(lower)alkenyl, lower alkoxycarbonyl(lower)alkenyl, amino, benzoylamino, pyrimidinyloxy, and pyridylamino which may have nitro; phenylsulfonylamino which may have one or two halogen; naphthoylamino which may have hydroxy, lower alkanoyloxy or lower alkoxycarbonyl; phenyl (lower)alkylsulfonylamino; cyclo(lower)alkylcarbonylamino; mono(or di)phenyl(lower)alkanoylamino; naphthyl(lower)alkanoylamino; lower alkadienoylamino; furylcarbonylamino; pyridylcarbonylamino which may have one or two halogen; thienylcarbonylamino; indolylcarbonylamino which may have lower alkyl; indolinylcarbonylamino; quinolylcarbonylamino; tetrahydroquinolylcarbonylamino; benzofurylcarbonylamino; benzothienylcarbonylamino; methylenedioxybenzoylamino; morpholinylcarbonylamino; phenyl(lower)alkenoylamino which may have lower alkyl, halogen, carboxy, lower alkoxycarbonyl or nitro; pyridyl(lower)alkenoylamino; carbamoylamino which may have one or two substituent(s) selected from the group consisting of lower alkyl, [phenyl which may have one or two substituent(s) selected from the group consisting of nitro, amino, acylamino, lower alkoxy, lower alkylthio, lower alkyl, phenyl, carboxy, lower alkoxycarbonyl, di(lower)alkylamino, trihalo(lower)alkyl and halogen]; naphthyl, phenylsulfonyl, phenyl(lower)alkyl, cyclo(lower)alkyl, thiazolyl, pyridyl, quinolyl, and morpholinyl; thiocarbamoylamino which may have phenyl, naphthyl, or benzoyl; lower alkylamino; N-lower alkanoyl-N-lower alkylamino; N-benzoyl-N-lower alkylamino; N-phenylcarbamoyl-N-lower alkylamino; N-[lower alkoxycarbonylphenyl](lower)alkenoyl-N-lower alkylamino; thiazolylamino which may have lower alkyl or phenyl; pyrimidinylamino; lower alkanoyl; carbamoyl which may have lower alkyl or phenyl which may have one or two halogen; benzoyl which may have lower alkoxy; morpholinylcarbonyl; indolizinylcarbonyl; carbamoyl(lower)alkyl which may have phenyl or naphthyl; phenyl which may have one or two substituent(s) selected from the group consisting of carboxy(lower)alkenyl, lower alkoxycarbonyl(lower)alkenyl, phenyl, lower alkoxy, cyclo(lower)alkyloxy, halogen, carboxy, lower alkoxycarbonyl, amino, lower alkanoylamino, benzoylamino which may have esterified carboxy or carboxy, mono- or di-lower alkylsulfonylamino, trihalo(lower)alkanoylamino, lower alkoxycarbonylamino, phenoxycarbonylamino, carboxy(lower)alkanoylamino, lower alkoxycarbonyl(lower)alkanoylamino, carboxy(lower)alkenoylamino, lower alkoxycarbonyl(lower)alkenoylamino, cyclo(lower)alkylcarbamoylamino, lower alkylglyoxyloylamino, phenylsulfonylamino which may have one or two halogen, phenyl(lower)alkenoylamino which may have esterified carboxy or carboxy, pyridyl(lower)alkenoylamino, quinoxalinylcarbonylamino, benzothienylcarbonylamino, carbamoylamino which may have one or two substituent(s) selected from the group consisting of lower alkyl and phenyl, bis(lower alkylsulfonyl)amino, carbamoyl which may have one or two substituent(s) selected from the group consisting of lower alkyl, phenyl and naphthyl; phenyl(lower)alkyl; naphthyl(lower)alkyl; phenyl(lower)alkenyl which may have two halogen; naphthyl(lower)alkenyl; benzoyl(lower)alkenyl; lower alkoxycarbonyl(lower)alkenyl; cyano(lower)alkenyl; pyridyl(lower)alkenyl which may have halogen; pyrimidinyl(lower)alkenyl; quinolyl(lower)alkenyl; pyridyl; thienyl which may have halogen; pyrrolyl which may have one or two substituent(s) selected from the group consisting of halogen, cyano and lower alkoxycarbonyl; pyrrolidinyl which may have oxo; indolyl which may have lower alkoxycarbonyl or lower alkanoyl; quinolyl; isoquinolyl; imidazolyl; thiazolyl which may have amino, acylamino or pyridyl; benzothiazolyl; triazolyl; and pyrimidinyloxy which may have phenyl; or pyridyl, provided that when $R^1$ is phenyl, trihalo(lower)alkyl, or carboxyethyl, then $R^2$ is not phenyl substituted by lower alkyl, by lower alkoxy, by halogen, by carboxy, by lower alkoxycarbonyl, by carboxy(lower)alkyl, by amino, or by mono(lower)alkylamino.

18. A compound of claim 17, wherein $R^2$ is phenyl, lower alkylphenyl, halophenyl, trihalo(lower)alkylphenyl, hydroxyphenyl, lower alkanoyloxyphenyl, carboxyphenyl, lower alkoxycarbonylphenyl, [phenyl(lower)alkoxycarbonyl]phenyl, [carboxy(lower)alkyl]phenyl, [lower alkoxycarbonyl(lower)alkyl]phenyl, lower alkoxyphenyl, cyanophenyl, nitrophenyl, aminophenyl, [lower alkanoylamino]phenyl, [phenoxycarbonylamino]phenyl, [lower alkoxycarbonylamino]phenyl, [lower alkoxyglyoxyloylamino]phenyl, [cyclo(lower)alkyloxycarbonylamino]phenyl, [cyclo(lower)alkylcarbonylamino]phenyl, [cyclo(lower)alkylidene(lower)alkanoylamino]phenyl, [benzoylamino]phenyl, [mono(or di)(lower alkyl)benzoylamino]phenyl, [mono(or di)halobenzoylamino]phenyl, [di(lower alkoxy)benzoylamino]phenyl, [bis(lower alkoxycarbonyl)benzoylamino]phenyl, [mono(or di)nitrobenzoylamino]phenyl, [hydroxybenzoylamino]phenyl, [lower alkanoyloxybenzoylamino]phenyl, [bis[trihalo(lower)alkyl]benzoylamino]phenyl, phenyl having benzoylamino substituted with lower alkoxycarbonyl and nitro, phenyl having benzoylamino substituted with lower alkoxy and cyclo(lower)alkyloxy, [phenylbenzoylamino]phenyl, [[lower alkoxycarbonyl(lower)alkenyl]benzoylamino]phenyl, [[benzoylamino]benzoylamino]phenyl, [pyrimidinyloxybenzoylamino]phenyl, [[nitropyridylamino]benzoylamino]phenyl, [naphthoylamino]phenyl, [hydroxynaphthoylamino]phenyl, [[lower alkanoyloxynaphthoyl]amino]phenyl, [[lower alkoxycarbonylnaphthoyl]amino]phenyl, [phenylsulfonylamino]phenyl, [dihalophenylsulfonylamino]phenyl, [phenyl(lower)alkylsulfonylamino]phenyl, [cyclo(lower)alkylcarbonylamino]phenyl, [mono(or di)phenyl(lower)alkanoylamino]phenyl, [naphthyl(lower)alkanoylamino]phenyl, [lower alkadienoylamino]phenyl, [furylcarbonylamino]phenyl, [pyridylcarbonylamino]phenyl, [dihalopyridylcarbonylamino]phenyl, [thienylcarbonylamino]phenyl, [indolinylcarbonylamino]phenyl, [quinolylcarbonylamino]phenyl, [tetrahydroquinolylcarbonylamino]phenyl, [benzofurylcarbonylamino]phenyl, [lower alkylindolylcarbonylamino]phenyl, [benzothienylcarbonylamino]phenyl, [methylenedioxybenzoylamino]phenyl, [morpholinylcarbonylamino]phenyl, [phenyl(lower)alkenoylamino]phenyl, [[lower alkylphenyl(lower)alkenoyl]amino]phenyl, [[mono(or di)halophenyl(lower)alkenoyl]amino]phenyl, [[lower alkoxycarbonylphenyl(lower)alkenoyl]amino]phenyl, [[nitrophenyl(lower)alkenoyl]amino]phenyl, [pyridyl (lower)alkenoylamino]phenyl, ureidophenyl, [lower alkylureido]phenyl, [phenylureido]phenyl, [[aminophenyl]ureido]phenyl, [[halophenyl]ureido]phenyl, [[nitrophenyl]ureido]phenyl, [[lower alkoxyphenyl]ureido]phenyl, [[lower alkylthiophenyl]ureido]phenyl, [[mono(or di)(lower alkyl)phenyl)ureido]phenyl, [biphenylylureido]phenyl, [[carboxyphenyl]ureido]phenyl, [[lower alkoxycarbonylphenyl]ureido]phenyl, [[di(lower)alkylaminophenyl]ureido]phenyl, [[trihalo(lower)alkylphenyl]ureido]phenyl, [[dihalophenyl]ureido]phenyl, [naphthylureido]phenyl, [phenylsulfonylureido]phenyl, [phenyl(lower)alkylureido]phenyl, [cyclo(lower)alkylureido]phenyl, [thiazolylureido]phenyl, [pyridylureido]phenyl, [quinolylureido]phenyl, [morpholinylureido]phenyl, [N-phenyl-N-lower alkylureido]phenyl, [phenyl(thioureido)]phenyl, [naphthyl(thioureido)]phenyl, [benzoyl(thioureido)]phenyl, [lower alkylamino]phenyl, [N-lower alkanoyl-N-lower alkylamino]phenyl, [N-benzoyl-N-lower alkylamino]phenyl, [N-phenylcarbamoyl-N-lower alkylamino]phenyl, [N-lower alkoxycarbonylphenyl(lower)alkenoyl-N-lower alkylamino]phenyl, [lower alkylthiazolylamino]phenyl, [phenylthiazolylamino]phenyl, [pyrimidinylamino]phenyl, lower alkanoylphenyl, carbamoylphenyl, [lower alkylcarbamoyl]phenyl, [phenylcarbamoyl]phenyl, [dihalophenylcarbamoyl]phenyl, [N-dihalophenyl-N-lower alkylcarbamoyl]phenyl, benzoylphenyl, [lower alkoxybenzoyl]phenyl, morpholinylcarbonylphenyl, indolizinylcarbonylphenyl, [phenylcarbamoyl(lower)alkyl]phenyl, [naphthylcarbamoyl(lower)alkyl]phenyl, phenylphenyl, [[lower alkoxycarbonyl(lower)alkenyl]phenyl]phenyl, biphenylylphenyl, phenyl having phenyl substituted with lower alkoxy and cyclo(lower)alkyloxy, [halophenyl]phenyl, [carboxyphenyl]phenyl, [lower alkoxycarbonylphenyl]phenyl, [aminophenyl]phenyl, [[lower alkanoylamino]phenyl]phenyl, [[benzoylamino]phenyl]phenyl, [[carboxybenzoylamino]phenyl]phenyl, [[mono(or bis)(lower alkylsulfonyl)amino]phenyl]phenyl, [[trihalo(lower)alkanoylamino]phenyl]phenyl, [[lower alkoxycarbonylamino]phenyl]phenyl, [[phenoxycarbonylamino]phenyl]phenyl, [[carboxy(lower)alkanoylamino]phenyl]phenyl, [[lower alkoxycarbonyl(lower)alkanoylamino]phenyl]phenyl, [[lower alkoxycarbonyl(lower)alkenoylamino]phenyl]phenyl, [[cyclo(lower)alkylcarbonylamino]phenyl]phenyl, [[lower alkylglyoxyloylamino]phenyl]phenyl, [[dihalophenylsulfonylamino]phenyl]phenyl, [[phenyl(lower)alkenoylamino]phenyl]phenyl, phenylphenyl substituted with (lower)alkenoylamino having phenyl and carboxy, [[pyridyl(lower)alkenoylamino]phenyl]phenyl, [[[halopyridyl(lower)alkenoyl]amino]phenyl]phenyl, [[quinoxalinylcarbonylamino]phenyl]phenyl, [[benzothienylcarbonylamino]phenyl]phenyl, [[lower alkylcarbamoylamino]phenyl]phenyl, [[phenylcarbamoylamino]phenyl]phenyl, [[naphthylcarbamoyl]phenyl]phenyl, naphthylphenyl, [lower alkoxynaphthyl]phenyl, [phenyl(lower)alkyl]phenyl, [naphthyl(lower)alkyl]phenyl, [phenyl(lower)alkenyl]phenyl, [dihalophenyl(lower)alkenyl]phenyl, [naphthyl(lower)alkenyl]phenyl, [benzoyl(lower)alkenyl]phenyl, [lower alkoxycarbonyl(lower)alkenyl]phenyl, [cyano(lower)alkenyl]phenyl, [pyridyl(lower)alkenyl]phenyl, [pyrimidinyl(lower)alkenyl]phenyl, [quinolyl(lower)alkenyl]phenyl, pyridylphenyl, thienylphenyl, [halothienyl]phenyl, pyrrolylphenyl, [dihalopyrrolyl]phenyl, [cyanopyrrolyl]phenyl, [lower alkoxycarbonylpyrrolyl]phenyl, [dioxopyrrolidinyl]phenyl, indolylphenyl, [lower alkoxycarbonylindolyl]phenyl, [lower alkanoylindolyl]phenyl, quinolylphenyl, isoquinolylphenyl, imidazolylphenyl, [aminothiazolyl]phenyl, [pyridylthiazolyl]phenyl, benzothiazolylphenyl, triazolylphenyl, pyrimidinyloxyphenyl, [phenylpyrimidinyloxy]phenyl, phenyl having halogen and amino, phenyl having halogen and (halophenyl)ureido, phenyl having halogen and (lower alkoxyphenyl)ureido, phenyl having halogen and lower alkanoylamino, bis(lower alkoxycarbonyl)phenyl, phenyl having lower alkoxycarbonyl and amino, phenyl having lower alkoxycarbonyl and lower alkanoylamino, phenyl having lower alkoxycarbonyl and naphthoylamino, phenyl having halogen and naphthoylamino, phenyl having cyclo(lower)alkyloxy and lower alkoxy, naphthyl or pyridyl, provided that when $R^1$ is phenyl, trihalo(lower)alkyl, or carboxyethyl, then $R^2$ is not phenyl, lower alkylphenyl, lower alkoxyphenyl, halophenyl, carboxyphenyl, lower alkoxycarbonylphenyl, [carboxy(lower)alkyl]phenyl, aminophenyl, or mono-[lower alkylamino]phenyl.

19. A pharmaceutical composition which comprises, as an active ingredient, a compound of claim 1 or a pharmaceutically acceptable salt thereof in admixture with a pharmaceutically acceptable carrier.

20. A pharmaceutical composition which comprises, as an active ingredient, a compound of claim 12 or a pharmaceutically acceptable salt thereof in admixture with a pharmaceutically acceptable carrier.

21. A process for preparing a compound of the formula:

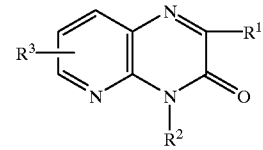

wherein $R^1$ is as defined in claim 1;

$R^2$ is aryl which may have suitable substituent(s) or heterocyclic group, and $R^3$ is hydrogen, lower alkoxy or arylthio, or a salt thereof, which comprises (1) reacting a compound of the formula:

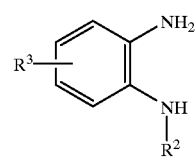

wherein $R^2$ and $R^3$ are each as defined above, or a salt thereof with a compound of the formula:

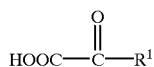

wherein R¹ is as defined above,
or a salt thereof to give a compound of the formula:

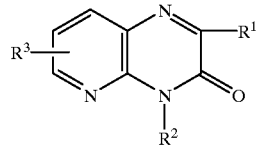

wherein R¹, R² and R³ are each as defined above, or a salt thereof, or (2) subjecting a compound of the formula:

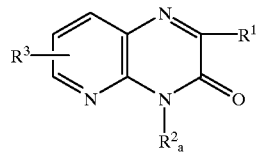

wherein R¹ and R³ are each as defined above, and $R_a^2$ is aryl having amino or aryl having aminoaryl,
or its reactive derivative at the amino group, or a salt thereof to acylation reaction to give a compound of the formula:

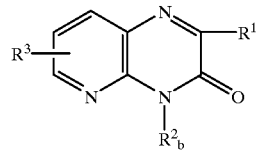

wherein R¹ and R³ are each as defined above and $R_b^2$ is aryl having acylamino or aryl having acylaminoaryl,
or a salt thereof, or (3) subjecting a compound of the formula:

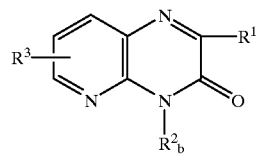

wherein R¹, $R_b^2$ and R³ are each as defined above, or a salt thereof to deacylation to give a compound of the formula:

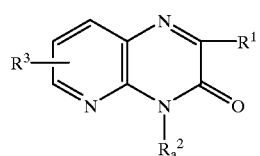

wherein R¹, $R_a^2$ and R³ are each as defined above, or a salt thereof, or (4) subjecting a compound of the formula:

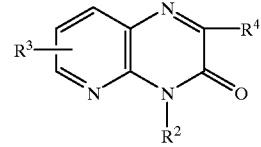

wherein R² and R³ are each as defined above, and R⁴ is lower alkyl, or a salt thereof to halogenation to give a compound of the formula:

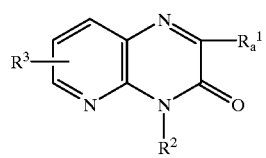

wherein R² and R³ are each as defined above, and $R_a^1$ is halo(lower)alkyl, or a salt thereof, or (5) subjecting a compound of the formula:

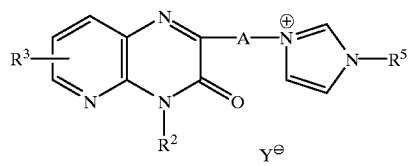

wherein R² and R³ are each as defined above,

R⁵ is N-protective group,

A is lower alkylene, and

Y⊖ is halide, or a salt thereof to elimination of N-protective group to give a compound of the formula:

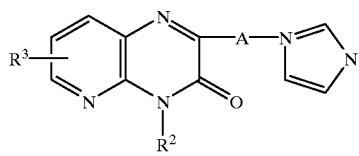

wherein R², R³ and A are each as defined above, or a salt thereof.

22. A process for preparing a pharmaceutical composition which comprises admixing a compound of claim 1 or a pharmaceutically acceptable salt thereof with a pharmaceutically acceptable carrier.

23. A process for preparing a pharmaceutical composition which comprises admixing a compound of claim 12 or a pharmaceutically acceptable salt thereof with a pharmaceutically acceptable carrier.

* * * * *

UNITED STATES PATENT AND TRADEMARK OFFICE
CERTIFICATE OF CORRECTION

PATENT NO. : 6,426,345 B1
DATED : July 30, 2002
INVENTOR(S) : Shimazaki et al.

It is certified that error appears in the above-identified patent and that said Letters Patent is hereby corrected as shown below:

<u>Title page,</u>
Item [86], should read:
-- [86]  PCT No.:     PCT/JP95/01366

§ 371 (c)(1),
         (2), (4) Date:   Jan. 30, 1998 --
Item [30], Foreign Application Priority Data should read:
-- [30]              Foreign Application Priority Data
Jul. 11, 1994    (GB) ....................................................... 9413975 --

Signed and Sealed this

Twenty-first Day of January, 2003

JAMES E. ROGAN
*Director of the United States Patent and Trademark Office*